(12) United States Patent
Aujame et al.

(10) Patent No.: US 6,835,384 B1
(45) Date of Patent: Dec. 28, 2004

(54) **NUCLEIC ACIDS AND POLYPEPTIDES SPECIFIC OF THE *NEISSERIA* GENUS PATHOGENIC STRAINS**

(75) Inventors: Luc Aujame, Fleurieux sur l'Abresle (FR); Annabelle Bouchardon, Lyons (FR); Geneviève Renauld-Mongenie, Chaponost (FR); Bachra Rokbi, Lyons (FR); Xavier Nassif, Paris (FR); Colin Tinsley, Paris (FR); Agnès Perrin, Paris (FR)

(73) Assignees: Aventis Pasteur, Lyons (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 09/830,433

(22) PCT Filed: Oct. 28, 1999

(86) PCT No.: PCT/FR99/02643

§ 371 (c)(1),
(2), (4) Date: Aug. 16, 2001

(87) PCT Pub. No.: WO00/26375

PCT Pub. Date: May 11, 2000

(30) Foreign Application Priority Data

Oct. 30, 1999 (FR) ............................................. 98 13693

(51) Int. Cl.$^7$ ..................... A61K 39/095; A61K 39/00; C12P 21/06; C07K 1/00; C12N 1/20
(52) U.S. Cl. ............................... 424/250.1; 424/249.1; 424/190.1; 424/185.1; 424/184.1; 530/300; 530/350; 536/23.1; 536/23.7; 536/24.1; 536/24.32; 435/69.1; 435/69.3; 435/243; 435/252.3
(58) Field of Search ........................... 424/184.1, 185.1, 424/190.1, 249.1, 250.1; 530/300, 350; 536/23.1, 23.7, 24.1, 26.32; 435/69.1, 69.3, 247, 253.3

(56) References Cited

U.S. PATENT DOCUMENTS 5,147,800 A * 9/1992 Hammond et al.

OTHER PUBLICATIONS

Biotecnologia Aplicada 1996, vol. 13, 1–7.*

Rudinger et al, in "Peptide Hormones", edited by Parsons, J.A., University Park Press, Jun. 1976, p. 6.*

Burgess et al., The Journal of Cell Biology, 111:2129–2138, 1990.*

Lazar et al., Molecular and Cellular Biology, 8(3): 1247–1252, 1988.*

Jobling et al. (Mol. Microbiol. 1991, 5(7): 1755–67.*

* cited by examiner

*Primary Examiner*—Lynette R. F. Smith
*Assistant Examiner*—Padma Baskar
(74) *Attorney, Agent, or Firm*—B. Aaron Schulman; Stites & Harbison PLLC

(57) ABSTRACT

The invention concerns nucleic acids coding for polypeptides specific of the *Neisseria* genus pathogenic strains, the corresponding polypeptides, and their diagnostic and therapeutic applications.

4 Claims, 1 Drawing Sheet

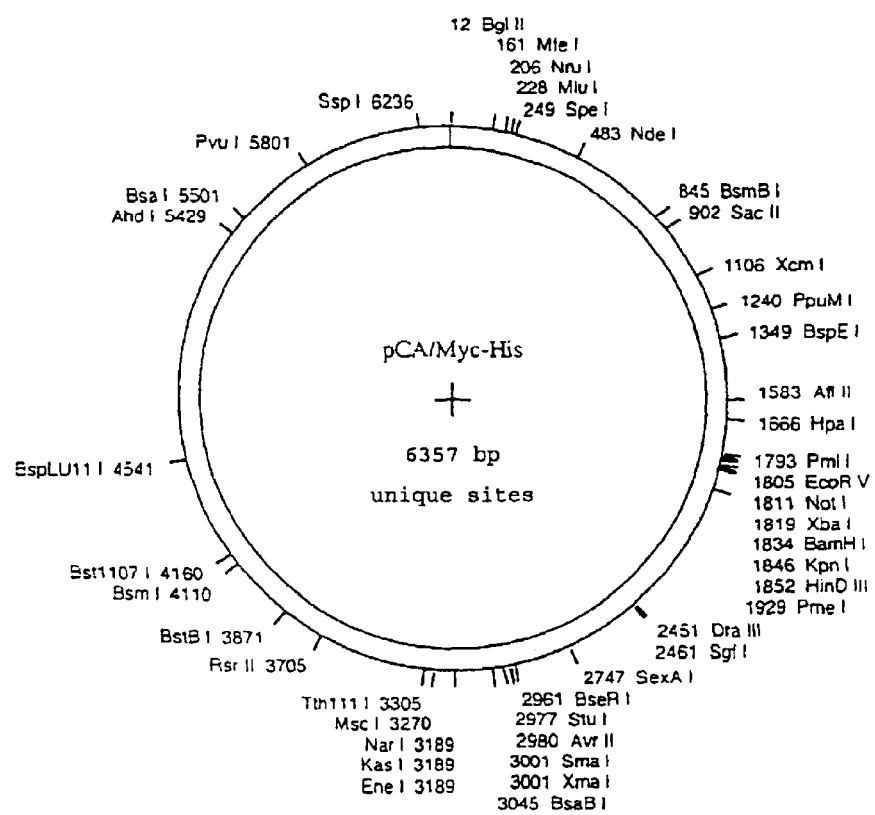

NUCLEIC ACIDS AND POLYPEPTIDES SPECIFIC OF THE *NEISSERIA* GENUS PATHOGENIC STRAINS

The present invention relates to nucleic acids encoding polypeptides specific for pathogenic strains of the *Neisseria* genus, in particular which are useful for preventing or treating a *Neisseria meningitidis* infection.

In general, meningitis is either of viral origin or of bacterial origin. The bacteria mainly responsible are: type b *Haemophilus influenzae, Neisseria meningitidis* and *Streptococcus pneumoniae*. The *Neisseria meningitidis* species is subdivided into serogroups according to the nature of the capsular polysaccharides. Although about a dozen serogroups exist, 90% of meningitis cases can be attributed to three serogroups: A, B and C.

Effective vaccines based on capsular polysaccharides exist for preventing meningitis caused by *Neisseria meningitidis* serogroups A and C. These polysaccharides, unmodified, are only slightly immunogenic, or not at all, in children under the age of two, and do not induce any immune memory. However, these drawbacks can be overcome by conjugating these polysaccharides to a carrier protein.

On the other hand, the polysaccharide of *Neisseria meningitidis* serogroup B is non-immunogenic, or relatively non-immunogenic in humans, whether or not it is in a conjugated form. Thus, it appears to be highly desirable to seek a vaccine against meningitis caused by *Neisseria meningitidis*, in particular *Neisseria meningitidis* serogroup B, other than a vaccine based on polysaccharide.

To this end, various proteins of the external membrane of *N. meningitidis* have already been proposed, such as the membrane-bound receptor for human transferrin (WO 90/12591 and WO 93/06861).

*Neisseria meningitidis* is genetically very close to *Neisseria gonorrhoeae* and *Neisseria lactamica*. *N. gonorrhoeae* is especially responsible for infections located in the urogenital tract. It colonizes the genital mucous membrane, crosses the epithelium and then invades the sub-epithelium, where it multiplies and is responsible for a severe inflammatory reaction. On the other hand, *N. lactamica* is considered to be a nonpathogenic species.

Sequences present in *N. gonorrhoeae* and *N. meningitidis*, but absent from *N. lactamica*, have been disclosed in patent application WO 98/02547, but this prior patent application does not locate or identify the coding sequences.

The authors of the present invention have now managed to identify some of these genes by searching, in the meningococcal genome, for the open reading frames specific for pathogenic strains of the *Neisseria* genus, using the following strategy:

Some of the sequences disclosed in patent application WO 98/02547 (referred to, in said prior application, as SEQ ID Nos 66, 67, 69, 70, 72 to 96, 98 and 99) were positioned on the sequence of the genome of the *N. meningitidis* serogroup B strain (ATCC 13090), available from the Pathoseq® bank of Incyte Pharmaceuticals, and also on the sequence of the genome of the *Neisseria meningitidis* strain Z2491 (Sanger Centre). This made it possible to identify, in the *N. meningitidis* genome which has 2.3 mega bases, 19 contigs representing 220000 base pairs.

The authors of the present invention then analysed, for each of the 19 contigs, the presence of open reading frames (ORFs) containing at least 100 amino acids (and, by definition, bordered by an initiation codon and a stop codon), using the Gene Jockey II sequence processor® program (Biosoft). This analysis made it possible to select approximately 400 candidate ORFs.

The sequences of each of these ORFs were then analysed using the Codon Use® program (Conrad Halling), which takes into account the codon use frequency in *N. meningitidis*. Only the ORFs with sequences having a maximum frequency of use of these codons were selected. At the end of this analysis, 197 candidate ORFs were selected.

The ORFs selected using this double analysis were subjected to a homology search through all of the available banks, using the BLASTX® program, from the access to the Pathoseq® bank of Incyte Pharmaceuticals. This homology search made it possible to exclude the ORFs encoding, a priori, cytoplasmic or periplasmic proteins, in particular metabolism proteins. The ORFs were also subjected to analysis of possible protein motifs, using the DNA Star Protean® program (Lasergene software).

The authors of the present invention then investigated whether the ORFs selected at the end of the previous step (118 in number) were effectively absent from *N. lactamica*, as predicted by the application of the prior art WO 98/02547.

To this end, a PCR amplification was carried out. This amplification proved to be ineffective for 78 of the 118 ORFs tested. Only the ORFs for which the amplification in *N. lactamica* was negative (sequences named "lactamica−") were selected. In order to verify that these negative results were not "false negatives", the lactamica− sequences selected were subjected to a control by dot blot. At the end of this step, only 23 ORFs were confirmed *N. meningitidis*+/ *N. lactamica*−.

Finally, these 23 ORFs were repositioned in their entirety on the *N. meningitides* ATCC13090 genome. This made it possible to demonstrate that three ORFs previously eliminated on the basis of their putative protein function appeared to be located close to, or were even framed by, some of the 23 *N. meningitidis*+/*N. lactamica*−ORFs. These three ORFs (SEQ ID Nos 29, 35 and 37) were reintroduced into the study, and it was proven that they were also *N. meningitidis*+/*N. lactamica*−.

The authors of the present invention then attempted to discover whether the ORFs identified using the genome of the *N. meningitidis* serogroup B strain ATCC 13090 were also present in the genomes of *N. meningitidis* serogroup A Z2491 (Sanger Centre) and of *N. gonorrhoeae* FA1090 (Advanced Centre of Genome Technology, Oklahoma University). Then, they compared the sequences derived from these various genomes, with multiple alignment (Clustal, Infobiogen). This made it possible to redefine, for some of the ORFs, the most probable position of the initiation codon and translation stop codon. The sequences of the open reading frames derived from the strain ATCC13090 are given in the SEQ ID Nos 1–51 (odd numbers) and the amino acid sequences which are deduced therefrom are given in the SEQ ID Nos 2–52 (even numbers).

A subject of the present invention is, therefore, a nucleic acid in isolated form encoding a polypeptide, or an antigenic fragment thereof, excluding the nucleic acids disclosed in SEQ ID Nos 70, 73, 74, 77, 80, 81, 87, 88, 89, 94, 95 and 98 of application WO 98/02547 (sequences attached to the present description and numbered SEQ ID Nos 70A, 73A, 74A, 77A, 80A, 81A, 87A, 88A, 89A, 94A, 95A and 98A so as to distinguish them from the sequences of the invention); said polypeptide having an amino acid sequence which is identical or homologous to a sequence selected from those of group II; group II consisting of the sequences shown in SEQ ID Nos 2–52 (even numbers) and the sequence SEQ ID No. 53.

Preferably, said nucleic acid can have a nucleotide sequence selected from those of group I, group I consisting of the sequences shown in SEQ ID Nos 1–51 (odd numbers).

The term "nucleic acid" includes and means equally ORF, gene, polynucleotide, DNA and RNA. The term "nucleic acid in isolated form" means a nucleic acid separated from the biological environment in which it is found under natural conditions. For example, a DNA molecule exists under natural conditions when it is integrated into a genome or when it forms part of a library of genes. In that case, it cannot be in isolated form. On the other hand, the same molecule separated from the genome by cloning (for example subsequent to a PCR amplification) should be considered as being in isolated form. Typically, a DNA molecule in isolated form does not contain the coding regions which are contiguous with it in 5' and 3' in the genome from which it is derived. The nucleic acids in isolated form can be integrated into vectors (for example plasmids, or viral or bacterial vectors) without, even so, abandoning their characteristic of being separated from their natural environment.

The authors of the present invention have more particularly found that the ORFs which, when they are derived from the strain ATCC 13090, are characterized by the sequences as shown in SEQ ID Nos 19, 27, 39, 45, 47 and 49 are specific for Neisseria meningitidis insofar as it has not been possible to demonstrate identical or homologous sequences in the N. gonorrhoeae genome. They have also found that the ORF characterized by the strain sequence as shown in SEQ ID No. 39 is specific for Neisseria meningitidis serogroup B.

A subject of the invention is also a polypeptide in isolated form, or a fragment thereof; said polypeptide having an amino acid sequence identical or homologous to a sequence selected from those of group II.

The amino acids framed in the sequence SEQ ID No. 8 correspond to the signal sequence, and the amino acid in bold represents the first amino acid of the mature form. The amino acid sequence of the mature protein form is represented in SEQ ID No. 53.

In the context of the present invention, the terms "polypeptide" and "protein" are equivalent and mutually interchangeable. They refer to any amino acid chain, whatever its length and its post-translational modifications (for example phosphorylation or glycosylation).

The expression "antigenic fragments of the polypeptides specific for pathogenic strains of the Neisseria genus" is intended to mean the polypeptides derived from the polypeptides of the invention as defined above, through deletions of portions of said polypeptides without destroying the antigenicity (for example, without notable loss of the antigenic activity) of said polypeptides. The specific antigenicity can be determined using various methods known to those skilled in the art, as explained later.

These fragments are preferably at least 12 amino acids long, more preferably at least 20 amino acids long, preferentially 50 amino acids long, more preferably still 75 amino acids long, preferentially 100 amino acids long.

These fragments can be used to reveal epitopes which may be masked in the parent polypeptides. They are also advantageous for inducing a T-lymphocyte-dependent protective immune response. The deletions can, in fact, make it possible to eliminate immunodominant regions which are highly variable between various strains.

Such fragments can be obtained using standard techniques known to those skilled in the art (for example, Ausubel et al., Current Protocols in Molecular Biology, John Wiley & Sons Inc, 1994), for example by PCR, RT-PCR or treatment with restriction enzymes for the cloned DNA molecules, or by the method of Kunkel et al. (Proc. Natl. Acad. Sci. USA (1985) 82:448).

The expression "homologous amino acid sequence" is intended to mean a sequence which differs from one of the sequences of group II by substitution, deletion and/or insertion of one or more amino acids, at positions such that these modifications do not destroy the specific antigenicity of the polypeptide in question.

Said substitutions are preferably conservative substitutions, i.e. substitutions of amino acids of the same class, such as substitutions of amino acids with uncharged side chains (for instance asparagine, glutamine, serine, threonine and tyrosine), of amino acids with basic side chains (for instance lysine, arginine and histidine), of amino acids with acid side chains (for instance aspartic acid and glutamic acid) or of amino acids with apolar side chains (for instance glycine, alanine, valine, leucine, isoleucine, proline, phenylalanine, methionine, tryptophan and cysteine).

Advantageously, a homologous amino acid sequence has at least a 75% degree of homology (i.e. of identity) with one of the sequences of group II; preferably this degree of homology is at least 80%, most preferably at least 90%. The homologous amino acid sequences include, in particular, the sequences which are substantially identical to one of the sequences of group II. The expression "substantially identical sequence" means a sequence which has at least a 90%, advantageously at least a 95%, preferably at least a 97%, and most preferably at least a 99%, degree of homology (i.e. of identity) with one of the sequences of group II. In addition, it may differ from the reference sequence only through mainly conservative substitutions.

The degree of homology (also named degree of identity) is generally determined using a sequence analysis program (for example, Sequence Analysis Software Package of the Genetics Computer Group, University of Wisconsin Biotechnology Centre, 1710 University Avenue, Madison, Wis. 53705). Similar amino acid sequences are aligned so as to obtain the maximum degree of homology (i.e. identity). To this end, it may be necessary to artificially introduce gaps into the sequence. Once optimal alignment has been produced, the degree of homology (i.e. identity) is established by recording all the positions for which the amino acids of the two sequences compared are identical, with respect to the total number of positions.

The expression "homologous nucleotide sequences" is intended to mean sequences which differ from the sequences of group I by substitution of one or more nucleotides, or by deletion and/or insertion of one or more codons, at positions such that these sequences (i) still encode polypeptides having the sequences of group II, due to the effect of the degeneracy of the genetic code; or (ii) encode polypeptides having homologous sequences as defined above.

Advantageously, a homologous nucleotide sequence has at least a 60% degree of homology with one of the sequences of group I; preferably this degree of homology is at least 80%, most preferably at least 90%.

Typically, a homologous nucleotide sequence hybridizes specifically to the sequences complementary to the sequences of group I, under stringent conditions. The temperature at which the hybridization assay is carried out constitutes an important factor which influences the stringency. Conventionally, this temperature, termed hybridization temperature (Th), is selected from 5 to 40° C., preferably from 20 to 25°0 C., below the temperature at which 50% of the paired strands separate (Tm). In general, it is considered that conditions of high stringency are satisfied when Th is lower than Tm by 5 to 25° C. approximately, for example by 5 to 10° C. or, most commonly, by 20 to 25° C. approximately. Moderate stringency is established when Th is lower than Tm by 30 to 40° C.

For sequences comprising more than 30 bases, the temperature Tm is defined by the equation: Tm=81.5+0.41(%G+C)+16.6Log(cation concentration)−0.63(%formamide)−(600/number of bases). Thus, ionic strength has a major impact on the value of Tm. The temperature Tm increases by 16.60° C. every time the monovalent cation concentration increases by a factor of 10. The addition of formamide into the hybridization buffer causes, on the other hand, the value of Tm to decrease. (For a complete reference, see Sambrook et al., Molecular Cloning, A laboratory manual, Cold Spring Harbor Laboratory Press, 1989, pages 9.54–9.62).

Conventionally, hybridization experiments are carried out at a temperature of 60 to 68° C., for example at 65° C. At this temperature, stringent hybridization conditions can, for example, be implemented in 6×SSC, advantageously in 2×SSC or 1×SSC, preferably in 0.5×SSC, 0.3×SSC or 0.1×SSC (in the absence of formamide). A solution of 1×SSC contains 0.15 M of NaCl and 0.015 M of sodium citrate.

For this reason, in other words, a subject of the invention is a polynucleotide in isolated form, which is capable of hybridizing, under stringent conditions, with a DNA molecule having one of the nucleotide sequences as shown in SEQ ID Nos 1–51 (odd numbers) or the sequences complementary thereto.

A specific class of homologous sequences consists of those encountered naturally by virtue of the extremely common phenomenon of allelic variation. A bacterial species, for example *N. meningitidis* or *N. gonorrhoeae*, consists of a large variety of strains which differ from one another through minor variations, termed allelic variations. Thus, a polypeptide which is present in various strains and which, of course, performs the same biological function in each of them, can have an amino acid sequence which is not identical from one strain to the other. In other words, the sequences derived from the allelic variation are purely sequences equivalent or alternative to those of group II. The class of sequences which are allelic variants of one of the sequences of group II consists of the sequences of the polypeptide as found in a pathogenic species of the *Neisseria* genus (for example, *N. meningitidis* or *N. gonorrhoeae*) other than the *N. meningitidis* strain ATCC 13090. The biological function which is associated with the allelic variant sequences is the same as that which is associated with the reference sequence. The differences (substitution, deletion or addition of one or more amino acids) which they exhibit between one another (including the reference sequence) do not modify the biological function of the polypeptide. The term "biological function" is intended to mean the function exercised by the polypeptide in the cells which produce it naturally.

The allelic variation is also expressed in the coding sequences. A polynucleotide, encoding a polypeptide, having a sequence which is an allelic variant of one of the sequences of group I can be easily cloned by amplifying the genomic DNA of the strains of pathogenic species of the *Neisseria* genus, for example by PCR (polymerase chain reaction), using synthetic oligonucleotide primers capable of hybridizing to the 5' and 3' ends of the coding region. The sequences of such primers can easily be established by those skilled in the art using the nucleotide sequences given in SEQ ID Nos 1–51 (odd numbers). The primers generally have from 10 to 40 nucleotides, preferably from 15 to 25 nucleotides.

For this reason, in other words, a subject of the invention is a DNA molecule in isolated form which can be amplified and/or cloned by PCR from the genome of a pathogenic *Neisseria* strain, using a pair of 5' and 3' PCR primers; the sequences of these primers being established using one of the nucleotide sequences as shown in SEQ ID Nos 1–51 (odd numbers). An example is given, for each pair of primers, in Example I.1 hereinafter.

A subject of the present invention is more particularly the allelic variants having the nucleotide sequences SEQ ID Nos 54 to 76 (even numbers) and the products encoded by these nucleotide sequences, having the amino acid sequences SEQ ID Nos 55 to 77 (odd numbers).

The polypeptides of the invention can be fused to other polypeptides, for example by translation of a hybrid gene. Vectors for expressing fusion polypeptides are commercially available, such as the vectors pMal-c2 or pMal-p2 from New England Biolabs, in which the protein to which the polypeptides of the invention can be fused is a maltose-binding protein, the glutathione-S-transferase system from Pharmacia or the His-Tag system from Novagen. Such systems are in particular useful for purifying the polypeptides of the invention. The polypeptides of the invention can be fused to polypeptides having adjuvant activity, such as for example the B subunit of cholera toxin or the B subunit of the *E. coli* heat-sensitive toxin.

The nucleic acids of the present invention can be used (i) in a process for producing the polypeptides encoded by said nucleic acids, in a recombinant host system, (ii) for the construction of vaccination vectors, such as poxviruses, intended to be used in methods and compositions for preventing and/or for treating an infection with pathogenic *Neisseria* strains, in particular with *Neisseria meningitidis*, (iii) as a vaccination agent in a naked form or in combination with a vehicle which promotes transfer to the target cells and, (iv) in the construction of attenuated *Neisseria* strains which can overexpress a nucleic acid of the invention, or express it in a non-toxic, mutated form.

The present invention also provides (i) an expression cassette containing a polynucleotide of the invention placed under the control of elements allowing its expression, in particular under the control of a suitable promoter; (ii) an expression vector containing said expression cassette; (iii) a host cell (prokaryotic or eukaryotic) transformed with an expression cassette and/or an expression vector as defined above, and (iv) a method for obtaining a polypeptide encoded by said polynucleotide of the invention, comprising culturing said transformed cell under conditions allowing the expression of the polynucleotide of the invention, and recovering the polypeptide from the cell culture.

Among the eukaryotic hosts which can be used, mention may be made in particular of yeast cells (for example *Saccharomyces cerevisiae* or *Pichia Pastoris*), mammalian cells (for example COS1, NIH3T3 or JEG3) arthropod cells (for example *Spodoptera frugiperda* (SF9)) and plant cells. Among the prokaryotic hosts which can be used, mention may be made in particular of *E. coli*.

The choice of the expression cassette depends on the host system chosen, and also on the characteristics desired for the expressed polypeptide. In general, expression cassettes include a promoter which is functional in the host system selected and which can be constitutive or inducible; a ribosome-binding site; an initiation codon (ATG); if necessary, a region encoding a signal peptide; a nucleotide sequence of the invention; a stop codon; and, optionally, a 3' terminal region (translation and/or transcription terminator). The open reading frame (ORF) consisting of the nucleotide sequence of the invention, alone or associated with the region encoding the signal peptide, is placed under the control of the promoter such that translation and transcription take place in the host system. The promoters and regions encoding the signal peptides are known to those skilled in the art. Among them, mention may be made in particular of the arabinose-inducible promoter (araB promoter) of *Salmonella typhimurium*, which is functional in Gram⁻ bacteria such as *E. coli* (U.S. Pat. No. 5,028,530 and Cagnon et al., Protein Engineering (1991) 4(7): 843), the promoter of the T7 bacteriophage gene encoding RNA polymerase (U.S. Pat. No. 4,952,496), and the OspA and RlpB signal peptide (Takase et al., J. Bact. (1987) 169:5692).

The polypeptide expressed can be recovered in a practically purified form from the cell extract or from the supernatant, after centrifuging the recombinant cell culture. The recombinant polypeptide can, in particular, be purified using methods of affinity purification with the aid of antibodies, or using any other method known to those skilled in the art, for instance by genetic fusion with a small binding domain.

The nucleic acids of the invention can also be used in the field of vaccination, either by using a viral or bacterial host as a vehicle for releasing the DNA, or by administering the nucleic acid of interest in a free form.

A subject of the present invention is also (i) a vaccination vector containing a nucleic acid of the invention, placed under the control of elements allowing its expression; (ii) a pharmaceutical composition containing a therapeutically or prophylactically effective amount of said vaccination vector; (iii) a method for inducing an immune response against *Neisseria* in a vertebrate, in particular a mammal, preferably a human, said method comprising the administration to said vertebrate of an immunologically effective amount of said vaccination vector so as to cause an immune response, in particular a protective or therapeutic response to *Neisseria meningitidis*; and (iv) a method for preventing and/or treating an infection with pathogenic *Neisseria* strains, in particular with *Neisseria meningitidis*, which comprises the administration of a prophylactic or therapeutic amount of said vaccination vector of the invention to an individual requiring such a treatment.

In combination with the polypeptides of the invention, the vaccination vector as defined above can also comprise nucleotide sequences the expression of which allows the immune response to be stimulated, such as the sequences encoding cytokines.

Said vaccination vector of the invention can be administered via any route which is conventional in the field of vaccination, in particular via the parenteral route (for example subcutaneous, intradermal, intramuscular, intravenous or intraperitoneal route). The dose depends on many parameters which are known to those skilled in the art, such as the vector itself, the route of administration, or the weight, age or sex of the animal or of the human to be vaccinated.

A subject of the present invention is also (i) a pharmaceutical composition containing a therapeutically or prophylactically effective amount of a polynucleotide of the invention; (ii) a method for inducing an immune response against pathogenic *Neisseria* strains, in particular *Neisseria meningitidis* in a vertebrate, by administering to said vertebrate an immunologically effective amount of said polynucleotide so as to cause an immune response, in particular a protective immune response against pathogenic *Neisseria* strains, especially *Neisseria meningitidis*; and (iii) a method for preventing and for treating an infection with pathogenic *Neisseria* strains, in particular with *Neisseria meningitidis*, by administering a therapeutic or prophylactic amount of said polynucleotide to an individual requiring such a treatment.

The polynucleotides of the invention (DNA or RNA) can be administered to a vertebrate as they are. When a DNA molecule of the invention is used, it can be in the form of a plasmid incapable of replicating in a vertebrate cell and incapable of integrating the genome of said vertebrate. Said DNA molecule is, typically, placed under the control of a promoter suitable for expression in a vertebrate cell. Said polynucleotide used as vaccine can be formulated according to various methods known to those skilled in the art. Said polynucleotide can, in particular, be used in a naked form, free of any vehicle which promotes transfer to the target cell, such as anionic liposomes, cationic lipids, microparticles, for example gold microparticles, precipitation agents, for example calcium phosphate, or any other agent which facilitates transfection. In this case, the polynucleotide can be simply diluted in a physiologically acceptable solution, such as a sterile solution or a sterile buffer solution, in the presence or absence of a vehicle. When it is present, this vehicle can be preferably isotonic, hypotonic or slightly hypertonic, and has a relatively low ionic strength. It can, for example, be a sucrose solution (for example a solution containing 20% of sucrose).

Alternatively, a polynucleotide of the invention can be combined with agents which facilitate transfection. It can be, inter alia, (i) combined with a chemical agent which modifies cell permeability, such as bupivacain (WO 94/16737); (ii) encapsulated in liposomes, optionally in the presence of additional substances which facilitate transfection (WO 93/18759, WO 93/19768, WO 94/25608 and WO 95/2397, WO 93/18759 and WO 93/19768); or (iii) combined with cationic lipids, or silica, gold or tungsten microparticles.

When the polynucleotides of the invention coat microparticles, these particles can be injected via the intradermal or intraepidermal route, using the "gene gun" technique (U.S. Pat. Nos. 4,945,050, 5,015,580 and WO 94/24263).

The amount of DNA to be used as a vaccine depends, in particular, on the strength of the promoter used in the DNA construct, on the immunogenicity of the product expressed, on the individual to which this DNA is administered, on the method of administration and on the type of formulation. In general, a therapeutically or prophylactically effective amount ranging from approximately 1 μg to approximately 1 mg, preferably from approximately 10 μg to approximately 800 μg, and preferentially from approximately 25 μg to approximately 250 μg, can be administered to human adults.

The polynucleotide of the invention can be administered via any conventional route of administration, such as in particular via the parenteral route. The choice of the route of administration depends, in particular, on the formulation chosen. A polynucleotide formulated in combination with bupivacain is advantageously administered into muscle. When neutral or anionic liposomes, or a cationic lipid such as DOTMA (N-[1-(2,3-dioleyloxy)propyl]-N,N,N-trimethylammonium chloride) or DC-Chol (3-beta-(N-(N', N'-dimethyl-aminomethane)carbamoyl)cholesterol) are used, the formulation can advantageously be injected via the intravenous, intramuscular, intradermal or subcutaneous route. A polynucleotide in a naked form can advantageously be administered via the intramuscular, intradermal or subcutaneous route.

The nucleotide sequences of the invention allow the construction of specific nucleotide probes and primers which can be used in diagnosis. Said probes or primers are nucleic acids having sequences identical or homologous to portions of the sequences of group I or to the sequences complementary thereto.

Preferably, said probes contain from approximately 5 to approximately 100, preferably from approximately 10 to approximately 80, nucleotides. They can contain modified bases, the sugar and phosphate residues possibly also being modified or substituted. The probes of the invention can be used in diagnostic tests, to capture or detect polynucleotides specific for pathogenic Neisseria strains. Such capture probes can conventionally be immobilized on a solid support directly or indirectly, by covalent bonding or by passive adsorption. A detection probe can be labelled, in particular with a radioactive isotope, an enzyme such as peroxidase or alkaline phosphatase, or enzymes capable of hydrolyzing a chromogenic, fluorogenic or luminescent substrate, or with compounds which are, themselves, chromogenic, fluorogenic or luminescent, nucleotide analogues; or biotin.

A primer generally contains from approximately 10 to approximately 40 nucleotides, and can be used to initiate enzymatic polymerization of the DNA in an amplification process (for example PCR), in an elongation process or in a reverse transcription method. A primer of the invention can in particular be a primer as described in Example II.1 hereinafter.

A subject of the present invention is also:

(i) a reagent containing a probe of the invention for detecting and/or identifying the presence of pathogenic Neisseria strains in a biological sample;

(ii) a process for detecting and/or for identifying the presence of pathogenic Neisseria strains in a biological sample, said method comprising the steps consisting in a) extracting the DNA or RNA from a biological sample and denaturing it; b) exposing said DNA or said RNA to a probe of the invention, under stringent hybridization conditions, so as to detect the hybridization; and (iii) a method for detecting and/or for identifying pathogenic Neisseria strains in a biological sample, in which the DNA is extracted from a biological sample and mixed together with at least one and preferably with two primers of the invention, and is amplified, for example by PCR.

As mentioned above, the polypeptides produced by the expression of the ORF sequences identified can be used as vaccination agents. The specific antigenicity of the polypeptides homologous to the polypeptides having sequences of group II can be evaluated by assaying the cross-reactivity with an antiserum directed against the polypeptides having sequences of group II. A monospecific hyperimmune antiserum can be produced against a purified polypeptide having a sequence of group II or a fusion polypeptide, for example an expression product of the MBP, GST or His-tag systems.

The specific antigenicity can be determined using various methods known to those skilled in the art, in particular the Western blot, dot blot and ELISA techniques, described below.

In the Western blot technique, the protein preparation to be tested is subjected to SDS-PAGE gel electrophoresis. After transfer onto a nitrocellulose membrane, the material is incubated with a monospecific hyperimmune antiserum obtained after having immunized an animal with the referent material; i.e., in the present case, with a polypeptide having an amino acid sequence of group II. This antiserum is diluted beforehand in a dilution range of approximately 1:50 to 1:5000, preferably of approximately 1:100 to 1:500. The specific antigenicity is revealed when a band corresponding to the product shows reactivity with one of the dilutions above.

In the ELISA assay, a purified protein preparation is preferably used, although a whole cell extract may also be used. Approximately 100 µl of a preparation at approximately 10 µg/ml are distributed into the wells of a plate. The plate is incubated for two hours at 37° C., and then overnight at 4° C. The plate is then washed with a phosphate buffered saline solution (PBS) comprising 0.05% of Tween 20. The wells are saturated with 250 µl of PBS containing 1% of bovine serum albumin (BSA) so as to prevent non-specific antibody binding. After incubation for one hour at 37° C., the plate is washed with the PBS/Tween buffer. The antiserum is serially diluted in PBS/Tween buffer containing 0.5% BSA. 100 µl of this dilution are added per well. The plate is incubated for 90 minutes at 37° C., washed and evaluated according to standard procedures. For example, when specific antibodies are produced in rabbits, a goat anti-rabbit peroxidase conjugate is added to the wells. The incubation is carried out for 90 minutes at 37° C. and the plate is then washed. The reaction is measured by colorimetry (the reaction is positive when the optical density value is 1, if the dilution is at least 1:50, preferably at least 1:500).

In the dot blot assay, a purified protein is preferably used, it being understood that it is also possible to use a whole cell extract. Two-fold serial dilutions of a protein solution at approximately 100 µg/ml are prepared in a 50 mM Tris-HCl buffer, pH: 7.5. 100 µl of each dilution are applied to a nitrocellulose membrane (BioRad apparatus). The buffer is removed by applying suction to the system. The wells are washed by adding 50 mM of Tris-HCl buffer (pH: 7.5) and the membrane is air-dried. The membrane is then saturated in a blocking buffer (50 mM Tris-HCl (pH: 7.5) 0.15 M NaCl, 10 g/l of skimmed milk) and incubated with a dilution of antiserum ranging from approximately 1:50 to 1:5000, preferably to approximately 1:500. The reaction is revealed in accordance with standard procedures. For example, when specific antibodies are produced in rabbits, a goat anti-rabbit peroxidase conjugate is added to the wells. The incubation is carried out for 90 minutes at 37° C. The reaction is developed with the suitable substrate and measured, for example by colorimetry, by the appearance of a coloured spot (a reaction is positive when a coloured spot appears in association with a dilution of at least 1:50, preferably of at least 1:500).

A subject of the present invention is also (i) a pharmaceutical composition containing a therapeutically or prophylactically effective amount of a polypeptide of the invention; (ii) a method for inducing an immune response against pathogenic Neisseria strains in a vertebrate, by administering to said vertebrate an immunogenically effective amount of a polypeptide of the invention so as to cause an immune response, in particular a protective immune response against pathogenic Neisseria strains; and (iii) a method for preventing and/or for treating an infection with pathogenic Neisseria strains, by administering a therapeutic or prophylactic amount of a polypeptide of the invention to an individual requiring such a treatment.

The immunogenic compositions of the invention can be administered via any route which is conventional in the field of vaccination, in particular via the parenteral route (for example subcutaneous, intradermal, intramuscular, intravenous or intra-peritoneal route). The choice of the route of administration depends on a certain number of parameters, such as the adjuvant combined with the polypeptide.

A composition of the invention contains at least one polypeptide as defined above. It can also contain at least one additional antigen of *Neisseria meningitidis* and/or *Neisseria gonorrhoeae*.

The polypeptides of the invention can be formulated with liposomes, preferably neutral or anionic liposomes, microspheres, ISCOMS or "virus-like" particles, in order to facilitate the transfer of the polypeptide and/or to increase the immune response.

The administration can be carried out with a single dose or with doses repeated, if necessary, at intervals which can be determined by those skilled in the art.

For example, an initial dose can be followed by three booster doses at intervals of one or more weeks or of one or more months. The suitable dose depends on many parameters, including the individual treated (adult or child), the specific vaccination antigen, the route of administration and the frequency of administration, the presence or absence or the type of adjuvant, and the desired effect (for example protection and/or treatment), and can be determined by those skilled in the art. If the route of administration is parenteral, the dose is preferentially less than 1 mg, preferably approximately 100 µg. The polypeptides and polynucleotides of the invention used as vaccination agents can be used sequentially, in a several-step immunization process. For example, a vertebrate can be initially sensitized with a vaccination vector of the invention, such as a poxvirus, for example via the parenteral route, and can then be stimulated twice with the polypeptide encoded by the vaccination vector.

A polypeptide of the invention can also be useful as a diagnostic agent for detecting the presence of anti-*Neisseria meningitidis* and/or anti-*Neisseria gonorrhoeae* antibodies in a biological sample such as a blood sample.

A subject of the present invention is also monospecific antibodies directed against the polypeptides of the invention.

The term "monospecific antibodies" is intended to mean an antibody capable of reacting specifically with a *Neisseria* polypeptide of the invention. Such antibodies can be polyclonal or monoclonal, and can be recombinant antibodies, for example chimeric (for example consisting of a variable region of murine origin associated with a constant region of human origin), humanized and/or single-chain antibodies. Said antibodies can also be in the form of immunoglobulin fragments, for example F(ab)'2 or Fab fragments. The antibodies of the invention can be of any isotype, for example IgA or IgG, the polyclonal antibodies possibly being of a single isotype or possibly containing a mixture of several isotypes.

The antibodies of the invention directed against the polypeptides of the invention can be produced and identified using standard immunological methods, for example Western blot analysis, a dot blot assay, an ELISA assay (Coligan et al., Current Protocols in Immunology (1994) John Wiley & Sons, Inc., New York, N.Y.). Said antibodies can be used in diagnostic processes for detecting the presence of a *Neisseria meningitidis* antigen in a sample such as, in particular, a biological sample (for example a blood sample).

The antibodies of the invention can also be used in affinity chromatography processes for purifying a polypeptide of the invention. Finally, such antibodies can also be used in prophylactic or therapeutic passive immunization methods.

A subject of the present invention is also a diagnostic method for detecting the presence of pathogenic *Neisseria* strains in a biological sample, comprising bringing said biological sample into contact with an antibody or a polypeptide of the invention, such that an immune complex is formed, and detecting said complex which indicates pathogenic *Neisseria* strains in the organism from which the sample originates. Those skilled in the art understand that the immune complex is formed between a component of the sample and the antibody or the polypeptide of the invention, any substance not bound possibly being eliminated prior to the detection of the complex.

Thus, a reagent of polypeptide type can be used for detecting the presence of anti-*Neisseria meningitidis* and/or *Neisseria gonorrhoeae* antibodies in a sample, whereas an antibody of the invention can be used as a reagent for assaying the presence of a *Neisseria meningitidis* and/or *Neisseria gonorrhoeae* polypeptide in a sample.

For use in diagnostic applications, the reagent (for example the antibody or the polypeptide of the invention) can be in the free state or immobilized on a solid support, by direct or indirect means.

The direct means include passive adsorption or covalent bonding between the support and the reagent.

The term "indirect means" is intended to mean that a substance which interacts with said reagent is attached to the solid support. For example, if a reagent of polypeptide type is used, an antibody which binds to this polypeptide can be used as an anti-reagent substance, it being understood that this substance binds to an antibody which is not involved in recognizing the antibodies in the biological samples.

Among the indirect means which can be used, mention may also be made of the ligand receptor system, a molecule such as a vitamin possibly being grafted onto the reagent of polypeptide type, and the corresponding receptor possibly being immobilized on the solid phase. This is illustrated by the biotin-streptavidin system. It is also possible to add a peptide tail to the reagent, by chemical engineering or genetic engineering, and to immobilize the grafted or fused product by passive adsorption or covalent bonding with the peptide tail.

A subject of the present invention is also a process for purifying, from a biological sample, a *Neisseria* polypeptide of the invention, by affinity chromatography with a monospecific antibody of the invention. Said antibody is preferably of isotype IgG.

According to an example of implementation; a biological sample, preferably in a buffer solution, is applied to a chromatographic material, preferably equilibrated with the buffer used to dilute the biological sample, such that the polypeptide of the invention (i.e. the antigen) may adsorb to the material. The unbound components are washed and the antigen is then eluted with a suitable elution buffer, such as a glycine buffer or a buffer containing chaotropic agent, for example guanidine HCl, or a high concentration of salt (for example 3 M $MgCl_2$). The eluted fractions are recovered and the presence of antigen is detected, for example by measuring the absorbence at 280 nm.

A subject of the present invention is also (i) a pharmaceutical composition containing a therapeutically or prophylactically effective amount of a monospecific antibody of the invention; and (ii) a method for preventing and/or for treating an infection with pathogenic *Neisseria* strains, by administering a therapeutic or prophylactic amount of a monospecific antibody of the invention to an individual requiring such a treatment.

To this end, the monospecific antibody of the invention is preferably of isotype IgG, and preferably fixes the complement. Said monospecific antibody according to the invention can be administered alone or in a mixture with at least one other monospecific antibody, specific for a different *Neisseria meningitidis* and/or *Neisseria gonorrhoeae* polypeptide, according to the invention. The amount of antibody can be determined easily by those skilled in the art. For example, a daily administration of approximately 100 to 1000 mg of antibodies over a week, or three daily doses of approximately 100 to 1000 mg of antibodies over two or three days, may be an effective dose.

The therapeutic or prophylactic effectiveness may be evaluated using standard methods known to those skilled in the art, for example by measuring the induction of an immune response or the induction of protective and/or therapeutic immunity (in newborn rats or mice), through evaluation of the bacterial load in the cerebrospinal fluid. The protection can be determined by comparing the degree of Neisseria infection to a control group. Protection is demonstrated when the infection is decreased in comparison with the control group. Such an evaluation can be carried out with the polynucleotides, the vaccination vectors, the polypeptides and also the antibodies according to the invention. The therapeutic or prophylactic effectiveness of a product according to the invention (polynucleotide or polypeptide) can also be evaluated in an assay for bactericidal activity, as described by Danve et al., Vaccine (1993) 11(12):1214 against the meningococcal strain of origin of the polynucleotide or polypeptide used. In the field of meningococcal vaccines, the bactericidal activity assay is, in fact, recognized as being the reference assay based upon which it is possible to make a valid prediction of the vaccination value of a product. Briefly, a product according to the invention is administered to animals such as rabbits in order to produce an antiserum against this product. Then, this antiserum is assayed for its lysis capacity. The bactericidal titre of an antiserum represents the inverse of the dilution of this antiserum for which 50% of the load of meningococci is lysed. The antiserum is considered to be bactericidal when the titre is higher than 4, with respect to the menigococcal strain of origin of the polynucleotide or polypeptide used. In that case, the product against which the antiserum was generated is demonstrated to be potentially advantageous from a pharmaceutical point of view.

The following examples illustrate the invention without limiting the scope thereof.

LEGEND OF THE FIGURE

The attached FIGURE represents the vector pCAMyc-His used as a cloning vector.

DETAILS OF THE STRATEGY FOR IDENTIFYING THE ORFs

In order to select the ORF sequences specific for the pathogenic strains of the Neisseria genus, a PCR amplification is carried out on the sequences of the 118 ORFs selected after analysis with the Gene Jockey®, Codon Use®, and homology search programs. Only the sequences for which the amplification in N. lactamica is negative (sequences named "lactamica⁻") are selected. In order to verify that these negative results are not "false negatives", the lactamica⁻ sequences selected are subjected to a dot blot.

A—PCR Amplification

A.1. Extraction of Genomic DNAs

The genomic DNAs of all of the Neisseria strains used in this study were prepared according to an identical protocol. The N. meningitidis, N. lactamica, N. flava, N. subflava and N. mucosa strains were cultured on tissues of MHA (Muller Hinton Agar, Difco) medium, and the N. gonorrhoeae were cultured on tissues of MHA medium supplemented with 10% of heat-treated horse blood (Biomérieux) and 1% of Isovitalex (Biomérieux). The culturing is carried out under an atmosphere containing 10% $CO_2$, overnight at 37° C. Then, the cells are harvested, and washed in PBS phosphate buffer (pH 7.2), and the DNA is extracted according to protocol D of the "Rapid Prep genomic DNA isolation kit for cells and tissue" (Pharmacia Biotech).

The genomic DNAs were then controlled on agarose gel for their completeness and by PCR reaction for their purity.

A.2. PCR Reaction for Screening the ORFs Absent in N. lactamica 2314

A PCR amplification was carried out on the genomic DNAs of the N. meningitidis strain ATCC 13090 and N. lactamica strain 2314 (ATCC 23970), according to the following protocol:

The PCR reaction was carried out on a 50 µl volume with 10 ng of genomic DNA, 250 µM of each of the dNTPs, 300 nM of each of the primers, 1×Taq DNA polymerase buffer and 2 u of Taq DNA polymerase (Appligène).

The amplification cycles are:

| | | |
|---|---|---|
| 97° C. | 45 seconds | 25 cycles |
| 56° C. | 1 minute | 25 cycles |
| 72° C. | 2.30 minutes | 25 cycles |

For each of the ORFs analysed, positive and negative controls for the PCR reaction were carried out. At this stage, only the N. meningitidis+ and N. lactamica− ORFs are selected.

B—Selection of the N. meningitidis⁺ N. lactamica⁻ ORFs by Dot Blot on Genomic DNA The absence of a product of PCR amplification of an ORF with genomic DNA of N. lactamica 2314 as the matrix does not guarantee the absence of this ORF in the N. lactamica 2314 genome. Specifically, a certain variability in the region to which the oligonucleotides should hybridize may be responsible for the absence of amplified product for a given ORF.

In this context, further verification is carried out by dot blot on genomic DNA, using, as probe, the products of genomic amplification on the N. meningitidis strain corresponding to each of the reading frames identified. The dot blot filters contain genomic DNA of the following strains: 2 N. lactamica strains 8064 and 2314, one N. flava strain ATCC 30008, one N. mucosa strain ATCC 9297, 3 N. meningitidis serogroup B strains ATCC13090, M982 and B16B6, one N. meningitidis serogroup A strain Z2491, one N. meningitidis serogroup C strain (strain Z4182) and 2 N. gonorrhoeae strains MS11 and FA1090. This dot blot analysis makes it possible to validate the absence of the ORF in N. lactamica 2314 and 8064, and it is also an indication of the degree of variability of an ORF within the Neisseria strains.

The dot blot technique used is as follows. Approximately 50 ng of genomic DNA, denatured for 5 min at 100° C., of the various Neisseria strains are loaded, with suction, onto a Hybond N+nitrocellulose membrane (Amersham) placed between the jaws of a dot blot apparatus (BioRad). Then, the DNA is fixed on the membranes for 5 min with UV radiation at 315 nm.

The membranes are incubated in a prehybridization buffer (containing denatured salmon sperm DNA). They are then hybridized with a probe corresponding to the product of amplification of the ORF of interest, labelled according to a cold labelling protocol, such as the "DIG DNA labelling and detection kit" system (Boehringer Mannheim).

The ORF which does not hybridize to the genomic DNA of N. lactamica 2314 and 8064 is definitively selected as a potential vaccination candidate.

EXAMPLE I

Cloning

1. PCR Amplification

Each of the ORFs was amplified by PCR using the genomic DNA of N. meningitidis serogroup B (strain ATCC 13090), according to standard protocol.

Two oligonucleotides, primers on the N-terminal side and on the C-terminal side were defined for each of the ORF sequences of the invention.

The primer on the N-terminal side comprises an enzyme restriction site for cloning, a CCACC Kozak sequence for translation initiation (M. Kozak, J. Mol. Biol. 196: 947–950), the ATG of the potential ORF and approximately 17 bases specific for the 5' portion of the ORF.

The primer on the C-terminal side was defined such that the ORF cloned is in fusion, in its 3' portion, with a repeat of 8 histidines and a stop codon which are present in the vector behind the multiple cloning site, hence the insertion of an "A" base in order to keep the correct reading frame after cloning and the disappearance of the stop codon of the ORF. The primer on the C-terminal side thus comprises an enzyme restriction site for cloning, an "A" base, and then approximately 20 bases specific for the 3' portion of the gene starting from the codon preceding the stop codon.

After searching for restriction sites which are absent in each of the ORFs, with the aid of the DNASTAR MapDraw subprogram (Lasergene Software), the XbaI restriction site in 5' and BglII restriction site in 3' are used for the ORF SEQ ID No. 19. For the ORF SEQ ID No. 41, the SpeI site in 5' and the BglII site in 3' are used. The XbaI restriction site in 5' and BamHI restriction site in 3' are used to clone the remaining ORFs.

The PCR mixture comprises, for a final volume of 100 μl, 10–50 ng of genomic DNA, the N-terminal and C-terminal primers each at 200 nM, the dNTPs each at 250 μM, the 1×PCR buffer (composition of the 10 ×PCR buffer: 200 mM Tris-HCl (pH 8.8), 20 mM $MgSO_4$, 100 mM KCl, 100 mM $(NH_4)_2SO_4$, 1% TritonX-100 and 1 mg/ml of nuclease-free bovine serum albumin) and 2.5 U of polymerase.

The amplification is carried out as follows:

| Step | Temperature (° C.) | Time (min.) | Number of cycles |
|---|---|---|---|
| Denaturation | 97 | 0.45 | 25 |
| Hybridization | cf. table | 1 | 25 |
| Elongation | 72 | 1/kb DNA | 25 |

The primers used and the PCR conditions given in the table below, in which "N. gallelic variant" means that an allelic variant is present in Neisseria gonorrhoeae and "N. m A allelic variant" means that an allelic variant is present in Neisseria meningitidis serogroup A.

| ORF No. (internal ref.) | SEQ ID No. | 5' Primer | 3' Primer | Polymerase | Hybridization T ° |
|---|---|---|---|---|---|
| 22 | 1–2 | GCT CTA GAC CAC CAT GTC TGA AGA | CGG GAT CCA GAA ATG GCT GGA TTC | Tfu | 56° C. |
|  | N.g allelic variant: 54, 55 | AAA ATT GAA AAT GAG (SEQ ID no 78) | GCT ATC AG (SEQ ID no 79) | (Appligene) |  |
| 41 | 3–4 | GCT CTA GAC CAC CAT GAA ACA CTT ACT CAT CG (SEQ ID no 80) | CGG GAT CCA ATA CGT AGG ACT TGG GTC (SEQ ID no 81) | Tfu (Appligene) | 43° C. |
| 42–43 | 5–6 | GCT CTA GAC CAC CAT GAA AAA ATC | CGG GAT CCA TTG CGG ATA AAC ATA | Tfu | 56° C. |
|  | N.g allelic variant: 56, 57 | CCT TTT CGT TC (SEQ ID no 82) | TTC CGC C (SEQ ID no 83) | (Appligene) |  |
| 47 | 7–8 | GCT CTA GAC CAC CAT GCG AAC GAC | CGG GAT CCA GAA CCG GTA GCC TAC | Tfu | 56° C. |
|  | N.g allelic variant: 58, 59 | CCC AAC CTT C (SEQ ID no 84) | GCC GAC (SEQ ID no 85) | (Appligene) |  |
| 55 | 9–10 | GCT CTA GAC CAC CAT GAA CAC ACG | CGG GAT CCA GCA ACG GCC TGC CGC | Pfu Turbo | 56° C. |
|  | N.g allelic variant: 60, 61 | CAT CAT CGT TTC (SEQ ID no 86) | TTT AAG (SEQ ID no 87) | (Stratagene) |  |
| 68 | 11–12 | GCT CTA GAC CAC CAT GCT GAC GTT TAT CGG ACT G (SEQ ID no 88) | CGG GAT CCA CGG CAG AGG CAC GAT TCC (SEQ ID no 89) | Tfu (Appligene) | 56° C. |
| 71 | 13–14 | GCT CTA GAC CAC CAT GGG CAT CCA TCT CGA CTT C (SEQ ID no 90) | CGG GAT CCA CAA AAG TTC CAG AAA ATC TAA CTC (SEQ ID no 91) | Tfu (Appligene) | 56° C. |
| 72 | 15–16 | GCT CTA GAC CAC CAT GAA TAG ACC | CGG GAT CCA TGC CGC TTG GGG GAG | Pfu Turbo | 56° C. |
|  | N.mA. allelic variant: 62, 63 | CAA GCA ACC (SEQ ID no 92) | GC (SEQ ID no 93) | (Stratagene) |  |
| 73 | 17–18 | GCT CTA GAC CAC CAT GAT GAA TGT | CGG GAT CCA CAG TTT GCC CGA CAT | Pfu Turbo | 56° C. |
|  | N.g allelic variant: 64, 65 | CGA GGC AGA G (SEQ ID no 94) | AC (SEQ ID no 95) | (Stratagene) |  |
| 74 | 19–20 | GCT CTA GAC CAC CAT GAA ATT TTT TCC TGC TCC (SEQ ID no 96) | GAA GAT CTA GAA ACT GTA ATT CAA GTT GAA G (SEQ ID no 97) | Pfu Turbo (Stratagene) | 56° C. |
| 98 | 21–22 | GCT CTA GAC CAC CAT GAT TGA ATT TGT CCG AGC (SEQ ID no 98) | CGG GAT CCA ACC CTG CGA CGA GTT GCG (SEQ ID no 99) | Pfu Turbo (Stratagene) | 56° C. |
| 116 | 23–24 | GCT CTA GAC CAC CAT GCA ATA CAG | CGG GAT CCA GTC CTT TTT CGC ACC | Pfu Turbo | 56° C. |
|  | N.g. allelic variant: 66, 67 | CAC ACT GGC (SEQ ID no 100) | TTG AAG (SEQ ID no 101) | (Stratagene) |  |
| 122 | 25–26 | GCT CTA GAC CAC CAT GGA GCA GTC GGG CAA ATT C (SEQ ID no 102) | CGG GAT CCA AGC TGT TTG GCG ATT TCG GTG (SEQ ID no 103) | Pfu Turbo (Stratagene) | 56° C. |
| 125 | 27–28 | GCT CTA GAC CAC CAT GCA AAA CGG CGG GGG AAA G C (SEQ ID no 104) | CGG GAT CCA GTG CCT GCG CAG CTT GGA ATC (SEQ ID no 105) | Pfu Turbo (Stratagene) | 56° C. |

-continued

| ORF No. (internal ref.) | SEQ ID No. | 5' Primer | 3' Primer | Polymerase | Hybridization T° |
|---|---|---|---|---|---|
| 128 | 29–30 N. mA. allelic variant: 68, 69 | GCT CTA GAC CAC CAT GAC ATT GCT CAA TCT AAT GAT AAT G (SEQ ID no 106) | CGG GAT CCA TTC CGC AAA TAC CTG TTT CCA ACC (SEQ ID no 107) | Tfu (Appligene) | 56° C. |
| 152 | 31–32 N.g allelic variant: 70, 71 | GCT CTA GAC CAC CAT GAA ACA ATC CGC CCG (SEQ ID no 108) | CGG GAT CCA TAC TTG GGC GCA ACA TGA C (SEQ ID no 109) | Pfu Turbo (Stratagene) | 56° C. |
| 153 | 33–34 | GCT CTA GAC CAC CAT GAA TGT TTA CGG TTT CCC (SEQ ID no 110) | CGG GAT CCA TTT TTT AGA CGT ATT TTT AGT CG (SEQ ID no 111) | Tfu (Appligene) | 56° C. |
| 155 | 35–36 | GCT CTA GAC CAC CAT GAT GAG TCA ACA CTC TGC C (SEQ ID no 112) | CGG GAT CCA TCC AGT TTT TGC TCG AAG GC (SEQ ID no 113) | Tfu (Appligene) | 56° C. |
| 156 | 37–38 | GCT CTA GAC CAC CAT GCC TTC GAG CAA AAA CTG G (SEQ ID no 114) | CGG GAT CCA TCG TTC TTC AAT CTC CAC AAA CG (SEQ ID no 115) | Tfu (Appligene) | 56° C. |
| 157 | 39–40 | GCT CTA GAC CAC CAT GCA CC TGG AAA G (SEQ ID no 116) | CGG GAT CCA TTC AAT TCG CTT CAA CAA TG (SEQ ID no 117) | Tfu (Appligene) | 56° C. |
| 158 | 41–42 N. mA. allelic variant: 72, 73 | GGA CTA GTC CAC CAT GGC TGC CAA CCA ACG TTA CCG (SEQ ID no 118) | GAA GAT CTA AGC CGC GTT CCC TTC CAA AAA ATC (SEQ ID no 119) | Tfu (Appligene) | 56° C. |
| 159 | 43–44 N.mA. allelic variant: 74, 75 | GCT CTA GAC CAC CAT GCC GCA AAT TAA AAT TCC C (SEQ ID no 120) | CGG GAT CCA AAA ACA ATC TTC CGG CAC CC (SEQ ID no 121) | Tfu (Appligene) | 56° C. |
| 161 | 45–46 | GCT CTA GAC CAG CAT GCG CAC GCC GTT TTG TTG (SEQ ID no 122) | CGG GAT CCA TTG GGC AAC GAC GAA GGC AC (SEQ ID no 123) | Tfu (Appligene) | 56° C. |
| 163-1 | 47–48 | GCT CTA GAC CAC CAT GAG AAT AGA GAT CAC ACC (SEQ ID no 124) | CGG GAT CCA TGG CTC AAT CCT TTC TGC (SEQ ID no 125) | Pfu Turbo (Stratagene) | 56° C. |
| 163-2 | 49–50 | GCT CTA GAC CAC CAT GAT TCA CGT TTC GGC AGT G (SEQ ID no 126) | CGG GAT CCA ACC TGC TTC ATG GGT GAT TC (SEQ ID no 127) | Tfu (Appligene) | 56° C. |
| 167–168 | 51–52 N. gallelic variant: 76, 77 | GCT CTA GAC CAC CAT GAA TTC GAC CGC AAG TAA AAC (SEQ ID no 128) | CGG GAT CCA AAT CCC TCT GCC GTA TTT G (SEQ ID no 129) | Tfu (Appligene) | 56° C. |

2—Cloning, Transformation and Selection of Recombinants

The cloning vector used is the 6.357 kb vector pCA/Myc-His or pM10710 (cf. figure), derived from the plasmid pCDNA 3.1 (Invitrogen). pCA/Myc-His comprises, in particular, the CMV ie1 promoter (bases 249–902), intron A of the CMV ie1 gene (Chapman et al., 1991 Nucleic Acids Research, 19, 3979–3986), a multiple cloning site (bases 1792–1852) with the PmlI, EcoRV, NotI, XbaI, BamHI, KpnI and HindIII sites, a sequence encoding a polyhistidine and a stop codon (bases 1908–1928), a bgh 3' termination sequence (bases 1853–2197) and the ampicillin resistance gene for selecting the recombinant clones in E. coli.

After purification (GeneClean Bio101 kit), the PCR amplification products are digested for 2 hours at 37° C. with the appropriate enzymes (XbaI-BamHI, XbaI-BglII or SpeI-BglII), in a final reaction volume of 20 µl. The digestion products are then ligated with the vector pCA/Myc-His, digested beforehand with XbaI and BamHI, according to the "Rapid DNA Ligation Kit" protocol (Boehringer Mannheim). 15 µl of the ligation is used to transform 100 µl of competent E. coli XLI-blue cells (Novagen). The cells are incubated for 30 minutes in ice, 30 seconds at 42° C. and 2 minutes in ice. Then, 500 µl of LB medium without antibiotics are added, and the mixture is incubated for 1 hour at 37° C. Next, 50 and 550 µl of the culture are plated out on plates containing LB medium plus ampicillin (50 µg/ml final concentration), and incubated overnight at 37° C.

The following day, 36 colonies are placed in culture in 2 ml of LB plus ampicillin (50 µg/ml) and incubated overnight at 37° C.

The following day, the plasmid DNA is extracted according to the Qiagen mini-prep protocol (Qiagen) and the recombinants are identified by enzymatic restriction followed by agarose gel electrophoresis. The cloning junctions are then verified by sequencing.

EXAMPLE II

Evaluation of the Protective Activity of the ORFs of the Invention

A. Preparation of the DNA Intended for the Immunization Experiments

An isolated colony of a recombinant clone is used to inoculate a preculture in LB medium+ampicillin, and 5 ml of this preculture represents the inoculum of a 2.5 liter culture in LB medium+ampicillin. The purification protocol for preparing the plasmid DNA is that described in the EndoFree Giga Kit (Qiagen). The purified DNA is eluted from the purification column with a 10 mM Tris-HCl, 1 mM EDTA buffer, pH 8, and stored at −20° C. Before injection, the purified recombinant plasmid is diluted to 100 µg/ml with water (of injectable preparation quality) and the NaCl concentration is brought to 150 mM.

B. Production of a Specific Polyclonal Serum

B.1. Hyperimmunization in an Animal Model

The animal model used is the mouse or the rabbit. The route of administration of the injected DNA is the intramuscular or intradermal route. The recombinant plasmids to be injected are optionally applied to beads if they are injected into animals using a gene gun apparatus (BioRad). The immunization protocol follows a scheme comprising two injections, 3 weeks apart.

B.2. Analysis of the Bactericidal Activity of the Antibodies Induced

Ten days after the final injection, the animals are bled and the sera are analysed using the bactericidal activity assay according to the protocol of Danve et al., Vaccine (1993) 11 (12) :1214. Briefly, the sera are incubated at various dilutions (2-fold) in the presence of rabbit complement and of meningococci cultured in the presence or absence of an iron-chelating agent. The bactericidal titre of a serum represents the inverse of the dilution of this antiserum for which 50% of the bacteria are lysed.

It is considered that the antiserum is not bactericidal when its titre is lower than 4 against the homologous strain.

When the bactericidal titre corresponds to a 4-fold seroconversion against the homologous strain, the bactericidal activity of the antiserum is analysed against other *Neisseria* strains in order to measure the extent of the cross-reactivity of the antiserum of interest.

EXAMPLE III

Production of Purified Recombinant Proteins

1. Recombinant Production of Proteins a. Preparation of Transformants

The PCR product obtained is then digested at 37° C. for two hours with restriction enzymes, in 20 μl of reaction volume. The digestion product is ligated into a plasmid pET28a (Novagen) which is cleaved in a similar way and which is dephosphorylated, before ligation, by treating with calf intestine alkaline phosphatase. The fusion gene constructed in this way allows the one-step affinity purification of the resulting fusion protein, due to the presence of histidine residues at the N-terminal end of the fusion protein, which are encoded by this vector.

The ligation reaction (20 μl) is carried out at 14° C. overnight, before transforming 100 μl of fresh competent *E. coli* XL1-blue cells (Novagen). The cells are incubated on ice for two hours, and then subjected to a heat shock at 42° C. for 30 seconds, before being returned to the ice for 90 seconds. The samples are then added to 1 ml of LB broth without selection, and cultured at 37° C. for two hours. The cells are then plated out on LB agar medium supplemented with kanamycin (50 μg/ml final concentration) at a 10×dilution, and are incubated overnight at 37° C. The following day, 50 colonies are subcultured on secondary plates and are incubated at 37° C. overnight.

b. Production of the Protein

The stored transformants (10 μl) are plated out onto selection plates and cultured overnight at 37° C. A few cells are harvested from the plate and used as an inoculum for an overnight starter culture (3 ml) at 37° C. The following day, a sample (time T=0) is taken and centrifuged at 14 000 rpm for 3 minutes. The starter culture is then used to inoculate an LB medium containing kanamycin (100 μg/ml) at a dilution of 1:50 (starting optical density $OD_{600}$=0.05–0.1). The cells are cultured to an $OD_{600}$ of 1.0, a sample is taken for SDS-PAGE (pre-induction sample) and the remaining culture is induced with 1 mM of IPTG. The cultures are cultured for four hours and samples are taken every hour. The culture is centrifuged at 600 g for 20 minutes at 4° C. The supernatant is discarded and the pellets are resuspended in 50 mM of Tris-HCl (pH: 8.0), 2 mM EDTA, and recentrifuged. The supernatant is discarded and the cells are stored at −70° C.

2. Protein Purification

The pellets obtained from one liter of culture prepared according to Example I.4 above are dried and resuspended in 20 ml of 20 mM Tris-HCl (pH 8.0), 0.5 M NaCl, 5 mM imidazole, cooled in ice. Lysozyme is added at a concentration of 0.1 mg/ml, and the suspension is homogenized using a high-speed homogenizer (Turrax), then treated with a sonicator (Sonifier 450, Branson). Benzonase (Merck) is used at a final concentration of 1 U/ml in order to eliminate the DNA. The suspension is centrifuged at 40 000 g for 20 minutes and the supernatant is filtered through a 0.45 μm membrane. The supernatant is loaded onto an IMAC column (12 ml of resin) which has been prepared by immobilizing $Ni^{++}$ cations according to the manufacturer's recommendations (Pharmacia). The column is washed with 10 column volumes of 20 mM Tris-HCl (pH 8.0), 0.5 M NaCl, 60 mM imidazole. The recombinant protein is eluted with six volumes of 20 mM Tris-HCl (pH: 7.9), 0.5 M NaCl, 500 mM imidazole, 0.1% Zwittergent 3–14.

The elution profile is controlled by measuring the absorbence of the fractions at an optical density of 280 nm. An aliquot fraction is analysed on an SDS-PAGE gel and stained with Coomassie blue (Phast System—Pharmacia), and the fractions corresponding to the protein peak are then pooled and concentrated. In order to eliminate the elution buffer, the fraction is passed over a G24 Sephadex column (Pharmacia) and equilibrated in PBS buffer (pH: 7.4). The protein solution is sterilized by filtration through a 0.45 μm membrane, and the protein concentration is determined using the BCA micromethod (Pierce). The protein solution is stored at −70° C.

EXAMPLE IV

Production of Monospecific Polyclonal Antibodies

1. Rabbit Hyperimmune Antiserum

100 μg (in total) of the polypeptide purified in Example III, in the presence of complete Freund's adjuvant in a total volume of approximately 2 ml, are injected into New Zealand rabbits, both subcutaneously and intravenously. 21 and 42 days after the initial injection, the booster doses, which are identical to the initial doses, are administered in the same way, with the exception that incomplete Freund's adjuvant is used. 15 days after the final injection, the animal's serum is recovered, decomplemented and filtered through a 0.45 μm membrane.

2. Mouse Hyperimmune Ascites Fluid

10–50 μg of the purified fusion polypeptide obtained in Example II, in the presence of complete Freund's adjuvant, in a volume of approximately 200 μl, are injected subcutaneously into 10 mice. 7 and 14 days after the initial injection, booster doses, which are identical to the initial doses, are administered in the same way, with the exception that incomplete Freund's adjuvant is used. 21 and 28 days after the initial injection, the mice receive 50 μg of the antigen alone, intraperitoneally. On the 21st day, the mice are also injected intraperitoneally with 180/TG CM26684 sarcoma cells (Lennette & Schmidt, Diagnostic procedures for viral, rickettsial, and chlamydial infections, (1979) 5th Ed. Washington D.C., American Public Health Association). The ascites fluids are harvested 10 to 13 days after the first injection.

EXAMPLE V

Purification of the Polypeptides of the Invention by Immunoaffinity

1. Purification of Specific IgG

An immune serum as prepared in Example IV is applied to a Fast Flow Sepharose 4 protein A column (Pharmacia) equilibrated with 100 mM Tris-HCl (pH: 8.0). The resin is washed by applying 10 column volumes of 100 mM Tris-HCl and 10 volumes of 10 mM Tris-HCl (pH: 8.0) to the column. The IgGs are eluted with a 0.1 M glycine buffer (pH: 3.0) and are collected by 5 ml fraction, to which 0.25 ml of 1 M Tris-HCl (pH: 8.0) are added. The optical density of the eluate is measured at 280 nm and the fractions containing the IgGs are pooled and, if necessary, stored at −70° C.

2. Column Preparation

A suitable amount of CNBr-activated Sepharose 4B gel (1 g of dried gel providing approximately 3.5 ml of hydrated gel, and the capacity of the gel ranging from 5 to 10 mg of coupled IgG per ml of gel) manufactured by Pharmacia (17-0430-01) is suspended in 1 mM HCl buffer and washed, using a Buchner funnel, by adding small amounts of 1 mM HCl buffer. The total volume of the buffer is 200 ml per gram of gel.

The purified IgGs are dialysed for four hours at 20±5° C. against 5 volumes of 500 mM PBS buffer (pH: 7.5). Then, they are diluted in 500 mM of PBS (pH: 7.5) for a final concentration of 3 mg/ml.

The IgGs are incubated with the gel overnight at 5±3° C., with stirring. The gel is packed into a chromatography column and washed with 2 column volumes of 500 mM phosphate buffer (pH: 7.5) and then one volume of 50 mM NaCl sodium buffer (pH: 7.5). The gel is then transferred to a tube, then incubated with 100 mM of ethanolamine (pH: 7.5) for 4 hours at room temperature with stirring, and then washed twice with two column volumes of PBS. The gel is then stored in PBS merthiolate at 1/10 000. The amount of IgG coupled to the gel is determined by measuring the optical density at 280 nm of the IgG solution and of the direct eluate.

3. Adsorption and Elution of the Antigen

A solution of antigen in 50 mM Tris-HCl (pH: 8.0), 2 mM EDTA, for example the supernatant obtained in Example III.2 after treatment with Benzonase, centrifugation and filtration through a 0.45 μm membrane, is applied to a column equilibrated with 50 mM Tris-HCl (pH: 8.0), 2 mM EDTA, at a flow rate of approximately 10 ml/hour. Then, the column is washed with 20 volumes of 50 mM Tris-HCl (pH: 8.0), 2 mM EDTA. Alternatively, batch adsorption can be carried out, in which the mixture is left overnight at 5±3° C., with stirring.

The gel is washed with 2 to 6 volumes of 10 mM PBS buffer (pH: 6.8). The antigen is eluted with a 100 mM glycine buffer (pH: 2.5). The eluate is collected in 3 ml fractions, to which 150 μl of 1 mM PBS buffer (pH: 8.0) are added. The optical density is measured at 280 nm for each fraction; those containing the antigen are recovered and stored at −20° C.

```
Fragments of the genome of N. meningitidis Z2491
described in patent application WO 98/02547

(2) INFORMATION FOR SEQ ID NO: 70A:
    (i)    SEQUENCE CHARACTERISTICS:
           (A) LENGTH: 243 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 70A:

GATCAGACCC ATTTTCAGCG CACCGTAAGC GCGGATTTTC TCGAATTTTT CCAAAGCTGC    60

GGCATCGTTG TTGATGTCGT CTTGCAACTC TTTGCCCGTG TAGCCCAAGT CGGCGGCATT   120

CAGGAAAACG GTCGGAATGC CCGCGTTGAT GAGCGTGGCT TTCAAACGGC CTATATTCGG   180

CACATCAATT TCATCGACCA AATTGCCGGT TGGGAACATA CTGCCTTCGC CGTCGGCTGG   240

ATC                                                                243

(2) INFORMATION FOR SEQ ID NO: 73A:
    (i)    SEQUENCE CHARACTERISTICS:
           (A) LENGTH: 120 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 73A:

CGGTCAGAAA CAGGCAAGGT AATGAAAATG CCTGAGGCAC GGACTGTGCT GCGAACGAAA    60

ACTCCTTACC GAAGTCTTCT ATACCCAGGC TCAATAGCCG CTCAAGGAGA GAGCTATCAT   120

(2) INFORMATION FOR SEQ ID NO: 74A:
    (i)    SEQUENCE CHARACTERISTICS:
           (A) LENGTH: 120 base pairs
           (B) TYPE: nucleotide
           (C) STRANDEDNESS: single
```

```
        (D) TOPOLOGY: linear (ii) MOLECULE TYPE: DNA (genomic)

(iii) HYPOTHETICAL: NO (iv) ANTISENS: NO (xi) SEQUENCE DESCRIPTION: SEQ ID NO: 74A:

CGGTCAGAAA CAGGCAAGGT AATGAAAATG CCTGAGGCAC GGACTGTGCT GCGAACGAAA    60

ACTCCTTACC GAAGTCTTCT ATACCCAGGC TCAATAGCCG CTCAAGGAGA GAGCTATCAT   120

(2) INFORMATION FOR SEQ ID NO: 77A
    (i) SEQUENCE CHARACTERISTICS:
        (A) LENGTH: 269 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTISENS: NO (xi) SEQUENCE DESCRIPTION: SEQ ID NO: 77A:

CGGAGCATAA AATCGTTATT AAAGATAATG GTATAGGAAC GAGCTTCGAT GAAATCAATG    60

ATTTTTATTT GAGAATCGGT CGGAACAGAA GGGAAGAAAA ACAAGCCTCC CCGTGCGGAA   120

GAATTCCAAC GGGTAAAAAA GGCCTTGGTA AATTGGCATT ATTCGGGCTT GGCAACAAAA   180

TTGAAATTTC TACTATCCAG GGAAACGAAA GGGTTACTTT TACTTTGGAT TATGCAGAGA   240

TTCGAAGAAG CAAGGGTATT TATCAACCG                                     269

(2) INFORMATION FOR SEQ ID NO: 80A:
    (i) SEQUENCE CHARACTERISTICS:
        (A) LENGTH: 207 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTISENS: NO (xi) SEQUENCE DESCRIPTION: SEQ ID NO: 80A:

CGGGTCGCTT TATTTGTGC AGGCATTATT TTTCATTTTT GGCTTGACAG TTTGGAAATA     60

TTGTGTATCG GGGGGGGGTA TTTGCTGACG TAAAAAACTA TAAACGCCGC GCAAAATATG   120

GCTGACTATA TTATTGACTT TGATTTTGTC CTGCGCGGTG ATGGATAAAA TCGCCAGCGA   180

TAAAGAATTT GCGAGAACCT GATGCCG                                       207

(2) INFORMATION FOR SEQ ID NO: 81A.:
    (i) SEQUENCE CHARACTERISTICS:
        (A) LENGTH: 224 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTISENS: NO (xi) SEQUENCE DESCRIPTION: SEQ ID NO: 81A:

CGGCAACGAT TTGAGCTATC GCCGTTACGA CATTCTGGAT TTGGCACAAA AATGCGAGTT    60
```

```
TGAAGAAGTC GCCCACCTGC TGATTCACGG CCATCTGCCC AACAAATTCG AGCTGGCCGC    120

TTATAAAACC AAGCTCAAAT CCATGCGCGG CCTGCCTATC CGTGTGATTA AAGTTTTGGA    180

AAGCCTGCCT GCACATACCC ATCCGATGGA CGTAATGCGT ACCG                     224
```

(2) INFORMATION FOR SEQ ID NO: 87A:

(i)    SEQUENCE CHARACTERISTICS:
           (A) LENGTH: 273 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 87A:

```
AATTTCCACC TATGCCCTAC GCAGCGATTA TCCGTGGTTT ACCCAAAGGG TGATTATGGC     60

AAAAGCGCGG GGTTGAGCGA CCGCCTTTTG TTGCCGGCGT TCAAACGGGT TTTGATAGGA    120

AATGCAGGCA CGAAGCCTCG GCTGATTGTG ATGCACCTGA TGGGTTCGCA CAGTGATTTT    180

TGCACACGTT TGGATAAGGA TGCGCGGCGG TTTCAGTATC AAACTGAAAA AATATCCTGC    240

TATGTTTCCA TCAATCGCGC AAACCGATAA ATT                                 273
```

(2) INFORMATION FOR SEQ ID NO: 88A:

(i)    SEQUENCE CHARACTERISTICS:
           (A) LENGTH: 270 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 88A:

```
AATTCTTCCG CACGGGGAGG CTTGTTTTTC TTCCCTTCTG TTCCGACCGA TTCTCAAATA     60

AAAATCATTG ATTTCATCGA AGTTCATTCC TATACCATTA TCTTTAATAA CGATTTTATG    120

CTCCGGTTTA TCGAATAACC TAACTTCCAC TTCCGTAGCA CATGCATCGT AGGCATTCGC    180

TATCAACTCG CCAATCGCAG GAACAGTGTG CGAATACAAT CTTTACACCC AAATGTTCGA    240

TTACGGTTGG CTCGAAACTC AATTTCAATT                                     270
```

(2) INFORMATION FOR SEQ ID NO: 89A:

(i)    SEQUENCE CHARACTERISTICS:
           (A) LENGTH: 267 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 89A:

```
AATTATGAAC ACACGCATCA TCGTTTCGGC TGCGTTCGTT GCGTTGGCAT TAGCAGGTTG     60

CGGCTCAATC AATAATGTAA CCGTTTCCGA CCAGAAACTT CAGGAACGTG CCGCGTTTGC    120

CTTGGGCGTC ACCAATGCCG TAAAAATCAG CAACCGCAGC AATGAAGGCA TACGCATCAA    180
```

```
CTTTACCGCA ACTGTGGGTA AGCGCGTGAC CAATGCTATG TTACCAGTGT AATCAGCACA    240

ATCGGCGTTA CCACTTCCGA TGCAATT                                       267
```

(2) INFORMATION FOR SEQ ID NO: 94A:

(i)    SEQUENCE CHARACTERISTICS:
           (A) LENGTH: 308 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 94A:

```
AATTTGTTGG GCAGATGGCC GTGAATCAGC AGGTGGGCGA CTTCTTCAAA CTCGCATTTT     60

TCTGCCAAAT CCAGAATGTC GTAACCGCGA TACGTCAAAT CGTTGCCGGT ACGCAACGGT    120

ACACAAAGCG GTATTACCGG CCGCAACGCC AGAAAGCGCA ACGGATTTTT AGGTTTGAGG    180

GTCGGGGTTT GACTAGTTTC AGTCATGGTA TTTCTCCTTT GTGTTTTTAT GGGTTTCGGG    240

TTTTCAGACG ACCGATGCGG ATTTGTTGAA AGGCAGTCTG AAAGCGGTAA ATCATTTTTG    300

AAACAATT                                                            308
```

(2) INFORMATION FOR SEQ ID NO: 95A:

(i)    SEQUENCE CHARACTERISTICS:
           (A) LENGTH: 286 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 95A:

```
AATTCGGAGG AGCAGTACCG CCAAGCGTTG CTCGCCTATT CCGGCGGTGA TAAAACAGAC     60

GAGGGTATCC GCCTGATGCA ACAGAGCGAT TACGGCAACT TGTCCTACCA CATCCGTAAT    120

AAAAACATGC TTTTCATTTT TTCGGCAAGC AATGACGCAC AAGCTCAGCC CAACACAACT    180

GACCCTATTG CCATTTTATG AAAAAGACGC TCAAAAAGGC ATTATACACAG TTGCAGGCGT    240

AGACCGCAGT GGAGAAAAGT TCAATGGCTC CAACCATTGC GGAATT                   286
```

(2) INFORMATION FOR SEQ ID NO: 98A:

(i)    SEQUENCE CHARACTERISTICS:
           (A) LENGTH: 316 base pairs
           (B) TYPE: nucleotide
           (C) STRANDEDNESS: single
           (D) TOPOLOGY: linear (ii)   MOLECULE TYPE: DNA (genomic)

(iii)  HYPOTHETICAL: NO (iv)   ANTISENS: NO (xi)   SEQUENCE DESCRIPTION: SEQ ID NO: 98A:

```
AATTTGTCGG CAATCTTCCC GGGTCGCTTT ATTTTGTGCA GGCATTATTT TTCATTTTTG     60

GCTTGACAGT TTGGAGATAT TGTGTATCGG GGGGGGGTAT TTGCTGACGT AAAAAACTAT    120

AAACGCCGCA GCAAAATATG GCTGACTATA TTATTGACTT TGATTTTGTC CTGCGCGGTG    180
```

-continued

```
ATGGATAAAA TCGCCAGCGA TAAAGATTTG CGAGAACCTG ATGCCGGCCT GTTGTTGAAT    240

ATTTTCGACC TGTAATTACG ATTTGGCTTC CGCGCCGGCA CAATATGCCG CCAAGCGGCG    300

CCCACATTTT GGAAGC                                                    316
```

---

What is claimed is:

1. An isolated nucleic acid which encodes the amino acid sequence as shown in SEQ ID NO: 8.

2. The isolated nucleic acid according to claim 1, which has the sequence SEQ ID NO: 7.

3. An expression vector comprising an expression cassette in which a nucleotide sequence as defined in claim 1 is placed under conditions allowing expression of said nucleotide sequence in a host cell.

4. A host cell transformed with the expression vector according to claim 3.

* * * * *

UNITED STATES PATENT AND TRADEMARK OFFICE
CERTIFICATE OF CORRECTION

PATENT NO. : 6,835,384 B1  Page 1 of 1
APPLICATION NO. : 09/830433
DATED : December 28, 2004
INVENTOR(S) : Aujame et al.

It is certified that error appears in the above-identified patent and that said Letters Patent is hereby corrected as shown below:

On The Title Page:

(30) Foreign Application Priority Data

Oct. 30, 1998        (FR).....................................98 13693

Signed and Sealed this

Twenty-fifth Day of July, 2006

JON W. DUDAS
*Director of the United States Patent and Trademark Office*

SEQUENCE LISTING

<160> NUMBER OF SEQ ID NOS: 129

<210> SEQ ID NO 1
<211> LENGTH: 858
<212> TYPE: DNA
<213> ORGANISM: Neisseria meningitidis
<220> FEATURE:
<221> NAME/KEY: CDS
<222> LOCATION: (1)..(855)

<400> SEQUENCE: 1

```
atg tct gaa gaa aaa ttg aaa atg agt ttc gag cca acc gta atc gaa      48
Met Ser Glu Glu Lys Leu Lys Met Ser Phe Glu Pro Thr Val Ile Glu
 1               5                  10                  15 cat ttg ggt gta aag atg tat tcg cac act gtt cct gcg att gcc gag      96
His Leu Gly Val Lys Met Tyr Ser His Thr Val Pro Ala Ile Ala Glu
                 20                  25                  30 ttg ata gcg aat gcc tac gat gca tgt gct acg gaa gtg gaa gtt agg     144
Leu Ile Ala Asn Ala Tyr Asp Ala Cys Ala Thr Glu Val Glu Val Arg
             35                  40                  45 tta ttc gat aaa ccg gag cat aaa atc gtt atc aaa gat aat ggt ata     192
Leu Phe Asp Lys Pro Glu His Lys Ile Val Ile Lys Asp Asn Gly Ile
         50                  55                  60 gga atg agc ttc gat gaa atc aat gat ttt tat ttg aga atc ggt cgg     240
Gly Met Ser Phe Asp Glu Ile Asn Asp Phe Tyr Leu Arg Ile Gly Arg
 65                  70                  75                  80 aac aga agg gaa gaa aaa caa gct tcc ccg tgc gga aga att cca acg     288
Asn Arg Arg Glu Glu Lys Gln Ala Ser Pro Cys Gly Arg Ile Pro Thr
                 85                  90                  95 ggt aaa aaa ggc ctt ggt aaa ttg gca tta ttc ggg ctt ggc aac aaa     336
Gly Lys Lys Gly Leu Gly Lys Leu Ala Leu Phe Gly Leu Gly Asn Lys
                100                 105                 110 att gaa att tct act atc cag gga aac gaa agg gtt act ttt act ttg     384
Ile Glu Ile Ser Thr Ile Gln Gly Asn Glu Arg Val Thr Phe Thr Leu
            115                 120                 125 gat tat gca gag att cga aga agc aag ggt att tat caa ccg gag ttt     432
Asp Tyr Ala Glu Ile Arg Arg Ser Lys Gly Ile Tyr Gln Pro Glu Phe
        130                 135                 140 cga aaa gaa tct gtt gaa tcc aat atc gaa agc ggg aca acc ata act     480
Arg Lys Glu Ser Val Glu Ser Asn Ile Glu Ser Gly Thr Thr Ile Thr
145                 150                 155                 160 tta acc gaa ctg acg aaa aag caa gga tat ccg tta gat aat tat gta     528
Leu Thr Glu Leu Thr Lys Lys Gln Gly Tyr Pro Leu Asp Asn Tyr Val
                165                 170                 175 gag cat ctt tcc cgc ttg ttt gat ttt ccg gct cag gat ttt aaa atc     576
Glu His Leu Ser Arg Leu Phe Asp Phe Pro Ala Gln Asp Phe Lys Ile
            180                 185                 190 aaa gta agc ttg aac ggc tct gaa cct aaa atc att gat gga aat cta     624
Lys Val Ser Leu Asn Gly Ser Glu Pro Lys Ile Ile Asp Gly Asn Leu
        195                 200                 205 aaa tat gat ctt gtt acc cca caa ttc gaa tgg gaa tac cag gat tta     672
Lys Tyr Asp Leu Val Thr Pro Gln Phe Glu Trp Glu Tyr Gln Asp Leu
```

```
                 210                 215                 220
gca acc aat att tca tcg tta tct tca aaa ttc gaa cag tat gaa tac      720
Ala Thr Asn Ile Ser Ser Leu Ser Ser Lys Phe Glu Gln Tyr Glu Tyr
225                 230                 235                 240 agc gga tta ata caa ggt aag ttc att aca acg gaa aaa cct tta aag      768
Ser Gly Leu Ile Gln Gly Lys Phe Ile Thr Thr Glu Lys Pro Leu Lys
                245                 250                 255 aat aat atg aaa ggt att acc ttg ttt gcc aac ggc aga atg gta aat      816
Asn Asn Met Lys Gly Ile Thr Leu Phe Ala Asn Gly Arg Met Val Asn
                260                 265                 270 atg ccc gag ttt ttc act gat agc gaa tcc agc cat ttc taa              858
Met Pro Glu Phe Phe Thr Asp Ser Glu Ser Ser His Phe
                275                 280                 285

<210> SEQ ID NO 2
<211> LENGTH: 285
<212> TYPE: PRT
<213> ORGANISM: Neisseria meningitidis

<400> SEQUENCE: 2

Met Ser Glu Glu Lys Leu Lys Met Ser Phe Glu Pro Thr Val Ile Glu
  1               5                  10                  15

His Leu Gly Val Lys Met Tyr Ser His Thr Val Pro Ala Ile Ala Glu
                 20                  25                  30

Leu Ile Ala Asn Ala Tyr Asp Ala Cys Ala Thr Glu Val Glu Val Arg
             35                  40                  45

Leu Phe Asp Lys Pro Glu His Lys Ile Val Ile Lys Asp Asn Gly Ile
         50                  55                  60

Gly Met Ser Phe Asp Glu Ile Asn Asp Phe Tyr Leu Arg Ile Gly Arg
 65                  70                  75                  80

Asn Arg Arg Glu Glu Lys Gln Ala Ser Pro Cys Gly Arg Ile Pro Thr
                 85                  90                  95

Gly Lys Lys Gly Leu Gly Lys Leu Ala Leu Phe Gly Leu Gly Asn Lys
            100                 105                 110

Ile Glu Ile Ser Thr Ile Gln Gly Asn Glu Arg Val Thr Phe Thr Leu
        115                 120                 125

Asp Tyr Ala Glu Ile Arg Arg Ser Lys Gly Ile Tyr Gln Pro Glu Phe
130                 135                 140

Arg Lys Glu Ser Val Glu Ser Asn Ile Glu Ser Gly Thr Thr Ile Thr
145                 150                 155                 160

Leu Thr Glu Leu Thr Lys Lys Gln Gly Tyr Pro Leu Asp Asn Tyr Val
                165                 170                 175

Glu His Leu Ser Arg Leu Phe Asp Phe Pro Ala Gln Asp Phe Lys Ile
            180                 185                 190

Lys Val Ser Leu Asn Gly Ser Glu Pro Lys Ile Ile Asp Gly Asn Leu
        195                 200                 205

Lys Tyr Asp Leu Val Thr Pro Gln Phe Glu Trp Glu Tyr Gln Asp Leu
    210                 215                 220

Ala Thr Asn Ile Ser Ser Leu Ser Ser Lys Phe Glu Gln Tyr Glu Tyr
225                 230                 235                 240

Ser Gly Leu Ile Gln Gly Lys Phe Ile Thr Thr Glu Lys Pro Leu Lys
                245                 250                 255

Asn Asn Met Lys Gly Ile Thr Leu Phe Ala Asn Gly Arg Met Val Asn
            260                 265                 270

Met Pro Glu Phe Phe Thr Asp Ser Glu Ser Ser His Phe
        275                 280                 285
```

<210> SEQ ID NO 3
<211> LENGTH: 1101
<212> TYPE: DNA
<213> ORGANISM: Neisseria meningitidis
<220> FEATURE:
<221> NAME/KEY: CDS
<222> LOCATION: (1)..(1098)

<400> SEQUENCE: 3

| | | | | | | | | | | | | | | | | |
|---|---|---|---|---|---|---|---|---|---|---|---|---|---|---|---|---|
| atg | aaa | cac | tta | ctc | atc | gat | ttt | gaa | aac | gtc | cag | ccg | caa | aac | tta | 48 |
| Met | Lys | His | Leu | Leu | Ile | Asp | Phe | Glu | Asn | Val | Gln | Pro | Gln | Asn | Leu | |
| 1 | | | | 5 | | | | | 10 | | | | | 15 | | |
| gac | aaa | tta | cta | acc | gaa | aat | acc | cat | att | tgg | cta | ttt | ata | ggt | gta | 96 |
| Asp | Lys | Leu | Leu | Thr | Glu | Asn | Thr | His | Ile | Trp | Leu | Phe | Ile | Gly | Val | |
| | | | 20 | | | | | 25 | | | | | 30 | | | |
| tta | cac | aaa | atg | tta | cct | att | agt | ctg | gtg | caa | tcc | cta | cta | cgt | ttc | 144 |
| Leu | His | Lys | Met | Leu | Pro | Ile | Ser | Leu | Val | Gln | Ser | Leu | Leu | Arg | Phe | |
| | | 35 | | | | | 40 | | | | | 45 | | | | |
| ggc | gaa | cgt | gtc | cat | ctt | gtc | cag | tta | caa | aaa | acg | ggg | aaa | aac | gca | 192 |
| Gly | Glu | Arg | Val | His | Leu | Val | Gln | Leu | Gln | Lys | Thr | Gly | Lys | Asn | Ala | |
| | 50 | | | | | 55 | | | | | 60 | | | | | |
| ttg | gat | ttt | tac | ctg | tcc | tat | tac | ctc | gga | caa | att | acc | gcc | aca | gac | 240 |
| Leu | Asp | Phe | Tyr | Leu | Ser | Tyr | Tyr | Leu | Gly | Gln | Ile | Thr | Ala | Thr | Asp | |
| 65 | | | | | 70 | | | | | 75 | | | | | 80 | |
| ccc | aat | gcc | caa | atc | ggc | ata | ctc | tcg | cgt | gat | gga | gga | tac | gat | gtt | 288 |
| Pro | Asn | Ala | Gln | Ile | Gly | Ile | Leu | Ser | Arg | Asp | Gly | Gly | Tyr | Asp | Val | |
| | | | | 85 | | | | | 90 | | | | | 95 | | |
| ctg | gtc | gaa | cat | att | ttg | aaa | aac | cac | cag | gcg | aag | ggt | atc | gtg | cgc | 336 |
| Leu | Val | Glu | His | Ile | Leu | Lys | Asn | His | Gln | Ala | Lys | Gly | Ile | Val | Arg | |
| | | | 100 | | | | | 105 | | | | | 110 | | | |
| cta | gcc | aat | ata | gat | gaa | gta | caa | cat | cag | aaa | att | gct | acc | gaa | ccg | 384 |
| Leu | Ala | Asn | Ile | Asp | Glu | Val | Gln | His | Gln | Lys | Ile | Ala | Thr | Glu | Pro | |
| | | 115 | | | | | 120 | | | | | 125 | | | | |
| ccg | tca | gca | ttg | ctg | gaa | aac | act | cct | cag | cct | gaa | acc | acc | ctc | aaa | 432 |
| Pro | Ser | Ala | Leu | Leu | Glu | Asn | Thr | Pro | Gln | Pro | Glu | Thr | Thr | Leu | Lys | |
| | 130 | | | | | 135 | | | | | 140 | | | | | |
| cca | cag | caa | cca | tta | act | tcc | tat | ttc | caa | gca | gcc | cta | act | gca | ctg | 480 |
| Pro | Gln | Gln | Pro | Leu | Thr | Ser | Tyr | Phe | Gln | Ala | Ala | Leu | Thr | Ala | Leu | |
| 145 | | | | | 150 | | | | | 155 | | | | | 160 | |
| cgc | cgc | ccc | gac | gct | ttc | cgc | ccc | tgc | cgc | ctg | cat | aac | ctg | cga | caa | 528 |
| Arg | Arg | Pro | Asp | Ala | Phe | Arg | Pro | Cys | Arg | Leu | His | Asn | Leu | Arg | Gln | |
| | | | | 165 | | | | | 170 | | | | | 175 | | |
| aat | ctg | cgt | aag | cat | att | ttg | agt | gat | ttg | ttt | aaa | gaa | aaa | acc | gat | 576 |
| Asn | Leu | Arg | Lys | His | Ile | Leu | Ser | Asp | Leu | Phe | Lys | Glu | Lys | Thr | Asp | |
| | | | 180 | | | | | 185 | | | | | 190 | | | |
| gaa | gaa | tgc | gaa | ata | acc | act | gct | aac | gtt | atc | aat | aaa | ctc | aaa | gca | 624 |
| Glu | Glu | Cys | Glu | Ile | Thr | Thr | Ala | Asn | Val | Ile | Asn | Lys | Leu | Lys | Ala | |
| | | 195 | | | | | 200 | | | | | 205 | | | | |
| caa | aac | ttc | atc | agc | att | gat | gaa | cag | gaa | acc | gtt | tcc | tac | cat | ctc | 672 |
| Gln | Asn | Phe | Ile | Ser | Ile | Asp | Glu | Gln | Glu | Thr | Val | Ser | Tyr | His | Leu | |
| | 210 | | | | | 215 | | | | | 220 | | | | | |
| agt | gat | aat | gat | ttg | tta | caa | aga | atc | caa | cgc | cat | att | tta | agc | caa | 720 |
| Ser | Asp | Asn | Asp | Leu | Leu | Gln | Arg | Ile | Gln | Arg | His | Ile | Leu | Ser | Gln | |
| 225 | | | | | 230 | | | | | 235 | | | | | 240 | |
| cgt | ccc | aaa | acc | tac | gct | gat | ttt | caa | gcc | gtc | gtg | caa | aac | cga | gca | 768 |
| Arg | Pro | Lys | Thr | Tyr | Ala | Asp | Phe | Gln | Ala | Val | Val | Gln | Asn | Arg | Ala | |
| | | | | 245 | | | | | 250 | | | | | 255 | | |
| gat | gca | ctt | cac | tta | aca | gtc | ggt | acc | aac | gac | att | caa | tcc | ttt | gcg | 816 |
| Asp | Ala | Leu | His | Leu | Thr | Val | Gly | Thr | Asn | Asp | Ile | Gln | Ser | Phe | Ala | |
| | | | 260 | | | | | 265 | | | | | 270 | | | |

```
cga cat ttg cgc gac caa aac ctg atc cgc caa aac aat ggg aaa att      864
Arg His Leu Arg Asp Gln Asn Leu Ile Arg Gln Asn Asn Gly Lys Ile
        275                 280                 285 gaa tat gca ccg ttt act gaa cct aaa cca cag cca acg ccc aag cag      912
Glu Tyr Ala Pro Phe Thr Glu Pro Lys Pro Gln Pro Thr Pro Lys Gln
290                 295                 300 cct aaa aaa acc gca tgg gaa cct gat gaa att att tgg aaa aaa gtg      960
Pro Lys Lys Thr Ala Trp Glu Pro Asp Glu Ile Ile Trp Lys Lys Val
305                 310                 315                 320 att gcc gcg tta tcg tta aag aac cgt cct aat aaa acc aaa act tta     1008
Ile Ala Ala Leu Ser Leu Lys Asn Arg Pro Asn Lys Thr Lys Thr Leu
                325                 330                 335 cgc aat aca atc cag gca ctc aca aaa tcc aat gca caa gaa act gac     1056
Arg Asn Thr Ile Gln Ala Leu Thr Lys Ser Asn Ala Gln Glu Thr Asp
            340                 345                 350 aaa ctg cta caa cat tta caa gat gac cca agt cct acg tat tga         1101
Lys Leu Leu Gln His Leu Gln Asp Asp Pro Ser Pro Thr Tyr
        355                 360                 365

<210> SEQ ID NO 4
<211> LENGTH: 366
<212> TYPE: PRT
<213> ORGANISM: Neisseria meningitidis

<400> SEQUENCE: 4

Met Lys His Leu Leu Ile Asp Phe Glu Asn Val Gln Pro Gln Asn Leu
1               5                   10                  15

Asp Lys Leu Leu Thr Glu Asn Thr His Ile Trp Leu Phe Ile Gly Val
                20                  25                  30

Leu His Lys Met Leu Pro Ile Ser Leu Val Gln Ser Leu Leu Arg Phe
            35                  40                  45

Gly Glu Arg Val His Leu Val Gln Leu Gln Lys Thr Gly Lys Asn Ala
        50                  55                  60

Leu Asp Phe Tyr Leu Ser Tyr Tyr Leu Gly Gln Ile Thr Ala Thr Asp
65                  70                  75                  80

Pro Asn Ala Gln Ile Gly Ile Leu Ser Arg Asp Gly Tyr Asp Val
                85                  90                  95

Leu Val Glu His Ile Leu Lys Asn His Gln Ala Lys Gly Ile Val Arg
            100                 105                 110

Leu Ala Asn Ile Asp Glu Val Gln His Gln Lys Ile Ala Thr Glu Pro
        115                 120                 125

Pro Ser Ala Leu Leu Glu Asn Thr Pro Gln Pro Glu Thr Thr Leu Lys
    130                 135                 140

Pro Gln Gln Pro Leu Thr Ser Tyr Phe Gln Ala Ala Leu Thr Ala Leu
145                 150                 155                 160

Arg Arg Pro Asp Ala Phe Arg Pro Cys Arg Leu His Asn Leu Arg Gln
                165                 170                 175

Asn Leu Arg Lys His Ile Leu Ser Asp Leu Phe Lys Glu Lys Thr Asp
            180                 185                 190

Glu Glu Cys Glu Ile Thr Thr Ala Asn Val Ile Asn Lys Leu Lys Ala
        195                 200                 205

Gln Asn Phe Ile Ser Ile Asp Glu Gln Glu Thr Val Ser Tyr His Leu
    210                 215                 220

Ser Asp Asn Asp Leu Leu Gln Arg Ile Gln Arg His Ile Leu Ser Gln
225                 230                 235                 240

Arg Pro Lys Thr Tyr Ala Asp Phe Gln Ala Val Val Gln Asn Arg Ala
```

-continued

```
                    245                 250                 255
Asp Ala Leu His Leu Thr Val Gly Thr Asn Asp Ile Gln Ser Phe Ala
                260                 265                 270

Arg His Leu Arg Asp Gln Asn Leu Ile Arg Gln Asn Gly Lys Ile
            275                 280                 285

Glu Tyr Ala Pro Phe Thr Glu Pro Lys Pro Gln Pro Thr Pro Lys Gln
            290                 295                 300

Pro Lys Lys Thr Ala Trp Glu Pro Asp Glu Ile Ile Trp Lys Lys Val
305                 310                 315                 320

Ile Ala Ala Leu Ser Leu Lys Asn Arg Pro Asn Lys Thr Lys Thr Leu
                325                 330                 335

Arg Asn Thr Ile Gln Ala Leu Thr Lys Ser Asn Ala Gln Glu Thr Asp
                340                 345                 350

Lys Leu Leu Gln His Leu Gln Asp Asp Pro Ser Pro Thr Tyr
                355                 360                 365

<210> SEQ ID NO 5
<211> LENGTH: 1572
<212> TYPE: DNA
<213> ORGANISM: Neisseria meningitidis
<220> FEATURE:
<221> NAME/KEY: CDS
<222> LOCATION: (1)..(1569)

<400> SEQUENCE: 5 atg aaa aaa tcc ctt ttc gtt ctc ttt ctg tat tca tcc cta ctt acc      48
Met Lys Lys Ser Leu Phe Val Leu Phe Leu Tyr Ser Ser Leu Leu Thr
  1               5                  10                  15 gcc agc gaa atc gcc tat cgc ttt gta ttc gga att gaa acc tta ccg      96
Ala Ser Glu Ile Ala Tyr Arg Phe Val Phe Gly Ile Glu Thr Leu Pro
                 20                  25                  30 gct gca aaa atg gca gaa acg ttt gcg ctg aca ttt atg att gct gcg     144
Ala Ala Lys Met Ala Glu Thr Phe Ala Leu Thr Phe Met Ile Ala Ala
             35                  40                  45 ctg tat ctg ttt gcg cgt tat aag gct tcg cgg ctg ctg att gcg gtg     192
Leu Tyr Leu Phe Ala Arg Tyr Lys Ala Ser Arg Leu Leu Ile Ala Val
         50                  55                  60 ttt ttc gcg ttc agc att att gcc aac aat gta cat tat gcg gtt tat     240
Phe Phe Ala Phe Ser Ile Ile Ala Asn Asn Val His Tyr Ala Val Tyr
 65                  70                  75                  80 caa agt tgg atg acg ggc atc aat tat tgg ctg atg ctg aaa gag att     288
Gln Ser Trp Met Thr Gly Ile Asn Tyr Trp Leu Met Leu Lys Glu Ile
                 85                  90                  95 acc gaa gtc ggc agt gcg ggc gcg tcg atg ttg gat aag ttg tgg ctg     336
Thr Glu Val Gly Ser Ala Gly Ala Ser Met Leu Asp Lys Leu Trp Leu
                100                 105                 110 cct gcg ttg tgg ggc gtg ttg gaa gtc atg ttg ttt tgc agc ctt gcc     384
Pro Ala Leu Trp Gly Val Leu Glu Val Met Leu Phe Cys Ser Leu Ala
            115                 120                 125 aag ttc cac cgt aag acg cat ttt tct gcc gat ata ctg ttt gcc ttc     432
Lys Phe His Arg Lys Thr His Phe Ser Ala Asp Ile Leu Phe Ala Phe
        130                 135                 140 cta atg ctg atg att ttc gtg cgt tcg ttc gac acg aaa caa gag cac     480
Leu Met Leu Met Ile Phe Val Arg Ser Phe Asp Thr Lys Gln Glu His
145                 150                 155                 160 ggt att tcg ccc aaa ccg aca tac agc cgc atc aaa gcc aat tat ttc     528
Gly Ile Ser Pro Lys Pro Thr Tyr Ser Arg Ile Lys Ala Asn Tyr Phe
                165                 170                 175 agc ttc ggt tat ttt gtc gga cgc gtg ttg ccg tat cag ttg ttt gat     576
```

```
                                                                    -continued Ser Phe Gly Tyr Phe Val Gly Arg Val Leu Pro Tyr Gln Leu Phe Asp
            180                 185                 190 tta agc agg att ccc gcc ttt aag cag cct gct cca agc aaa atc ggg        624
Leu Ser Arg Ile Pro Ala Phe Lys Gln Pro Ala Pro Ser Lys Ile Gly
        195                 200                 205 cag ggc agt gtt caa aat atc gtc ctg att atg ggc gaa agc gaa agc        672
Gln Gly Ser Val Gln Asn Ile Val Leu Ile Met Gly Glu Ser Glu Ser
    210                 215                 220 gcg gcg cat ttg aag ctg ttt ggc tac gga cgc gaa act tcg ccg ttt        720
Ala Ala His Leu Lys Leu Phe Gly Tyr Gly Arg Glu Thr Ser Pro Phe
225                 230                 235                 240 tta acc cgg ctg tcg caa gcc gat ttt aag ccg att gtg aaa caa agt        768
Leu Thr Arg Leu Ser Gln Ala Asp Phe Lys Pro Ile Val Lys Gln Ser
                245                 250                 255 tat tcc gca ggc ttt atg act gca gtg tcc ctg ccc agt ttt ttc aat        816
Tyr Ser Ala Gly Phe Met Thr Ala Val Ser Leu Pro Ser Phe Phe Asn
            260                 265                 270 gcg ata ccg cac gcc aac ggc ttg gaa caa atc agc ggc ggc gat act        864
Ala Ile Pro His Ala Asn Gly Leu Glu Gln Ile Ser Gly Gly Asp Thr
        275                 280                 285 aat atg ttc cgc ctc gcc aaa gag cag ggc tat gaa acg tat ttt tac        912
Asn Met Phe Arg Leu Ala Lys Glu Gln Gly Tyr Glu Thr Tyr Phe Tyr
    290                 295                 300 agc gca cag gcg gaa aac gag atg gcg att ttg aac tta atc ggt aag        960
Ser Ala Gln Ala Glu Asn Glu Met Ala Ile Leu Asn Leu Ile Gly Lys
305                 310                 315                 320 aaa tgg ata gac cat ctg att cag ccg acg cag ctt ggc tac ggc aac       1008
Lys Trp Ile Asp His Leu Ile Gln Pro Thr Gln Leu Gly Tyr Gly Asn
                325                 330                 335 ggc gac aat atg ccc gat gag aag ctg ctg ccg ctg ttc gac aaa atc       1056
Gly Asp Asn Met Pro Asp Glu Lys Leu Leu Pro Leu Phe Asp Lys Ile
            340                 345                 350 aat ttg cag cag ggc agg cat ttt atc gtg ttg cac caa cgt ggt tcg       1104
Asn Leu Gln Gln Gly Arg His Phe Ile Val Leu His Gln Arg Gly Ser
        355                 360                 365 cac gcc cca tac agc gca ttg ttg cag cct caa gat aaa gta ttc ggc       1152
His Ala Pro Tyr Ser Ala Leu Leu Gln Pro Gln Asp Lys Val Phe Gly
    370                 375                 380 gaa ctt att gtg gat aag tac gac aac acc atc cac aaa acc gac caa       1200
Glu Leu Ile Val Asp Lys Tyr Asp Asn Thr Ile His Lys Thr Asp Gln
385                 390                 395                 400 atg att caa acc gta ttc gag cag ctg caa aag cag cct gac ggc aac       1248
Met Ile Gln Thr Val Phe Glu Gln Leu Gln Lys Gln Pro Asp Gly Asn
                405                 410                 415 tgg ctg ttt gcc tat acc tcc gat cat ggc cag tat gtt cgc caa gat       1296
Trp Leu Phe Ala Tyr Thr Ser Asp His Gly Gln Tyr Val Arg Gln Asp
            420                 425                 430 atc tac aat caa ggc acg gtg cag ccc gac agc tat ctc gtg ccg ctg       1344
Ile Tyr Asn Gln Gly Thr Val Gln Pro Asp Ser Tyr Leu Val Pro Leu
        435                 440                 445 gtg ttg tac agc tcg aat aag gcc gtg caa cag gct gcc aac cag gct       1392
Val Leu Tyr Ser Ser Asn Lys Ala Val Gln Gln Ala Ala Asn Gln Ala
    450                 455                 460 ttt gcg cct tgc gag att gcc ttc cat cag cag ctt tca acg ttc ctg       1440
Phe Ala Pro Cys Glu Ile Ala Phe His Gln Gln Leu Ser Thr Phe Leu
465                 470                 475                 480 att cac acg ttg ggc tac gat atg ccg gtt tca ggt tgt cgc gaa ggc       1488
Ile His Thr Leu Gly Tyr Asp Met Pro Val Ser Gly Cys Arg Glu Gly
                485                 490                 495
```

```
tcg gta acg ggc aac ctg att acg ggt gat gca ggc agc ttg aac att    1536
Ser Val Thr Gly Asn Leu Ile Thr Gly Asp Ala Gly Ser Leu Asn Ile
        500                 505                 510 cgc gac ggc aag gcg gaa tat gtt tat ccg caa tga                    1572
Arg Asp Gly Lys Ala Glu Tyr Val Tyr Pro Gln
        515                 520
```

<210> SEQ ID NO 6
<211> LENGTH: 523
<212> TYPE: PRT
<213> ORGANISM: Neisseria meningitidis

<400> SEQUENCE: 6

```
Met Lys Lys Ser Leu Phe Val Leu Phe Leu Tyr Ser Ser Leu Leu Thr
  1               5                  10                  15

Ala Ser Glu Ile Ala Tyr Arg Phe Val Phe Gly Ile Glu Thr Leu Pro
             20                  25                  30

Ala Ala Lys Met Ala Glu Thr Phe Ala Leu Thr Phe Met Ile Ala Ala
         35                  40                  45

Leu Tyr Leu Phe Ala Arg Tyr Lys Ala Ser Arg Leu Leu Ile Ala Val
 50                  55                  60

Phe Phe Ala Phe Ser Ile Ile Ala Asn Asn Val His Tyr Ala Val Tyr
 65                  70                  75                  80

Gln Ser Trp Met Thr Gly Ile Asn Tyr Trp Leu Met Leu Lys Glu Ile
             85                  90                  95

Thr Glu Val Gly Ser Ala Gly Ala Ser Met Leu Asp Lys Leu Trp Leu
            100                 105                 110

Pro Ala Leu Trp Gly Val Leu Glu Val Met Leu Phe Cys Ser Leu Ala
            115                 120                 125

Lys Phe His Arg Lys Thr His Phe Ser Ala Asp Ile Leu Phe Ala Phe
        130                 135                 140

Leu Met Leu Met Ile Phe Val Arg Ser Phe Asp Thr Lys Gln Glu His
145                 150                 155                 160

Gly Ile Ser Pro Lys Pro Thr Tyr Ser Arg Ile Lys Ala Asn Tyr Phe
            165                 170                 175

Ser Phe Gly Tyr Phe Val Gly Arg Val Leu Pro Tyr Gln Leu Phe Asp
            180                 185                 190

Leu Ser Arg Ile Pro Ala Phe Lys Gln Pro Ala Pro Ser Lys Ile Gly
        195                 200                 205

Gln Gly Ser Val Gln Asn Ile Val Leu Ile Met Gly Glu Ser Glu Ser
    210                 215                 220

Ala Ala His Leu Lys Leu Phe Gly Tyr Gly Arg Glu Thr Ser Pro Phe
225                 230                 235                 240

Leu Thr Arg Leu Ser Gln Ala Asp Phe Lys Pro Ile Val Lys Gln Ser
            245                 250                 255

Tyr Ser Ala Gly Phe Met Thr Ala Val Ser Leu Pro Ser Phe Phe Asn
            260                 265                 270

Ala Ile Pro His Ala Asn Gly Leu Glu Gln Ile Ser Gly Gly Asp Thr
        275                 280                 285

Asn Met Phe Arg Leu Ala Lys Glu Gln Gly Tyr Glu Thr Tyr Phe Tyr
    290                 295                 300

Ser Ala Gln Ala Glu Asn Glu Met Ala Ile Leu Asn Leu Ile Gly Lys
305                 310                 315                 320

Lys Trp Ile Asp His Leu Ile Gln Pro Thr Gln Leu Gly Tyr Gly Asn
                325                 330                 335
```

```
Gly Asp Asn Met Pro Asp Glu Lys Leu Leu Pro Leu Phe Asp Lys Ile
            340                 345                 350

Asn Leu Gln Gln Gly Arg His Phe Ile Val Leu His Gln Arg Gly Ser
            355                 360                 365

His Ala Pro Tyr Ser Ala Leu Leu Gln Pro Gln Asp Lys Val Phe Gly
            370                 375                 380

Glu Leu Ile Val Asp Lys Tyr Asp Asn Thr Ile His Lys Thr Asp Gln
385                 390                 395                 400

Met Ile Gln Thr Val Phe Glu Gln Leu Gln Lys Gln Pro Asp Gly Asn
                405                 410                 415

Trp Leu Phe Ala Tyr Thr Ser Asp His Gly Gln Tyr Val Arg Gln Asp
                420                 425                 430

Ile Tyr Asn Gln Gly Thr Val Gln Pro Asp Ser Tyr Leu Val Pro Leu
            435                 440                 445

Val Leu Tyr Ser Ser Asn Lys Ala Val Gln Gln Ala Ala Asn Gln Ala
        450                 455                 460

Phe Ala Pro Cys Glu Ile Ala Phe His Gln Gln Leu Ser Thr Phe Leu
465                 470                 475                 480

Ile His Thr Leu Gly Tyr Asp Met Pro Val Ser Gly Cys Arg Glu Gly
                485                 490                 495

Ser Val Thr Gly Asn Leu Ile Thr Gly Asp Ala Gly Ser Leu Asn Ile
            500                 505                 510

Arg Asp Gly Lys Ala Glu Tyr Val Tyr Pro Gln
        515                 520

<210> SEQ ID NO 7
<211> LENGTH: 3204
<212> TYPE: DNA
<213> ORGANISM: Neisseria meningitidis
<220> FEATURE:
<221> NAME/KEY: CDS
<222> LOCATION: (1)..(3201)

<400> SEQUENCE: 7 atg cga acg acc cca acc ttc cct aca aaa act ttc aaa ccg gct gcc    48
Met Arg Thr Thr Pro Thr Phe Pro Thr Lys Thr Phe Lys Pro Ala Ala
1               5                   10                  15 atg gcg tta gct gtt gca aca aca ctt tct gcc tgc tta ggc ggc ggc    96
Met Ala Leu Ala Val Ala Thr Thr Leu Ser Ala Cys Leu Gly Gly Gly
                20                  25                  30 ggc ggc act tct gcg ccc gac ttc aat gca ggc ggc acc ggt atc ggc   144
Gly Gly Thr Ser Ala Pro Asp Phe Asn Ala Gly Gly Thr Gly Ile Gly
            35                  40                  45 agc aac agc aga gca aca aca gcg aaa tca gca gca gta tct tac gcc   192
Ser Asn Ser Arg Ala Thr Thr Ala Lys Ser Ala Ala Val Ser Tyr Ala
        50                  55                  60 ggt atc aag aac gaa atg tgc aaa gac aga agc atg ctc tgt gcc ggt   240
Gly Ile Lys Asn Glu Met Cys Lys Asp Arg Ser Met Leu Cys Ala Gly
65                  70                  75                  80 cgg gat gac gtt gcg gtt aca gac agg gat gcc aaa atc aat gcc ccc   288
Arg Asp Asp Val Ala Val Thr Asp Arg Asp Ala Lys Ile Asn Ala Pro
                85                  90                  95 ccc ccg aat ctg cat acc gga gac ttt aca aac cca aat gac gca tac   336
Pro Pro Asn Leu His Thr Gly Asp Phe Thr Asn Pro Asn Asp Ala Tyr
                100                 105                 110 aag aat ttg atc aac ctc aaa cct gca att gaa gca ggc tat aca gga   384
Lys Asn Leu Ile Asn Leu Lys Pro Ala Ile Glu Ala Gly Tyr Thr Gly
            115                 120                 125
```

-continued

| | | |
|---|---|---|
| cgc ggg gta gag gta ggt atc gtc gat aca ggc gaa tcc gtc ggc agc<br>Arg Gly Val Glu Val Gly Ile Val Asp Thr Gly Glu Ser Val Gly Ser<br>130                        135                   140 | 432 |
| ata tcc ttt ccc gaa ctg tat ggc aga aaa gaa cac ggc tat aac gaa<br>Ile Ser Phe Pro Glu Leu Tyr Gly Arg Lys Glu His Gly Tyr Asn Glu<br>145                        150                 155                  160 | 480 |
| aat tac aaa aac tat acg gcg tat atg cgg aag gaa gcg cct gaa gac<br>Asn Tyr Lys Asn Tyr Thr Ala Tyr Met Arg Lys Glu Ala Pro Glu Asp<br>                    165                   170                  175 | 528 |
| gga ggc ggt aaa gac att aaa gct tct ttc gac gat gag gcc gtt ata<br>Gly Gly Gly Lys Asp Ile Lys Ala Ser Phe Asp Asp Glu Ala Val Ile<br>                  180                   185                  190 | 576 |
| gag act gaa gca aag ccg acg gat atc cgc cac gta aaa gaa atc gga<br>Glu Thr Glu Ala Lys Pro Thr Asp Ile Arg His Val Lys Glu Ile Gly<br>          195                   200                 205 | 624 |
| cac atc gat gtg gtc tcc cat att att ggc ggg cgt tcc gtg gac ggc<br>His Ile Asp Val Val Ser His Ile Ile Gly Gly Arg Ser Val Asp Gly<br>210                        215                   220 | 672 |
| aga cct gca ggc ggt att gcg ccc gat gcg acg cta cac ata atg aat<br>Arg Pro Ala Gly Gly Ile Ala Pro Asp Ala Thr Leu His Ile Met Asn<br>225                        230                 235                  240 | 720 |
| acg cat gat gga acc aag aac gaa ata atg tct gca gcc atc cgc aat<br>Thr His Asp Gly Thr Lys Asn Glu Ile Met Ser Ala Ala Ile Arg Asn<br>                    245                   250                  255 | 768 |
| gca tgg gtc aag ctg ggc gaa cgt ggc gtg cgc atc gtc aat aac agt<br>Ala Trp Val Lys Leu Gly Glu Arg Gly Val Arg Ile Val Asn Asn Ser<br>                  260                   265                  270 | 816 |
| ttt gga aca aca tcg agg gca ggc act gcc gac cat ttc caa ata gcc<br>Phe Gly Thr Thr Ser Arg Ala Gly Thr Ala Asp His Phe Gln Ile Ala<br>          275                   280                 285 | 864 |
| aat tcg gag gag cag tac cgc caa gcg ttg ctc gcc tat tcc ggc ggt<br>Asn Ser Glu Glu Gln Tyr Arg Gln Ala Leu Leu Ala Tyr Ser Gly Gly<br>290                        295                 300 | 912 |
| gat aaa aca gac gag ggt atc cgc ctg atg caa cag agc gat tac ggc<br>Asp Lys Thr Asp Glu Gly Ile Arg Leu Met Gln Gln Ser Asp Tyr Gly<br>305                        310                 315                  320 | 960 |
| aac ttg tcc tac cac atc cgt aat aaa aac atg ctt ttc att ttt tcg<br>Asn Leu Ser Tyr His Ile Arg Asn Lys Asn Met Leu Phe Ile Phe Ser<br>                    325                   330                  335 | 1008 |
| gca agc aat gac gca caa gct cag ccc aac aca ctg acc cta ttg cca<br>Ala Ser Asn Asp Ala Gln Ala Gln Pro Asn Thr Leu Thr Leu Leu Pro<br>                  340                   345                  350 | 1056 |
| ttt tat gaa aaa gat gct caa aaa ggc att atc aca gtc gca ggc gta<br>Phe Tyr Glu Lys Asp Ala Gln Lys Gly Ile Ile Thr Val Ala Gly Val<br>          355                   360                 365 | 1104 |
| gac cgc agt gga gaa aag ttc aat ggc tcc aac cat tgc gga att act<br>Asp Arg Ser Gly Glu Lys Phe Asn Gly Ser Asn His Cys Gly Ile Thr<br>370                        375                 380 | 1152 |
| gcc atg tgg tgc cta tcg gca ccc tat gaa gca agc gtc cgt ttc acc<br>Ala Met Trp Cys Leu Ser Ala Pro Tyr Glu Ala Ser Val Arg Phe Thr<br>385                        390                 395                  400 | 1200 |
| cgt aca aac ccg att caa att gcc gga aca tcc ttt tcc gca ccc atc<br>Arg Thr Asn Pro Ile Gln Ile Ala Gly Thr Ser Phe Ser Ala Pro Ile<br>                    405                   410                  415 | 1248 |
| gta acc ggc acg gcg gct ctg ctg ctg cag aaa tac ccg tgg atg agc<br>Val Thr Gly Thr Ala Ala Leu Leu Leu Gln Lys Tyr Pro Trp Met Ser<br>                  420                   425                  430 | 1296 |
| aac gac aac ctg cgt acc acg ctg ctg aca acg gct cag gac atc ggt<br>Asn Asp Asn Leu Arg Thr Thr Leu Leu Thr Thr Ala Gln Asp Ile Gly<br>          435                   440                 445 | 1344 |

```
gca gtc ggc gtg gac agc aag ttc ggc tgg gga ctg ctg gat gcg ggt   1392
Ala Val Gly Val Asp Ser Lys Phe Gly Trp Gly Leu Leu Asp Ala Gly
450                 455                 460 aag gcc atg aac gga ccc gcg tcc ttt ccg ttc ggc gac ttt acc gcc   1440
Lys Ala Met Asn Gly Pro Ala Ser Phe Pro Phe Gly Asp Phe Thr Ala
465                 470                 475                 480 gat acg aaa ggt aca tcc gat att gcc tac tcc ttc cgt aac gac att   1488
Asp Thr Lys Gly Thr Ser Asp Ile Ala Tyr Ser Phe Arg Asn Asp Ile
                485                 490                 495 tca ggc acg ggc ggc ctg atc aaa aaa ggc ggc agc caa ctg caa ctg   1536
Ser Gly Thr Gly Gly Leu Ile Lys Lys Gly Gly Ser Gln Leu Gln Leu
            500                 505                 510 cac ggc aac aac acc tat acg ggc aaa acc att atc gaa ggc ggt tcg   1584
His Gly Asn Asn Thr Tyr Thr Gly Lys Thr Ile Ile Glu Gly Gly Ser
        515                 520                 525 ctg gtg ttg tac ggc aac aac aaa tcg gat atg cgc gtc gaa acc aaa   1632
Leu Val Leu Tyr Gly Asn Asn Lys Ser Asp Met Arg Val Glu Thr Lys
530                 535                 540 ggt gcg ctg att tat aac ggg gcg gca tcc ggc ggt agc ctg aac agc   1680
Gly Ala Leu Ile Tyr Asn Gly Ala Ala Ser Gly Gly Ser Leu Asn Ser
545                 550                 555                 560 gac ggc att gtc tat ctg gca gat acc gac cga tcc ggc gca aac gaa   1728
Asp Gly Ile Val Tyr Leu Ala Asp Thr Asp Arg Ser Gly Ala Asn Glu
                565                 570                 575 acc gtg cac atc aaa ggc gat ctg cag ctg ggc ggc gaa ggt acg ctg   1776
Thr Val His Ile Lys Gly Asp Leu Gln Leu Gly Gly Glu Gly Thr Leu
            580                 585                 590 tac aca cgt ttg ggc aaa ctg ctg aaa gtg gac ggt acg gcg atg acc   1824
Tyr Thr Arg Leu Gly Lys Leu Leu Lys Val Asp Gly Thr Ala Met Thr
        595                 600                 605 ggc ggc aag ctg tac atg tcg gca cgc ggc aaa ggg gca ggc tat ctc   1872
Gly Gly Lys Leu Tyr Met Ser Ala Arg Gly Lys Gly Ala Gly Tyr Leu
610                 615                 620 aac cgt acc gga caa cgt gtt ccc ttc ctg agt gcc gcc aaa atc ggg   1920
Asn Arg Thr Gly Gln Arg Val Pro Phe Leu Ser Ala Ala Lys Ile Gly
625                 630                 635                 640 cgg gat tat tct ttc ttc aca aac atc gaa acc gac ggt ggt ctg ctg   1968
Arg Asp Tyr Ser Phe Phe Thr Asn Ile Glu Thr Asp Gly Gly Leu Leu
                645                 650                 655 gct tcc ctc gac agc gtc gaa aaa aca gcg ggc agt gaa ggc gac acg   2016
Ala Ser Leu Asp Ser Val Glu Lys Thr Ala Gly Ser Glu Gly Asp Thr
            660                 665                 670 ctg tcc tat tat gtc cgt cgc ggc aat gcg gca cgg act gct tcg gca   2064
Leu Ser Tyr Tyr Val Arg Arg Gly Asn Ala Ala Arg Thr Ala Ser Ala
        675                 680                 685 gcg gca cat tcc gcg ccc gcc ggt ctg aaa cac gcc gta gaa cag ggc   2112
Ala Ala His Ser Ala Pro Ala Gly Leu Lys His Ala Val Glu Gln Gly
690                 695                 700 ggc agc aat ctg gaa aac ctg atg gtc gaa ctg gat gcc tcc gaa tca   2160
Gly Ser Asn Leu Glu Asn Leu Met Val Glu Leu Asp Ala Ser Glu Ser
705                 710                 715                 720 tcc gca aca ccc gag acg gtt gaa act gcg gcc gcc gac cgc aca gat   2208
Ser Ala Thr Pro Glu Thr Val Glu Thr Ala Ala Ala Asp Arg Thr Asp
                725                 730                 735 atg ccg ggc atc cgc ccc tac ggc gca act ttc cgc gca gcg gca gcc   2256
Met Pro Gly Ile Arg Pro Tyr Gly Ala Thr Phe Arg Ala Ala Ala Ala
            740                 745                 750 gta cag cat gcg aat gcc gcc gac ggt gta cgc atc ttc aac agt ctc   2304
Val Gln His Ala Asn Ala Ala Asp Gly Val Arg Ile Phe Asn Ser Leu
```

```
                     755                 760                 765
gcc gct acc gtc tat gcc gac agt acc gcc gcc cat gcc gat atg cag     2352
Ala Ala Thr Val Tyr Ala Asp Ser Thr Ala Ala His Ala Asp Met Gln
    770                 775                 780 gga cgc cgg ctg aaa gcc gta tcg gac ggg ttg gac cac aac gct acg     2400
Gly Arg Arg Leu Lys Ala Val Ser Asp Gly Leu Asp His Asn Ala Thr
785                 790                 795                 800 ggt ctg cgc gtc atc gcg caa acc caa cag gac ggt gga acg tgg gaa     2448
Gly Leu Arg Val Ile Ala Gln Thr Gln Gln Asp Gly Gly Thr Trp Glu
                805                 810                 815 cag ggc ggt gtt gaa ggc aaa atg cgc ggc agt acc caa acc gtc ggc     2496
Gln Gly Gly Val Glu Gly Lys Met Arg Gly Ser Thr Gln Thr Val Gly
        820                 825                 830 att gcc gcg aaa acc ggc gaa aat acg aca gca gcc gcc aca ctg ggc     2544
Ile Ala Ala Lys Thr Gly Glu Asn Thr Thr Ala Ala Ala Thr Leu Gly
            835                 840                 845 atg gga cac agc aca tgg agc gaa aac agt gca aat gca aaa acc gac     2592
Met Gly His Ser Thr Trp Ser Glu Asn Ser Ala Asn Ala Lys Thr Asp
850                 855                 860 agc att agt ctg ttt gca ggc ata cgg cac gat gcg ggc gat atc ggc     2640
Ser Ile Ser Leu Phe Ala Gly Ile Arg His Asp Ala Gly Asp Ile Gly
865                 870                 875                 880 tat ctc aaa ggc ctg ttc tcc tac gga cgc tac aaa aac agc atc agc     2688
Tyr Leu Lys Gly Leu Phe Ser Tyr Gly Arg Tyr Lys Asn Ser Ile Ser
                885                 890                 895 cgc agc acc ggt gcg gac gaa cat gcg gaa ggc agc gtc aac ggc acg     2736
Arg Ser Thr Gly Ala Asp Glu His Ala Glu Gly Ser Val Asn Gly Thr
            900                 905                 910 ctg atg cag ctg ggc gca ctg ggt gtc aac gtt ccg ttt gcc gca         2784
Leu Met Gln Leu Gly Ala Leu Gly Gly Val Asn Val Pro Phe Ala Ala
        915                 920                 925 acg gga gat ttg acg gtc gaa ggc ggt ctg cgc tac gac ctg ctc aaa     2832
Thr Gly Asp Leu Thr Val Glu Gly Gly Leu Arg Tyr Asp Leu Leu Lys
    930                 935                 940 cag gat gca ttc gcc gaa aaa ggc agt gct ttg ggc tgg agc ggc aac     2880
Gln Asp Ala Phe Ala Glu Lys Gly Ser Ala Leu Gly Trp Ser Gly Asn
945                 950                 955                 960 agc ctc act gaa ggc aca ctg gtc gga ctc gcg ggt ctg aag ctg tcg     2928
Ser Leu Thr Glu Gly Thr Leu Val Gly Leu Ala Gly Leu Lys Leu Ser
                965                 970                 975 caa ccc ttg agc gat aaa gcc gtc ctg ttt gca acg gcg ggc gtg gaa     2976
Gln Pro Leu Ser Asp Lys Ala Val Leu Phe Ala Thr Ala Gly Val Glu
            980                 985                 990 cgc gac ctg aac gga cgc gac tac acg gta acg ggc ggc ttt acc ggc     3024
Arg Asp Leu Asn Gly Arg Asp Tyr Thr Val Thr Gly Gly Phe Thr Gly
        995                 1000                1005 gcg act gca gca acc ggc aag acg ggg gca cgc aat atg ccg cac acc     3072
Ala Thr Ala Ala Thr Gly Lys Thr Gly Ala Arg Asn Met Pro His Thr
    1010                1015                1020 cgc ctg gtt gcc ggt ctg ggc gcg gat gtc gaa ttc ggc aac ggc tgg     3120
Arg Leu Val Ala Gly Leu Gly Ala Asp Val Glu Phe Gly Asn Gly Trp
1025                1030                1035                1040 aac ggc ttg gca cgt tac agc tac gcc ggt tcc aaa cag tac ggc aac     3168
Asn Gly Leu Ala Arg Tyr Ser Tyr Ala Gly Ser Lys Gln Tyr Gly Asn
                1045                1050                1055 cac agc gga cga gtc ggc gta ggc tac cgg ttc tga                     3204
His Ser Gly Arg Val Gly Val Gly Tyr Arg Phe
            1060                1065
```

<210> SEQ ID NO 8
<211> LENGTH: 1067
<212> TYPE: PRT
<213> ORGANISM: Neisseria meningitidis

<400> SEQUENCE: 8

```
Met Arg Thr Thr Pro Thr Phe Pro Thr Lys Thr Phe Lys Pro Ala Ala
 1               5                  10                  15

Met Ala Leu Ala Val Ala Thr Thr Leu Ser Ala Cys Leu Gly Gly Gly
             20                  25                  30

Gly Gly Thr Ser Ala Pro Asp Phe Asn Ala Gly Gly Thr Gly Ile Gly
         35                  40                  45

Ser Asn Ser Arg Ala Thr Thr Ala Lys Ser Ala Ala Val Ser Tyr Ala
 50                  55                  60

Gly Ile Lys Asn Glu Met Cys Lys Asp Arg Ser Met Leu Cys Ala Gly
 65                  70                  75                  80

Arg Asp Asp Val Ala Val Thr Asp Arg Asp Ala Lys Ile Asn Ala Pro
                 85                  90                  95

Pro Pro Asn Leu His Thr Gly Asp Phe Thr Asn Pro Asn Asp Ala Tyr
            100                 105                 110

Lys Asn Leu Ile Asn Leu Lys Pro Ala Ile Glu Ala Gly Tyr Thr Gly
        115                 120                 125

Arg Gly Val Glu Val Gly Ile Val Asp Thr Gly Glu Ser Val Gly Ser
    130                 135                 140

Ile Ser Phe Pro Glu Leu Tyr Gly Arg Lys Glu His Gly Tyr Asn Glu
145                 150                 155                 160

Asn Tyr Lys Asn Tyr Thr Ala Tyr Met Arg Lys Glu Ala Pro Glu Asp
                165                 170                 175

Gly Gly Gly Lys Asp Ile Lys Ala Ser Phe Asp Asp Glu Ala Val Ile
            180                 185                 190

Glu Thr Glu Ala Lys Pro Thr Asp Ile Arg His Val Lys Glu Ile Gly
        195                 200                 205

His Ile Asp Val Val Ser His Ile Ile Gly Gly Arg Ser Val Asp Gly
    210                 215                 220

Arg Pro Ala Gly Gly Ile Ala Pro Asp Ala Thr Leu His Ile Met Asn
225                 230                 235                 240

Thr His Asp Gly Thr Lys Asn Glu Ile Met Ser Ala Ala Ile Arg Asn
                245                 250                 255

Ala Trp Val Lys Leu Gly Glu Arg Gly Val Arg Ile Val Asn Asn Ser
            260                 265                 270

Phe Gly Thr Thr Ser Arg Ala Gly Thr Ala Asp His Phe Gln Ile Ala
        275                 280                 285

Asn Ser Glu Glu Gln Tyr Arg Gln Ala Leu Leu Ala Tyr Ser Gly Gly
    290                 295                 300

Asp Lys Thr Asp Glu Gly Ile Arg Leu Met Gln Gln Ser Asp Tyr Gly
305                 310                 315                 320

Asn Leu Ser Tyr His Ile Arg Asn Lys Asn Met Leu Phe Ile Phe Ser
                325                 330                 335

Ala Ser Asn Asp Ala Gln Ala Gln Pro Asn Thr Leu Thr Leu Leu Pro
            340                 345                 350

Phe Tyr Glu Lys Asp Ala Gln Lys Gly Ile Ile Thr Val Ala Gly Val
        355                 360                 365

Asp Arg Ser Gly Glu Lys Phe Asn Gly Ser Asn His Cys Gly Ile Thr
    370                 375                 380
```

-continued

```
Ala Met Trp Cys Leu Ser Ala Pro Tyr Glu Ala Ser Val Arg Phe Thr
385             390             395             400

Arg Thr Asn Pro Ile Gln Ile Ala Gly Thr Ser Phe Ser Ala Pro Ile
            405             410             415

Val Thr Gly Thr Ala Ala Leu Leu Gln Lys Tyr Pro Trp Met Ser
            420             425             430

Asn Asp Asn Leu Arg Thr Thr Leu Leu Thr Thr Ala Gln Asp Ile Gly
            435             440             445

Ala Val Gly Val Asp Ser Lys Phe Gly Trp Gly Leu Leu Asp Ala Gly
450             455             460

Lys Ala Met Asn Gly Pro Ala Ser Phe Pro Phe Gly Asp Phe Thr Ala
465             470             475             480

Asp Thr Lys Gly Thr Ser Asp Ile Ala Tyr Ser Phe Arg Asn Asp Ile
            485             490             495

Ser Gly Thr Gly Gly Leu Ile Lys Lys Gly Ser Gln Leu Gln Leu
            500             505             510

His Gly Asn Asn Thr Tyr Thr Gly Lys Thr Ile Ile Glu Gly Gly Ser
            515             520             525

Leu Val Leu Tyr Gly Asn Asn Lys Ser Asp Met Arg Val Glu Thr Lys
            530             535             540

Gly Ala Leu Ile Tyr Asn Gly Ala Ala Ser Gly Gly Ser Leu Asn Ser
545             550             555             560

Asp Gly Ile Val Tyr Leu Ala Asp Thr Asp Arg Ser Gly Ala Asn Glu
            565             570             575

Thr Val His Ile Lys Gly Asp Leu Gln Leu Gly Gly Glu Gly Thr Leu
            580             585             590

Tyr Thr Arg Leu Gly Lys Leu Leu Lys Val Asp Gly Thr Ala Met Thr
            595             600             605

Gly Gly Lys Leu Tyr Met Ser Ala Arg Gly Lys Gly Ala Gly Tyr Leu
610             615             620

Asn Arg Thr Gly Gln Arg Val Pro Phe Leu Ser Ala Ala Lys Ile Gly
625             630             635             640

Arg Asp Tyr Ser Phe Phe Thr Asn Ile Glu Thr Asp Gly Gly Leu Leu
            645             650             655

Ala Ser Leu Asp Ser Val Glu Lys Thr Ala Gly Ser Glu Gly Asp Thr
            660             665             670

Leu Ser Tyr Tyr Val Arg Arg Gly Asn Ala Ala Arg Thr Ala Ser Ala
            675             680             685

Ala Ala His Ser Ala Pro Ala Gly Leu Lys His Ala Val Glu Gln Gly
690             695             700

Gly Ser Asn Leu Glu Asn Leu Met Val Glu Leu Asp Ala Ser Glu Ser
705             710             715             720

Ser Ala Thr Pro Glu Thr Val Glu Thr Ala Ala Ala Asp Arg Thr Asp
            725             730             735

Met Pro Gly Ile Arg Pro Tyr Gly Ala Thr Phe Arg Ala Ala Ala
            740             745             750

Val Gln His Ala Asn Ala Ala Asp Gly Val Arg Ile Phe Asn Ser Leu
            755             760             765

Ala Ala Thr Val Tyr Ala Asp Ser Thr Ala His Ala Asp Met Gln
770             775             780

Gly Arg Arg Leu Lys Ala Val Ser Asp Gly Leu Asp His Asn Ala Thr
785             790             795             800

Gly Leu Arg Val Ile Ala Gln Thr Gln Gln Asp Gly Gly Thr Trp Glu
```

```
                805                 810                 815
Gln Gly Gly Val Glu Gly Lys Met Arg Gly Ser Thr Gln Thr Val Gly
            820                 825                 830

Ile Ala Ala Lys Thr Gly Glu Asn Thr Thr Ala Ala Thr Leu Gly
        835                 840                 845

Met Gly His Ser Thr Trp Ser Glu Asn Ser Ala Asn Ala Lys Thr Asp
    850                 855                 860

Ser Ile Ser Leu Phe Ala Gly Ile Arg His Asp Ala Gly Asp Ile Gly
865                 870                 875                 880

Tyr Leu Lys Gly Leu Phe Ser Tyr Gly Arg Tyr Lys Asn Ser Ile Ser
                885                 890                 895

Arg Ser Thr Gly Ala Asp Glu His Ala Glu Gly Ser Val Asn Gly Thr
            900                 905                 910

Leu Met Gln Leu Gly Ala Leu Gly Val Asn Val Pro Phe Ala Ala
        915                 920                 925

Thr Gly Asp Leu Thr Val Glu Gly Gly Leu Arg Tyr Asp Leu Leu Lys
    930                 935                 940

Gln Asp Ala Phe Ala Glu Lys Gly Ser Ala Leu Gly Trp Ser Gly Asn
945                 950                 955                 960

Ser Leu Thr Glu Gly Thr Leu Val Gly Leu Ala Gly Leu Lys Leu Ser
                965                 970                 975

Gln Pro Leu Ser Asp Lys Ala Val Leu Phe Ala Thr Ala Gly Val Glu
            980                 985                 990

Arg Asp Leu Asn Gly Arg Asp Tyr Thr Val Thr Gly Gly Phe Thr Gly
        995                 1000                1005

Ala Thr Ala Ala Thr Gly Lys Thr Gly Ala Arg Asn Met Pro His Thr
    1010                1015                1020

Arg Leu Val Ala Gly Leu Gly Ala Asp Val Glu Phe Gly Asn Gly Trp
1025                1030                1035                1040

Asn Gly Leu Ala Arg Tyr Ser Tyr Ala Gly Ser Lys Gln Tyr Gly Asn
                1045                1050                1055

His Ser Gly Arg Val Gly Val Gly Tyr Arg Phe
            1060                1065

<210> SEQ ID NO 9
<211> LENGTH: 339
<212> TYPE: DNA
<213> ORGANISM: Neisseria meningitidis
<220> FEATURE:
<221> NAME/KEY: CDS
<222> LOCATION: (1)..(336)

<400> SEQUENCE: 9 atg aac aca cgc atc atc gtt tcg gct gcg ttc gtt gcg ttg gca tta      48
Met Asn Thr Arg Ile Ile Val Ser Ala Ala Phe Val Ala Leu Ala Leu
 1               5                  10                  15 gca ggt tgc ggc tca atc aat aat gta acc gtt tcc gac cag aaa ctt      96
Ala Gly Cys Gly Ser Ile Asn Asn Val Thr Val Ser Asp Gln Lys Leu
            20                  25                  30 cag gaa cgt gcc gcg ttt gcc ttg ggc gtc agc caa aat gcc gta aaa     144
Gln Glu Arg Ala Ala Phe Ala Leu Gly Val Ser Gln Asn Ala Val Lys
        35                  40                  45 atc agc aac cgc agc aat gaa agc ata cgc atc aac ttt acc gca act     192
Ile Ser Asn Arg Ser Asn Glu Ser Ile Arg Ile Asn Phe Thr Ala Thr
    50                  55                  60 gtg ggt aag cgc gtg agc caa tgc tat gtt acc agt gta atc agc aca     240
Val Gly Lys Arg Val Ser Gln Cys Tyr Val Thr Ser Val Ile Ser Thr
```

| | | | | |
|---|---|---|---|---|
| 65 | 70 | 75 | 80 | |

```
atc ggc gtt acc act tcc gat gca att tgt ttg gga ggc gga acg cac        288
Ile Gly Val Thr Thr Ser Asp Ala Ile Cys Leu Gly Gly Gly Thr His
                85                  90                  95 aaa ggc aaa agt caa tgc aat gct ttg ctt aaa gcg gca ggc cgt tgc        336
Lys Gly Lys Ser Gln Cys Asn Ala Leu Leu Lys Ala Ala Gly Arg Cys
        100                 105                 110 taa                                                                    339
```

<210> SEQ ID NO 10
<211> LENGTH: 112
<212> TYPE: PRT
<213> ORGANISM: Neisseria meningitidis

<400> SEQUENCE: 10

```
Met Asn Thr Arg Ile Ile Val Ser Ala Ala Phe Val Ala Leu Ala Leu
 1               5                  10                  15

Ala Gly Cys Gly Ser Ile Asn Asn Val Thr Val Ser Asp Gln Lys Leu
            20                  25                  30

Gln Glu Arg Ala Ala Phe Ala Leu Gly Val Ser Gln Asn Ala Val Lys
        35                  40                  45

Ile Ser Asn Arg Ser Asn Glu Ser Ile Arg Ile Asn Phe Thr Ala Thr
    50                  55                  60

Val Gly Lys Arg Val Ser Gln Cys Tyr Val Thr Ser Val Ile Ser Thr
65                  70                  75                  80

Ile Gly Val Thr Thr Ser Asp Ala Ile Cys Leu Gly Gly Gly Thr His
                85                  90                  95

Lys Gly Lys Ser Gln Cys Asn Ala Leu Leu Lys Ala Ala Gly Arg Cys
        100                 105                 110
```

<210> SEQ ID NO 11
<211> LENGTH: 1314
<212> TYPE: DNA
<213> ORGANISM: Neisseria meningitidis
<220> FEATURE:
<221> NAME/KEY: CDS
<222> LOCATION: (1)..(1311)

<400> SEQUENCE: 11

```
atg ctg acg ttt atc gga ctg ctg att atc ggg gtc atc gta tgg ctg         48
Met Leu Thr Phe Ile Gly Leu Leu Ile Ile Gly Val Ile Val Trp Leu
 1               5                  10                  15 ctg ctg acg gaa aaa gtg tcg ccc atc atc gca tta atc ttg gtg ccg         96
Leu Leu Thr Glu Lys Val Ser Pro Ile Ile Ala Leu Ile Leu Val Pro
            20                  25                  30 ctg ttt ggg gcg ttg ctg gcg ggg ttt gat gta tcc caa tta aaa gaa        144
Leu Phe Gly Ala Leu Leu Ala Gly Phe Asp Val Ser Gln Leu Lys Glu
        35                  40                  45 ttt tat tcg ggc ggc acc aaa tcg gtg atg cag att gtg att atg ttt        192
Phe Tyr Ser Gly Gly Thr Lys Ser Val Met Gln Ile Val Ile Met Phe
    50                  55                  60 atg ttt tcc att ttg ttt ttt gga atc atg aac gat gtg ggg ctg ttc        240
Met Phe Ser Ile Leu Phe Phe Gly Ile Met Asn Asp Val Gly Leu Phe
65                  70                  75                  80 cgt ccg atg ata ggc ggt ttg att aag ctg act cgg ggt aat atc gtg        288
Arg Pro Met Ile Gly Gly Leu Ile Lys Leu Thr Arg Gly Asn Ile Val
                85                  90                  95 gca gtg agt gtg ggg acg gtc ttg gtg tcg gtg gtg gcg cag ttg gac        336
Ala Val Ser Val Gly Thr Val Leu Val Ser Val Val Ala Gln Leu Asp
        100                 105                 110
```

```
                                                           -continued ggg gcg ggt gcg acg acg ttt tta ttg gtc gtc ccc gcc ctt ttg ccg      384
Gly Ala Gly Ala Thr Thr Phe Leu Leu Val Val Pro Ala Leu Leu Pro
            115                 120                 125 ctt tac aag cgt ctg cat atg aat cct tac ctg ctg ttt ttg ctg ctg      432
Leu Tyr Lys Arg Leu His Met Asn Pro Tyr Leu Leu Phe Leu Leu Leu
130                 135                 140 act tcc agt gcg gga ttg att aac ctt ctg ccg tgg ggc ggg ccg acc      480
Thr Ser Ser Ala Gly Leu Ile Asn Leu Leu Pro Trp Gly Gly Pro Thr
145                 150                 155                 160 ggg cgg gtt gca agc gtg ttg ggc gca gat gtg ggc gaa ttg tat aaa      528
Gly Arg Val Ala Ser Val Leu Gly Ala Asp Val Gly Glu Leu Tyr Lys
                165                 170                 175 cct ttg ttg acg gtg caa att atc ggt gtg gtg ttt atc ctt gcg ctg      576
Pro Leu Leu Thr Val Gln Ile Ile Gly Val Val Phe Ile Leu Ala Leu
            180                 185                 190 tcc ctg ctt ttg ggt gtg cgt gaa aaa agg cgg att gtc cgg gag ttg      624
Ser Leu Leu Leu Gly Val Arg Glu Lys Arg Arg Ile Val Arg Glu Leu
        195                 200                 205 ggc gcg ttg ccc gcc gtg gcg gat ttg ata aag ccg gtg cct ttg tcg      672
Gly Ala Leu Pro Ala Val Ala Asp Leu Ile Lys Pro Val Pro Leu Ser
210                 215                 220 gaa gaa gaa caa aaa ttg gcg cgt ccg aaa ctg ttt tgg tgg aat gtc      720
Glu Glu Glu Gln Lys Leu Ala Arg Pro Lys Leu Phe Trp Trp Asn Val
225                 230                 235                 240 ctg ctg ttt ttg gcg gcg atg agc ctg ctt ttt tcg ggc atc ttc ccg      768
Leu Leu Phe Leu Ala Ala Met Ser Leu Leu Phe Ser Gly Ile Phe Pro
                245                 250                 255 ccg ggt tat gta ttt atg ctg gct gca acg gcg gcg ttg ctt ttg aat      816
Pro Gly Tyr Val Phe Met Leu Ala Ala Thr Ala Ala Leu Leu Leu Asn
            260                 265                 270 tac cgc agc ccg cag gaa cag atg gag cgg att tat gcc cac gcc ggc      864
Tyr Arg Ser Pro Gln Glu Gln Met Glu Arg Ile Tyr Ala His Ala Gly
        275                 280                 285 ggc gcg gtg atg atg gcg tcc att att ttg gcg gca ggt acg ttt ttg      912
Gly Ala Val Met Met Ala Ser Ile Ile Leu Ala Ala Gly Thr Phe Leu
290                 295                 300 ggg att ttg aag ggt gcg ggg atg ttg gac gcg att tcc aaa gac att      960
Gly Ile Leu Lys Gly Ala Gly Met Leu Asp Ala Ile Ser Lys Asp Ile
305                 310                 315                 320 gtg cat atc ctg ccg gac gcg ctg ctg cct tat ctg cat att gcc atc     1008
Val His Ile Leu Pro Asp Ala Leu Leu Pro Tyr Leu His Ile Ala Ile
                325                 330                 335 ggt gtg ttg ggc att ccg ctt gag ttg gtt ttg agt acg gac gct tat     1056
Gly Val Leu Gly Ile Pro Leu Glu Leu Val Leu Ser Thr Asp Ala Tyr
            340                 345                 350 tat ttc gga ctg ttt ccg att gtg gag cag att acc tcg cag gcg ggc     1104
Tyr Phe Gly Leu Phe Pro Ile Val Glu Gln Ile Thr Ser Gln Ala Gly
        355                 360                 365 gtg gcg ccc gaa gca gca ggt tat gcg atg ttg atc ggc agt atc gtc     1152
Val Ala Pro Glu Ala Ala Gly Tyr Ala Met Leu Ile Gly Ser Ile Val
370                 375                 380 ggc act ttt gtt acg ccg ctt tcg ccg gct ttg tgg atg ggc ttg ggt     1200
Gly Thr Phe Val Thr Pro Leu Ser Pro Ala Leu Trp Met Gly Leu Gly
385                 390                 395                 400 ttg gcg aaa ttg tcg atg ggc aaa cac atc cgt tat tcg ttt ttt tgg     1248
Leu Ala Lys Leu Ser Met Gly Lys His Ile Arg Tyr Ser Phe Phe Trp
                405                 410                 415 gcg tgg ggt ttg tcg ctg gcg ata ttg gcc agt tcg ata gcg gca gga     1296
Ala Trp Gly Leu Ser Leu Ala Ile Leu Ala Ser Ser Ile Ala Ala Gly
```

-continued

```
               420           425           430
atc gtg cct ctg ccg taa                              1314
Ile Val Pro Leu Pro
    435
```

<210> SEQ ID NO 12
<211> LENGTH: 437
<212> TYPE: PRT
<213> ORGANISM: Neisseria meningitidis

<400> SEQUENCE: 12

```
Met Leu Thr Phe Ile Gly Leu Ile Ile Gly Val Ile Val Trp Leu
 1               5                  10                  15

Leu Leu Thr Glu Lys Val Ser Pro Ile Ile Ala Leu Ile Leu Val Pro
            20                  25                  30

Leu Phe Gly Ala Leu Leu Ala Gly Phe Asp Val Ser Gln Leu Lys Glu
        35                  40                  45

Phe Tyr Ser Gly Gly Thr Lys Ser Val Met Gln Ile Val Ile Met Phe
    50                  55                  60

Met Phe Ser Ile Leu Phe Phe Gly Ile Met Asn Asp Val Gly Leu Phe
65                  70                  75                  80

Arg Pro Met Ile Gly Gly Leu Ile Lys Leu Thr Arg Gly Asn Ile Val
                85                  90                  95

Ala Val Ser Val Gly Thr Val Leu Val Ser Val Val Ala Gln Leu Asp
            100                 105                 110

Gly Ala Gly Ala Thr Thr Phe Leu Leu Val Val Pro Ala Leu Leu Pro
        115                 120                 125

Leu Tyr Lys Arg Leu His Met Asn Pro Tyr Leu Leu Phe Leu Leu Leu
    130                 135                 140

Thr Ser Ser Ala Gly Leu Ile Asn Leu Leu Pro Trp Gly Gly Pro Thr
145                 150                 155                 160

Gly Arg Val Ala Ser Val Leu Gly Ala Asp Val Gly Glu Leu Tyr Lys
                165                 170                 175

Pro Leu Leu Thr Val Gln Ile Ile Gly Val Val Phe Ile Leu Ala Leu
            180                 185                 190

Ser Leu Leu Leu Gly Val Arg Glu Lys Arg Ile Val Arg Glu Leu
        195                 200                 205

Gly Ala Leu Pro Ala Val Ala Asp Leu Ile Lys Pro Val Pro Leu Ser
    210                 215                 220

Glu Glu Glu Gln Lys Leu Ala Arg Pro Lys Leu Phe Trp Trp Asn Val
225                 230                 235                 240

Leu Leu Phe Leu Ala Ala Met Ser Leu Leu Phe Ser Gly Ile Phe Pro
                245                 250                 255

Pro Gly Tyr Val Phe Met Leu Ala Ala Thr Ala Ala Leu Leu Leu Asn
            260                 265                 270

Tyr Arg Ser Pro Gln Glu Gln Met Glu Arg Ile Tyr Ala His Ala Gly
        275                 280                 285

Gly Ala Val Met Met Ala Ser Ile Ile Leu Ala Ala Gly Thr Phe Leu
    290                 295                 300

Gly Ile Leu Lys Gly Ala Gly Met Leu Asp Ala Ile Ser Lys Asp Ile
305                 310                 315                 320

Val His Ile Leu Pro Asp Ala Leu Leu Pro Tyr Leu His Ile Ala Ile
                325                 330                 335

Gly Val Leu Gly Ile Pro Leu Glu Leu Val Leu Ser Thr Asp Ala Tyr
            340                 345                 350
```

```
Tyr Phe Gly Leu Phe Pro Ile Val Glu Gln Ile Thr Ser Gln Ala Gly
        355                 360                 365

Val Ala Pro Glu Ala Ala Gly Tyr Ala Met Leu Ile Gly Ser Ile Val
    370                 375                 380

Gly Thr Phe Val Thr Pro Leu Ser Pro Ala Leu Trp Met Gly Leu Gly
385                 390                 395                 400

Leu Ala Lys Leu Ser Met Gly Lys His Ile Arg Tyr Ser Phe Phe Trp
                405                 410                 415

Ala Trp Gly Leu Ser Leu Ala Ile Leu Ala Ser Ser Ile Ala Ala Gly
            420                 425                 430

Ile Val Pro Leu Pro
        435

<210> SEQ ID NO 13
<211> LENGTH: 1155
<212> TYPE: DNA
<213> ORGANISM: Neisseria meningitidis
<220> FEATURE:
<221> NAME/KEY: CDS
<222> LOCATION: (1)..(1152)

<400> SEQUENCE: 13
```

| | | | | | | | | | | | | | | | | |
|---|---|---|---|---|---|---|---|---|---|---|---|---|---|---|---|---|
| atg | ggc | atc | cat | ctc | gac | ttc | ggc | att | agt | cct | aaa | acg | ttc | cga | cag | 48 |
| Met | Gly | Ile | His | Leu | Asp | Phe | Gly | Ile | Ser | Pro | Lys | Thr | Phe | Arg | Gln | |
| 1 | | | | 5 | | | | | 10 | | | | | 15 | | |
| act | tat | ctg | tat | caa | aag | ccc | aag | ctc | ttt | aaa | gga | gcg | gtt | cgg | aat | 96 |
| Thr | Tyr | Leu | Tyr | Gln | Lys | Pro | Lys | Leu | Phe | Lys | Gly | Ala | Val | Arg | Asn | |
| | | | 20 | | | | | 25 | | | | | 30 | | | |
| ctc | gaa | gcc | gca | tct | tgt | aaa | tat | atc | aac | gag | ata | tac | caa | cga | gca | 144 |
| Leu | Glu | Ala | Ala | Ser | Cys | Lys | Tyr | Ile | Asn | Glu | Ile | Tyr | Gln | Arg | Ala | |
| | | 35 | | | | | 40 | | | | | 45 | | | | |
| gac | cca | acc | gca | ccg | ctg | ttt | cat | ctg | cgt | aaa | aaa | ggc | gca | atc | gtt | 192 |
| Asp | Pro | Thr | Ala | Pro | Leu | Phe | His | Leu | Arg | Lys | Lys | Gly | Ala | Ile | Val | |
| | 50 | | | | | 55 | | | | | 60 | | | | | |
| cct | aaa | gaa | gaa | tac | gtc | gaa | agt | ttc | gac | gat | ttg | ggc | aaa | act | cgc | 240 |
| Pro | Lys | Glu | Glu | Tyr | Val | Glu | Ser | Phe | Asp | Asp | Leu | Gly | Lys | Thr | Arg | |
| 65 | | | | 70 | | | | | 75 | | | | | 80 | | |
| tac | cgt | ttt | att | aaa | tcc | gtt | atc | tac | gaa | cat | atg | aag | aat | ggt | gcg | 288 |
| Tyr | Arg | Phe | Ile | Lys | Ser | Val | Ile | Tyr | Glu | His | Met | Lys | Asn | Gly | Ala | |
| | | | 85 | | | | | 90 | | | | | 95 | | | |
| tcg | tta | gtc | tat | aac | cat | att | aac | aac | gag | ccg | ttt | tca | gac | cat | atc | 336 |
| Ser | Leu | Val | Tyr | Asn | His | Ile | Asn | Asn | Glu | Pro | Phe | Ser | Asp | His | Ile | |
| | | | 100 | | | | | 105 | | | | | 110 | | | |
| gcc | cgt | caa | gtc | gcc | cgc | ttt | gcc | ggc | gca | cat | act | att | gtt | agt | gga | 384 |
| Ala | Arg | Gln | Val | Ala | Arg | Phe | Ala | Gly | Ala | His | Thr | Ile | Val | Ser | Gly | |
| | | 115 | | | | | 120 | | | | | 125 | | | | |
| tat | ctt | gct | ttt | ggc | agc | gac | gaa | tct | tat | aaa | aac | cat | tgg | gat | acc | 432 |
| Tyr | Leu | Ala | Phe | Gly | Ser | Asp | Glu | Ser | Tyr | Lys | Asn | His | Trp | Asp | Thr | |
| | 130 | | | | | 135 | | | | | 140 | | | | | |
| cgc | gat | gtg | tat | gcc | atc | cag | ctt | ttc | ggc | aag | aaa | cgt | tgg | caa | ctt | 480 |
| Arg | Asp | Val | Tyr | Ala | Ile | Gln | Leu | Phe | Gly | Lys | Lys | Arg | Trp | Gln | Leu | |
| 145 | | | | 150 | | | | | 155 | | | | | 160 | | |
| act | gcc | cct | gat | ttc | cct | atg | cca | ttg | tat | atg | caa | cag | act | aaa | gat | 528 |
| Thr | Ala | Pro | Asp | Phe | Pro | Met | Pro | Leu | Tyr | Met | Gln | Gln | Thr | Lys | Asp | |
| | | | 165 | | | | | 170 | | | | | 175 | | | |
| act | gat | att | tcc | att | cct | gaa | cat | atc | gat | atg | gat | att | atc | ctt | gaa | 576 |
| Thr | Asp | Ile | Ser | Ile | Pro | Glu | His | Ile | Asp | Met | Asp | Ile | Ile | Leu | Glu | |
| | | | 180 | | | | | 185 | | | | | 190 | | | |
| gca | ggt | gat | gtc | ctc | tac | atc | cca | cgc | ggt | tgg | tgg | cac | aga | cct | atc | 624 |

-continued

| | | |
|---|---|---|
| Ala Gly Asp Val Leu Tyr Ile Pro Arg Gly Trp Trp His Arg Pro Ile<br>195 200 205 | | |
| ccg ctc ggc tgt gaa acc ttc cac ttc gct gtc ggt acc ttc ccg ccc<br>Pro Leu Gly Cys Glu Thr Phe His Phe Ala Val Gly Thr Phe Pro Pro<br>210 215 220 | | 672 |
| aac ggc tat aat tac ctc gag tgg cta atg aag aaa ttc ccc acg ata<br>Asn Gly Tyr Asn Tyr Leu Glu Trp Leu Met Lys Lys Phe Pro Thr Ile<br>225 230 235 240 | | 720 |
| gaa agt ctg cgc cac agt ttc tca gac tgg gag caa gat agg acg cgt<br>Glu Ser Leu Arg His Ser Phe Ser Asp Trp Glu Gln Asp Arg Thr Arg<br>245 250 255 | | 768 |
| atc aac gat act gcc gca caa att gct gcc atg att gcc gac ccc gtc<br>Ile Asn Asp Thr Ala Ala Gln Ile Ala Ala Met Ile Ala Asp Pro Val<br>260 265 270 | | 816 |
| aat tac gaa gcc ttc agt gaa gac ttc ctc ggc aaa gaa cgc acc gat<br>Asn Tyr Glu Ala Phe Ser Glu Asp Phe Leu Gly Lys Glu Arg Thr Asp<br>275 280 285 | | 864 |
| acc gct ttt cat ctc gaa cag ttc gcg aat ccc aac gct act ccg ctt<br>Thr Ala Phe His Leu Glu Gln Phe Ala Asn Pro Asn Ala Thr Pro Leu<br>290 295 300 | | 912 |
| tca gac gac gtc agg ttg aga cta aat gcc aat aat ttg gat acg ttg<br>Ser Asp Asp Val Arg Leu Arg Leu Asn Ala Asn Asn Leu Asp Thr Leu<br>305 310 315 320 | | 960 |
| gaa aag gga tat ttg att ggg aat ggg atg aag ata agc gta gat gaa<br>Glu Lys Gly Tyr Leu Ile Gly Asn Gly Met Lys Ile Ser Val Asp Glu<br>325 330 335 | | 1008 |
| ttg ggg aaa aaa gtg tta gaa cac atc ggt aag aat gaa ccg tta ttg<br>Leu Gly Lys Lys Val Leu Glu His Ile Gly Lys Asn Glu Pro Leu Leu<br>340 345 350 | | 1056 |
| ttg aaa aat cta ctg gtt aac ttc aat cag gga aaa cat gaa gaa gtt<br>Leu Lys Asn Leu Leu Val Asn Phe Asn Gln Gly Lys His Glu Glu Val<br>355 360 365 | | 1104 |
| agg aag ttg att tat cag ttg ata gag tta gat ttt ctg gaa ctt ttg<br>Arg Lys Leu Ile Tyr Gln Leu Ile Glu Leu Asp Phe Leu Glu Leu Leu<br>370 375 380 | | 1152 |
| tga | | 1155 |

<210> SEQ ID NO 14
<211> LENGTH: 384
<212> TYPE: PRT
<213> ORGANISM: Neisseria meningitidis

<400> SEQUENCE: 14

Met Gly Ile His Leu Asp Phe Gly Ile Ser Pro Lys Thr Phe Arg Gln
1               5                   10                  15

Thr Tyr Leu Tyr Gln Lys Pro Lys Leu Phe Lys Gly Ala Val Arg Asn
                20                  25                  30

Leu Glu Ala Ala Ser Cys Lys Tyr Ile Asn Glu Ile Tyr Gln Arg Ala
            35                  40                  45

Asp Pro Thr Ala Pro Leu Phe His Leu Arg Lys Lys Gly Ala Ile Val
        50                  55                  60

Pro Lys Glu Glu Tyr Val Glu Ser Phe Asp Asp Leu Gly Lys Thr Arg
65                  70                  75                  80

Tyr Arg Phe Ile Lys Ser Val Ile Tyr Glu His Met Lys Asn Gly Ala
                85                  90                  95

Ser Leu Val Tyr Asn His Ile Asn Asn Glu Pro Phe Ser Asp His Ile
            100                 105                 110

Ala Arg Gln Val Ala Arg Phe Ala Gly Ala His Thr Ile Val Ser Gly

```
                    115                 120                 125
Tyr Leu Ala Phe Gly Ser Asp Glu Ser Tyr Lys Asn His Trp Asp Thr
    130                 135                 140

Arg Asp Val Tyr Ala Ile Gln Leu Phe Gly Lys Lys Arg Trp Gln Leu
145                 150                 155                 160

Thr Ala Pro Asp Phe Pro Met Pro Leu Tyr Met Gln Gln Thr Lys Asp
                165                 170                 175

Thr Asp Ile Ser Ile Pro Glu His Ile Asp Met Asp Ile Ile Leu Glu
            180                 185                 190

Ala Gly Asp Val Leu Tyr Ile Pro Arg Gly Trp Trp His Arg Pro Ile
        195                 200                 205

Pro Leu Gly Cys Glu Thr Phe His Phe Ala Val Gly Thr Phe Pro Pro
    210                 215                 220

Asn Gly Tyr Asn Tyr Leu Glu Trp Leu Met Lys Lys Phe Pro Thr Ile
225                 230                 235                 240

Glu Ser Leu Arg His Ser Phe Ser Asp Trp Glu Gln Asp Arg Thr Arg
                245                 250                 255

Ile Asn Asp Thr Ala Ala Gln Ile Ala Ala Met Ile Ala Asp Pro Val
            260                 265                 270

Asn Tyr Glu Ala Phe Ser Glu Asp Phe Leu Gly Lys Glu Arg Thr Asp
        275                 280                 285

Thr Ala Phe His Leu Glu Gln Phe Ala Asn Pro Asn Ala Thr Pro Leu
    290                 295                 300

Ser Asp Asp Val Arg Leu Arg Leu Asn Ala Asn Asn Leu Asp Thr Leu
305                 310                 315                 320

Glu Lys Gly Tyr Leu Ile Gly Asn Gly Met Lys Ile Ser Val Asp Glu
                325                 330                 335

Leu Gly Lys Lys Val Leu Glu His Ile Gly Lys Asn Glu Pro Leu Leu
            340                 345                 350

Leu Lys Asn Leu Leu Val Asn Phe Asn Gln Gly Lys His Glu Glu Val
        355                 360                 365

Arg Lys Leu Ile Tyr Gln Leu Ile Glu Leu Asp Phe Leu Glu Leu Leu
    370                 375                 380

<210> SEQ ID NO 15
<211> LENGTH: 717
<212> TYPE: DNA
<213> ORGANISM: Neisseria meningitidis
<220> FEATURE:
<221> NAME/KEY: CDS
<222> LOCATION: (1)..(714)

<400> SEQUENCE: 15 atg aat aga ccc aag caa ccc ttc ttc cgt ccc gaa gtc gcc gtt gcc    48
Met Asn Arg Pro Lys Gln Pro Phe Phe Arg Pro Glu Val Ala Val Ala
 1               5                  10                  15 cgc caa acc agc ctg acg ggt aaa gtg att ctg aca cga ccg ttg tca    96
Arg Gln Thr Ser Leu Thr Gly Lys Val Ile Leu Thr Arg Pro Leu Ser
             20                  25                  30 ttt tcc cta tgg acg aca ttt gca tcg ata tct gcg tta ttg att atc   144
Phe Ser Leu Trp Thr Thr Phe Ala Ser Ile Ser Ala Leu Leu Ile Ile
         35                  40                  45 ctg ttt ttg ata ttt ggt aac tat acg cga aag aca aca gtg gag gga   192
Leu Phe Leu Ile Phe Gly Asn Tyr Thr Arg Lys Thr Thr Val Glu Gly
     50                  55                  60 caa att tta cct gca tcg ggc gta atc agg gtg tat gca ccg gat acg   240
Gln Ile Leu Pro Ala Ser Gly Val Ile Arg Val Tyr Ala Pro Asp Thr
```

```
                 65                  70                  75                  80
ggg aca att aca gcg aaa ttc gtg gaa gat gga gaa aag gtt aag gct       288
Gly Thr Ile Thr Ala Lys Phe Val Glu Asp Gly Glu Lys Val Lys Ala
                     85                  90                  95 ggc gac aag cta ttt gcg ctt tcg acc tca cgt ttc ggc gca gga gat       336
Gly Asp Lys Leu Phe Ala Leu Ser Thr Ser Arg Phe Gly Ala Gly Asp
                100                 105                 110 agc gtg cag cag cag ttg aaa acg gag gca gtt ttg aag aaa acg ttg       384
Ser Val Gln Gln Gln Leu Lys Thr Glu Ala Val Leu Lys Lys Thr Leu
            115                 120                 125 gca gaa cag gaa ctg ggt cgt ctg aag ctg ata cac ggg aat gaa acg       432
Ala Glu Gln Glu Leu Gly Arg Leu Lys Leu Ile His Gly Asn Glu Thr
        130                 135                 140 cgc agc ctt aaa gca act gtc gaa cgt ttg gaa aac cag aaa ctc cat       480
Arg Ser Leu Lys Ala Thr Val Glu Arg Leu Glu Asn Gln Lys Leu His
145                 150                 155                 160 att tcg caa cag ata gac ggt cag aaa agg cgc att aga ctt gcg gaa       528
Ile Ser Gln Gln Ile Asp Gly Gln Lys Arg Arg Ile Arg Leu Ala Glu
                165                 170                 175 gaa atg ttg cag aaa tat cgt ttc cta tcc gcc aat gat gca gtg cca       576
Glu Met Leu Gln Lys Tyr Arg Phe Leu Ser Ala Asn Asp Ala Val Pro
                180                 185                 190 aaa caa gaa atg atg aat gtc aag gca gag ctt tta gag cag aaa gcc       624
Lys Gln Glu Met Met Asn Val Lys Ala Glu Leu Leu Glu Gln Lys Ala
            195                 200                 205 aaa ctt gat gcc tac cgc cga gaa gaa gtc ggg ctg ctt cag gaa atc       672
Lys Leu Asp Ala Tyr Arg Arg Glu Glu Val Gly Leu Leu Gln Glu Ile
        210                 215                 220 cgc acg cag aat ctg aca ttg gcc agc ctc ccc caa gcg gca tga           717
Arg Thr Gln Asn Leu Thr Leu Ala Ser Leu Pro Gln Ala Ala
225                 230                 235

<210> SEQ ID NO 16
<211> LENGTH: 238
<212> TYPE: PRT
<213> ORGANISM: Neisseria meningitidis

<400> SEQUENCE: 16

Met Asn Arg Pro Lys Gln Pro Phe Phe Arg Pro Glu Val Ala Val Ala
1               5                   10                  15

Arg Gln Thr Ser Leu Thr Gly Lys Val Ile Leu Thr Arg Pro Leu Ser
                20                  25                  30

Phe Ser Leu Trp Thr Thr Phe Ala Ser Ile Ser Ala Leu Leu Ile Ile
            35                  40                  45

Leu Phe Leu Ile Phe Gly Asn Tyr Thr Arg Lys Thr Thr Val Glu Gly
        50                  55                  60

Gln Ile Leu Pro Ala Ser Gly Val Ile Arg Val Tyr Ala Pro Asp Thr
65                  70                  75                  80

Gly Thr Ile Thr Ala Lys Phe Val Glu Asp Gly Glu Lys Val Lys Ala
                85                  90                  95

Gly Asp Lys Leu Phe Ala Leu Ser Thr Ser Arg Phe Gly Ala Gly Asp
            100                 105                 110

Ser Val Gln Gln Gln Leu Lys Thr Glu Ala Val Leu Lys Lys Thr Leu
        115                 120                 125

Ala Glu Gln Glu Leu Gly Arg Leu Lys Leu Ile His Gly Asn Glu Thr
    130                 135                 140

Arg Ser Leu Lys Ala Thr Val Glu Arg Leu Glu Asn Gln Lys Leu His
145                 150                 155                 160
```

Ile Ser Gln Gln Ile Asp Gly Gln Lys Arg Arg Ile Arg Leu Ala Glu
        165                 170                 175

Glu Met Leu Gln Lys Tyr Arg Phe Leu Ser Ala Asn Asp Ala Val Pro
        180                 185                 190

Lys Gln Glu Met Met Asn Val Lys Ala Glu Leu Leu Glu Gln Lys Ala
        195                 200                 205

Lys Leu Asp Ala Tyr Arg Arg Glu Val Gly Leu Leu Gln Glu Ile
        210                 215                 220

Arg Thr Gln Asn Leu Thr Leu Ala Ser Leu Pro Gln Ala Ala
225                 230                 235

<210> SEQ ID NO 17
<211> LENGTH: 690
<212> TYPE: DNA
<213> ORGANISM: Neisseria meningitidis
<220> FEATURE:
<221> NAME/KEY: CDS
<222> LOCATION: (1)..(687)

<400> SEQUENCE: 17

| | |
|---|---|
| atg atg aat gtc gag gca gag ctt tta gag cag aaa gcc aaa ctt gat<br>Met Met Asn Val Glu Ala Glu Leu Leu Glu Gln Lys Ala Lys Leu Asp<br>1               5                   10                  15 | 48 |
| gcc tac ggc cga gaa gaa gcc ggg ctg ctt cag gaa atc cgc acg cag<br>Ala Tyr Gly Arg Glu Glu Ala Gly Leu Leu Gln Glu Ile Arg Thr Gln<br>            20                  25                  30 | 96 |
| aat ctg aca ttg gcc agc ctc ccc aaa cgg cat gag aca gaa caa agc<br>Asn Leu Thr Leu Ala Ser Leu Pro Lys Arg His Glu Thr Glu Gln Ser<br>        35                  40                  45 | 144 |
| cag ctt gaa cgc acc atg gcc gat att tct caa gaa gtt ttg gat ttt<br>Gln Leu Glu Arg Thr Met Ala Asp Ile Ser Gln Glu Val Leu Asp Phe<br>    50                  55                  60 | 192 |
| gaa atg cgc tct gaa caa atc atc cgt gca gga cgg tcg ggt tat ata<br>Glu Met Arg Ser Glu Gln Ile Ile Arg Ala Gly Arg Ser Gly Tyr Ile<br>65                  70                  75                  80 | 240 |
| gca ata ccg aac gtc gaa gtc gga cag cag gtt gat cct tcc aaa ctg<br>Ala Ile Pro Asn Val Glu Val Gly Gln Gln Val Asp Pro Ser Lys Leu<br>                85                  90                  95 | 288 |
| ctc ttg agc att gtt ccc gaa cgt acc gag cta tat gcc cat cta tat<br>Leu Leu Ser Ile Val Pro Glu Arg Thr Glu Leu Tyr Ala His Leu Tyr<br>            100                 105                 110 | 336 |
| atc ccc agc agt gca gca ggc ttt atc aag ccg aaa gac aag gtt gtc<br>Ile Pro Ser Ser Ala Ala Gly Phe Ile Lys Pro Lys Asp Lys Val Val<br>        115                 120                 125 | 384 |
| cta cgt tat cag gca tat ccc tat caa aaa ttc ggg ctt gct tcc ggc<br>Leu Arg Tyr Gln Ala Tyr Pro Tyr Gln Lys Phe Gly Leu Ala Ser Gly<br>    130                 135                 140 | 432 |
| agt gtc gta tca gta gca aaa acg gca ctg ggc aga cag gaa ttg tcg<br>Ser Val Val Ser Val Ala Lys Thr Ala Leu Gly Arg Gln Glu Leu Ser<br>145                 150                 155                 160 | 480 |
| gga ttg ggc atg gta tcc tcc gat ttg gcg aag agc aac gaa cct gtt<br>Gly Leu Gly Met Val Ser Ser Asp Leu Ala Lys Ser Asn Glu Pro Val<br>                165                 170                 175 | 528 |
| tat ctc gtg aaa ata aaa ccc gac aaa cca acc atc act gca tac ggt<br>Tyr Leu Val Lys Ile Lys Pro Asp Lys Pro Thr Ile Thr Ala Tyr Gly<br>            180                 185                 190 | 576 |
| gag gaa aaa ccg ctg caa atc ggc atg acg ttg gaa gca gac atc ctg<br>Glu Glu Lys Pro Leu Gln Ile Gly Met Thr Leu Glu Ala Asp Ile Leu<br>        195                 200                 205 | 624 |

-continued

```
cac gag aaa cgg cgg ctg tac gaa tgg gta ttg gag ctg att tat agt      672
His Glu Lys Arg Arg Leu Tyr Glu Trp Val Leu Glu Leu Ile Tyr Ser
    210                 215                 220 atg tcg ggc aaa ctg taa                                              690
Met Ser Gly Lys Leu
225
```

<210> SEQ ID NO 18
<211> LENGTH: 229
<212> TYPE: PRT
<213> ORGANISM: Neisseria meningitidis

<400> SEQUENCE: 18

```
Met Met Asn Val Glu Ala Glu Leu Leu Glu Gln Lys Ala Lys Leu Asp
  1               5                  10                  15

Ala Tyr Gly Arg Glu Ala Gly Leu Leu Gln Glu Ile Arg Thr Gln
             20                  25                  30

Asn Leu Thr Leu Ala Ser Leu Pro Lys Arg His Glu Thr Glu Gln Ser
         35                  40                  45

Gln Leu Glu Arg Thr Met Ala Asp Ile Ser Gln Glu Val Leu Asp Phe
     50                  55                  60

Glu Met Arg Ser Glu Gln Ile Ile Arg Ala Gly Arg Ser Gly Tyr Ile
 65                  70                  75                  80

Ala Ile Pro Asn Val Glu Val Gly Gln Gln Val Asp Pro Ser Lys Leu
                 85                  90                  95

Leu Leu Ser Ile Val Pro Glu Arg Thr Glu Leu Tyr Ala His Leu Tyr
            100                 105                 110

Ile Pro Ser Ser Ala Ala Gly Phe Ile Lys Pro Lys Asp Lys Val Val
        115                 120                 125

Leu Arg Tyr Gln Ala Tyr Pro Tyr Gln Lys Phe Gly Leu Ala Ser Gly
    130                 135                 140

Ser Val Val Ser Val Ala Lys Thr Ala Leu Gly Arg Gln Glu Leu Ser
145                 150                 155                 160

Gly Leu Gly Met Val Ser Ser Asp Leu Ala Lys Ser Asn Glu Pro Val
                165                 170                 175

Tyr Leu Val Lys Ile Lys Pro Asp Lys Pro Thr Ile Thr Ala Tyr Gly
            180                 185                 190

Glu Glu Lys Pro Leu Gln Ile Gly Met Thr Leu Glu Ala Asp Ile Leu
        195                 200                 205

His Glu Lys Arg Arg Leu Tyr Glu Trp Val Leu Glu Leu Ile Tyr Ser
    210                 215                 220

Met Ser Gly Lys Leu
225
```

<210> SEQ ID NO 19
<211> LENGTH: 1743
<212> TYPE: DNA
<213> ORGANISM: Neisseria meningitidis
<220> FEATURE:
<221> NAME/KEY: CDS
<222> LOCATION: (1)..(1740)

<400> SEQUENCE: 19

```
atg aaa ttt ttt cct gct cca tgt ctg ttg gtt atc ctg gct gtc ata       48
Met Lys Phe Phe Pro Ala Pro Cys Leu Leu Val Ile Leu Ala Val Ile
  1               5                  10                  15 ccc ctt aaa acc tta gct gcc gat gaa aac gat gca gaa ctt atc cgt       96
Pro Leu Lys Thr Leu Ala Ala Asp Glu Asn Asp Ala Glu Leu Ile Arg
             20                  25                  30
```

-continued

```
tcc atg cag cgt cag cag cac ata gat gct gaa ttg tta act gat gca    144
Ser Met Gln Arg Gln Gln His Ile Asp Ala Glu Leu Leu Thr Asp Ala
        35                  40                  45 aat gtc cgt ttc gag caa cca ttg gag aag aac aat tat gtc ctg agt    192
Asn Val Arg Phe Glu Gln Pro Leu Glu Lys Asn Asn Tyr Val Leu Ser
 50                  55                  60 gaa gat gaa aca ccg tgt act cgg gta aat tac att agt tta gat gat    240
Glu Asp Glu Thr Pro Cys Thr Arg Val Asn Tyr Ile Ser Leu Asp Asp
 65                  70                  75                  80 aag acg gcg cgc aaa ttt tct ttt ctt cct tct gtg ctc atg aaa gaa    288
Lys Thr Ala Arg Lys Phe Ser Phe Leu Pro Ser Val Leu Met Lys Glu
                 85                  90                  95 aca gct ttt aaa act ggg atg tgt tta ggt tcc aat aat ttg agc agg    336
Thr Ala Phe Lys Thr Gly Met Cys Leu Gly Ser Asn Asn Leu Ser Arg
            100                 105                 110 cta caa aaa gcc gcg caa cag ata ctg att gtg cgt ggc tac ctc act    384
Leu Gln Lys Ala Ala Gln Gln Ile Leu Ile Val Arg Gly Tyr Leu Thr
        115                 120                 125 tcc caa gct att atc caa cca cag aat atg gat tcg gga att ctg aaa    432
Ser Gln Ala Ile Ile Gln Pro Gln Asn Met Asp Ser Gly Ile Leu Lys
130                 135                 140 tta cgg gta tca gca ggc gaa atc agg gat atc cgc tat gaa gaa aaa    480
Leu Arg Val Ser Ala Gly Glu Ile Arg Asp Ile Arg Tyr Glu Glu Lys
145                 150                 155                 160 cgg gat gcg aag tct gcc gag ggc agt att agt gca ttc aat aac aaa    528
Arg Asp Ala Lys Ser Ala Glu Gly Ser Ile Ser Ala Phe Asn Asn Lys
                165                 170                 175 ctt ccc tta tat agg aac aaa att ctc aat ctt cgc gat gta gag cag    576
Leu Pro Leu Tyr Arg Asn Lys Ile Leu Asn Leu Arg Asp Val Glu Gln
            180                 185                 190 ggc ttg gaa aac ctg cgt cgt ttg ccg agt gtt aaa aca gat att cag    624
Gly Leu Glu Asn Leu Arg Arg Leu Pro Ser Val Lys Thr Asp Ile Gln
        195                 200                 205 att ata ccg tcc gaa gaa gaa ggc aaa agc gat tta cag atc aaa tgg    672
Ile Ile Pro Ser Glu Glu Glu Gly Lys Ser Asp Leu Gln Ile Lys Trp
210                 215                 220 cag cag aat aaa ccc ata cgg ttc agt atc ggt ata gat gat gcg ggc    720
Gln Gln Asn Lys Pro Ile Arg Phe Ser Ile Gly Ile Asp Asp Ala Gly
225                 230                 235                 240 ggc aaa acg acc ggc aaa tat caa gga aat gtc gct tta tcg tcc gat    768
Gly Lys Thr Thr Gly Lys Tyr Gln Gly Asn Val Ala Leu Ser Ser Asp
                245                 250                 255 aac cct ttg ggc tta agc gat tcg ttt tat gtt tca tat gga cgc ggt    816
Asn Pro Leu Gly Leu Ser Asp Ser Phe Tyr Val Ser Tyr Gly Arg Gly
            260                 265                 270 ttg gtg cac aaa acg gac ttg act gct gcc acc ggt acg gaa act gaa    864
Leu Val His Lys Thr Asp Leu Thr Ala Ala Thr Gly Thr Glu Thr Glu
        275                 280                 285 agc gga tcc aga agt tac agc gtg cat tat tcg gtg ccc gta aaa aaa    912
Ser Gly Ser Arg Ser Tyr Ser Val His Tyr Ser Val Pro Val Lys Lys
        290                 295                 300 tgg ctg ttt tct ttt aat cac aat gga cat cgt tac cac gaa gca acc    960
Trp Leu Phe Ser Phe Asn His Asn Gly His Arg Tyr His Glu Ala Thr
305                 310                 315                 320 gaa ggc tat tcc gtc aat tac gat tac aac ggc aaa caa tat cag agc    1008
Glu Gly Tyr Ser Val Asn Tyr Asp Tyr Asn Gly Lys Gln Tyr Gln Ser
                325                 330                 335 agc ctg gcc gcc gag cgc atg ctt tgg ccc ccc agc ttt cct caa act    1056
Ser Leu Ala Ala Glu Arg Met Leu Trp Pro Pro Ser Phe Pro Gln Thr
```

```
                    340                 345                 350
tca gtc cga atg aaa tta tgg aca cgc caa acc tat aaa tac atc gac      1104
Ser Val Arg Met Lys Leu Trp Thr Arg Gln Thr Tyr Lys Tyr Ile Asp
        355                 360                 365 gat gcc gaa atc gaa gtg caa cgc cgc cgc tct gca ggc tgg gaa gcc      1152
Asp Ala Glu Ile Glu Val Gln Arg Arg Arg Ser Ala Gly Trp Glu Ala
        370                 375                 380 gaa ttg cgc cac cgt gct tac ctc cac cgt tgg cag ctt gac ggc aag      1200
Glu Leu Arg His Arg Ala Tyr Leu His Arg Trp Gln Leu Asp Gly Lys
385                 390                 395                 400 ttg tct tac aaa cgc ggg acc ggc atg cgc caa agt atg ccc gca cct      1248
Leu Ser Tyr Lys Arg Gly Thr Gly Met Arg Gln Ser Met Pro Ala Pro
                405                 410                 415 gaa gaa aac ggc ggc ggt act att cca gcc aca tcc cgt atg aaa atc      1296
Glu Glu Asn Gly Gly Gly Thr Ile Pro Ala Thr Ser Arg Met Lys Ile
            420                 425                 430 ata acc gcc gga ttg gat gca gcg gcc ccg tct atg ttg ggc aaa cag      1344
Ile Thr Ala Gly Leu Asp Ala Ala Ala Pro Ser Met Leu Gly Lys Gln
        435                 440                 445 cag ttt ttc tac gca acc gcc att caa gct caa tgg aac aaa acg cct      1392
Gln Phe Phe Tyr Ala Thr Ala Ile Gln Ala Gln Trp Asn Lys Thr Pro
    450                 455                 460 ttg gtt gcc caa gac aag ttg tct atc ggc agc cgc tac acc gtt cgc      1440
Leu Val Ala Gln Asp Lys Leu Ser Ile Gly Ser Arg Tyr Thr Val Arg
465                 470                 475                 480 gga ttt gat ggg gag cag agt ctt ttc gga gag cga ggt ttc tac tgg      1488
Gly Phe Asp Gly Glu Gln Ser Leu Phe Gly Glu Arg Gly Phe Tyr Trp
                485                 490                 495 cag aat act tta act tgg tat ttt cat ccg aac cat cag ttc tat ctc      1536
Gln Asn Thr Leu Thr Trp Tyr Phe His Pro Asn His Gln Phe Tyr Leu
            500                 505                 510 ggt gcg gac tat ggc cgc gta tct ggc gaa agt gca caa tat gta tcg      1584
Gly Ala Asp Tyr Gly Arg Val Ser Gly Glu Ser Ala Gln Tyr Val Ser
        515                 520                 525 ggc aag cag ctg atg ggt gca gtg gtc ggc ttc aga gga ggg cat aaa      1632
Gly Lys Gln Leu Met Gly Ala Val Val Gly Phe Arg Gly Gly His Lys
    530                 535                 540 gta ggc ggt atg ttt gct tat gat ctg ttt gcc ggc aag ccg ctt cat      1680
Val Gly Gly Met Phe Ala Tyr Asp Leu Phe Ala Gly Lys Pro Leu His
545                 550                 555                 560 aaa ccc aaa ggc ttt cag acg acc aac acc gtt tac ggc ttc aac ttg      1728
Lys Pro Lys Gly Phe Gln Thr Thr Asn Thr Val Tyr Gly Phe Asn Leu
                565                 570                 575 aat tac agt ttc taa                                                   1743
Asn Tyr Ser Phe
        580

<210> SEQ ID NO 20
<211> LENGTH: 580
<212> TYPE: PRT
<213> ORGANISM: Neisseria meningitidis

<400> SEQUENCE: 20

Met Lys Phe Phe Pro Ala Pro Cys Leu Leu Val Ile Leu Ala Val Ile
 1               5                  10                  15

Pro Leu Lys Thr Leu Ala Ala Asp Glu Asn Asp Ala Glu Leu Ile Arg
            20                  25                  30

Ser Met Gln Arg Gln Gln His Ile Asp Ala Glu Leu Leu Thr Asp Ala
        35                  40                  45
```

```
Asn Val Arg Phe Glu Gln Pro Leu Glu Lys Asn Asn Tyr Val Leu Ser
     50                  55                  60

Glu Asp Glu Thr Pro Cys Thr Arg Val Asn Tyr Ile Ser Leu Asp Asp
 65                  70                  75                  80

Lys Thr Ala Arg Lys Phe Ser Phe Leu Pro Ser Val Leu Met Lys Glu
                 85                  90                  95

Thr Ala Phe Lys Thr Gly Met Cys Leu Gly Ser Asn Asn Leu Ser Arg
                100                 105                 110

Leu Gln Lys Ala Ala Gln Gln Ile Leu Ile Val Arg Gly Tyr Leu Thr
            115                 120                 125

Ser Gln Ala Ile Ile Gln Pro Gln Asn Met Asp Ser Gly Ile Leu Lys
    130                 135                 140

Leu Arg Val Ser Ala Gly Glu Ile Arg Asp Ile Arg Tyr Glu Glu Lys
145                 150                 155                 160

Arg Asp Ala Lys Ser Ala Glu Gly Ser Ile Ser Ala Phe Asn Asn Lys
                165                 170                 175

Leu Pro Leu Tyr Arg Asn Lys Ile Leu Asn Leu Arg Asp Val Glu Gln
                180                 185                 190

Gly Leu Glu Asn Leu Arg Arg Leu Pro Ser Val Lys Thr Asp Ile Gln
            195                 200                 205

Ile Ile Pro Ser Glu Glu Gly Lys Ser Asp Leu Gln Ile Lys Trp
    210                 215                 220

Gln Gln Asn Lys Pro Ile Arg Phe Ser Ile Gly Ile Asp Asp Ala Gly
225                 230                 235                 240

Gly Lys Thr Thr Gly Lys Tyr Gln Gly Asn Val Ala Leu Ser Ser Asp
                245                 250                 255

Asn Pro Leu Gly Leu Ser Asp Ser Phe Tyr Val Ser Tyr Gly Arg Gly
                260                 265                 270

Leu Val His Lys Thr Asp Leu Thr Ala Ala Thr Gly Thr Glu Thr Glu
            275                 280                 285

Ser Gly Ser Arg Ser Tyr Ser Val His Tyr Ser Val Pro Val Lys Lys
    290                 295                 300

Trp Leu Phe Ser Phe Asn His Asn Gly His Arg Tyr His Glu Ala Thr
305                 310                 315                 320

Glu Gly Tyr Ser Val Asn Tyr Asp Tyr Asn Gly Lys Gln Tyr Gln Ser
                325                 330                 335

Ser Leu Ala Ala Glu Arg Met Leu Trp Pro Pro Ser Phe Pro Gln Thr
                340                 345                 350

Ser Val Arg Met Lys Leu Trp Thr Arg Gln Thr Tyr Lys Tyr Ile Asp
            355                 360                 365

Asp Ala Glu Ile Glu Val Gln Arg Arg Ser Ala Gly Trp Glu Ala
    370                 375                 380

Glu Leu Arg His Arg Ala Tyr Leu His Arg Trp Gln Leu Asp Gly Lys
385                 390                 395                 400

Leu Ser Tyr Lys Arg Gly Thr Gly Met Arg Gln Ser Met Pro Ala Pro
                405                 410                 415

Glu Glu Asn Gly Gly Thr Ile Pro Ala Thr Ser Arg Met Lys Ile
                420                 425                 430

Ile Thr Ala Gly Leu Asp Ala Ala Pro Ser Met Leu Gly Lys Gln
            435                 440                 445

Gln Phe Phe Tyr Ala Thr Ala Ile Gln Ala Gln Trp Asn Lys Thr Pro
    450                 455                 460

Leu Val Ala Gln Asp Lys Leu Ser Ile Gly Ser Arg Tyr Thr Val Arg
```

```
                465                 470                 475                 480
            Gly Phe Asp Gly Glu Gln Ser Leu Phe Gly Glu Arg Gly Phe Tyr Trp
                            485                 490                 495
            Gln Asn Thr Leu Thr Trp Tyr Phe His Pro Asn His Gln Phe Tyr Leu
                        500                 505                 510
            Gly Ala Asp Tyr Gly Arg Val Ser Gly Glu Ser Ala Gln Tyr Val Ser
                        515                 520                 525
            Gly Lys Gln Leu Met Gly Ala Val Val Gly Phe Arg Gly Gly His Lys
                    530                 535                 540
            Val Gly Gly Met Phe Ala Tyr Asp Leu Phe Ala Gly Lys Pro Leu His
            545                 550                 555                 560
            Lys Pro Lys Gly Phe Gln Thr Thr Asn Thr Val Tyr Gly Phe Asn Leu
                            565                 570                 575
            Asn Tyr Ser Phe
                        580

<210> SEQ ID NO 21
<211> LENGTH: 411
<212> TYPE: DNA
<213> ORGANISM: Neisseria meningitidis
<220> FEATURE:
<221> NAME/KEY: CDS
<222> LOCATION: (1)..(408)

<400> SEQUENCE: 21 atg att gaa ttt gtc cga gcc aaa aaa cgg ctg ctt tgg gca ttt gtg        48
Met Ile Glu Phe Val Arg Ala Lys Lys Arg Leu Leu Trp Ala Phe Val
 1               5                  10                  15 ctt ttg ctt gtg tgg acg tgc ggt tac cga tac gcc gcc gac aag gcc        96
Leu Leu Leu Val Trp Thr Cys Gly Tyr Arg Tyr Ala Ala Asp Lys Ala
             20                  25                  30 gaa gcg aaa caa acc gcc ctg att gcc acc tat cgg cat tct tct atg       144
Glu Ala Lys Gln Thr Ala Leu Ile Ala Thr Tyr Arg His Ser Ser Met
         35                  40                  45 gtt gcg gcg gaa caa tac gcc ttg cag ctt aaa aaa gcg cag gac gaa       192
Val Ala Ala Glu Gln Tyr Ala Leu Gln Leu Lys Lys Ala Gln Asp Glu
     50                  55                  60 agg cag cgg tgg tac gac ttt tcc caa aaa caa gga aga aag ccc gtg       240
Arg Gln Arg Trp Tyr Asp Phe Ser Gln Lys Gln Gly Arg Lys Pro Val
 65                  70                  75                  80 aaa aaa cag tat ccg ccg caa acg aaa aaa gcc ggc tat ctg aaa acc       288
Lys Lys Gln Tyr Pro Pro Gln Thr Lys Lys Ala Gly Tyr Leu Lys Thr
                 85                  90                  95 aag gaa gaa ctg ctt gcg gaa ttg gct tgc ctt aaa gcg gaa atg gct       336
Lys Glu Glu Leu Leu Ala Glu Leu Ala Cys Leu Lys Ala Glu Met Ala
            100                 105                 110 gcc cta aaa aag ctc gat gcc tta atc tat ggg aaa gaa gtg cgg cag       384
Ala Leu Lys Lys Leu Asp Ala Leu Ile Tyr Gly Lys Glu Val Arg Gln
        115                 120                 125 aaa gaa cgc aac tcg tcg cag ggt taa                                   411
Lys Glu Arg Asn Ser Ser Gln Gly
    130                 135

<210> SEQ ID NO 22
<211> LENGTH: 136
<212> TYPE: PRT
<213> ORGANISM: Neisseria meningitidis

<400> SEQUENCE: 22

Met Ile Glu Phe Val Arg Ala Lys Lys Arg Leu Leu Trp Ala Phe Val
```

-continued

```
                1               5              10              15
        Leu Leu Leu Val Trp Thr Cys Gly Tyr Arg Tyr Ala Ala Asp Lys Ala
                        20                  25                  30

Glu Ala Lys Gln Thr Ala Leu Ile Ala Thr Tyr Arg His Ser Ser Met
                    35                  40                  45

Val Ala Ala Glu Gln Tyr Ala Leu Gln Leu Lys Lys Ala Gln Asp Glu
                50                  55                  60

Arg Gln Arg Trp Tyr Asp Phe Ser Gln Lys Gln Gly Arg Lys Pro Val
        65                  70                  75                  80

Lys Lys Gln Tyr Pro Pro Gln Thr Lys Lys Ala Gly Tyr Leu Lys Thr
                        85                  90                  95

Lys Glu Glu Leu Leu Ala Glu Leu Ala Cys Leu Lys Ala Glu Met Ala
                    100                 105                 110

Ala Leu Lys Lys Leu Asp Ala Leu Ile Tyr Gly Lys Glu Val Arg Gln
                    115                 120                 125

Lys Glu Arg Asn Ser Ser Gln Gly
                    130                 135
```

<210> SEQ ID NO 23
<211> LENGTH: 924
<212> TYPE: DNA
<213> ORGANISM: Neisseria meningitidis
<220> FEATURE:
<221> NAME/KEY: CDS
<222> LOCATION: (1)..(921)

<400> SEQUENCE: 23

```
atg caa tac agc aca ctg gca gga caa acc gac aac tcc ctc gtt tcc      48
Met Gln Tyr Ser Thr Leu Ala Gly Gln Thr Asp Asn Ser Leu Val Ser
  1               5                  10                  15 aat aat ttc ggg ttt ttg cgc ctg ccg ctt aat ttt atg ccg tat gaa      96
Asn Asn Phe Gly Phe Leu Arg Leu Pro Leu Asn Phe Met Pro Tyr Glu
                 20                  25                  30 agt cat gcc gat tgg gtt att acc ggc gtg cct tat gat atg gcg gtt     144
Ser His Ala Asp Trp Val Ile Thr Gly Val Pro Tyr Asp Met Ala Val
             35                  40                  45 tca ggg cgt tcc ggc gcg cgt ttc ggt cct gaa gcc atc cgg cgc gcc     192
Ser Gly Arg Ser Gly Ala Arg Phe Gly Pro Glu Ala Ile Arg Arg Ala
         50                  55                  60 tcc gtc aac ctc gct tgg gag cac cgc agg ttt cca tgg aca ttt gat     240
Ser Val Asn Leu Ala Trp Glu His Arg Arg Phe Pro Trp Thr Phe Asp
 65                  70                  75                  80 gtg cgc gaa cgc ctg aac att att gat tgc ggc gac ttg gtt ttt tct     288
Val Arg Glu Arg Leu Asn Ile Ile Asp Cys Gly Asp Leu Val Phe Ser
                 85                  90                  95 ttt ggc gac agc agg gat ttt gtc gaa aaa atg gaa gcg cac gcc ggc     336
Phe Gly Asp Ser Arg Asp Phe Val Glu Lys Met Glu Ala His Ala Gly
                100                 105                 110 aaa tta ctt tct tcc ggc aaa cgc tgt ttg agt ttg ggc ggc gac cat     384
Lys Leu Leu Ser Ser Gly Lys Arg Cys Leu Ser Leu Gly Gly Asp His
             115                 120                 125 ttc att acc ctc ccg ttg ttg cgc gcc cac gcc cgc tat ttc ggc aaa     432
Phe Ile Thr Leu Pro Leu Leu Arg Ala His Ala Arg Tyr Phe Gly Lys
         130                 135                 140 ctc gca ctg att cat ttt gac gcg cac acc gac acc tac gac aac ggc     480
Leu Ala Leu Ile His Phe Asp Ala His Thr Asp Thr Tyr Asp Asn Gly
145                 150                 155                 160 agc gaa tac gac cac ggt acg atg ttc tat acc gcc ccc aag gaa ggc     528
Ser Glu Tyr Asp His Gly Thr Met Phe Tyr Thr Ala Pro Lys Glu Gly
```

-continued

```
                    165                 170                 175
ctc atc gac ccg tcc cgt tcc gta caa atc ggc ata cgt acc gaa cac      576
Leu Ile Asp Pro Ser Arg Ser Val Gln Ile Gly Ile Arg Thr Glu His
            180                 185                 190 agt aaa aaa ttg cct ttt act gtg ttg acc gcc ccc caa gtt aat gaa      624
Ser Lys Lys Leu Pro Phe Thr Val Leu Thr Ala Pro Gln Val Asn Glu
        195                 200                 205 gac agt gtt gaa gag acc gtc cgt aaa atc aaa gaa acc gtc ggc aat      672
Asp Ser Val Glu Glu Thr Val Arg Lys Ile Lys Glu Thr Val Gly Asn
    210                 215                 220 atg ccc gtt tac ctg act ttc gac ata gac tgc ctc gac ccg tcg ttc      720
Met Pro Val Tyr Leu Thr Phe Asp Ile Asp Cys Leu Asp Pro Ser Phe
225                 230                 235                 240 gcc ccc ggg acc ggt acg ccc gta tgc ggc ggc ttg agc agc gac agg      768
Ala Pro Gly Thr Gly Thr Pro Val Cys Gly Gly Leu Ser Ser Asp Arg
                245                 250                 255 gca tta aaa atc cta cgt ggg ctg acg gat ctc gac atc gtc ggt atg      816
Ala Leu Lys Ile Leu Arg Gly Leu Thr Asp Leu Asp Ile Val Gly Met
            260                 265                 270 gat gtt gta gaa gtt gcc ccc tct tac gac caa tcc gac att acc gct      864
Asp Val Val Glu Val Ala Pro Ser Tyr Asp Gln Ser Asp Ile Thr Ala
        275                 280                 285 ttg gcc ggc gcc aca att gcc ttg gaa atg ctt tac ctt caa ggt gcg      912
Leu Ala Gly Ala Thr Ile Ala Leu Glu Met Leu Tyr Leu Gln Gly Ala
    290                 295                 300 aaa aag gac tga                                                      924
Lys Lys Asp
305
```

<210> SEQ ID NO 24
<211> LENGTH: 307
<212> TYPE: PRT
<213> ORGANISM: Neisseria meningitidis

<400> SEQUENCE: 24

```
Met Gln Tyr Ser Thr Leu Ala Gly Gln Thr Asp Asn Ser Leu Val Ser
 1               5                  10                  15

Asn Asn Phe Gly Phe Leu Arg Leu Pro Leu Asn Phe Met Pro Tyr Glu
            20                  25                  30

Ser His Ala Asp Trp Val Ile Thr Gly Val Pro Tyr Asp Met Ala Val
        35                  40                  45

Ser Gly Arg Ser Gly Ala Arg Phe Gly Pro Glu Ala Ile Arg Arg Ala
    50                  55                  60

Ser Val Asn Leu Ala Trp Glu His Arg Arg Phe Pro Trp Thr Phe Asp
65                  70                  75                  80

Val Arg Glu Arg Leu Asn Ile Ile Asp Cys Gly Asp Leu Val Phe Ser
                85                  90                  95

Phe Gly Asp Ser Arg Asp Phe Val Glu Lys Met Glu Ala His Ala Gly
            100                 105                 110

Lys Leu Leu Ser Ser Gly Lys Arg Cys Leu Ser Leu Gly Gly Asp His
        115                 120                 125

Phe Ile Thr Leu Pro Leu Leu Arg Ala His Ala Arg Tyr Phe Gly Lys
    130                 135                 140

Leu Ala Leu Ile His Phe Asp Ala His Thr Asp Thr Tyr Asp Asn Gly
145                 150                 155                 160

Ser Glu Tyr Asp His Gly Thr Met Phe Tyr Thr Ala Pro Lys Glu Gly
                165                 170                 175
```

```
Leu Ile Asp Pro Ser Arg Ser Val Gln Ile Gly Ile Arg Thr Glu His
            180                 185                 190

Ser Lys Lys Leu Pro Phe Thr Val Leu Thr Ala Pro Gln Val Asn Glu
        195                 200                 205

Asp Ser Val Glu Glu Thr Val Arg Lys Ile Lys Glu Thr Val Gly Asn
    210                 215                 220

Met Pro Val Tyr Leu Thr Phe Asp Ile Asp Cys Leu Asp Pro Ser Phe
225                 230                 235                 240

Ala Pro Gly Thr Gly Thr Pro Val Cys Gly Gly Leu Ser Ser Asp Arg
                245                 250                 255

Ala Leu Lys Ile Leu Arg Gly Leu Thr Asp Leu Asp Ile Val Gly Met
            260                 265                 270

Asp Val Val Glu Val Ala Pro Ser Tyr Asp Gln Ser Asp Ile Thr Ala
        275                 280                 285

Leu Ala Gly Ala Thr Ile Ala Leu Glu Met Leu Tyr Leu Gln Gly Ala
    290                 295                 300

Lys Lys Asp
305

<210> SEQ ID NO 25
<211> LENGTH: 426
<212> TYPE: DNA
<213> ORGANISM: Neisseria meningitidis
<220> FEATURE:
<221> NAME/KEY: CDS
<222> LOCATION: (1)..(423)

<400> SEQUENCE: 25 atg gag cag tcg ggc aaa ttc agt tgg tct gcg gca gct ttt tgg gac      48
Met Glu Gln Ser Gly Lys Phe Ser Trp Ser Ala Ala Ala Phe Trp Asp
 1               5                  10                  15 att ccc tac ccc gtc acc agg cgg att gcc tca agt ttg tat tcg acc      96
Ile Pro Tyr Pro Val Thr Arg Arg Ile Ala Ser Ser Leu Tyr Ser Thr
                20                  25                  30 gaa tat ttt gtc gta tgc ttt ctg cgt ttg atg cca ctc tct ccg tgt     144
Glu Tyr Phe Val Val Cys Phe Leu Arg Leu Met Pro Leu Ser Pro Cys
            35                  40                  45 aat ctg tat ttt gtc acc cat ctg cgt acc aat gaa tcg gaa ata gaa     192
Asn Leu Tyr Phe Val Thr His Leu Arg Thr Asn Glu Ser Glu Ile Glu
        50                  55                  60 aga tgg tct gct gtt ccc tgc caa ata gta ttg aac gac ggc aag tcg     240
Arg Trp Ser Ala Val Pro Cys Gln Ile Val Leu Asn Asp Gly Lys Ser
 65                  70                  75                  80 gaa ttc ggc gga ttc gca ttt gaa gtg caa ctt tcc cta aca gaa aaa     288
Glu Phe Gly Gly Phe Ala Phe Glu Val Gln Leu Ser Leu Thr Glu Lys
                 85                  90                  95 ggc cag tat gcg gta gca tac gac ctt tcc tgc aag aaa gat tgc cat     336
Gly Gln Tyr Ala Val Ala Tyr Asp Leu Ser Cys Lys Lys Asp Cys His
                100                 105                 110 gag cta cac gca act gac cca agg cga acg ata cca cat cca ata cct     384
Glu Leu His Ala Thr Asp Pro Arg Arg Thr Ile Pro His Pro Ile Pro
            115                 120                 125 gtc ccg cca ctg cac cgt cac cga aat cgc caa aca gct taa             426
Val Pro Pro Leu His Arg His Arg Asn Arg Gln Thr Ala
        130                 135                 140

<210> SEQ ID NO 26
<211> LENGTH: 141
<212> TYPE: PRT
<213> ORGANISM: Neisseria meningitidis
```

<400> SEQUENCE: 26

Met Glu Gln Ser Gly Lys Phe Ser Trp Ser Ala Ala Phe Trp Asp
 1               5                  10                  15

Ile Pro Tyr Pro Val Thr Arg Arg Ile Ala Ser Ser Leu Tyr Ser Thr
                 20                  25                  30

Glu Tyr Phe Val Val Cys Phe Leu Arg Leu Met Pro Leu Ser Pro Cys
             35                  40                  45

Asn Leu Tyr Phe Val Thr His Leu Arg Thr Asn Glu Ser Glu Ile Glu
         50                  55                  60

Arg Trp Ser Ala Val Pro Cys Gln Ile Val Leu Asn Asp Gly Lys Ser
 65                  70                  75                  80

Glu Phe Gly Gly Phe Ala Phe Glu Val Gln Leu Ser Leu Thr Glu Lys
                 85                  90                  95

Gly Gln Tyr Ala Val Ala Tyr Asp Leu Ser Cys Lys Lys Asp Cys His
            100                 105                 110

Glu Leu His Ala Thr Asp Pro Arg Arg Thr Ile Pro His Pro Ile Pro
        115                 120                 125

Val Pro Pro Leu His Arg His Arg Asn Arg Gln Thr Ala
    130                 135                 140

<210> SEQ ID NO 27
<211> LENGTH: 351
<212> TYPE: DNA
<213> ORGANISM: Neisseria meningitidis
<220> FEATURE:
<221> NAME/KEY: CDS
<222> LOCATION: (1)..(348)

<400> SEQUENCE: 27 atg caa aac ggc ggg gga aag att tac cag acg gcg gac aat gtg gaa      48
Met Gln Asn Gly Gly Gly Lys Ile Tyr Gln Thr Ala Asp Asn Val Glu
 1               5                  10                  15 ggg att atg ctg ttg aag gta gta cct gag cgt acc gtt tcg gca gat      96
Gly Ile Met Leu Leu Lys Val Val Pro Glu Arg Thr Val Ser Ala Asp
             20                  25                  30 gca aaa acc aga gac ccg atg tgg gac aat gcg gct tta cag acc agc     144
Ala Lys Thr Arg Asp Pro Met Trp Asp Asn Ala Ala Leu Gln Thr Ser
         35                  40                  45 gaa ggc gta aat ttt att gct cgt ttc cta gga ttt ttt agc gat ggg     192
Glu Gly Val Asn Phe Ile Ala Arg Phe Leu Gly Phe Phe Ser Asp Gly
     50                  55                  60 gaa tac cgc tat gtg gat gtc ctg caa ccc aac cat tcc gat att att     240
Glu Tyr Arg Tyr Val Asp Val Leu Gln Pro Asn His Ser Asp Ile Ile
 65                  70                  75                  80 cgg tat tca ggt aaa gat ttt ccg cta aat caa ata ctt aac cat ata     288
Arg Tyr Ser Gly Lys Asp Phe Pro Leu Asn Gln Ile Leu Asn His Ile
                 85                  90                  95 cac ccc gcc cgt tat gcg gta acg ttc gaa aac aat gtc gat tcc aag     336
His Pro Ala Arg Tyr Ala Val Thr Phe Glu Asn Asn Val Asp Ser Lys
            100                 105                 110 ctg cgc agg cac tga                                                 351
Leu Arg Arg His
        115

<210> SEQ ID NO 28
<211> LENGTH: 116
<212> TYPE: PRT
<213> ORGANISM: Neisseria meningitidis

```
<400> SEQUENCE: 28

Met Gln Asn Gly Gly Lys Ile Tyr Gln Thr Ala Asp Asn Val Glu
 1               5                  10                  15

Gly Ile Met Leu Leu Lys Val Val Pro Glu Arg Thr Val Ser Ala Asp
             20                  25                  30

Ala Lys Thr Arg Asp Pro Met Trp Asp Asn Ala Ala Leu Gln Thr Ser
         35                  40                  45

Glu Gly Val Asn Phe Ile Ala Arg Phe Leu Gly Phe Phe Ser Asp Gly
     50                  55                  60

Glu Tyr Arg Tyr Val Asp Val Leu Gln Pro Asn His Ser Asp Ile Ile
 65                  70                  75                  80

Arg Tyr Ser Gly Lys Asp Phe Pro Leu Asn Gln Ile Leu Asn His Ile
                 85                  90                  95

His Pro Ala Arg Tyr Ala Val Thr Phe Glu Asn Asn Val Asp Ser Lys
            100                 105                 110

Leu Arg Arg His
        115

<210> SEQ ID NO 29
<211> LENGTH: 1404
<212> TYPE: DNA
<213> ORGANISM: Neisseria meningitidis
<220> FEATURE:
<221> NAME/KEY: CDS
<222> LOCATION: (1)..(1401)

<400> SEQUENCE: 29 atg aca ttg ctc aat cta atg ata atg caa gat tac ggt att tcc gtt      48
Met Thr Leu Leu Asn Leu Met Ile Met Gln Asp Tyr Gly Ile Ser Val
 1               5                  10                  15 tgc ctg aca ctg acg ccc tat ttg caa cat gaa cta ttt tcg gct atg      96
Cys Leu Thr Leu Thr Pro Tyr Leu Gln His Glu Leu Phe Ser Ala Met
             20                  25                  30 aaa tcc tat ttt tcc aaa tat atc cta ccc gtt tca ctt ttt acc ttg     144
Lys Ser Tyr Phe Ser Lys Tyr Ile Leu Pro Val Ser Leu Phe Thr Leu
         35                  40                  45 cca cta tcc ctt tcc cca tcc gtt tcg gct ttt acg ctg cct gaa gca     192
Pro Leu Ser Leu Ser Pro Ser Val Ser Ala Phe Thr Leu Pro Glu Ala
     50                  55                  60 tgg cgg gcg gcg cag caa cat tcg gct gat ttt caa gcg tcc cat tac     240
Trp Arg Ala Ala Gln Gln His Ser Ala Asp Phe Gln Ala Ser His Tyr
 65                  70                  75                  80 cag cgt gat gca gtg cgc gca cgg caa caa caa gcc aag gcc gca ttc     288
Gln Arg Asp Ala Val Arg Ala Arg Gln Gln Gln Ala Lys Ala Ala Phe
                 85                  90                  95 ctt ccc cat gta tcc gcc aat gcc agc tac cag cgc cag ccg cca tcg     336
Leu Pro His Val Ser Ala Asn Ala Ser Tyr Gln Arg Gln Pro Pro Ser
            100                 105                 110 att tct tcc acc cgc gaa aca cag gga tgg agc gtg cag gtg gga caa     384
Ile Ser Ser Thr Arg Glu Thr Gln Gly Trp Ser Val Gln Val Gly Gln
        115                 120                 125 acc tta ttt gac gct gcc aaa ttt gca caa tac cgc caa agc agg ttc     432
Thr Leu Phe Asp Ala Ala Lys Phe Ala Gln Tyr Arg Gln Ser Arg Phe
    130                 135                 140 gat acg cag gct gca gaa cag cgt ttc gat gcg gca cgc gaa gaa ttg     480
Asp Thr Gln Ala Ala Glu Gln Arg Phe Asp Ala Ala Arg Glu Glu Leu
145                 150                 155                 160 ctg ttg aaa gtt gcc gaa agt tat ttc aac gtt tta ctc agc cga gac     528
Leu Leu Lys Val Ala Glu Ser Tyr Phe Asn Val Leu Leu Ser Arg Asp
```

-continued

```
              165                 170                 175
acc gtt gcc gcc cat gcg gcg gaa aaa gag gct tat gcg cag cag gta      576
Thr Val Ala Ala His Ala Ala Glu Lys Glu Ala Tyr Ala Gln Gln Val
                180                 185                 190 agg cag gcg cag gct tta ttc aat aaa ggt gct gcc acc gcg ctg gat      624
Arg Gln Ala Gln Ala Leu Phe Asn Lys Gly Ala Ala Thr Ala Leu Asp
            195                 200                 205 att cac gaa gcc aaa gcc ggt tac gac aat gcc ctg gcc caa gaa atc      672
Ile His Glu Ala Lys Ala Gly Tyr Asp Asn Ala Leu Ala Gln Glu Ile
        210                 215                 220 gcc gta ttg gct gag aaa caa acc tat gaa aac cag ttg aac gac tac      720
Ala Val Leu Ala Glu Lys Gln Thr Tyr Glu Asn Gln Leu Asn Asp Tyr
225                 230                 235                 240 acc gac ctg gat agc aaa caa atc gag gcc ata gat acc gcc aac ctg      768
Thr Asp Leu Asp Ser Lys Gln Ile Glu Ala Ile Asp Thr Ala Asn Leu
                245                 250                 255 ttg gca cgc tat ctg ccc aag ctg gaa cgt tac agt ctg gat gaa tgg      816
Leu Ala Arg Tyr Leu Pro Lys Leu Glu Arg Tyr Ser Leu Asp Glu Trp
            260                 265                 270 cag cgc att gcc tta tcc aac aat cat gaa tac cgg atg cag cag ctt      864
Gln Arg Ile Ala Leu Ser Asn Asn His Glu Tyr Arg Met Gln Gln Leu
        275                 280                 285 gcc ctg caa agc agc gga cag gcg ctt cgg gca gca cag aac agc cgc      912
Ala Leu Gln Ser Ser Gly Gln Ala Leu Arg Ala Ala Gln Asn Ser Arg
    290                 295                 300 tat ccc acc gtt tct gcc cat gtc ggc tat cag aat aac ctc tac act      960
Tyr Pro Thr Val Ser Ala His Val Gly Tyr Gln Asn Asn Leu Tyr Thr
305                 310                 315                 320 tca tct gcg cag aat aat gac tac cac tat cgg ggc aaa ggg atg agc     1008
Ser Ser Ala Gln Asn Asn Asp Tyr His Tyr Arg Gly Lys Gly Met Ser
                325                 330                 335 gtc ggc gta cag ttg aat ttg ccg ctt tat acc ggc gga gaa ttg tcg     1056
Val Gly Val Gln Leu Asn Leu Pro Leu Tyr Thr Gly Gly Glu Leu Ser
            340                 345                 350 ggc aaa atc cat gaa gcc gaa gcg caa tac ggg gcc gcc gaa gca cag     1104
Gly Lys Ile His Glu Ala Glu Ala Gln Tyr Gly Ala Ala Glu Ala Gln
        355                 360                 365 ctg acc gca acc gag cgg cac atc aaa ctc gcc gta cgc cag gct tat     1152
Leu Thr Ala Thr Glu Arg His Ile Lys Leu Ala Val Arg Gln Ala Tyr
    370                 375                 380 acc gaa agc ggt gcg gcg cgt tac caa atc atg gcg caa gaa cgg gtt     1200
Thr Glu Ser Gly Ala Ala Arg Tyr Gln Ile Met Ala Gln Glu Arg Val
385                 390                 395                 400 ttg gaa agc agc cgt ttg aaa ctg aaa tcg acc gaa acc ggc caa caa     1248
Leu Glu Ser Ser Arg Leu Lys Leu Lys Ser Thr Glu Thr Gly Gln Gln
                405                 410                 415 tac ggc atc cgc aac cgg ctg gaa gta ata cgg gcg cgg cag gaa gtc     1296
Tyr Gly Ile Arg Asn Arg Leu Glu Val Ile Arg Ala Arg Gln Glu Val
            420                 425                 430 gcc caa gca gaa cag aaa ctg gct caa gca cgg tat aaa ttc atg ctg     1344
Ala Gln Ala Glu Gln Lys Leu Ala Gln Ala Arg Tyr Lys Phe Met Leu
        435                 440                 445 gct tat ttg cgc ttg gtg aaa gag agc ggg tta ggg ttg gaa acg gta     1392
Ala Tyr Leu Arg Leu Val Lys Glu Ser Gly Leu Gly Leu Glu Thr Val
    450                 455                 460 ttt gcg gaa taa                                                     1404
Phe Ala Glu
465
```

-continued

<210> SEQ ID NO 30
<211> LENGTH: 467
<212> TYPE: PRT
<213> ORGANISM: Neisseria meningitidis

<400> SEQUENCE: 30

| Met | Thr | Leu | Leu | Asn | Leu | Met | Ile | Met | Gln | Asp | Tyr | Gly | Ile | Ser | Val |
|---|---|---|---|---|---|---|---|---|---|---|---|---|---|---|---|
| 1 | | | | 5 | | | | | 10 | | | | | 15 | |

| Cys | Leu | Thr | Leu | Thr | Pro | Tyr | Leu | Gln | His | Glu | Leu | Phe | Ser | Ala | Met |
| | | | 20 | | | | | 25 | | | | | 30 | | |

| Lys | Ser | Tyr | Phe | Ser | Lys | Tyr | Ile | Leu | Pro | Val | Ser | Leu | Phe | Thr | Leu |
| | | 35 | | | | | 40 | | | | | 45 | | | |

| Pro | Leu | Ser | Leu | Ser | Pro | Ser | Val | Ser | Ala | Phe | Thr | Leu | Pro | Glu | Ala |
| | 50 | | | | | 55 | | | | | 60 | | | | |

| Trp | Arg | Ala | Ala | Gln | Gln | His | Ser | Ala | Asp | Phe | Gln | Ala | Ser | His | Tyr |
| 65 | | | | | 70 | | | | | 75 | | | | | 80 |

| Gln | Arg | Asp | Ala | Val | Arg | Ala | Arg | Gln | Gln | Ala | Lys | Ala | Ala | Phe |
| | | | | 85 | | | | | 90 | | | | | 95 |

| Leu | Pro | His | Val | Ser | Ala | Asn | Ala | Ser | Tyr | Gln | Arg | Gln | Pro | Pro | Ser |
| | | | | 100 | | | | | 105 | | | | | 110 | |

| Ile | Ser | Ser | Thr | Arg | Glu | Thr | Gln | Gly | Trp | Ser | Val | Gln | Val | Gly | Gln |
| | | | | 115 | | | | | 120 | | | | | 125 | |

| Thr | Leu | Phe | Asp | Ala | Ala | Lys | Phe | Ala | Gln | Tyr | Arg | Gln | Ser | Arg | Phe |
| | 130 | | | | | 135 | | | | | 140 | | | | |

| Asp | Thr | Gln | Ala | Ala | Glu | Gln | Arg | Phe | Asp | Ala | Ala | Arg | Glu | Glu | Leu |
| 145 | | | | | 150 | | | | | 155 | | | | | 160 |

| Leu | Leu | Lys | Val | Ala | Glu | Ser | Tyr | Phe | Asn | Val | Leu | Leu | Ser | Arg | Asp |
| | | | | 165 | | | | | 170 | | | | | 175 | |

| Thr | Val | Ala | Ala | His | Ala | Ala | Glu | Lys | Glu | Ala | Tyr | Ala | Gln | Gln | Val |
| | | | | 180 | | | | | 185 | | | | | 190 | |

| Arg | Gln | Ala | Gln | Ala | Leu | Phe | Asn | Lys | Gly | Ala | Ala | Thr | Ala | Leu | Asp |
| | | 195 | | | | | 200 | | | | | 205 | | | |

| Ile | His | Glu | Ala | Lys | Ala | Gly | Tyr | Asp | Asn | Ala | Leu | Ala | Gln | Glu | Ile |
| | 210 | | | | | 215 | | | | | 220 | | | | |

| Ala | Val | Leu | Ala | Glu | Lys | Gln | Thr | Tyr | Glu | Asn | Gln | Leu | Asn | Asp | Tyr |
| 225 | | | | | 230 | | | | | 235 | | | | | 240 |

| Thr | Asp | Leu | Asp | Ser | Lys | Gln | Ile | Glu | Ala | Ile | Asp | Thr | Ala | Asn | Leu |
| | | | | 245 | | | | | 250 | | | | | 255 | |

| Leu | Ala | Arg | Tyr | Leu | Pro | Lys | Leu | Glu | Arg | Tyr | Ser | Leu | Asp | Glu | Trp |
| | | | 260 | | | | | 265 | | | | | 270 | | |

| Gln | Arg | Ile | Ala | Leu | Ser | Asn | Asn | His | Glu | Tyr | Arg | Met | Gln | Gln | Leu |
| | | | 275 | | | | | 280 | | | | | 285 | | |

| Ala | Leu | Gln | Ser | Ser | Gly | Gln | Ala | Leu | Arg | Ala | Ala | Gln | Asn | Ser | Arg |
| | | 290 | | | | | 295 | | | | | 300 | | | |

| Tyr | Pro | Thr | Val | Ser | Ala | His | Val | Gly | Tyr | Gln | Asn | Asn | Leu | Tyr | Thr |
| 305 | | | | | 310 | | | | | 315 | | | | | 320 |

| Ser | Ser | Ala | Gln | Asn | Asn | Asp | Tyr | His | Tyr | Arg | Gly | Lys | Gly | Met | Ser |
| | | | | 325 | | | | | 330 | | | | | 335 | |

| Val | Gly | Val | Gln | Leu | Asn | Leu | Pro | Leu | Tyr | Thr | Gly | Gly | Glu | Leu | Ser |
| | | | 340 | | | | | 345 | | | | | 350 | | |

| Gly | Lys | Ile | His | Glu | Ala | Glu | Ala | Gln | Tyr | Gly | Ala | Ala | Glu | Ala | Gln |
| | | | 355 | | | | | 360 | | | | | 365 | | |

| Leu | Thr | Ala | Thr | Glu | Arg | His | Ile | Lys | Leu | Ala | Val | Arg | Gln | Ala | Tyr |
| | 370 | | | | | 375 | | | | | 380 | | | | |

```
Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
            405                 410                 415

Tyr Gly Ile Arg Asn Arg Leu Glu Val Ile Arg Ala Arg Gln Glu Val
        420                 425                 430

Ala Gln Ala Glu Gln Lys Leu Ala Gln Ala Arg Tyr Lys Phe Met Leu
    435                 440                 445

Ala Tyr Leu Arg Leu Val Lys Glu Ser Gly Leu Gly Leu Glu Thr Val
450                 455                 460

Phe Ala Glu
465

<210> SEQ ID NO 31
<211> LENGTH: 696
<212> TYPE: DNA
<213> ORGANISM: Neisseria meningitidis
<220> FEATURE:
<221> NAME/KEY: CDS
<222> LOCATION: (1)..(693)

<400> SEQUENCE: 31 atg aaa caa tcc gcc cga ata aaa aat atg gat cag aca tta aaa aat    48
Met Lys Gln Ser Ala Arg Ile Lys Asn Met Asp Gln Thr Leu Lys Asn
1               5                   10                  15 aca ttg ggc att tgc gcg ctt tta gcc ttt tgt ttt ggc gcg gcc atc    96
Thr Leu Gly Ile Cys Ala Leu Leu Ala Phe Cys Phe Gly Ala Ala Ile
                20                  25                  30 gca tca ggt tat cac ttg gaa tat gaa tac ggc tac cgt tat tct gcc   144
Ala Ser Gly Tyr His Leu Glu Tyr Glu Tyr Gly Tyr Arg Tyr Ser Ala
            35                  40                  45 gtg ggt gct ttg gct tcg gtt gta ttt tta tta tta ttg gca cgc ggt   192
Val Gly Ala Leu Ala Ser Val Val Phe Leu Leu Leu Ala Arg Gly
    50                  55                  60 ttc ccg cgc gtt tct tca gtt gtt tta ctg att tac gtc ggc aca acc   240
Phe Pro Arg Val Ser Ser Val Val Leu Leu Ile Tyr Val Gly Thr Thr
65                  70                  75                  80 gcc cta tat ttg ccg gtc ggc tgg ctg tat ggt gcg ccg tct tat cag   288
Ala Leu Tyr Leu Pro Val Gly Trp Leu Tyr Gly Ala Pro Ser Tyr Gln
                85                  90                  95 ata gtc ggt tcg ata ttg gaa agc aat cct gcc gag gcg cgt gaa ttt   336
Ile Val Gly Ser Ile Leu Glu Ser Asn Pro Ala Glu Ala Arg Glu Phe
            100                 105                 110 gtc ggc aat ctt ccc ggg tcg ctt tat ttt gtg cag gca tta ttt ttc   384
Val Gly Asn Leu Pro Gly Ser Leu Tyr Phe Val Gln Ala Leu Phe Phe
        115                 120                 125 att ttt ggc ttg aca gtt tgg aga tat tgt gta tcg ggg ggg gta ttt   432
Ile Phe Gly Leu Thr Val Trp Arg Tyr Cys Val Ser Gly Gly Val Phe
    130                 135                 140 gct gac gta aaa aac tat aaa cgc cgc agc aaa ata tgg ctg act ata   480
Ala Asp Val Lys Asn Tyr Lys Arg Arg Ser Lys Ile Trp Leu Thr Ile
145                 150                 155                 160 tta ttg act ttg att ttg tcc tgc gcg gtg atg gat aaa atc gcc agc   528
Leu Leu Thr Leu Ile Leu Ser Cys Ala Val Met Asp Lys Ile Ala Ser
                165                 170                 175 gat aaa gat ttg cga gaa cct gat gcc ggc ctg ttg ttg aat att ttc   576
Asp Lys Asp Leu Arg Glu Pro Asp Ala Gly Leu Leu Leu Asn Ile Phe
            180                 185                 190 gac ctg tat tac gat ttg gct tcc gcg ccg gca cca ata tgt cgc caa   624
Asp Leu Tyr Tyr Asp Leu Ala Ser Ala Pro Ala Pro Ile Cys Arg Gln
```

```
gcg cgc cca cat ttt gga agc agc aaa aaa agc gtc aac atg gca tat      672
Ala Arg Pro His Phe Gly Ser Ser Lys Lys Ser Val Asn Met Ala Tyr
    210                 215                 220 ccg tca tgt tgc gcc caa gta taa                                      696
Pro Ser Cys Cys Ala Gln Val
225                 230
```

<210> SEQ ID NO 32
<211> LENGTH: 231
<212> TYPE: PRT
<213> ORGANISM: Neisseria meningitidis

<400> SEQUENCE: 32

```
Met Lys Gln Ser Ala Arg Ile Lys Asn Met Asp Gln Thr Leu Lys Asn
 1               5                  10                  15

Thr Leu Gly Ile Cys Ala Leu Leu Ala Phe Cys Phe Gly Ala Ala Ile
             20                  25                  30

Ala Ser Gly Tyr His Leu Glu Tyr Glu Tyr Gly Tyr Arg Tyr Ser Ala
         35                  40                  45

Val Gly Ala Leu Ala Ser Val Val Phe Leu Leu Leu Ala Arg Gly
     50                  55                  60

Phe Pro Arg Val Ser Ser Val Val Leu Ile Tyr Val Gly Thr Thr
 65                  70                  75                  80

Ala Leu Tyr Leu Pro Val Gly Trp Leu Tyr Gly Ala Pro Ser Tyr Gln
                 85                  90                  95

Ile Val Gly Ser Ile Leu Glu Ser Asn Pro Ala Glu Ala Arg Glu Phe
            100                 105                 110

Val Gly Asn Leu Pro Gly Ser Leu Tyr Phe Val Gln Ala Leu Phe Phe
        115                 120                 125

Ile Phe Gly Leu Thr Val Trp Arg Tyr Cys Val Ser Gly Gly Val Phe
    130                 135                 140

Ala Asp Val Lys Asn Tyr Lys Arg Arg Ser Lys Ile Trp Leu Thr Ile
145                 150                 155                 160

Leu Leu Thr Leu Ile Leu Ser Cys Ala Val Met Asp Lys Ile Ala Ser
                165                 170                 175

Asp Lys Asp Leu Arg Glu Pro Asp Ala Gly Leu Leu Leu Asn Ile Phe
            180                 185                 190

Asp Leu Tyr Tyr Asp Leu Ala Ser Ala Pro Ala Pro Ile Cys Arg Gln
        195                 200                 205

Ala Arg Pro His Phe Gly Ser Ser Lys Lys Ser Val Asn Met Ala Tyr
    210                 215                 220

Pro Ser Cys Cys Ala Gln Val
225                 230
```

<210> SEQ ID NO 33
<211> LENGTH: 909
<212> TYPE: DNA
<213> ORGANISM: Neisseria meningitidis
<220> FEATURE:
<221> NAME/KEY: CDS
<222> LOCATION: (1)..(906)

<400> SEQUENCE: 33

```
atg aat gtt tac ggt ttc cca ttg ccc gat acg cct ttt ttg agt cgg      48
Met Asn Val Tyr Gly Phe Pro Leu Pro Asp Thr Pro Phe Leu Ser Arg
 1               5                  10                  15 acc aaa ggg ctg ttg ata aac ggt tac cat ttc acc gcc cac gcg acg      96
```

| | | |
|---|---|---|
| Thr Lys Gly Leu Leu Ile Asn Gly Tyr His Phe Thr Ala His Ala Thr<br>               20                       25                    30 | |

```
aat ctt tcg ctg ccg cag act ttg ggg ctg ccg gga gag ccg aac aat       144
Asn Leu Ser Leu Pro Gln Thr Leu Gly Leu Pro Gly Glu Pro Asn Asn
         35                  40                  45 aac att gtc agc ttg gcg aag cag gcg ggt ttt cgg acg gcg tgg ctg       192
Asn Ile Val Ser Leu Ala Lys Gln Ala Gly Phe Arg Thr Ala Trp Leu
     50                  55                  60 tct aat caa gga atg ttg ggg cat ttt gcc aac gaa att tcc acc tat       240
Ser Asn Gln Gly Met Leu Gly His Phe Ala Asn Glu Ile Ser Thr Tyr
 65                  70                  75                  80 gcc cta cgc agc gat tat ccg tgg ttt acc caa agg ggt gat tat ggc       288
Ala Leu Arg Ser Asp Tyr Pro Trp Phe Thr Gln Arg Gly Asp Tyr Gly
                 85                  90                  95 aaa agc gcg ggg ttg agc gac cgc ctt ttg ttg ccg gcg ttc aaa cgg       336
Lys Ser Ala Gly Leu Ser Asp Arg Leu Leu Leu Pro Ala Phe Lys Arg
            100                 105                 110 gtt ttg ata gga aat gca ggc acg aag cct cgg ctg att gtg atg cac       384
Val Leu Ile Gly Asn Ala Gly Thr Lys Pro Arg Leu Ile Val Met His
        115                 120                 125 ctg atg ggt tcg cac agt gat ttt tgc aca cgt ttg gat aag gat gcg       432
Leu Met Gly Ser His Ser Asp Phe Cys Thr Arg Leu Asp Lys Asp Ala
    130                 135                 140 cgg cgg ttt cag tat caa act gaa aaa ata tcc tgc tat gtt tcc acc       480
Arg Arg Phe Gln Tyr Gln Thr Glu Lys Ile Ser Cys Tyr Val Ser Thr
145                 150                 155                 160 atc gcg caa acc gat aaa ttt tta gaa gat aca gtt aag ata ttg aat       528
Ile Ala Gln Thr Asp Lys Phe Leu Glu Asp Thr Val Lys Ile Leu Asn
                165                 170                 175 gaa aat aaa gaa agc tgg tct ttg gtt tac ttt tcc gac cac ggt ttg       576
Glu Asn Lys Glu Ser Trp Ser Leu Val Tyr Phe Ser Asp His Gly Leu
            180                 185                 190 atg cat gtc ggt aaa ggc ggc gag cga acg ttg aca cat ggt gcg tgg       624
Met His Val Gly Lys Gly Gly Glu Arg Thr Leu Thr His Gly Ala Trp
        195                 200                 205 aag cgt caa agc tac ggc gtg ccg ctg gtt aaa att tcg tcc gat gac       672
Lys Arg Gln Ser Tyr Gly Val Pro Leu Val Lys Ile Ser Ser Asp Asp
    210                 215                 220 acg cgg cgc gaa atg att aaa gtg agg cgc agc gcg ttt aat ttt tta       720
Thr Arg Arg Glu Met Ile Lys Val Arg Arg Ser Ala Phe Asn Phe Leu
225                 230                 235                 240 cgc gga ttc ggc agt tgg acg ggt atc gaa acc gac gag ttg ccc gat       768
Arg Gly Phe Gly Ser Trp Thr Gly Ile Glu Thr Asp Glu Leu Pro Asp
                245                 250                 255 gac ggc tat gat ttt tgg ggg aat gtt ccc gat gtg cag ggc gaa ggc       816
Asp Gly Tyr Asp Phe Trp Gly Asn Val Pro Asp Val Gln Gly Glu Gly
            260                 265                 270 aat aac ctt gcc ttt atc gac gga ctg ccc gac gac ccc gcg ccg tgg       864
Asn Asn Leu Ala Phe Ile Asp Gly Leu Pro Asp Asp Pro Ala Pro Trp
        275                 280                 285 tat gcg gga aaa ggc aaa tcg act aaa aat acg tct aaa aaa tga           909
Tyr Ala Gly Lys Gly Lys Ser Thr Lys Asn Thr Ser Lys Lys
    290                 295                 300
```

<210> SEQ ID NO 34
<211> LENGTH: 302
<212> TYPE: PRT
<213> ORGANISM: Neisseria meningitidis

<400> SEQUENCE: 34

```
Met Asn Val Tyr Gly Phe Pro Leu Pro Asp Thr Pro Phe Leu Ser Arg
 1               5                  10                  15

Thr Lys Gly Leu Leu Ile Asn Gly Tyr His Phe Thr Ala His Ala Thr
                20                  25                  30

Asn Leu Ser Leu Pro Gln Thr Leu Gly Leu Pro Gly Glu Pro Asn Asn
            35                  40                  45

Asn Ile Val Ser Leu Ala Lys Gln Ala Gly Phe Arg Thr Ala Trp Leu
 50                  55                  60

Ser Asn Gln Gly Met Leu Gly His Phe Ala Asn Glu Ile Ser Thr Tyr
 65                  70                  75                  80

Ala Leu Arg Ser Asp Tyr Pro Trp Phe Thr Gln Arg Gly Asp Tyr Gly
                85                  90                  95

Lys Ser Ala Gly Leu Ser Asp Arg Leu Leu Pro Ala Phe Lys Arg
                100                 105                 110

Val Leu Ile Gly Asn Ala Gly Thr Lys Pro Arg Leu Ile Val Met His
            115                 120                 125

Leu Met Gly Ser His Ser Asp Phe Cys Thr Arg Leu Asp Lys Asp Ala
        130                 135                 140

Arg Arg Phe Gln Tyr Gln Thr Glu Lys Ile Ser Cys Tyr Val Ser Thr
145                 150                 155                 160

Ile Ala Gln Thr Asp Lys Phe Leu Glu Asp Thr Val Lys Ile Leu Asn
                165                 170                 175

Glu Asn Lys Glu Ser Trp Ser Leu Val Tyr Phe Ser Asp His Gly Leu
            180                 185                 190

Met His Val Gly Lys Gly Gly Glu Arg Thr Leu Thr His Gly Ala Trp
        195                 200                 205

Lys Arg Gln Ser Tyr Gly Val Pro Leu Val Lys Ile Ser Ser Asp Asp
    210                 215                 220

Thr Arg Arg Glu Met Ile Lys Val Arg Arg Ser Ala Phe Asn Phe Leu
225                 230                 235                 240

Arg Gly Phe Gly Ser Trp Thr Gly Ile Glu Thr Asp Glu Leu Pro Asp
                245                 250                 255

Asp Gly Tyr Asp Phe Trp Gly Asn Val Pro Asp Val Gln Gly Glu Gly
            260                 265                 270

Asn Asn Leu Ala Phe Ile Asp Gly Leu Pro Asp Pro Ala Pro Trp
        275                 280                 285

Tyr Ala Gly Lys Gly Lys Ser Thr Lys Asn Thr Ser Lys Lys
290                 295                 300
```

<210> SEQ ID NO 35
<211> LENGTH: 864
<212> TYPE: DNA
<213> ORGANISM: Neisseria meningitidis
<220> FEATURE:
<221> NAME/KEY: CDS
<222> LOCATION: (1)..(861)

<400> SEQUENCE: 35

```
atg atg agt caa cac tct gcc gga gca cgt ttc cgc caa gcc gtg aaa      48
Met Met Ser Gln His Ser Ala Gly Ala Arg Phe Arg Gln Ala Val Lys
 1               5                  10                  15 gaa tcg aat ccg ctt gcc gtc gcc ggt tgc gtc aat gct tat ttt gca      96
Glu Ser Asn Pro Leu Ala Val Ala Gly Cys Val Asn Ala Tyr Phe Ala
                20                  25                  30 cga ttg gcc acc caa agc ggt ttc aaa gcc atc tat ctg tcc ggc ggc     144
Arg Leu Ala Thr Gln Ser Gly Phe Lys Ala Ile Tyr Leu Ser Gly Gly
            35                  40                  45
```

```
ggc gtg gca gcc tgt tct tgc ggt atc cct gat ttg ggc att acc aca      192
Gly Val Ala Ala Cys Ser Cys Gly Ile Pro Asp Leu Gly Ile Thr Thr
    50                  55                  60 atg gaa gat gtg ctg atc gac gca cga cgc att acg gac aac gtg gat      240
Met Glu Asp Val Leu Ile Asp Ala Arg Arg Ile Thr Asp Asn Val Asp
65                  70                  75                  80 acg cct ctg ctg gtg gac atc gat gtg ggt tgg ggc ggt gca ttc aat      288
Thr Pro Leu Leu Val Asp Ile Asp Val Gly Trp Gly Gly Ala Phe Asn
                85                  90                  95 att gcc cgt acc att cgc aac ttt gaa cgc gcc ggt gtt gca gcg gtt      336
Ile Ala Arg Thr Ile Arg Asn Phe Glu Arg Ala Gly Val Ala Ala Val
            100                 105                 110 cac atc gaa gat cag gta gcg caa aaa cgc tgc ggc cac cgt ccg aac      384
His Ile Glu Asp Gln Val Ala Gln Lys Arg Cys Gly His Arg Pro Asn
        115                 120                 125 aaa gcc att gta tct aaa gat gaa atg gtc gac cgt atc aaa gct gcc      432
Lys Ala Ile Val Ser Lys Asp Glu Met Val Asp Arg Ile Lys Ala Ala
    130                 135                 140 gta gat gcg cgc gtt gat gag aac ttc gtg att atg gcg cgt acc gat      480
Val Asp Ala Arg Val Asp Glu Asn Phe Val Ile Met Ala Arg Thr Asp
145                 150                 155                 160 gcg ctg gcg gta gaa ggt ttg gat gcc gct atc gaa cgc gcc caa gct      528
Ala Leu Ala Val Glu Gly Leu Asp Ala Ala Ile Glu Arg Ala Gln Ala
                165                 170                 175 tgt gtc gaa gcc ggt gcg gac atg att ttc cct gaa gcc atg acc gat      576
Cys Val Glu Ala Gly Ala Asp Met Ile Phe Pro Glu Ala Met Thr Asp
            180                 185                 190 ttg aac atg tac cgc caa ttt gca gat gcg gtg aaa gtg ccc gtg ttg      624
Leu Asn Met Tyr Arg Gln Phe Ala Asp Ala Val Lys Val Pro Val Leu
        195                 200                 205 gcg aac att acc gag ttt ggt tcc act ccg ctt tat acc caa agc gag      672
Ala Asn Ile Thr Glu Phe Gly Ser Thr Pro Leu Tyr Thr Gln Ser Glu
    210                 215                 220 ctg gct gaa aac ggc gtg tcg ctg gtg ctg tat ccg ctg tca tcg ttc      720
Leu Ala Glu Asn Gly Val Ser Leu Val Leu Tyr Pro Leu Ser Ser Phe
225                 230                 235                 240 cgt gca gca agc aaa gcc gct ctg aat gtt tac gaa gcg att atg cgc      768
Arg Ala Ala Ser Lys Ala Ala Leu Asn Val Tyr Glu Ala Ile Met Arg
                245                 250                 255 gat ggc act tca ggc ggc ggt ggt gga cag tat gca aac ccg tgc cga      816
Asp Gly Thr Ser Gly Gly Gly Gly Gln Tyr Ala Asn Pro Cys Arg
            260                 265                 270 gct gta cga gca tct gaa cta tca tgc ctt cga gca aaa act gga taa     864
Ala Val Arg Ala Ser Glu Leu Ser Cys Leu Arg Ala Lys Thr Gly
        275                 280                 285

<210> SEQ ID NO 36
<211> LENGTH: 287
<212> TYPE: PRT
<213> ORGANISM: Neisseria meningitidis

<400> SEQUENCE: 36

Met Met Ser Gln His Ser Ala Gly Ala Arg Phe Arg Gln Ala Val Lys
 1               5                  10                  15

Glu Ser Asn Pro Leu Ala Val Ala Gly Cys Val Asn Ala Tyr Phe Ala
            20                  25                  30

Arg Leu Ala Thr Gln Ser Gly Phe Lys Ala Ile Tyr Leu Ser Gly Gly
        35                  40                  45

Gly Val Ala Ala Cys Ser Cys Gly Ile Pro Asp Leu Gly Ile Thr Thr
```

```
                50                   55                   60
Met Glu Asp Val Leu Ile Asp Ala Arg Arg Ile Thr Asp Asn Val Asp
 65                   70                   75                   80

Thr Pro Leu Leu Val Asp Ile Asp Val Gly Trp Gly Ala Phe Asn
                 85                   90                   95

Ile Ala Arg Thr Ile Arg Asn Phe Glu Arg Ala Gly Val Ala Ala Val
                100                  105                  110

His Ile Glu Asp Gln Val Ala Gln Lys Arg Cys Gly His Arg Pro Asn
                115                  120                  125

Lys Ala Ile Val Ser Lys Asp Glu Met Val Asp Arg Ile Lys Ala Ala
130                  135                  140

Val Asp Ala Arg Val Asp Glu Asn Phe Val Ile Met Ala Arg Thr Asp
145                  150                  155                  160

Ala Leu Ala Val Glu Gly Leu Asp Ala Ala Ile Glu Arg Ala Gln Ala
                165                  170                  175

Cys Val Glu Ala Gly Ala Asp Met Ile Phe Pro Glu Ala Met Thr Asp
                180                  185                  190

Leu Asn Met Tyr Arg Gln Phe Ala Asp Ala Val Lys Val Pro Val Leu
                195                  200                  205

Ala Asn Ile Thr Glu Phe Gly Ser Thr Pro Leu Tyr Thr Gln Ser Glu
                210                  215                  220

Leu Ala Glu Asn Gly Val Ser Leu Val Leu Tyr Pro Leu Ser Ser Phe
225                  230                  235                  240

Arg Ala Ala Ser Lys Ala Ala Leu Asn Val Tyr Glu Ala Ile Met Arg
                245                  250                  255

Asp Gly Thr Ser Gly Gly Gly Gly Gln Tyr Ala Asn Pro Cys Arg
                260                  265                  270

Ala Val Arg Ala Ser Glu Leu Ser Cys Leu Arg Ala Lys Thr Gly
                275                  280                  285

<210> SEQ ID NO 37
<211> LENGTH: 921
<212> TYPE: DNA
<213> ORGANISM: Neisseria meningitidis
<220> FEATURE:
<221> NAME/KEY: CDS
<222> LOCATION: (1)..(918)

<400> SEQUENCE: 37 atg cct tcg agc aaa aac tgg ata aat tgt ttc aaa aat gat tta ccg      48
Met Pro Ser Ser Lys Asn Trp Ile Asn Cys Phe Lys Asn Asp Leu Pro
  1               5                  10                  15 ctt tca gac tgc ctt tca aca aat ccg cat cgg tcg tct gaa aac ccg     96
Leu Ser Asp Cys Leu Ser Thr Asn Pro His Arg Ser Ser Glu Asn Pro
                 20                  25                  30 aaa ccc ata aaa aca caa agg aga aat acc atg act gaa act act caa    144
Lys Pro Ile Lys Thr Gln Arg Arg Asn Thr Met Thr Glu Thr Thr Gln
             35                  40                  45 acc ccg acc ctc aaa cct aaa aaa tcc gtt gcg ctt tct ggc gtt gcg    192
Thr Pro Thr Leu Lys Pro Lys Lys Ser Val Ala Leu Ser Gly Val Ala
 50                  55                  60 gcc ggt aat acc gct ttg tgt acc gtt ggc cgt acc ggc aac gat ttg    240
Ala Gly Asn Thr Ala Leu Cys Thr Val Gly Arg Thr Gly Asn Asp Leu
 65                  70                  75                  80 agc tat cgc ggt tac gac att ctg gat ttg gca caa aaa tgt gag ttt    288
Ser Tyr Arg Gly Tyr Asp Ile Leu Asp Leu Ala Gln Lys Cys Glu Phe
                 85                  90                  95
```

-continued

| | |
|---|---|
| gaa gaa gtt gcc cac ctg ctg att cac ggc cat tta ccc aac aaa ttc<br>Glu Glu Val Ala His Leu Leu Ile His Gly His Leu Pro Asn Lys Phe<br>100 105 110 | 336 |
| gag ctg gcc gct tat aaa gcc aag ctc aaa tcc atg cgc ggc ctg cct<br>Glu Leu Ala Ala Tyr Lys Ala Lys Leu Lys Ser Met Arg Gly Leu Pro<br>115 120 125 | 384 |
| atc cgt gtg att aaa gtt ttg gaa agc ctg cct gca cat acc cat ccg<br>Ile Arg Val Ile Lys Val Leu Glu Ser Leu Pro Ala His Thr His Pro<br>130 135 140 | 432 |
| atg gac gtg atg cgt acc ggc gta tcc atg ctg ggc tgt gtt cat cct<br>Met Asp Val Met Arg Thr Gly Val Ser Met Leu Gly Cys Val His Pro<br>145 150 155 160 | 480 |
| gaa cgt gaa ggc cat ccg gaa agc gaa gcg cgc gac att gcc gac aaa<br>Glu Arg Glu Gly His Pro Glu Ser Glu Ala Arg Asp Ile Ala Asp Lys<br>165 170 175 | 528 |
| ctg atc gcc agc ctc ggc agt atc ctc ttg tac tgg tat caa tat tcg<br>Leu Ile Ala Ser Leu Gly Ser Ile Leu Leu Tyr Trp Tyr Gln Tyr Ser<br>180 185 190 | 576 |
| cac aac ggc aaa cgc att gaa gtt gaa agc gaa gaa gag acc atc ggc<br>His Asn Gly Lys Arg Ile Glu Val Glu Ser Glu Glu Glu Thr Ile Gly<br>195 200 205 | 624 |
| ggt cat ttc ctg cac ctg ttg cac ggc aaa cgc cca agc gaa tca cac<br>Gly His Phe Leu His Leu Leu His Gly Lys Arg Pro Ser Glu Ser His<br>210 215 220 | 672 |
| atc aaa gcc atg cac gtt tca ctg att ctg tat gcc gaa cac gag ttc<br>Ile Lys Ala Met His Val Ser Leu Ile Leu Tyr Ala Glu His Glu Phe<br>225 230 235 240 | 720 |
| aac gct tct acc ttt acc gcc cgc gtg atc gcc ggt aca ggc tct gat<br>Asn Ala Ser Thr Phe Thr Ala Arg Val Ile Ala Gly Thr Gly Ser Asp<br>245 250 255 | 768 |
| atg tac tcc agc att acc gga gca atc ggc gcg ttg aaa ggt ccg aaa<br>Met Tyr Ser Ser Ile Thr Gly Ala Ile Gly Ala Leu Lys Gly Pro Lys<br>260 265 270 | 816 |
| cac ggc ggc gcg aac gaa ggg ctt acg ata ttc aaa aac gct acc gca<br>His Gly Gly Ala Asn Glu Gly Leu Thr Ile Phe Lys Asn Ala Thr Ala<br>275 280 285 | 864 |
| atg ccg acg aag ccg aag ccg aca tcc gcg aac gca tcg gcc gca aag<br>Met Pro Thr Lys Pro Lys Pro Thr Ser Ala Asn Ala Ser Ala Ala Lys<br>290 295 300 | 912 |
| aaa tcg tga<br>Lys Ser<br>305 | 921 |

<210> SEQ ID NO 38
<211> LENGTH: 306
<212> TYPE: PRT
<213> ORGANISM: Neisseria meningitidis

<400> SEQUENCE: 38

Met Pro Ser Ser Lys Asn Trp Ile Asn Cys Phe Lys Asn Asp Leu Pro
1               5                   10                  15

Leu Ser Asp Cys Leu Ser Thr Asn Pro His Arg Ser Glu Asn Pro
            20                  25                  30

Lys Pro Ile Lys Thr Gln Arg Arg Asn Thr Met Thr Glu Thr Thr Gln
        35                  40                  45

Thr Pro Thr Leu Lys Pro Lys Lys Ser Val Ala Leu Ser Gly Val Ala
    50                  55                  60

Ala Gly Asn Thr Ala Leu Cys Thr Val Gly Arg Thr Gly Asn Asp Leu
65                  70                  75                  80

-continued

```
Ser Tyr Arg Gly Tyr Asp Ile Leu Asp Leu Ala Gln Lys Cys Glu Phe
                 85                  90                  95

Glu Glu Val Ala His Leu Leu Ile His Gly His Leu Pro Asn Lys Phe
            100                 105                 110

Glu Leu Ala Ala Tyr Lys Ala Lys Leu Lys Ser Met Arg Gly Leu Pro
        115                 120                 125

Ile Arg Val Ile Lys Val Leu Glu Ser Leu Pro Ala His Thr His Pro
    130                 135                 140

Met Asp Val Met Arg Thr Gly Val Ser Met Leu Gly Cys Val His Pro
145                 150                 155                 160

Glu Arg Glu Gly His Pro Glu Ser Glu Ala Arg Asp Ile Ala Asp Lys
                165                 170                 175

Leu Ile Ala Ser Leu Gly Ser Ile Leu Leu Tyr Trp Tyr Gln Tyr Ser
            180                 185                 190

His Asn Gly Lys Arg Ile Glu Val Glu Ser Glu Glu Thr Ile Gly
        195                 200                 205

Gly His Phe Leu His Leu Leu His Gly Lys Arg Pro Ser Glu Ser His
    210                 215                 220

Ile Lys Ala Met His Val Ser Leu Ile Leu Tyr Ala Glu His Glu Phe
225                 230                 235                 240

Asn Ala Ser Thr Phe Thr Ala Arg Val Ile Ala Gly Thr Gly Ser Asp
                245                 250                 255

Met Tyr Ser Ser Ile Thr Gly Ala Ile Gly Ala Leu Lys Gly Pro Lys
            260                 265                 270

His Gly Gly Ala Asn Glu Gly Leu Thr Ile Phe Lys Asn Ala Thr Ala
        275                 280                 285

Met Pro Thr Lys Pro Lys Pro Thr Ser Ala Asn Ala Ser Ala Ala Lys
    290                 295                 300

Lys Ser
305
```

<210> SEQ ID NO 39
<211> LENGTH: 945
<212> TYPE: DNA
<213> ORGANISM: Neisseria meningitidis
<220> FEATURE:
<221> NAME/KEY: CDS
<222> LOCATION: (1)..(942)

<400> SEQUENCE: 39

```
atg cac cta tgt gga aag tat tat gga gta aat atg aag ctg cgt gat      48
Met His Leu Cys Gly Lys Tyr Tyr Gly Val Asn Met Lys Leu Arg Asp
  1               5                  10                  15 tta ctg atg gga ata ttc ttg gca gtt tct gcg gcc ctt ctg aat gca      96
Leu Leu Met Gly Ile Phe Leu Ala Val Ser Ala Ala Leu Leu Asn Ala
             20                  25                  30 acc atc ggc ata ttc agc aag ata ttg atg gag cag ggc ttg tct gtt     144
Thr Ile Gly Ile Phe Ser Lys Ile Leu Met Glu Gln Gly Leu Ser Val
         35                  40                  45 cag cat att gca ttt ttg aaa act ttg aca ggt ttc gtg ttt atc agc     192
Gln His Ile Ala Phe Leu Lys Thr Leu Thr Gly Phe Val Phe Ile Ser
     50                  55                  60 att ttg ctt tgc cgt acc ggt ttt acc aga cag att gcg gat att tca     240
Ile Leu Leu Cys Arg Thr Gly Phe Thr Arg Gln Ile Ala Asp Ile Ser
 65                  70                  75                  80 aga aag aaa gag gca att ttg ccg ttg ctg tta aaa gta gca att tgt     288
Arg Lys Lys Glu Ala Ile Leu Pro Leu Leu Leu Lys Val Ala Ile Cys
                 85                  90                  95
```

-continued

```
gct ttt ttc gga att tat acg ttg ttt ttc ttt gaa acc aca gct tat    336
Ala Phe Phe Gly Ile Tyr Thr Leu Phe Phe Phe Glu Thr Thr Ala Tyr
            100                 105                 110 caa tat ggc aat gct gcg aat gta gta gtt gta tta atg gca tcg gct    384
Gln Tyr Gly Asn Ala Ala Asn Val Val Val Val Leu Met Ala Ser Ala
        115                 120                 125 gcc gta tct gcc ttg ata ttg gac agc ata ctg tta gat gaa cgt att    432
Ala Val Ser Ala Leu Ile Leu Asp Ser Ile Leu Leu Asp Glu Arg Ile
    130                 135                 140 tgc att tct tca gtc gtc ggt gtg ggt ttg gca gta ttg ggg atc gca    480
Cys Ile Ser Ser Val Val Gly Val Gly Leu Ala Val Leu Gly Ile Ala
145                 150                 155                 160 atg att tct tgg act gga gaa gga agt tta ggg ttg att ctg aat gcc    528
Met Ile Ser Trp Thr Gly Glu Gly Ser Leu Gly Leu Ile Leu Asn Ala
                165                 170                 175 gca ctg gcg ggc tcg ggc tac ggt tgt ttt tcc gtt tty att aag aaa    576
Ala Leu Ala Gly Ser Gly Tyr Gly Cys Phe Ser Val Leu Ile Lys Lys
            180                 185                 190 ttc ggc cta aac ggc ggt att tat ttg aca cgg ata ttg atg ttt ttt    624
Phe Gly Leu Asn Gly Gly Ile Tyr Leu Thr Arg Ile Leu Met Phe Phe
        195                 200                 205 gga agt att ttt ttg ttt atc cct tca ttg gaa ggt att gag gat ata    672
Gly Ser Ile Phe Leu Phe Ile Pro Ser Leu Glu Gly Ile Glu Asp Ile
    210                 215                 220 cat tgg caa tgg tct ttt att ccg cca ctc ttg gca ttg tct tta ttg    720
His Trp Gln Trp Ser Phe Ile Pro Pro Leu Leu Ala Leu Ser Leu Leu
225                 230                 235                 240 ccg acg att tta gga ttt tat tgt aca act aaa gca ttg gat tat ttg    768
Pro Thr Ile Leu Gly Phe Tyr Cys Thr Thr Lys Ala Leu Asp Tyr Leu
                245                 250                 255 agt gct gcg aag gta cag gta act gaa ttg gcc gag cca ttg ttt gct    816
Ser Ala Ala Lys Val Gln Val Thr Glu Leu Ala Glu Pro Leu Phe Ala
            260                 265                 270 gcc gta ctg gct tgg ttg ttt ttg aat gaa ata ccg gaa gga cgc ttc    864
Ala Val Leu Ala Trp Leu Phe Leu Asn Glu Ile Pro Glu Gly Arg Phe
        275                 280                 285 ttt gtc ggc gcc att ctg att att gcc ggt att gtg tct atc aat ggg    912
Phe Val Gly Ala Ile Leu Ile Ile Ala Gly Ile Val Ser Ile Asn Gly
    290                 295                 300 ctg tat cga cca ttg ttg aag cga att gaa taa                        945
Leu Tyr Arg Pro Leu Leu Lys Arg Ile Glu
305                 310
```

<210> SEQ ID NO 40
<211> LENGTH: 314
<212> TYPE: PRT
<213> ORGANISM: Neisseria meningitidis

<400> SEQUENCE: 40

```
Met His Leu Cys Gly Lys Tyr Tyr Gly Val Asn Met Lys Leu Arg Asp
 1               5                  10                  15

Leu Leu Met Gly Ile Phe Leu Ala Val Ser Ala Ala Leu Leu Asn Ala
            20                  25                  30

Thr Ile Gly Ile Phe Ser Lys Ile Leu Met Glu Gln Gly Leu Ser Val
        35                  40                  45

Gln His Ile Ala Phe Leu Lys Thr Leu Thr Gly Phe Val Phe Ile Ser
    50                  55                  60

Ile Leu Leu Cys Arg Thr Gly Phe Thr Arg Gln Ile Ala Asp Ile Ser
65                  70                  75                  80
```

```
Arg Lys Lys Glu Ala Ile Leu Pro Leu Leu Lys Val Ala Ile Cys
                85                  90                  95

Ala Phe Phe Gly Ile Tyr Thr Leu Phe Phe Glu Thr Thr Ala Tyr
            100                 105                 110

Gln Tyr Gly Asn Ala Ala Asn Val Val Val Leu Met Ala Ser Ala
        115                 120                 125

Ala Val Ser Ala Leu Ile Leu Asp Ser Ile Leu Leu Asp Glu Arg Ile
    130                 135                 140

Cys Ile Ser Ser Val Val Gly Val Gly Leu Ala Val Leu Gly Ile Ala
145                 150                 155                 160

Met Ile Ser Trp Thr Gly Glu Gly Ser Leu Gly Leu Ile Leu Asn Ala
                165                 170                 175

Ala Leu Ala Gly Ser Gly Tyr Gly Cys Phe Ser Val Leu Ile Lys Lys
            180                 185                 190

Phe Gly Leu Asn Gly Gly Ile Tyr Leu Thr Arg Ile Leu Met Phe Phe
        195                 200                 205

Gly Ser Ile Phe Leu Phe Ile Pro Ser Leu Glu Gly Ile Glu Asp Ile
    210                 215                 220

His Trp Gln Trp Ser Phe Ile Pro Pro Leu Leu Ala Leu Ser Leu Leu
225                 230                 235                 240

Pro Thr Ile Leu Gly Phe Tyr Cys Thr Thr Lys Ala Leu Asp Tyr Leu
                245                 250                 255

Ser Ala Ala Lys Val Gln Val Thr Glu Leu Ala Glu Pro Leu Phe Ala
            260                 265                 270

Ala Val Leu Ala Trp Leu Phe Leu Asn Glu Ile Pro Glu Gly Arg Phe
        275                 280                 285

Phe Val Gly Ala Ile Leu Ile Ala Gly Ile Val Ser Ile Asn Gly
    290                 295                 300

Leu Tyr Arg Pro Leu Leu Lys Arg Ile Glu
305                 310

<210> SEQ ID NO 41
<211> LENGTH: 2610
<212> TYPE: DNA
<213> ORGANISM: Neisseria meningitidis
<220> FEATURE:
<221> NAME/KEY: CDS
<222> LOCATION: (1)..(2607)

<400> SEQUENCE: 41 atg gct gcc aac caa cgt tac cgc aaa ccg ctg ccc ggt acg gat ttg      48
Met Ala Ala Asn Gln Arg Tyr Arg Lys Pro Leu Pro Gly Thr Asp Leu
  1               5                  10                  15 gaa tac tac gac gcg cgt gcg gcg tgt gag gac atc aag ccc ggc tct      96
Glu Tyr Tyr Asp Ala Arg Ala Ala Cys Glu Asp Ile Lys Pro Gly Ser
             20                  25                  30 tac gac aag ctg cct tac acg agc cgc att ttg gcg gag aat ttg gtc     144
Tyr Asp Lys Leu Pro Tyr Thr Ser Arg Ile Leu Ala Glu Asn Leu Val
         35                  40                  45 aac cgc gcg gac aaa gtc gat ttg ccg acg ctg caa agc tgg ctg ggt     192
Asn Arg Ala Asp Lys Val Asp Leu Pro Thr Leu Gln Ser Trp Leu Gly
     50                  55                  60 cag ctg att gag gga aaa cag gaa atc gac ttt cct tgg tat ccg gcg     240
Gln Leu Ile Glu Gly Lys Gln Glu Ile Asp Phe Pro Trp Tyr Pro Ala
 65                  70                  75                  80 cgg gtg gtg tgc cac gat att ctg ggg cag acc gcg ttg gtg gat ttg     288
Arg Val Val Cys His Asp Ile Leu Gly Gln Thr Ala Leu Val Asp Leu
                 85                  90                  95
```

|  |  |  |  |  |  |  |  |  |  |  |  |  |
|---|---|---|---|---|---|---|---|---|---|---|---|---|
|  |  |  | 85 |  |  |  | 90 |  |  |  | 95 |  |
| gca | ggt | ctg | cgc | gat | gcg | att | gcc | gaa | aaa | ggc | ggc | gat | cct | gcc | aaa | 336 |
| Ala | Gly | Leu | Arg | Asp | Ala | Ile | Ala | Glu | Lys | Gly | Gly | Asp | Pro | Ala | Lys |  |
|  |  | 100 |  |  |  | 105 |  |  |  | 110 |  |

```
            85                   90                   95
gca ggt ctg cgc gat gcg att gcc gaa aaa ggc ggc gat cct gcc aaa        336
Ala Gly Leu Arg Asp Ala Ile Ala Glu Lys Gly Gly Asp Pro Ala Lys
            100                 105                 110 gtg aat ccg gtg gtt gca aaa ccc agc ttc atc gtc gac cac tct ctg        384
Val Asn Pro Val Val Ala Lys Pro Ser Phe Ile Val Asp His Ser Leu
        115                 120                 125 gcc gtt gaa tgc ggc ggc tac gac ccc gat gcc ttc cgc aaa aac cgc        432
Ala Val Glu Cys Gly Gly Tyr Asp Pro Asp Ala Phe Arg Lys Asn Arg
    130                 135                 140 caa atc gaa gac aga cgt aac gaa gac cgt ttc cac ttc atc aac tgg        480
Gln Ile Glu Asp Arg Arg Asn Glu Asp Arg Phe His Phe Ile Asn Trp
145                 150                 155                 160 aca aaa acc gca ttt gaa aat gtg gac gtg att ccg gcg ggc aac ggc        528
Thr Lys Thr Ala Phe Glu Asn Val Asp Val Ile Pro Ala Gly Asn Gly
                165                 170                 175 atg atg cac caa atc aat cta gaa aaa atg tcg ccc gtc gtc caa gtc        576
Ile Met His Gln Ile Asn Leu Glu Lys Met Ser Pro Val Val Gln Val
            180                 185                 190 aaa aac ggc gtg gcg ttc ccc gat acc tgc gtc ggc acg gat tcg cac        624
Lys Asn Gly Val Ala Phe Pro Asp Thr Cys Val Gly Thr Asp Ser His
        195                 200                 205 acg ccg cac gtc gat gcg ctg ggc gtg att tcc gtg ggc gtg ggc gga        672
Thr Pro His Val Asp Ala Leu Gly Val Ile Ser Val Gly Val Gly Gly
    210                 215                 220 ttg gaa gcg gaa acc gtg atg ctg ggt cgc gcg tcc atg atg cgc ctg        720
Leu Glu Ala Glu Thr Val Met Leu Gly Arg Ala Ser Met Met Arg Leu
225                 230                 235                 240 ccc gat att gtc ggc gtt gag ctg aac ggc aaa cgg cag gcg ggc att        768
Pro Asp Ile Val Gly Val Glu Leu Asn Gly Lys Arg Gln Ala Gly Ile
                245                 250                 255 acg gcg acg gat att gtg ttg gca ctg acc gag ttt ctg cgc aaa gaa        816
Thr Ala Thr Asp Ile Val Leu Ala Leu Thr Glu Phe Leu Arg Lys Glu
            260                 265                 270 cgc gtg gtc ggg gcg ttt gtc gaa ttc ttc ggc gag ggc gcg aga agc        864
Arg Val Val Gly Ala Phe Val Glu Phe Phe Gly Glu Gly Ala Arg Ser
        275                 280                 285 ctg tct atc ggc gac cgc gcg acc att tcc aac atg acg ccg gag ttc        912
Leu Ser Ile Gly Asp Arg Ala Thr Ile Ser Asn Met Thr Pro Glu Phe
    290                 295                 300 ggc gcg act gcc gcg atg ttc gct att gat gag caa acc att gat tat        960
Gly Ala Thr Ala Ala Met Phe Ala Ile Asp Glu Gln Thr Ile Asp Tyr
305                 310                 315                 320 ttg aaa ctg acc gga cgc gac gac gcg cag gtg aaa ttg gtg gaa acc       1008
Leu Lys Leu Thr Gly Arg Asp Asp Ala Gln Val Lys Leu Val Glu Thr
                325                 330                 335 tac gcc aaa acc gca ggc tta tgg gca gat gcc ttg aaa acc gcc gtt       1056
Tyr Ala Lys Thr Ala Gly Leu Trp Ala Asp Ala Leu Lys Thr Ala Val
            340                 345                 350 tat ccg cgc gtt ttg aaa ttt gat ttg agc agc gta acg cgc aat atg       1104
Tyr Pro Arg Val Leu Lys Phe Asp Leu Ser Ser Val Thr Arg Asn Met
        355                 360                 365 gca ggc ccg agc aac ccg cac gcg cgt ttt gcg acc gcc gat ttg gcc       1152
Ala Gly Pro Ser Asn Pro His Ala Arg Phe Ala Thr Ala Asp Leu Ala
    370                 375                 380 agc aaa ggc ttg gct aaa cct tac gaa gag cct tca gac ggc caa atg       1200
Ser Lys Gly Leu Ala Lys Pro Tyr Glu Glu Pro Ser Asp Gly Gln Met
385                 390                 395                 400 ccc gac ggc gcg gtc atc atc gcc gcg att acc agt tgc acc aac act       1248
```

```
Pro Asp Gly Ala Val Ile Ile Ala Ala Ile Thr Ser Cys Thr Asn Thr
            405                 410                 415 tcc aac ccg cgc aac gtt gtt gcc gcc gcg ctc ttg gcg cgc aac gcc   1296
Ser Asn Pro Arg Asn Val Val Ala Ala Ala Leu Leu Ala Arg Asn Ala
            420                 425                 430 aac tgc ttc ggg ctg aaa cgc aaa ccg tgg gtc aaa acc tcg ttt gcc   1344
Asn Cys Phe Gly Leu Lys Arg Lys Pro Trp Val Lys Thr Ser Phe Ala
            435                 440                 445 ccc ggt tcg aaa gtg gcg gaa att tat ttg aaa gaa gca ggc ctg ctg   1392
Pro Gly Ser Lys Val Ala Glu Ile Tyr Leu Lys Glu Ala Gly Leu Leu
    450                 455                 460 ccc gaa atg gaa aaa ctc ggc ttc ggt atc gtc gcc ttc gcc tgc acc   1440
Pro Glu Met Glu Lys Leu Gly Phe Gly Ile Val Ala Phe Ala Cys Thr
465                 470                 475                 480 acc tgc aac ggc atg agt ggc gcg ctg gat ccg aaa atc cag aaa gaa   1488
Thr Cys Asn Gly Met Ser Gly Ala Leu Asp Pro Lys Ile Gln Lys Glu
                485                 490                 495 atc atc gac cgc gat ttg tac gcc acc gcc gta tta tca ggc aac cgc   1536
Ile Ile Asp Arg Asp Leu Tyr Ala Thr Ala Val Leu Ser Gly Asn Arg
                500                 505                 510 aac ttc gac ggc cgt gtc cat ccg tat gcg aaa cag gct ttc ctc gct   1584
Asn Phe Asp Gly Arg Val His Pro Tyr Ala Lys Gln Ala Phe Leu Ala
            515                 520                 525 tcg cct ccg ttg gtc gtt gcc tac gcg ctg gca ggc agt atc cgt ttc   1632
Ser Pro Pro Leu Val Val Ala Tyr Ala Leu Ala Gly Ser Ile Arg Phe
    530                 535                 540 gat att gaa aac gac gta ctc ggc gtt gca gac ggc aag gaa atc cgc   1680
Asp Ile Glu Asn Asp Val Leu Gly Val Ala Asp Gly Lys Glu Ile Arg
545                 550                 555                 560 ctg aaa gac att tgg cct gcc gat gaa gaa atc gat gcc gtc gtt gcc   1728
Leu Lys Asp Ile Trp Pro Ala Asp Glu Glu Ile Asp Ala Val Val Ala
                565                 570                 575 gaa tat gtg aaa ccg cag cag ttc cgc gat gtg tat gta ccg atg ttc   1776
Glu Tyr Val Lys Pro Gln Gln Phe Arg Asp Val Tyr Val Pro Met Phe
                580                 585                 590 gac acc ggc aca gcg caa aaa gca cct agt ccg ctg tac gat tgg cgt   1824
Asp Thr Gly Thr Ala Gln Lys Ala Pro Ser Pro Leu Tyr Asp Trp Arg
            595                 600                 605 ccg atg tcc acc tac atc cgc cgt ccg cct tac tgg gaa ggc gcg ctg   1872
Pro Met Ser Thr Tyr Ile Arg Arg Pro Pro Tyr Trp Glu Gly Ala Leu
    610                 615                 620 gca ggg gaa cgc aca tta aga ggt atg cgt ccg ctg gcg att ttg ccc   1920
Ala Gly Glu Arg Thr Leu Arg Gly Met Arg Pro Leu Ala Ile Leu Pro
625                 630                 635                 640 gac aac atc acc acc gac cac ctc tcg ccg tcc aat gcg att ttg gcc   1968
Asp Asn Ile Thr Thr Asp His Leu Ser Pro Ser Asn Ala Ile Leu Ala
                645                 650                 655 gtc agt gcc gca ggc gag tat ttg gcg aaa atg ggt ttg cct gaa gaa   2016
Val Ser Ala Ala Gly Glu Tyr Leu Ala Lys Met Gly Leu Pro Glu Glu
            660                 665                 670 gac ttc aac tct tac gca acc cac cgc ggc gac cac ttg acc gcc caa   2064
Asp Phe Asn Ser Tyr Ala Thr His Arg Gly Asp His Leu Thr Ala Gln
            675                 680                 685 cgc gct acc ttc gcc aat ccg aaa ctg ttt aac gaa atg gtg aaa aac   2112
Arg Ala Thr Phe Ala Asn Pro Lys Leu Phe Asn Glu Met Val Lys Asn
    690                 695                 700 gaa gac ggc agc gtg cgc caa ggc tcg ttc gcc cgc gtc gaa ccc gaa   2160
Glu Asp Gly Ser Val Arg Gln Gly Ser Phe Ala Arg Val Glu Pro Glu
705                 710                 715                 720
```

| | | |
|---|---|---|
| ggc gaa acc atg cgc atg tgg gaa gcc atc gaa acc tat atg aac cgc<br>Gly Glu Thr Met Arg Met Trp Glu Ala Ile Glu Thr Tyr Met Asn Arg<br>725                      730                   735 | | 2208 |
| aaa cag ccg ctc atc atc att gcc ggt gcg gac tat ggt caa ggc tca<br>Lys Gln Pro Leu Ile Ile Ile Ala Gly Ala Asp Tyr Gly Gln Gly Ser<br>     740                   745                       750 | | 2256 |
| agc cgc gac tgg gct gca aaa ggc gta cgc ctc gcc ggc gta gaa gcg<br>Ser Arg Asp Trp Ala Ala Lys Gly Val Arg Leu Ala Gly Val Glu Ala<br>         755                   760                  765 | | 2304 |
| att gtt gcc gaa ggc ttc gag cgt atc cac cgc acc aac ctt atc ggc<br>Ile Val Ala Glu Gly Phe Glu Arg Ile His Arg Thr Asn Leu Ile Gly<br>770                      775                   780 | | 2352 |
| atg ggc gtg ttg ccg ctg cag ttc aaa ccc gac acc aac cgc cat acc<br>Met Gly Val Leu Pro Leu Gln Phe Lys Pro Asp Thr Asn Arg His Thr<br>785                      790                   795                  800 | | 2400 |
| ctg caa ctg gac ggt acg gaa acc tac gac gtg gtc ggc gaa cgc aca<br>Leu Gln Leu Asp Gly Thr Glu Thr Tyr Asp Val Val Gly Glu Arg Thr<br>                 805                   810                  815 | | 2448 |
| ccg cgc tgc gac ctg acc ctc gtg att cac cgt aaa aac ggc gaa acc<br>Pro Arg Cys Asp Leu Thr Leu Val Ile His Arg Lys Asn Gly Glu Thr<br>         820                   825                  830 | | 2496 |
| gtc gaa gtt ccc gtt acc tgc cgc ctc gat act gca gaa gaa gta ttg<br>Val Glu Val Pro Val Thr Cys Arg Leu Asp Thr Ala Glu Glu Val Leu<br>835                      840                   845 | | 2544 |
| gta tat gaa gcc ggc ggc gtg ttg caa cgg ttt gca cag gat ttt ttg<br>Val Tyr Glu Ala Gly Gly Val Leu Gln Arg Phe Ala Gln Asp Phe Leu<br>     850                   855                       860 | | 2592 |
| gaa ggg aac gcg gct tag<br>Glu Gly Asn Ala Ala<br>865 | | 2610 |

<210> SEQ ID NO 42
<211> LENGTH: 869
<212> TYPE: PRT
<213> ORGANISM: Neisseria meningitidis

<400> SEQUENCE: 42

Met Ala Ala Asn Gln Arg Tyr Arg Lys Pro Leu Pro Gly Thr Asp Leu
1               5                   10                  15

Glu Tyr Tyr Asp Ala Arg Ala Ala Cys Glu Asp Ile Lys Pro Gly Ser
            20                  25                  30

Tyr Asp Lys Leu Pro Tyr Thr Ser Arg Ile Leu Ala Glu Asn Leu Val
        35                  40                  45

Asn Arg Ala Asp Lys Val Asp Leu Pro Thr Leu Gln Ser Trp Leu Gly
    50                  55                  60

Gln Leu Ile Glu Gly Lys Gln Glu Ile Asp Phe Pro Trp Tyr Pro Ala
65                  70                  75                  80

Arg Val Val Cys His Asp Ile Leu Gly Gln Thr Ala Leu Val Asp Leu
                85                  90                  95

Ala Gly Leu Arg Asp Ala Ile Ala Glu Lys Gly Gly Asp Pro Ala Lys
            100                 105                 110

Val Asn Pro Val Ala Lys Pro Ser Phe Ile Val Asp His Ser Leu
        115                 120                 125

Ala Val Glu Cys Gly Gly Tyr Asp Pro Asp Ala Phe Arg Lys Asn Arg
    130                 135                 140

Gln Ile Glu Asp Arg Arg Asn Glu Asp Arg Phe His Phe Ile Asn Trp
145                 150                 155                 160

Thr Lys Thr Ala Phe Glu Asn Val Asp Val Ile Pro Ala Gly Asn Gly

-continued

```
                165                 170                 175
Ile Met His Gln Ile Asn Leu Glu Lys Met Ser Pro Val Gln Val
            180                 185                 190
Lys Asn Gly Val Ala Phe Pro Asp Thr Cys Val Gly Thr Asp Ser His
        195                 200                 205
Thr Pro His Val Asp Ala Leu Gly Val Ile Ser Val Gly Val Gly Gly
    210                 215                 220
Leu Glu Ala Glu Thr Val Met Leu Gly Arg Ala Ser Met Met Arg Leu
225                 230                 235                 240
Pro Asp Ile Val Gly Val Glu Leu Asn Gly Lys Arg Gln Ala Gly Ile
            245                 250                 255
Thr Ala Thr Asp Ile Val Leu Ala Leu Thr Glu Phe Leu Arg Lys Glu
        260                 265                 270
Arg Val Val Gly Ala Phe Val Glu Phe Phe Gly Glu Gly Ala Arg Ser
    275                 280                 285
Leu Ser Ile Gly Asp Arg Ala Thr Ile Ser Asn Met Thr Pro Glu Phe
290                 295                 300
Gly Ala Thr Ala Ala Met Phe Ala Ile Asp Glu Gln Thr Ile Asp Tyr
305                 310                 315                 320
Leu Lys Leu Thr Gly Arg Asp Asp Ala Gln Val Lys Leu Val Glu Thr
            325                 330                 335
Tyr Ala Lys Thr Ala Gly Leu Trp Ala Asp Ala Leu Lys Thr Ala Val
            340                 345                 350
Tyr Pro Arg Val Leu Lys Phe Asp Leu Ser Ser Val Thr Arg Asn Met
        355                 360                 365
Ala Gly Pro Ser Asn Pro His Ala Arg Phe Ala Thr Ala Asp Leu Ala
    370                 375                 380
Ser Lys Gly Leu Ala Lys Pro Tyr Glu Glu Pro Ser Asp Gly Gln Met
385                 390                 395                 400
Pro Asp Gly Ala Val Ile Ile Ala Ala Ile Thr Ser Cys Thr Asn Thr
            405                 410                 415
Ser Asn Pro Arg Asn Val Val Ala Ala Leu Leu Ala Arg Asn Ala
        420                 425                 430
Asn Cys Phe Gly Leu Lys Arg Lys Pro Trp Val Lys Thr Ser Phe Ala
        435                 440                 445
Pro Gly Ser Lys Val Ala Glu Ile Tyr Leu Lys Glu Ala Gly Leu Leu
    450                 455                 460
Pro Glu Met Glu Lys Leu Gly Phe Gly Ile Val Ala Phe Ala Cys Thr
465                 470                 475                 480
Thr Cys Asn Gly Met Ser Gly Ala Leu Asp Pro Lys Ile Gln Lys Glu
            485                 490                 495
Ile Ile Asp Arg Asp Leu Tyr Ala Thr Ala Val Leu Ser Gly Asn Arg
        500                 505                 510
Asn Phe Asp Gly Arg Val His Pro Tyr Ala Lys Gln Ala Phe Leu Ala
        515                 520                 525
Ser Pro Pro Leu Val Val Ala Tyr Ala Leu Ala Gly Ser Ile Arg Phe
    530                 535                 540
Asp Ile Glu Asn Asp Val Leu Gly Val Ala Asp Gly Lys Glu Ile Arg
545                 550                 555                 560
Leu Lys Asp Ile Trp Pro Ala Asp Glu Glu Ile Asp Ala Val Val Ala
            565                 570                 575
Glu Tyr Val Lys Pro Gln Gln Phe Arg Asp Val Tyr Val Pro Met Phe
        580                 585                 590
```

```
Asp Thr Gly Thr Ala Gln Lys Ala Pro Ser Pro Leu Tyr Asp Trp Arg
            595                 600                 605

Pro Met Ser Thr Tyr Ile Arg Arg Pro Pro Tyr Trp Glu Gly Ala Leu
        610                 615                 620

Ala Gly Glu Arg Thr Leu Arg Gly Met Arg Pro Leu Ala Ile Leu Pro
625                 630                 635                 640

Asp Asn Ile Thr Thr Asp His Leu Ser Pro Ser Asn Ala Ile Leu Ala
                645                 650                 655

Val Ser Ala Ala Gly Glu Tyr Leu Ala Lys Met Gly Leu Pro Glu Glu
            660                 665                 670

Asp Phe Asn Ser Tyr Ala Thr His Arg Gly Asp His Leu Thr Ala Gln
        675                 680                 685

Arg Ala Thr Phe Ala Asn Pro Lys Leu Phe Asn Glu Met Val Lys Asn
690                 695                 700

Glu Asp Gly Ser Val Arg Gln Gly Ser Phe Ala Arg Val Glu Pro Glu
705                 710                 715                 720

Gly Glu Thr Met Arg Met Trp Glu Ala Ile Glu Thr Tyr Met Asn Arg
                725                 730                 735

Lys Gln Pro Leu Ile Ile Ile Ala Gly Ala Asp Tyr Gly Gln Gly Ser
            740                 745                 750

Ser Arg Asp Trp Ala Ala Lys Gly Val Arg Leu Ala Gly Val Glu Ala
        755                 760                 765

Ile Val Ala Glu Gly Phe Glu Arg Ile His Arg Thr Asn Leu Ile Gly
770                 775                 780

Met Gly Val Leu Pro Leu Gln Phe Lys Pro Asp Thr Asn Arg His Thr
785                 790                 795                 800

Leu Gln Leu Asp Gly Thr Glu Thr Tyr Asp Val Val Gly Glu Arg Thr
                805                 810                 815

Pro Arg Cys Asp Leu Thr Leu Val Ile His Arg Lys Asn Gly Glu Thr
            820                 825                 830

Val Glu Val Pro Val Thr Cys Arg Leu Asp Thr Ala Glu Glu Val Leu
        835                 840                 845

Val Tyr Glu Ala Gly Gly Val Leu Gln Arg Phe Ala Gln Asp Phe Leu
850                 855                 860

Glu Gly Asn Ala Ala
865

<210> SEQ ID NO 43
<211> LENGTH: 1170
<212> TYPE: DNA
<213> ORGANISM: Neisseria meningitidis
<220> FEATURE:
<221> NAME/KEY: CDS
<222> LOCATION: (1)..(1167)

<400> SEQUENCE: 43 atg ccg caa att aaa att ccc gcc gtt tac tac cgt ggc ggt aca tca      48
Met Pro Gln Ile Lys Ile Pro Ala Val Tyr Tyr Arg Gly Gly Thr Ser
 1               5                  10                  15 aaa ggc gtg ttt ttc aaa cgt tcc gac ctg ccc gag gcg gcg cgg gaa      96
Lys Gly Val Phe Phe Lys Arg Ser Asp Leu Pro Glu Ala Ala Arg Glu
             20                  25                  30 gcg gga agc gca cgc gac aaa atc ctc ttg cgc gta ctc ggc agc ccg     144
Ala Gly Ser Ala Arg Asp Lys Ile Leu Leu Arg Val Leu Gly Ser Pro
         35                  40                  45 gac ccc tac ggc aag cag ata gac ggt ttg ggc aac gcc agt tcg tcc     192
```

```
                -continued

Asp Pro Tyr Gly Lys Gln Ile Asp Gly Leu Gly Asn Ala Ser Ser Ser
    50              55                  60 acc agc aaa gcc gtg att ttg gac aag tcc gaa cgc acc gat cac gat      240
Thr Ser Lys Ala Val Ile Leu Asp Lys Ser Glu Arg Thr Asp His Asp
 65              70                  75                  80 gtc gat tac ctt ttc ggg caa gtt tcc atc gac aaa cct ttt gtc gat      288
Val Asp Tyr Leu Phe Gly Gln Val Ser Ile Asp Lys Pro Phe Val Asp
                 85                  90                  95 tgg agt ggc aac tgc ggc aac ctc acc gcc gcc gtg ggc gca ttt gcc      336
Trp Ser Gly Asn Cys Gly Asn Leu Thr Ala Ala Val Gly Ala Phe Ala
            100                 105                 110 atc gag caa ggc ttg gtc gat aaa tcc aaa atc cct tca gac ggc ccg      384
Ile Glu Gln Gly Leu Val Asp Lys Ser Lys Ile Pro Ser Asp Gly Pro
        115                 120                 125 tgt acc gtc aaa atc tgg cag aaa aac atc ggc aaa acc att att gcc      432
Cys Thr Val Lys Ile Trp Gln Lys Asn Ile Gly Lys Thr Ile Ile Ala
    130                 135                 140 cat gta ccg atg caa aac ggc gca gtt ttg gaa aca ggc gat ttt gag      480
His Val Pro Met Gln Asn Gly Ala Val Leu Glu Thr Gly Asp Phe Glu
145                 150                 155                 160 ctc gac ggc gta acg ttc ccg gca gcc gaa gta caa atc gaa ttt ctt      528
Leu Asp Gly Val Thr Phe Pro Ala Ala Glu Val Gln Ile Glu Phe Leu
                165                 170                 175 gat cca gcc gac ggc gaa ggc agt atg ttc cca acc ggc aat ttg gtc      576
Asp Pro Ala Asp Gly Glu Gly Ser Met Phe Pro Thr Gly Asn Leu Val
            180                 185                 190 gat gaa att gat gtg ccg aat ata ggc cgt ttg aaa gcc acg ctc atc      624
Asp Glu Ile Asp Val Pro Asn Ile Gly Arg Leu Lys Ala Thr Leu Ile
        195                 200                 205 aac gcg ggc att ccg acc gtt ttc ctg aat gcc gcc gac ttg ggc tac      672
Asn Ala Gly Ile Pro Thr Val Phe Leu Asn Ala Ala Asp Leu Gly Tyr
    210                 215                 220 acg ggc aaa gag ttg caa gac gac atc aac aac gat gcc gca gct ttg      720
Thr Gly Lys Glu Leu Gln Asp Asp Ile Asn Asn Asp Ala Ala Ala Leu
225                 230                 235                 240 gaa aaa ttc gag aaa atc cgc gct tac ggt gcg ctg aaa atg ggt cta      768
Glu Lys Phe Glu Lys Ile Arg Ala Tyr Gly Ala Leu Lys Met Gly Leu
                245                 250                 255 atc agc gac gta tcc gaa gct gcc gcc cgc gcg cac acg ccg aaa gtc      816
Ile Ser Asp Val Ser Glu Ala Ala Ala Arg Ala His Thr Pro Lys Val
            260                 265                 270 gcc ttc gtc gcg ccc gcc gcc gat tac acc gcc tcc agt ggc aaa acc      864
Ala Phe Val Ala Pro Ala Ala Asp Tyr Thr Ala Ser Ser Gly Lys Thr
        275                 280                 285 gtg aat gcc gcc gac atc gat ttg ctg gta cgc gcc ctg agc atg ggc      912
Val Asn Ala Ala Asp Ile Asp Leu Leu Val Arg Ala Leu Ser Met Gly
    290                 295                 300 aaa ttg cac cac gcg atg atg ggt acc gcc tct gtt gcc att gcg acc      960
Lys Leu His His Ala Met Met Gly Thr Ala Ser Val Ala Ile Ala Thr
305                 310                 315                 320 gcc gcc gcc gtg ccc ggt acg ctg gtc aac ctt gcc gca ggg gcg gga     1008
Ala Ala Ala Val Pro Gly Thr Leu Val Asn Leu Ala Ala Gly Ala Gly
                325                 330                 335 acg cgt aaa gaa gtg cgc ttc ggg cat cct tcc ggc aca ttg cgc gtc     1056
Thr Arg Lys Glu Val Arg Phe Gly His Pro Ser Gly Thr Leu Arg Val
            340                 345                 350 ggt gca gcc gcc gaa tgt cag gac gga caa tgg acg gcc acc aaa gcg     1104
Gly Ala Ala Ala Glu Cys Gln Asp Gly Gln Trp Thr Ala Thr Lys Ala
        355                 360                 365
```

```
gtt atg agc cgc agc gca cgc gtg atg atg gaa ggt tgg gtc agg gtg    1152
Val Met Ser Arg Ser Ala Arg Val Met Met Glu Gly Trp Val Arg Val
    370             375                 380 ccg gaa gat tgt ttt taa                                             1170
Pro Glu Asp Cys Phe
385

<210> SEQ ID NO 44
<211> LENGTH: 389
<212> TYPE: PRT
<213> ORGANISM: Neisseria meningitidis

<400> SEQUENCE: 44

Met Pro Gln Ile Lys Ile Pro Ala Val Tyr Tyr Arg Gly Gly Thr Ser
  1               5                  10                  15

Lys Gly Val Phe Phe Lys Arg Ser Asp Leu Pro Glu Ala Ala Arg Glu
                 20                  25                  30

Ala Gly Ser Ala Arg Asp Lys Ile Leu Leu Arg Val Leu Gly Ser Pro
             35                  40                  45

Asp Pro Tyr Gly Lys Gln Ile Asp Gly Leu Gly Asn Ala Ser Ser Ser
         50                  55                  60

Thr Ser Lys Ala Val Ile Leu Asp Lys Ser Glu Arg Thr Asp His Asp
 65                  70                  75                  80

Val Asp Tyr Leu Phe Gly Gln Val Ser Ile Asp Lys Pro Phe Val Asp
                 85                  90                  95

Trp Ser Gly Asn Cys Gly Asn Leu Thr Ala Ala Val Gly Ala Phe Ala
                100                 105                 110

Ile Glu Gln Gly Leu Val Asp Lys Ser Lys Ile Pro Ser Asp Gly Pro
            115                 120                 125

Cys Thr Val Lys Ile Trp Gln Lys Asn Ile Gly Lys Thr Ile Ile Ala
130                 135                 140

His Val Pro Met Gln Asn Gly Ala Val Leu Glu Thr Gly Asp Phe Glu
145                 150                 155                 160

Leu Asp Gly Val Thr Phe Pro Ala Ala Glu Val Gln Ile Glu Phe Leu
                165                 170                 175

Asp Pro Ala Asp Gly Glu Gly Ser Met Phe Pro Thr Gly Asn Leu Val
            180                 185                 190

Asp Glu Ile Asp Val Pro Asn Ile Gly Arg Leu Lys Ala Thr Leu Ile
        195                 200                 205

Asn Ala Gly Ile Pro Thr Val Phe Leu Asn Ala Asp Leu Gly Tyr
    210                 215                 220

Thr Gly Lys Glu Leu Gln Asp Ile Asn Asn Asp Ala Ala Leu
225                 230                 235                 240

Glu Lys Phe Glu Lys Ile Arg Ala Tyr Gly Ala Leu Lys Met Gly Leu
                245                 250                 255

Ile Ser Asp Val Ser Glu Ala Ala Arg Ala His Thr Pro Lys Val
            260                 265                 270

Ala Phe Val Ala Pro Ala Ala Asp Tyr Thr Ala Ser Ser Gly Lys Thr
        275                 280                 285

Val Asn Ala Ala Asp Ile Asp Leu Leu Val Arg Ala Leu Ser Met Gly
    290                 295                 300

Lys Leu His His Ala Met Met Gly Thr Ala Ser Val Ala Ile Ala Thr
305                 310                 315                 320

Ala Ala Ala Val Pro Gly Thr Leu Val Asn Leu Ala Ala Gly Ala Gly
                325                 330                 335
```

```
                    Thr Arg Lys Glu Val Arg Phe Gly His Pro Ser Gly Thr Leu Arg Val
                                    340                 345                 350

Gly Ala Ala Ala Glu Cys Gln Asp Gly Gln Trp Thr Ala Thr Lys Ala
                                355                 360                 365

Val Met Ser Arg Ser Ala Arg Val Met Met Glu Gly Trp Val Arg Val
                            370                 375                 380

Pro Glu Asp Cys Phe
                    385

<210> SEQ ID NO 45
<211> LENGTH: 954
<212> TYPE: DNA
<213> ORGANISM: Neisseria meningitidis
<220> FEATURE:
<221> NAME/KEY: CDS
<222> LOCATION: (1)..(951)

<400> SEQUENCE: 45 atg cgc acg ccg ttt tgt tgg gca tac gcc aat gcc gcc cga ata tcg        48
Met Arg Thr Pro Phe Cys Trp Ala Tyr Ala Asn Ala Ala Arg Ile Ser
  1               5                  10                  15 gca atg ctg ccg gcg tgt tgg gcg cag gcg atg ttg gcc gaa gta atc        96
Ala Met Leu Pro Ala Cys Trp Ala Gln Ala Met Leu Ala Glu Val Ile
             20                  25                  30 agc tgc aac aag gct tcg tcg ctg ccg cag cct tcg gcg aga tcg gcg       144
Ser Cys Asn Lys Ala Ser Ser Leu Pro Gln Pro Ser Ala Arg Ser Ala
         35                  40                  45 ttt aaa tca acc tgc ttc atg ggt gat tct ccg tat ttg gtt cag ata       192
Phe Lys Ser Thr Cys Phe Met Gly Asp Ser Pro Tyr Leu Val Gln Ile
     50                  55                  60 gac ttg gtt ttt gcg ccg cag ggc ggt ggc ttc ttt caa gcc gat tat       240
Asp Leu Val Phe Ala Pro Gln Gly Gly Gly Phe Phe Gln Ala Asp Tyr
 65                  70                  75                  80 ttt gaa ttt gac ttt gct gcc gaa gcg cac ctg tgc cag cct gcc caa       288
Phe Glu Phe Asp Phe Ala Ala Glu Ala His Leu Cys Gln Pro Ala Gln
                 85                  90                  95 atc ggc ggc ggc aac ggt agc gat ttt cgg ata acc gcc ggt ggt ttg       336
Ile Gly Gly Gly Asn Gly Ser Asp Phe Arg Ile Thr Ala Gly Gly Leu
            100                 105                 110 cgc atc ggc cag cag gat aat cgg ttt gcc gcc ggg cgg cac ctg cac       384
Arg Ile Gly Gln Gln Asp Asn Arg Phe Ala Ala Gly Arg His Leu His
        115                 120                 125 ggt tcc tgc ctg aac agc gtg gga cag cat ttc caa agg ttg cga cag       432
Gly Ser Cys Leu Asn Ser Val Gly Gln His Phe Gln Arg Leu Arg Gln
    130                 135                 140 ggt cag cgg ctg tcc gtc gaa gcg gta gcc cat gcg gtt gct atc gct       480
Gly Gln Arg Leu Ser Val Glu Ala Val Ala His Ala Val Ala Ile Ala
145                 150                 155                 160 ttg cag cgt cca cgt ttc ccg ttc cag att cag acg ccc ttt ttc act       528
Leu Gln Arg Pro Arg Phe Pro Phe Gln Ile Gln Thr Pro Phe Phe Thr
                165                 170                 175 gaa agc ggc ata ttc cga cga agg aac aag gtg gat ggt atc ggt aaa       576
Glu Ser Gly Ile Phe Arg Arg Arg Asn Lys Val Asp Gly Ile Gly Lys
            180                 185                 190 cgg tat cgg ggc aat gcc gac ttt gga caa ttc ctg cgc acc ttt gcc       624
Arg Tyr Arg Gly Asn Ala Asp Phe Gly Gln Phe Leu Arg Thr Phe Ala
        195                 200                 205 gat ggg gag ata atc gcc ttt ttg cag cat tct gcc ctg atg gcc gcc       672
Asp Gly Glu Ile Ile Ala Phe Leu Gln His Ser Ala Leu Met Ala Ala
    210                 215                 220
```

-continued

| | |
|---|---|
| gaa acc ggc ttt cag gtc ggt gct tct cga acc cat cac ttc cgg cac<br>Glu Thr Gly Phe Gln Val Gly Ala Ser Arg Thr His His Phe Arg His<br>225                             230                             235                             240 | 720 |
| atc aaa tcc gcc cgc cac gca cac ata gcc gta cat gcc ctg cac ggc<br>Ile Lys Ser Ala Arg His Ala His Ile Ala Val His Ala Leu His Gly<br>245                             250                             255 | 768 |
| acg cac cat ttt caa ggt ctg ccc ttt gcg ggc ggt ata acg cca ata<br>Thr His His Phe Gln Gly Leu Pro Phe Ala Gly Gly Ile Thr Pro Ile<br>             260                             265                             270 | 816 |
| cga ata gac cgg ttc gcc gtc caa ttc gcc ctg ata cac ggc acc ggt<br>Arg Ile Asp Arg Phe Ala Val Gln Phe Arg Leu Ile His Gly Thr Gly<br>275                             280                             285 | 864 |
| gag aca aaa cgg cgt atc ccg ttc aaa cac cag cat tat ccc gcc caa<br>Glu Thr Lys Arg Arg Ile Pro Phe Lys His Gln His Tyr Pro Ala Gln<br>             290                             295                             300 | 912 |
| agc gat ttc gat tgc ggc cgt gcc ttc gtc gtt gcc caa taa<br>Ser Asp Phe Asp Cys Gly Arg Ala Phe Val Val Ala Gln<br>305                             310                             315 | 954 |

<210> SEQ ID NO 46
<211> LENGTH: 317
<212> TYPE: PRT
<213> ORGANISM: Neisseria meningitidis

<400> SEQUENCE: 46

Met Arg Thr Pro Phe Cys Trp Ala Tyr Ala Asn Ala Ala Arg Ile Ser
 1               5                  10                  15

Ala Met Leu Pro Ala Cys Trp Ala Gln Ala Met Leu Ala Glu Val Ile
            20                  25                  30

Ser Cys Asn Lys Ala Ser Ser Leu Pro Gln Pro Ser Ala Arg Ser Ala
        35                  40                  45

Phe Lys Ser Thr Cys Phe Met Gly Asp Ser Pro Tyr Leu Val Gln Ile
    50                  55                  60

Asp Leu Val Phe Ala Pro Gln Gly Gly Gly Phe Gln Ala Asp Tyr
65                  70                  75                  80

Phe Glu Phe Asp Phe Ala Ala Glu Ala His Leu Cys Gln Pro Ala Gln
                85                  90                  95

Ile Gly Gly Gly Asn Gly Ser Asp Phe Arg Ile Thr Ala Gly Gly Leu
           100                 105                 110

Arg Ile Gly Gln Gln Asp Asn Arg Phe Ala Ala Gly Arg His Leu His
       115                 120                 125

Gly Ser Cys Leu Asn Ser Val Gly Gln His Phe Gln Arg Leu Arg Gln
   130                 135                 140

Gly Gln Arg Leu Ser Val Glu Ala Val Ala His Ala Val Ala Ile Ala
145                 150                 155                 160

Leu Gln Arg Pro Arg Phe Pro Phe Gln Ile Gln Thr Pro Phe Phe Thr
                165                 170                 175

Glu Ser Gly Ile Phe Arg Arg Asn Lys Val Asp Gly Ile Gly Lys
            180                 185                 190

Arg Tyr Arg Gly Asn Ala Asp Phe Gly Gln Phe Leu Arg Thr Phe Ala
        195                 200                 205

Asp Gly Glu Ile Ile Ala Phe Leu Gln His Ser Ala Leu Met Ala Ala
    210                 215                 220

Glu Thr Gly Phe Gln Val Gly Ala Ser Arg Thr His His Phe Arg His
225                 230                 235                 240

Ile Lys Ser Ala Arg His Ala His Ile Ala Val His Ala Leu His Gly
                245                 250                 255

-continued

```
Thr His His Phe Gln Gly Leu Pro Phe Ala Gly Ile Thr Pro Ile
        260                 265                 270

Arg Ile Asp Arg Phe Ala Val Gln Phe Arg Leu Ile His Gly Thr Gly
    275                 280                 285

Glu Thr Lys Arg Arg Ile Pro Phe Lys His Gln His Tyr Pro Ala Gln
290                 295                 300

Ser Asp Phe Asp Cys Gly Arg Ala Phe Val Val Ala Gln
305                 310                 315

<210> SEQ ID NO 47
<211> LENGTH: 648
<212> TYPE: DNA
<213> ORGANISM: Neisseria meningitidis
<220> FEATURE:
<221> NAME/KEY: CDS
<222> LOCATION: (1)..(645)

<400> SEQUENCE: 47 atg aga ata gag atc aca cca atc agc gaa tcc gct ttg gtc tgc cga      48
Met Arg Ile Glu Ile Thr Pro Ile Ser Glu Ser Ala Leu Val Cys Arg
 1               5                  10                  15 ctg aat gcg cct tcc gaa ctg ggc aaa cag caa aag ttg tgg gcg ttt      96
Leu Asn Ala Pro Ser Glu Leu Gly Lys Gln Gln Lys Leu Trp Ala Phe
                20                  25                  30 gcc gct gcg ctc ggg cag cac gac agg att gag gaa gtg gtg gtc ggc     144
Ala Ala Ala Leu Gly Gln His Asp Arg Ile Glu Glu Val Val Val Gly
            35                  40                  45 atg aac aat ctg acc gtg ttc acc cgt ttc gat acc gat ttg gcg acg     192
Met Asn Asn Leu Thr Val Phe Thr Arg Phe Asp Thr Asp Leu Ala Thr
        50                  55                  60 ctt gcc gat gaa ttg caa tat gtg tgg gaa cac acc gcc gtt aca gac     240
Leu Ala Asp Glu Leu Gln Tyr Val Trp Glu His Thr Ala Val Thr Asp
 65                  70                  75                  80 cat cag ggc aaa ctg gtg gaa att ccc gtc tgc tac ggc ggc gaa tac     288
His Gln Gly Lys Leu Val Glu Ile Pro Val Cys Tyr Gly Gly Glu Tyr
                85                  90                  95 ggc ccg gat ttg gcg gaa gtc gct gct ttc cat cag acg gtt att tcc     336
Gly Pro Asp Leu Ala Glu Val Ala Ala Phe His Gln Thr Val Ile Ser
            100                 105                 110 gaa atc gtc cgc cgc cat acg gcg caa act tat acc gta ttt atg atg     384
Glu Ile Val Arg Arg His Thr Ala Gln Thr Tyr Thr Val Phe Met Met
        115                 120                 125 ggc ttc cag cct ggt ttc cct tat ctg ggc ggc ttg ccc gaa gca ttg     432
Gly Phe Gln Pro Gly Phe Pro Tyr Leu Gly Gly Leu Pro Glu Ala Leu
    130                 135                 140 cac acg ccc cgc cgt gcc gtg ccg aga acg tcc gtt cct gcc ggt tcg     480
His Thr Pro Arg Arg Ala Val Pro Arg Thr Ser Val Pro Ala Gly Ser
145                 150                 155                 160 gtc ggt atc ggc ggc agt cag acc ggt gtg tat ccg ttc gct tcg ccc     528
Val Gly Ile Gly Gly Ser Gln Thr Gly Val Tyr Pro Phe Ala Ser Pro
                165                 170                 175 ggc ggc tgg cag att atc ggc aga acc gaa tta ccc ttg ttc cga gcc     576
Gly Gly Trp Gln Ile Ile Gly Arg Thr Glu Leu Pro Leu Phe Arg Ala
            180                 185                 190 gat ttg aat ccg ccg acc ctg ctg gcg gcg ggt gac caa gtc cgc ttt     624
Asp Leu Asn Pro Pro Thr Leu Leu Ala Ala Gly Asp Gln Val Arg Phe
        195                 200                 205 gtt gca gaa agg att gag cca tga                                      648
Val Ala Glu Arg Ile Glu Pro
    210                 215
```

<210> SEQ ID NO 48
<211> LENGTH: 215
<212> TYPE: PRT
<213> ORGANISM: Neisseria meningitidis

<400> SEQUENCE: 48

```
Met Arg Ile Glu Ile Thr Pro Ile Ser Glu Ser Ala Leu Val Cys Arg
 1               5                  10                  15

Leu Asn Ala Pro Ser Glu Leu Gly Lys Gln Gln Lys Leu Trp Ala Phe
            20                  25                  30

Ala Ala Ala Leu Gly Gln His Asp Arg Ile Glu Glu Val Val Val Gly
        35                  40                  45

Met Asn Asn Leu Thr Val Phe Thr Arg Phe Asp Thr Asp Leu Ala Thr
    50                  55                  60

Leu Ala Asp Glu Leu Gln Tyr Val Trp Glu His Thr Ala Val Thr Asp
65                  70                  75                  80

His Gln Gly Lys Leu Val Glu Ile Pro Val Cys Tyr Gly Gly Glu Tyr
                85                  90                  95

Gly Pro Asp Leu Ala Glu Val Ala Ala Phe His Gln Thr Val Ile Ser
            100                 105                 110

Glu Ile Val Arg Arg His Thr Ala Gln Thr Tyr Thr Val Phe Met Met
        115                 120                 125

Gly Phe Gln Pro Gly Phe Pro Tyr Leu Gly Gly Leu Pro Glu Ala Leu
    130                 135                 140

His Thr Pro Arg Arg Ala Val Pro Arg Thr Ser Val Pro Ala Gly Ser
145                 150                 155                 160

Val Gly Ile Gly Gly Ser Gln Thr Gly Val Tyr Pro Phe Ala Ser Pro
                165                 170                 175

Gly Gly Trp Gln Ile Ile Gly Arg Thr Glu Leu Pro Leu Phe Arg Ala
            180                 185                 190

Asp Leu Asn Pro Pro Thr Leu Leu Ala Ala Gly Asp Gln Val Arg Phe
        195                 200                 205

Val Ala Glu Arg Ile Glu Pro
    210                 215
```

<210> SEQ ID NO 49
<211> LENGTH: 930
<212> TYPE: DNA
<213> ORGANISM: Neisseria meningitidis
<220> FEATURE:
<221> NAME/KEY: CDS
<222> LOCATION: (1)..(927)

<400> SEQUENCE: 49

```
atg att cac gtt tcg gca gtg cag gca ccg gcg cat att cag gat acc      48
Met Ile His Val Ser Ala Val Gln Ala Pro Ala His Ile Gln Asp Thr
 1               5                  10                  15 gga cgc tac gga cac cgg cgt tac ggc atc ggt cat gcc ggt gcg atg      96
Gly Arg Tyr Gly His Arg Arg Tyr Gly Ile Gly His Ala Gly Ala Met
            20                  25                  30 gac acg gtt gct ttg gcg gcg ggt aat att tta ttg gca aac gac gaa     144
Asp Thr Val Ala Leu Ala Ala Gly Asn Ile Leu Leu Gly Asn Asp Glu
        35                  40                  45 ggc acg gcc gca atc gaa atc gct ttg ggc ggg ata atg ctg gtg ttt     192
Gly Thr Ala Ala Ile Glu Ile Ala Leu Gly Gly Ile Met Leu Val Phe
    50                  55                  60 gaa cgg gat acg ccg ttt tgt ctc acc ggt gcc gtg tat cag gcg gaa     240
```

```
Glu Arg Asp Thr Pro Phe Cys Leu Thr Gly Ala Val Tyr Gln Ala Glu
 65                  70                  75                  80 ttg gac ggc gaa ccg gtc tat tcg tat tgg cgt tat acc gcc cgc aaa    288
Leu Asp Gly Glu Pro Val Tyr Ser Tyr Trp Arg Tyr Thr Ala Arg Lys
                 85                  90                  95 ggg cag acc ttg aaa atg gtg cgt gcc gtg cag ggc atg tac ggc tat    336
Gly Gln Thr Leu Lys Met Val Arg Ala Val Gln Gly Met Tyr Gly Tyr
            100                 105                 110 gtg tgc gtg gcg ggc gga ttt gat gtg ccg gaa gtg atg ggt tcg aga    384
Val Cys Val Ala Gly Gly Phe Asp Val Pro Glu Val Met Gly Ser Arg
        115                 120                 125 agc acc gac ctg aaa gcc ggt ttc ggc ggc cat cag ggc aga atg ctg    432
Ser Thr Asp Leu Lys Ala Gly Phe Gly Gly His Gln Gly Arg Met Leu
    130                 135                 140 caa aaa ggc gat tat ctc ccc atc ggc aaa ggt gcg cag gaa ttg tcc    480
Gln Lys Gly Asp Tyr Leu Pro Ile Gly Lys Gly Ala Gln Glu Leu Ser
145                 150                 155                 160 aaa gtc ggc att gcc ccg ata ccg ttt acc gat acc atc cac ctt gtt    528
Lys Val Gly Ile Ala Pro Ile Pro Phe Thr Asp Thr Ile His Leu Val
                165                 170                 175 cct tcg tcg gaa tat gcc gct ttc agt gaa aaa ggg cgt ctg aat ctg    576
Pro Ser Ser Glu Tyr Ala Ala Phe Ser Glu Lys Gly Arg Leu Asn Leu
            180                 185                 190 gaa cgg gaa acg tgg acg ctg caa agc gat agc aac cgc atg ggc tac    624
Glu Arg Glu Thr Trp Thr Leu Gln Ser Asp Ser Asn Arg Met Gly Tyr
        195                 200                 205 cgc ttc gac gga cag ccg ctg acc ctg tcg caa cct ttg gaa atg ctg    672
Arg Phe Asp Gly Gln Pro Leu Thr Leu Ser Gln Pro Leu Glu Met Leu
    210                 215                 220 tcc cac gct gtt cag gca gga acc gtg cag gtg ccg ccc ggc ggc aaa    720
Ser His Ala Val Gln Ala Gly Thr Val Gln Val Pro Pro Gly Gly Lys
225                 230                 235                 240 ccg att atc ctg ctg gcc gat gcg caa acc acc ggc ggt tat ccg aaa    768
Pro Ile Ile Leu Leu Ala Asp Ala Gln Thr Thr Gly Gly Tyr Pro Lys
                245                 250                 255 atc gct acc gtt gcc gcc gcc gat ttg ggc agg ctg gca cag gtg cgc    816
Ile Ala Thr Val Ala Ala Ala Asp Leu Gly Arg Leu Ala Gln Val Arg
            260                 265                 270 ttc ggc agc aaa gtc aaa ttc aaa ata atc ggc ttg aaa gaa gcc acc    864
Phe Gly Ser Lys Val Lys Phe Lys Ile Ile Gly Leu Lys Glu Ala Thr
        275                 280                 285 gcc ctg cgg cgc aaa aac caa gtc tat ctg aac caa ata cgg aga atc    912
Ala Leu Arg Arg Lys Asn Gln Val Tyr Leu Asn Gln Ile Arg Arg Ile
    290                 295                 300 acc cat gaa gca ggt tga                                            930
Thr His Glu Ala Gly
305

<210> SEQ ID NO 50
<211> LENGTH: 309
<212> TYPE: PRT
<213> ORGANISM: Neisseria meningitidis

<400> SEQUENCE: 50

Met Ile His Val Ser Ala Val Gln Ala Pro His Ile Gln Asp Thr
  1               5                  10                  15

Gly Arg Tyr Gly His Arg Arg Tyr Gly Ile Gly His Ala Gly Ala Met
                 20                  25                  30

Asp Thr Val Ala Leu Ala Ala Gly Asn Ile Leu Leu Gly Asn Asp Glu
            35                  40                  45
```

```
Gly Thr Ala Ala Ile Glu Ile Ala Leu Gly Gly Ile Met Leu Val Phe
 50                  55                  60

Glu Arg Asp Thr Pro Phe Cys Leu Thr Gly Ala Val Tyr Gln Ala Glu
 65                  70                  75                  80

Leu Asp Gly Glu Pro Val Tyr Ser Tyr Trp Arg Tyr Thr Ala Arg Lys
                 85                  90                  95

Gly Gln Thr Leu Lys Met Val Arg Ala Val Gln Gly Met Tyr Gly Tyr
            100                 105                 110

Val Cys Val Ala Gly Gly Phe Asp Val Pro Glu Val Met Gly Ser Arg
        115                 120                 125

Ser Thr Asp Leu Lys Ala Gly Phe Gly Gly His Gln Gly Arg Met Leu
130                 135                 140

Gln Lys Gly Asp Tyr Leu Pro Ile Gly Lys Gly Ala Gln Glu Leu Ser
145                 150                 155                 160

Lys Val Gly Ile Ala Pro Ile Pro Phe Thr Asp Thr Ile His Leu Val
                165                 170                 175

Pro Ser Ser Glu Tyr Ala Ala Phe Ser Glu Lys Gly Arg Leu Asn Leu
            180                 185                 190

Glu Arg Glu Thr Trp Thr Leu Gln Ser Asp Ser Asn Arg Met Gly Tyr
        195                 200                 205

Arg Phe Asp Gly Gln Pro Leu Thr Leu Ser Gln Pro Leu Glu Met Leu
210                 215                 220

Ser His Ala Val Gln Ala Gly Thr Val Gln Val Pro Gly Gly Lys
225                 230                 235                 240

Pro Ile Ile Leu Leu Ala Asp Ala Gln Thr Thr Gly Gly Tyr Pro Lys
                245                 250                 255

Ile Ala Thr Val Ala Ala Ala Asp Leu Gly Arg Leu Ala Gln Val Arg
            260                 265                 270

Phe Gly Ser Lys Val Lys Phe Lys Ile Ile Gly Leu Lys Glu Ala Thr
        275                 280                 285

Ala Leu Arg Arg Lys Asn Gln Val Tyr Leu Asn Gln Ile Arg Arg Ile
290                 295                 300

Thr His Glu Ala Gly
305

<210> SEQ ID NO 51
<211> LENGTH: 2094
<212> TYPE: DNA
<213> ORGANISM: Neisseria meningitidis
<220> FEATURE:
<221> NAME/KEY: CDS
<222> LOCATION: (1)..(2091)

<400> SEQUENCE: 51 atg aat tcg acc gca agt aaa acc ctg aaa gga ttg tcg ctg gtg ttt     48
Met Asn Ser Thr Ala Ser Lys Thr Leu Lys Gly Leu Ser Leu Val Phe
 1               5                  10                  15 ttc gcc tct gga ttc tgc gcc ctg att tac cag gtc agc tgg cag agg     96
Phe Ala Ser Gly Phe Cys Ala Leu Ile Tyr Gln Val Ser Trp Gln Arg
             20                  25                  30 ctt cta ttc agt cac ata ggt atc gat ttg agt tcg att act gtc att    144
Leu Leu Phe Ser His Ile Gly Ile Asp Leu Ser Ser Ile Thr Val Ile
         35                  40                  45 att tct gta ttt atg gtc ggc ttg ggt gta ggt gcg tat ttc ggt gga    192
Ile Ser Val Phe Met Val Gly Leu Gly Val Gly Ala Tyr Phe Gly Gly
     50                  55                  60
```

| | | |
|---|---|---|
| cgc att gct gac cgt ttt cct tca agt atc atc ccc ctg ttt tgc atc<br>Arg Ile Ala Asp Arg Phe Pro Ser Ser Ile Ile Pro Leu Phe Cys Ile<br>65                            70                        75                        80 | | 240 |
| gct gaa gta tcc atc ggt ctg ttc ggt ttg gta agc agg ggt ctg att<br>Ala Glu Val Ser Ile Gly Leu Phe Gly Leu Val Ser Arg Gly Leu Ile<br>                          85                        90                        95 | | 288 |
| tcc ggc ttg ggg cat ctt tta gtt gag gct gat ttg ccc atc atc gct<br>Ser Gly Leu Gly His Leu Leu Val Glu Ala Asp Leu Pro Ile Ile Ala<br>                        100                     105                     110 | | 336 |
| gct gcc aat ttc ctc tta ttg ctg ctt cct acc ttt atg atg ggc gcg<br>Ala Ala Asn Phe Leu Leu Leu Leu Leu Pro Thr Phe Met Met Gly Ala<br>              115                     120                     125 | | 384 |
| acc ttg ccc ttg ctg acc tgt ttt ttt aac cgg aaa ata cat aat gtt<br>Thr Leu Pro Leu Leu Thr Cys Phe Phe Asn Arg Lys Ile His Asn Val<br>130                          135                     140 | | 432 |
| ggc gag tct atc ggt acc tta tat ttt ttc aac act ttg ggt gcg gca<br>Gly Glu Ser Ile Gly Thr Leu Tyr Phe Phe Asn Thr Leu Gly Ala Ala<br>145                          150                     155                     160 | | 480 |
| ctc gga tcg ctt gcc gcc gcc gaa ttt ttc tac gtc ttt ttt acc ctc<br>Leu Gly Ser Leu Ala Ala Ala Glu Phe Phe Tyr Val Phe Phe Thr Leu<br>                        165                     170                     175 | | 528 |
| tcc caa acc att gcg ctg aca gcc tgc ttt aac ctt ctg att gct gct<br>Ser Gln Thr Ile Ala Leu Thr Ala Cys Phe Asn Leu Leu Ile Ala Ala<br>                      180                     185                     190 | | 576 |
| tca gta tgc tgc gtt aca gaa agg atg gat ata gtg aac act aaa ccg<br>Ser Val Cys Cys Val Thr Glu Arg Met Asp Ile Val Asn Thr Lys Pro<br>              195                     200                     205 | | 624 |
| aat act agt ttg att tat atg ctt tct ttc ctt agc ggc tta ttg agc<br>Asn Thr Ser Leu Ile Tyr Met Leu Ser Phe Leu Ser Gly Leu Leu Ser<br>210                          215                     220 | | 672 |
| ttg ggt ata gaa gtc ttg tgg gta agg atg ttt tcg ttc gca gca cag<br>Leu Gly Ile Glu Val Leu Trp Val Arg Met Phe Ser Phe Ala Ala Gln<br>225                          230                     235                     240 | | 720 |
| tcc gtg cct cag gca ttt tca ttt act ctt gcc tat ttt ctg acc ggt<br>Ser Val Pro Gln Ala Phe Ser Phe Thr Leu Ala Tyr Phe Leu Thr Gly<br>                        245                     250                     255 | | 768 |
| atc gcc gtc ggc gcg tat ttt ggc aaa cgg att tgc cgc agc cgc ttt<br>Ile Ala Val Gly Ala Tyr Phe Gly Lys Arg Ile Cys Arg Ser Arg Phe<br>                        260                     265                     270 | | 816 |
| gtt gat att ccc ttt atc ggg cag tgc ttc ttg tgg gcg ggt att gcc<br>Val Asp Ile Pro Phe Ile Gly Gln Cys Phe Leu Trp Ala Gly Ile Ala<br>              275                     280                     285 | | 864 |
| gac ttt ttg att ttg ggt gct gcg tgg ttg ttg acg ggt ttt tcc ggc<br>Asp Phe Leu Ile Leu Gly Ala Ala Trp Leu Leu Thr Gly Phe Ser Gly<br>290                          295                     300 | | 912 |
| ttc gtc cac cac gcc ggt atc ttc att acc ctg tct gcc gtc gtc aga<br>Phe Val His His Ala Gly Ile Phe Ile Thr Leu Ser Ala Val Val Arg<br>305                          310                     315                     320 | | 960 |
| ggg ttg att ttc ccg ctc gta cac cat gtg ggt acg gat ggc aac aaa<br>Gly Leu Ile Phe Pro Leu Val His His Val Gly Thr Asp Gly Asn Lys<br>              325                     330                     335 | | 1008 |
| tcc gga cga cag gtt tcc aat gtt tat ttc gcc aac gtt gcc ggc agt<br>Ser Gly Arg Gln Val Ser Asn Val Tyr Phe Ala Asn Val Ala Gly Ser<br>                      340                     345                     350 | | 1056 |
| gca ttg ggt ccg gtc ctt atc ggc ttt gtg ata ctt gat ttc ttg tcc<br>Ala Leu Gly Pro Val Leu Ile Gly Phe Val Ile Leu Asp Phe Leu Ser<br>              355                     360                     365 | | 1104 |
| acc caa cag att tac ctg ctc atc tgt ttg att tct gct gct gtc cct<br>Thr Gln Gln Ile Tyr Leu Leu Ile Cys Leu Ile Ser Ala Ala Val Pro<br>370                          375                     380 | | 1152 |

```
                                                                -continued ttg ttt tgt aca ctg ttc caa aaa agt ctc cga ctg aat gca gtg tcg     1200
Leu Phe Cys Thr Leu Phe Gln Lys Ser Leu Arg Leu Asn Ala Val Ser
385                 390                 395                 400 gta gca gtt tcc cta atg ttc ggc atc ctc atg ttc cta ctg ccg gat     1248
Val Ala Val Ser Leu Met Phe Gly Ile Leu Met Phe Leu Leu Pro Asp
            405                 410                 415 tct gtc ttt caa aat att gct gac cgt ccg gat cgg ctg att gaa aac     1296
Ser Val Phe Gln Asn Ile Ala Asp Arg Pro Asp Arg Leu Ile Glu Asn
        420                 425                 430 aaa cac ggc att gtt gcg gtt tac cat aga gat ggt gat aag gtt gtt     1344
Lys His Gly Ile Val Ala Val Tyr His Arg Asp Gly Asp Lys Val Val
    435                 440                 445 tat ggg gcg aat gta tac gac ggc gca tac aat acc gat gta ttc aat     1392
Tyr Gly Ala Asn Val Tyr Asp Gly Ala Tyr Asn Thr Asp Val Phe Asn
450                 455                 460 agt gtc aac ggc atc gaa cgt gcc tat ctg cta ccc tcc ctg aag tct     1440
Ser Val Asn Gly Ile Glu Arg Ala Tyr Leu Leu Pro Ser Leu Lys Ser
465                 470                 475                 480 ggc ata cgc cgc att ttc gtc gtt gga ttg agt aca ggt tcg tgg gcg     1488
Gly Ile Arg Arg Ile Phe Val Val Gly Leu Ser Thr Gly Ser Trp Ala
            485                 490                 495 cgc gtc ttg tct gcc att ccg gaa atg cag tcg atg atc gtt gcg gaa     1536
Arg Val Leu Ser Ala Ile Pro Glu Met Gln Ser Met Ile Val Ala Glu
        500                 505                 510 atc aat ccg gca tac cgt agc ctt atc gcg gac gag ccg caa atc gcc     1584
Ile Asn Pro Ala Tyr Arg Ser Leu Ile Ala Asp Glu Pro Gln Ile Ala
    515                 520                 525 ccg ctt ttg cag gac aaa cgt gtt gaa att gta ttg gat gac ggt agg     1632
Pro Leu Leu Gln Asp Lys Arg Val Glu Ile Val Leu Asp Asp Gly Arg
530                 535                 540 aaa tgg ctg cgt cgc cat cct gat gaa aaa ttc gac ctg att ttg atg     1680
Lys Trp Leu Arg Arg His Pro Asp Glu Lys Phe Asp Leu Ile Leu Met
545                 550                 555                 560 aat acg act tgg tac tgg cgt gcc tat tcc acc aac ctg ttg agt gcg     1728
Asn Thr Thr Trp Tyr Trp Arg Ala Tyr Ser Thr Asn Leu Leu Ser Ala
            565                 570                 575 gaa ttt tta aaa cag gtg caa agc cac ctt acc ccg gat ggt att gta     1776
Glu Phe Leu Lys Gln Val Gln Ser His Leu Thr Pro Asp Gly Ile Val
        580                 585                 590 atg ttt aat acc acg cac agc ccg cat gct ttt gct acc gcc gta cac     1824
Met Phe Asn Thr Thr His Ser Pro His Ala Phe Ala Thr Ala Val His
    595                 600                 605 agt att ccc tat gca tac cgc tat ggg cat atg gta gtc ggc tcg gca     1872
Ser Ile Pro Tyr Ala Tyr Arg Tyr Gly His Met Val Val Gly Ser Ala
610                 615                 620 acc ccg gta gtt ttc cct aat aaa gaa ctg ctc aag caa cgt ctc tcc     1920
Thr Pro Val Val Phe Pro Asn Lys Glu Leu Leu Lys Gln Arg Leu Ser
625                 630                 635                 640 cgg ttg att tgg ccg gaa agc ggc agg cac gta ttt gac agc agc acc     1968
Arg Leu Ile Trp Pro Glu Ser Gly Arg His Val Phe Asp Ser Ser Thr
            645                 650                 655 gtg gat gct gca gca caa aag gtt gtc tct cgt atg ctg att cag atg     2016
Val Asp Ala Ala Ala Gln Lys Val Val Ser Arg Met Leu Ile Gln Met
        660                 665                 670 acg gaa cct tcg gct ggg gcg gaa gtc att acc gac gat aat atg att     2064
Thr Glu Pro Ser Ala Gly Ala Glu Val Ile Thr Asp Asp Asn Met Ile
    675                 680                 685 gta gaa tac aaa tac ggc aga ggg att taa                             2094
Val Glu Tyr Lys Tyr Gly Arg Gly Ile
```

690              695

<210> SEQ ID NO 52
<211> LENGTH: 697
<212> TYPE: PRT
<213> ORGANISM: Neisseria meningitidis

<400> SEQUENCE: 52

Met Asn Ser Thr Ala Ser Lys Thr Leu Lys Gly Leu Ser Leu Val Phe
 1               5                  10                  15

Phe Ala Ser Gly Phe Cys Ala Leu Ile Tyr Gln Val Ser Trp Gln Arg
            20                  25                  30

Leu Leu Phe Ser His Ile Gly Ile Asp Leu Ser Ser Ile Thr Val Ile
        35                  40                  45

Ile Ser Val Phe Met Val Gly Leu Gly Val Gly Ala Tyr Phe Gly Gly
    50                  55                  60

Arg Ile Ala Asp Arg Phe Pro Ser Ser Ile Ile Pro Leu Phe Cys Ile
65                  70                  75                  80

Ala Glu Val Ser Ile Gly Leu Phe Gly Leu Val Ser Arg Gly Leu Ile
                85                  90                  95

Ser Gly Leu Gly His Leu Leu Val Glu Ala Asp Leu Pro Ile Ile Ala
            100                 105                 110

Ala Ala Asn Phe Leu Leu Leu Leu Pro Thr Phe Met Met Gly Ala
        115                 120                 125

Thr Leu Pro Leu Leu Thr Cys Phe Phe Asn Arg Lys Ile His Asn Val
130                 135                 140

Gly Glu Ser Ile Gly Thr Leu Tyr Phe Phe Asn Thr Leu Gly Ala Ala
145                 150                 155                 160

Leu Gly Ser Leu Ala Ala Ala Glu Phe Phe Tyr Val Phe Phe Thr Leu
                165                 170                 175

Ser Gln Thr Ile Ala Leu Thr Ala Cys Phe Asn Leu Leu Ile Ala Ala
            180                 185                 190

Ser Val Cys Cys Val Thr Glu Arg Met Asp Ile Val Asn Thr Lys Pro
        195                 200                 205

Asn Thr Ser Leu Ile Tyr Met Leu Ser Phe Leu Ser Gly Leu Leu Ser
210                 215                 220

Leu Gly Ile Glu Val Leu Trp Val Arg Met Phe Ser Phe Ala Ala Gln
225                 230                 235                 240

Ser Val Pro Gln Ala Phe Ser Phe Thr Leu Ala Tyr Phe Leu Thr Gly
                245                 250                 255

Ile Ala Val Gly Ala Tyr Phe Gly Lys Arg Ile Cys Arg Ser Arg Phe
            260                 265                 270

Val Asp Ile Pro Phe Ile Gly Gln Cys Phe Leu Trp Ala Gly Ile Ala
        275                 280                 285

Asp Phe Leu Ile Leu Gly Ala Ala Trp Leu Leu Thr Gly Phe Ser Gly
290                 295                 300

Phe Val His His Ala Gly Ile Phe Ile Thr Leu Ser Ala Val Val Arg
305                 310                 315                 320

Gly Leu Ile Phe Pro Leu Val His Val Gly Thr Asp Gly Asn Lys
                325                 330                 335

Ser Gly Arg Gln Val Ser Asn Val Tyr Phe Ala Asn Val Ala Gly Ser
            340                 345                 350

Ala Leu Gly Pro Val Leu Ile Gly Phe Val Ile Leu Asp Phe Leu Ser
        355                 360                 365

```
Thr Gln Gln Ile Tyr Leu Leu Ile Cys Leu Ile Ser Ala Ala Val Pro
    370                 375                 380

Leu Phe Cys Thr Leu Phe Gln Lys Ser Leu Arg Leu Asn Ala Val Ser
385                 390                 395                 400

Val Ala Val Ser Leu Met Phe Gly Ile Leu Met Phe Leu Leu Pro Asp
                405                 410                 415

Ser Val Phe Gln Asn Ile Ala Asp Arg Pro Asp Arg Leu Ile Glu Asn
            420                 425                 430

Lys His Gly Ile Val Ala Val Tyr His Arg Asp Gly Asp Lys Val Val
        435                 440                 445

Tyr Gly Ala Asn Val Tyr Asp Gly Ala Tyr Asn Thr Asp Val Phe Asn
    450                 455                 460

Ser Val Asn Gly Ile Glu Arg Ala Tyr Leu Leu Pro Ser Leu Lys Ser
465                 470                 475                 480

Gly Ile Arg Arg Ile Phe Val Val Gly Leu Ser Thr Gly Ser Trp Ala
                485                 490                 495

Arg Val Leu Ser Ala Ile Pro Glu Met Gln Ser Met Ile Val Ala Glu
            500                 505                 510

Ile Asn Pro Ala Tyr Arg Ser Leu Ile Ala Asp Glu Pro Gln Ile Ala
        515                 520                 525

Pro Leu Leu Gln Asp Lys Arg Val Glu Ile Val Leu Asp Asp Gly Arg
    530                 535                 540

Lys Trp Leu Arg Arg His Pro Asp Glu Lys Phe Asp Leu Ile Leu Met
545                 550                 555                 560

Asn Thr Thr Trp Tyr Trp Arg Ala Tyr Ser Thr Asn Leu Leu Ser Ala
                565                 570                 575

Glu Phe Leu Lys Gln Val Gln Ser His Leu Thr Pro Asp Gly Ile Val
            580                 585                 590

Met Phe Asn Thr Thr His Ser Pro His Ala Phe Ala Thr Ala Val His
        595                 600                 605

Ser Ile Pro Tyr Ala Tyr Arg Tyr Gly His Met Val Val Gly Ser Ala
    610                 615                 620

Thr Pro Val Val Phe Pro Asn Lys Glu Leu Leu Lys Gln Arg Leu Ser
625                 630                 635                 640

Arg Leu Ile Trp Pro Glu Ser Gly Arg His Val Phe Asp Ser Ser Thr
                645                 650                 655

Val Asp Ala Ala Gln Lys Val Val Ser Arg Met Leu Ile Gln Met
            660                 665                 670

Thr Glu Pro Ser Ala Gly Ala Glu Val Ile Thr Asp Asp Asn Met Ile
    675                 680                 685

Val Glu Tyr Lys Tyr Gly Arg Gly Ile
    690                 695

<210> SEQ ID NO 53
<211> LENGTH: 1040
<212> TYPE: PRT
<213> ORGANISM: Neisseria meningitidis

<400> SEQUENCE: 53

Cys Leu Gly Gly Gly Gly Gly Thr Ser Ala Pro Asp Phe Asn Ala Gly
  1               5                  10                  15

Gly Thr Gly Ile Gly Ser Asn Ser Arg Ala Thr Thr Ala Lys Ser Ala
             20                  25                  30

Ala Val Ser Tyr Ala Gly Ile Lys Asn Glu Met Cys Lys Asp Arg Ser
         35                  40                  45
```

```
Met Leu Cys Ala Gly Arg Asp Asp Val Ala Val Thr Asp Arg Asp Ala
     50                  55                  60

Lys Ile Asn Ala Pro Pro Asn Leu His Thr Gly Asp Phe Thr Asn
 65              70                  75                  80

Pro Asn Asp Ala Tyr Lys Asn Leu Ile Asn Leu Lys Pro Ala Ile Glu
                 85                  90                  95

Ala Gly Tyr Thr Gly Arg Gly Val Glu Val Gly Ile Val Asp Thr Gly
            100                 105                 110

Glu Ser Val Gly Ser Ile Ser Phe Pro Glu Leu Tyr Gly Arg Lys Glu
        115                 120                 125

His Gly Tyr Asn Glu Asn Tyr Lys Asn Tyr Thr Ala Tyr Met Arg Lys
    130                 135                 140

Glu Ala Pro Glu Asp Gly Gly Lys Asp Ile Lys Ala Ser Phe Asp
145                 150                 155                 160

Asp Glu Ala Val Ile Glu Thr Glu Ala Lys Pro Thr Asp Ile Arg His
                165                 170                 175

Val Lys Glu Ile Gly His Ile Asp Val Val Ser His Ile Ile Gly Gly
            180                 185                 190

Arg Ser Val Asp Gly Arg Pro Ala Gly Gly Ile Ala Pro Asp Ala Thr
        195                 200                 205

Leu His Ile Met Asn Thr His Asp Gly Thr Lys Asn Glu Ile Met Ser
    210                 215                 220

Ala Ala Ile Arg Asn Ala Trp Val Lys Leu Gly Glu Arg Gly Val Arg
225                 230                 235                 240

Ile Val Asn Asn Ser Phe Gly Thr Thr Ser Arg Ala Gly Thr Ala Asp
                245                 250                 255

His Phe Gln Ile Ala Asn Ser Glu Glu Gln Tyr Arg Gln Ala Leu Leu
            260                 265                 270

Ala Tyr Ser Gly Gly Asp Lys Thr Asp Glu Gly Ile Arg Leu Met Gln
        275                 280                 285

Gln Ser Asp Tyr Gly Asn Leu Ser Tyr His Ile Arg Asn Lys Asn Met
    290                 295                 300

Leu Phe Ile Phe Ser Ala Ser Asn Asp Ala Gln Ala Gln Pro Asn Thr
305                 310                 315                 320

Leu Thr Leu Leu Pro Phe Tyr Glu Lys Asp Ala Gln Lys Gly Ile Ile
                325                 330                 335

Thr Val Ala Gly Val Asp Arg Ser Gly Glu Lys Phe Asn Gly Ser Asn
            340                 345                 350

His Cys Gly Ile Thr Ala Met Trp Cys Leu Ser Ala Pro Tyr Glu Ala
        355                 360                 365

Ser Val Arg Phe Thr Arg Thr Asn Pro Ile Gln Ile Ala Gly Thr Ser
    370                 375                 380

Phe Ser Ala Pro Ile Val Thr Gly Thr Ala Ala Leu Leu Leu Gln Lys
385                 390                 395                 400

Tyr Pro Trp Met Ser Asn Asp Asn Leu Arg Thr Thr Leu Leu Thr Thr
                405                 410                 415

Ala Gln Asp Ile Gly Ala Val Gly Val Asp Ser Lys Phe Gly Trp Gly
            420                 425                 430

Leu Leu Asp Ala Gly Lys Ala Met Asn Gly Pro Ala Ser Phe Pro Phe
        435                 440                 445

Gly Asp Phe Thr Ala Asp Thr Lys Gly Thr Ser Asp Ile Ala Tyr Ser
    450                 455                 460
```

-continued

```
Phe Arg Asn Asp Ile Ser Gly Thr Gly Gly Leu Ile Lys Lys Gly Gly
465                 470                 475                 480

Ser Gln Leu Gln Leu His Gly Asn Asn Thr Tyr Thr Gly Lys Thr Ile
            485                 490                 495

Ile Glu Gly Gly Ser Leu Val Leu Tyr Gly Asn Asn Lys Ser Asp Met
        500                 505                 510

Arg Val Glu Thr Lys Gly Ala Leu Ile Tyr Asn Gly Ala Ala Ser Gly
        515                 520                 525

Gly Ser Leu Asn Ser Asp Gly Ile Val Tyr Leu Ala Asp Thr Asp Arg
    530                 535                 540

Ser Gly Ala Asn Glu Thr Val His Ile Lys Gly Asp Leu Gln Leu Gly
545                 550                 555                 560

Gly Glu Gly Thr Leu Tyr Thr Arg Leu Gly Lys Leu Leu Lys Val Asp
            565                 570                 575

Gly Thr Ala Met Thr Gly Gly Lys Leu Tyr Met Ser Ala Arg Gly Lys
        580                 585                 590

Gly Ala Gly Tyr Leu Asn Arg Thr Gly Gln Arg Val Pro Phe Leu Ser
        595                 600                 605

Ala Ala Lys Ile Gly Arg Asp Tyr Ser Phe Phe Thr Asn Ile Glu Thr
    610                 615                 620

Asp Gly Gly Leu Leu Ala Ser Leu Asp Ser Val Glu Lys Thr Ala Gly
625                 630                 635                 640

Ser Glu Gly Asp Thr Leu Ser Tyr Tyr Val Arg Arg Gly Asn Ala Ala
            645                 650                 655

Arg Thr Ala Ser Ala Ala Ala His Ser Ala Pro Ala Gly Leu Lys His
        660                 665                 670

Ala Val Glu Gln Gly Gly Ser Asn Leu Glu Asn Leu Met Val Glu Leu
    675                 680                 685

Asp Ala Ser Glu Ser Ser Ala Thr Pro Glu Thr Val Glu Thr Ala Ala
690                 695                 700

Ala Asp Arg Thr Asp Met Pro Gly Ile Arg Pro Tyr Gly Ala Thr Phe
705                 710                 715                 720

Arg Ala Ala Ala Val Gln His Ala Asn Ala Asp Gly Val Arg
            725                 730                 735

Ile Phe Asn Ser Leu Ala Ala Thr Val Tyr Ala Asp Ser Thr Ala Ala
        740                 745                 750

His Ala Asp Met Gln Gly Arg Arg Leu Lys Ala Val Ser Asp Gly Leu
        755                 760                 765

Asp His Asn Ala Thr Gly Leu Arg Val Ile Ala Gln Thr Gln Gln Asp
    770                 775                 780

Gly Gly Thr Trp Glu Gln Gly Val Glu Gly Lys Met Arg Gly Ser
785                 790                 795                 800

Thr Gln Thr Val Gly Ile Ala Ala Lys Thr Gly Glu Asn Thr Thr Ala
            805                 810                 815

Ala Ala Thr Leu Gly Met Gly His Ser Thr Trp Ser Glu Asn Ser Ala
        820                 825                 830

Asn Ala Lys Thr Asp Ser Ile Ser Leu Phe Ala Gly Ile Arg His Asp
        835                 840                 845

Ala Gly Asp Ile Gly Tyr Leu Lys Gly Leu Phe Ser Tyr Gly Arg Tyr
    850                 855                 860

Lys Asn Ser Ile Ser Arg Ser Thr Gly Ala Asp Glu His Ala Glu Gly
865                 870                 875                 880

Ser Val Asn Gly Thr Leu Met Gln Leu Gly Ala Leu Gly Gly Val Asn
```

-continued

```
                        885                 890                 895
Val Pro Phe Ala Ala Thr Gly Asp Leu Thr Val Glu Gly Gly Leu Arg
                900                 905                 910

Tyr Asp Leu Leu Lys Gln Asp Ala Phe Ala Glu Lys Gly Ser Ala Leu
            915                 920                 925

Gly Trp Ser Gly Asn Ser Leu Thr Glu Gly Thr Leu Val Gly Leu Ala
        930                 935                 940

Gly Leu Lys Leu Ser Gln Pro Leu Ser Asp Lys Ala Val Leu Phe Ala
945                 950                 955                 960

Thr Ala Gly Val Glu Arg Asp Leu Asn Gly Arg Asp Tyr Thr Val Thr
                965                 970                 975

Gly Gly Phe Thr Gly Ala Thr Ala Thr Gly Lys Thr Gly Ala Arg
            980                 985                 990

Asn Met Pro His Thr Arg Leu Val Ala Gly Leu Gly Ala Asp Val Glu
        995                1000                1005

Phe Gly Asn Gly Trp Asn Gly Leu Ala Arg Tyr Ser Tyr Ala Gly Ser
    1010                1015                1020

Lys Gln Tyr Gly Asn His Ser Gly Arg Val Gly Val Gly Tyr Arg Phe
1025                1030                1035                1040
```

<210> SEQ ID NO 54
<211> LENGTH: 858
<212> TYPE: DNA
<213> ORGANISM: Neisseria gonorrhoeae
<220> FEATURE:
<221> NAME/KEY: CDS
<222> LOCATION: (1)..(855)

<400> SEQUENCE: 54

```
atg tct gaa gaa aaa ttg aaa atg agt ttc gag cca acc gta atc gaa      48
Met Ser Glu Glu Lys Leu Lys Met Ser Phe Glu Pro Thr Val Ile Glu
  1               5                  10                  15 cat ttg ggt gta aag atg tat tcg cac act gtt cct gcg att gcc gag      96
His Leu Gly Val Lys Met Tyr Ser His Thr Val Pro Ala Ile Ala Glu
             20                  25                  30 ttg ata gcg aat gcc tac gat gca tgt gct acg gaa gtg gaa gtt agg     144
Leu Ile Ala Asn Ala Tyr Asp Ala Cys Ala Thr Glu Val Glu Val Arg
         35                  40                  45 tta ttc gat aaa ccg gag cat aaa atc gtt att aaa gat aat ggc ata     192
Leu Phe Asp Lys Pro Glu His Lys Ile Val Ile Lys Asp Asn Gly Ile
     50                  55                  60 gga atg agc ttc gat gaa atc aat gat ttt tat ttg aga atc ggt cgg     240
Gly Met Ser Phe Asp Glu Ile Asn Asp Phe Tyr Leu Arg Ile Gly Arg
 65                  70                  75                  80 aac aga agg gaa gaa aaa caa gcc tcc ccg tgc gga aga att cca acg     288
Asn Arg Arg Glu Glu Lys Gln Ala Ser Pro Cys Gly Arg Ile Pro Thr
                 85                  90                  95 ggt aaa aaa ggt ctt ggt aaa ttg gca tta ttc agg ctt ggc aac aaa     336
Gly Lys Lys Gly Leu Gly Lys Leu Ala Leu Phe Arg Leu Gly Asn Lys
            100                 105                 110 atc gaa atc tct act atc caa gga aac gaa cgg gtt act ttt act ttg     384
Ile Glu Ile Ser Thr Ile Gln Gly Asn Glu Arg Val Thr Phe Thr Leu
        115                 120                 125 gat tat gca gag att aaa aaa agt gag cgt att tat caa ccg gag ttt     432
Asp Tyr Ala Glu Ile Lys Lys Ser Glu Arg Ile Tyr Gln Pro Glu Phe
    130                 135                 140 cag aaa gag tct gtt aaa ccc aat acc gaa aac gga aca act ata act     480
Gln Lys Glu Ser Val Lys Pro Asn Thr Glu Asn Gly Thr Thr Ile Thr
145                 150                 155                 160
```

-continued

```
tta acc gag ctg acg aaa aaa caa gga tac ccg tta gat aat tat gtg      528
Leu Thr Glu Leu Thr Lys Lys Gln Gly Tyr Pro Leu Asp Asn Tyr Val
                165                 170                 175 ggg cat ctt tcc cgt tta ttt gat ttt ccg gct cag gat ttt aaa atc      576
Gly His Leu Ser Arg Leu Phe Asp Phe Pro Ala Gln Asp Phe Lys Ile
            180                 185                 190 aaa gta agc ttg aac ggc tcg gaa cca aga atc att gac gga aac cta      624
Lys Val Ser Leu Asn Gly Ser Glu Pro Arg Ile Ile Asp Gly Asn Leu
        195                 200                 205 aaa tat aat ctt gtt acc cca caa ttc gaa tgg gaa tac cag gat cta      672
Lys Tyr Asn Leu Val Thr Pro Gln Phe Glu Trp Glu Tyr Gln Asp Leu
    210                 215                 220 gca acc aat att tca tcg tta tct tca aaa ttc gaa cag tat gaa tac      720
Ala Thr Asn Ile Ser Ser Leu Ser Ser Lys Phe Glu Gln Tyr Glu Tyr
225                 230                 235                 240 agc gga tta ata caa ggt aag ttc att aca acg gaa aaa cct tta aag      768
Ser Gly Leu Ile Gln Gly Lys Phe Ile Thr Thr Glu Lys Pro Leu Lys
                245                 250                 255 aat aat atg aaa ggt att acc ttg ttt gcc aac ggc aga atg gta aat      816
Asn Asn Met Lys Gly Ile Thr Leu Phe Ala Asn Gly Arg Met Val Asn
            260                 265                 270 atg ccc gag ttt ttc act gat agc gaa tcc agc cat ttc taa              858
Met Pro Glu Phe Phe Thr Asp Ser Glu Ser Ser His Phe
        275                 280                 285
```

<210> SEQ ID NO 55
<211> LENGTH: 285
<212> TYPE: PRT
<213> ORGANISM: Neisseria gonorrhoeae

<400> SEQUENCE: 55

```
Met Ser Glu Glu Lys Leu Lys Met Ser Phe Glu Pro Thr Val Ile Glu
  1               5                  10                  15

His Leu Gly Val Lys Met Tyr Ser His Thr Val Pro Ala Ile Ala Glu
                 20                  25                  30

Leu Ile Ala Asn Ala Tyr Asp Ala Cys Ala Thr Glu Val Glu Val Arg
             35                  40                  45

Leu Phe Asp Lys Pro Glu His Lys Ile Val Ile Lys Asp Asn Gly Ile
         50                  55                  60

Gly Met Ser Phe Asp Glu Ile Asn Asp Phe Tyr Leu Arg Ile Gly Arg
 65                  70                  75                  80

Asn Arg Arg Glu Glu Lys Gln Ala Ser Pro Cys Gly Arg Ile Pro Thr
                 85                  90                  95

Gly Lys Lys Gly Leu Gly Lys Leu Ala Leu Phe Arg Leu Gly Asn Lys
            100                 105                 110

Ile Glu Ile Ser Thr Ile Gln Gly Asn Glu Arg Val Thr Phe Thr Leu
        115                 120                 125

Asp Tyr Ala Glu Ile Lys Lys Ser Glu Arg Ile Tyr Gln Pro Glu Phe
    130                 135                 140

Gln Lys Glu Ser Val Lys Pro Asn Thr Glu Asn Gly Thr Thr Ile Thr
145                 150                 155                 160

Leu Thr Glu Leu Thr Lys Lys Gln Gly Tyr Pro Leu Asp Asn Tyr Val
                165                 170                 175

Gly His Leu Ser Arg Leu Phe Asp Phe Pro Ala Gln Asp Phe Lys Ile
            180                 185                 190

Lys Val Ser Leu Asn Gly Ser Glu Pro Arg Ile Ile Asp Gly Asn Leu
        195                 200                 205
```

```
Lys Tyr Asn Leu Val Thr Pro Gln Phe Glu Trp Glu Tyr Gln Asp Leu
            210                 215                 220

Ala Thr Asn Ile Ser Ser Leu Ser Ser Lys Phe Glu Gln Tyr Glu Tyr
225                 230                 235                 240

Ser Gly Leu Ile Gln Gly Lys Phe Ile Thr Thr Glu Lys Pro Leu Lys
                245                 250                 255

Asn Asn Met Lys Gly Ile Thr Leu Phe Ala Asn Gly Arg Met Val Asn
            260                 265                 270

Met Pro Glu Phe Phe Thr Asp Ser Glu Ser Ser His Phe
        275                 280                 285
```

<210> SEQ ID NO 56
<211> LENGTH: 1575
<212> TYPE: DNA
<213> ORGANISM: Neisseria gonorrhoeae
<220> FEATURE:
<221> NAME/KEY: CDS
<222> LOCATION: (1)..(1572)

<400> SEQUENCE: 56

```
atg aaa aaa tcc ctt ttc gtt ctc ttt ctg tat tca tcc cta ctt acc        48
Met Lys Lys Ser Leu Phe Val Leu Phe Leu Tyr Ser Ser Leu Leu Thr
  1               5                  10                  15 gcc agc gaa atc gcc tat cgc ttt gta ttc gga att gaa acc tta ccg        96
Ala Ser Glu Ile Ala Tyr Arg Phe Val Phe Gly Ile Glu Thr Leu Pro
             20                  25                  30 gct gca aaa atg gcg gaa acg ttt gcg ctg aca ttt atg att gct gcg       144
Ala Ala Lys Met Ala Glu Thr Phe Ala Leu Thr Phe Met Ile Ala Ala
         35                  40                  45 ctg tat ctg ttt gcg cgt tat aag gct tcg cgg ctg ctg att gcg gtg       192
Leu Tyr Leu Phe Ala Arg Tyr Lys Ala Ser Arg Leu Leu Ile Ala Val
     50                  55                  60 ttt ttc gcg ttc agc atg att gcc aac aat gtg cat tac gcg gtt tat       240
Phe Phe Ala Phe Ser Met Ile Ala Asn Asn Val His Tyr Ala Val Tyr
 65                  70                  75                  80 caa agc tgg atg acg ggt att aac tat tgg ctg atg ctg aaa gag gtt       288
Gln Ser Trp Met Thr Gly Ile Asn Tyr Trp Leu Met Leu Lys Glu Val
                 85                  90                  95 acc gaa gtc ggc agc gcg ggc gcg tcg atg ttg gat aag ttg tgg ctg       336
Thr Glu Val Gly Ser Ala Gly Ala Ser Met Leu Asp Lys Leu Trp Leu
            100                 105                 110 cct gct ttg tgg ggc gtg gcg gaa gtc atg ttg ttt tgc agc ctt gcc       384
Pro Ala Leu Trp Gly Val Ala Glu Val Met Leu Phe Cys Ser Leu Ala
        115                 120                 125 aag ttc cgc cgt aag acg cat ttt tct gcc gat ata ctg ttt gcc ttc       432
Lys Phe Arg Arg Lys Thr His Phe Ser Ala Asp Ile Leu Phe Ala Phe
    130                 135                 140 cta atg ctg atg att ttc gtg cgt tcg ttc gac acg aaa caa gag cac       480
Leu Met Leu Met Ile Phe Val Arg Ser Phe Asp Thr Lys Gln Glu His
145                 150                 155                 160 ggt att tcg ccc aaa ccg aca tac agc cgc atc aaa gcc aat tat ttc       528
Gly Ile Ser Pro Lys Pro Thr Tyr Ser Arg Ile Lys Ala Asn Tyr Phe
                165                 170                 175 agc ttc ggt tat ttt gtc ggg cgc gtg ttg ccg tat cag ttg ttt gat       576
Ser Phe Gly Tyr Phe Val Gly Arg Val Leu Pro Tyr Gln Leu Phe Asp
            180                 185                 190 tta agc aag atc cct gtg ttc aaa cag cct gct cca agc aaa atc ggg       624
Leu Ser Lys Ile Pro Val Phe Lys Gln Pro Ala Pro Ser Lys Ile Gly
        195                 200                 205
```

|  |  |
|---|---|
| caa ggc agt att caa aat atc gtc ctg att atg ggc gaa agc gaa agc<br>Gln Gly Ser Ile Gln Asn Ile Val Leu Ile Met Gly Glu Ser Glu Ser<br>210                              215                      220 | 672 |
| gcg gcg cat ttg aaa ttg ttt ggt tac ggg cgc gaa act tcg ccg ttt<br>Ala Ala His Leu Lys Leu Phe Gly Tyr Gly Arg Glu Thr Ser Pro Phe<br>225                       230                          235                240 | 720 |
| tta acc cgg ctg tcg caa gcc gat ttt aag ccg att gtg aaa caa agt<br>Leu Thr Arg Leu Ser Gln Ala Asp Phe Lys Pro Ile Val Lys Gln Ser<br>                       245                          250                          255 | 768 |
| tat tcc gca ggc ttt atg acg gca gta tcc ctg ccc agt ttc ttt aac<br>Tyr Ser Ala Gly Phe Met Thr Ala Val Ser Leu Pro Ser Phe Phe Asn<br>                       260                          265                          270 | 816 |
| gtc ata ccg cac gcc aac ggc ttg gaa caa atc agc ggc ggc gat acc<br>Val Ile Pro His Ala Asn Gly Leu Glu Gln Ile Ser Gly Gly Asp Thr<br>              275                          280                          285 | 864 |
| aat atg ttc cgc ctc gcc aaa gag cag ggc tat gaa acg tat ttt tac<br>Asn Met Phe Arg Leu Ala Lys Glu Gln Gly Tyr Glu Thr Tyr Phe Tyr<br>290                              295                          300 | 912 |
| agt gcc cag gct gaa aac caa atg gca att ttg aac tta atc ggt aag<br>Ser Ala Gln Ala Glu Asn Gln Met Ala Ile Leu Asn Leu Ile Gly Lys<br>305                              310                          315                320 | 960 |
| aaa tgg ata gac cat ctg att cag ccg acg caa ctt ggc tac ggc aac<br>Lys Trp Ile Asp His Leu Ile Gln Pro Thr Gln Leu Gly Tyr Gly Asn<br>                       325                          330                          335 | 1008 |
| ggc gac aat atg ccc gat gag aag ctg ctg ccg ttg ttc gac aaa atc<br>Gly Asp Asn Met Pro Asp Glu Lys Leu Leu Pro Leu Phe Asp Lys Ile<br>                       340                          345                          350 | 1056 |
| aat ttg cag cag ggc agg cat ttt atc gtg ttg cac caa cgc ggt tcg<br>Asn Leu Gln Gln Gly Arg His Phe Ile Val Leu His Gln Arg Gly Ser<br>                      355                          360                          365 | 1104 |
| cac gcc cca tac ggc gca ttg ttg cag cct caa gat aaa gta ttc ggc<br>His Ala Pro Tyr Gly Ala Leu Leu Gln Pro Gln Asp Lys Val Phe Gly<br>370                              375                          380 | 1152 |
| gaa gcc gat att gtg gat aag tac gac aac acc atc cac aaa acc gac<br>Glu Ala Asp Ile Val Asp Lys Tyr Asp Asn Thr Ile His Lys Thr Asp<br>385                              390                          395                400 | 1200 |
| caa atg att caa acc gta ttc gag cag ctg caa aag cag cct gac ggc<br>Gln Met Ile Gln Thr Val Phe Glu Gln Leu Gln Lys Gln Pro Asp Gly<br>                       405                          410                          415 | 1248 |
| aac tgg ctg ttt gcc tat acc tcc gat cat ggc cag tat gtg cgc caa<br>Asn Trp Leu Phe Ala Tyr Thr Ser Asp His Gly Gln Tyr Val Arg Gln<br>                    420                          425                          430 | 1296 |
| gat atc tac aat caa ggc acg gtg cag ccc gac agc tat att gtg cct<br>Asp Ile Tyr Asn Gln Gly Thr Val Gln Pro Asp Ser Tyr Ile Val Pro<br>                       435                          440                          445 | 1344 |
| ctg gtt ttg tac agc ccg gat aag gcc gtg caa cag gct gcc aac cag<br>Leu Val Leu Tyr Ser Pro Asp Lys Ala Val Gln Gln Ala Ala Asn Gln<br>450                              455                          460 | 1392 |
| gct ttt gcg cct tgc gag att gcc ttc cat cag cag ctt tca acg ttc<br>Ala Phe Ala Pro Cys Glu Ile Ala Phe His Gln Gln Leu Ser Thr Phe<br>465                              470                          475                480 | 1440 |
| ctg att cac acg ttg ggc tac gat atg ccg gtt tca ggt tgt cgc gaa<br>Leu Ile His Thr Leu Gly Tyr Asp Met Pro Val Ser Gly Cys Arg Glu<br>                           485                          490                          495 | 1488 |
| ggc tcg gta aca ggc aac ctg att acg ggc gat gca ggc agc ttg aac<br>Gly Ser Val Thr Gly Asn Leu Ile Thr Gly Asp Ala Gly Ser Leu Asn<br>                       500                          505                          510 | 1536 |
| att cgc aac ggc aag gcg gaa tat gtt tat ccg caa taa<br>Ile Arg Asn Gly Lys Ala Glu Tyr Val Tyr Pro Gln<br>                       515                          520 | 1575 |

```
<210> SEQ ID NO 57
<211> LENGTH: 524
<212> TYPE: PRT
<213> ORGANISM: Neisseria gonorrhoeae

<400> SEQUENCE: 57
```

| | | | | | | | | | | | | | | |
|---|---|---|---|---|---|---|---|---|---|---|---|---|---|---|
| Met | Lys | Lys | Ser | Leu | Phe | Val | Leu | Phe | Leu | Tyr | Ser | Ser | Leu | Leu | Thr |
| 1 | | | | 5 | | | | | 10 | | | | | 15 | |

Ala Ser Glu Ile Ala Tyr Arg Phe Val Phe Gly Ile Glu Thr Leu Pro
             20                  25                  30

Ala Ala Lys Met Ala Glu Thr Phe Ala Leu Thr Phe Met Ile Ala Ala
         35                  40                  45

Leu Tyr Leu Phe Ala Arg Tyr Lys Ala Ser Arg Leu Leu Ile Ala Val
     50                  55                  60

Phe Phe Ala Phe Ser Met Ile Ala Asn Asn Val His Tyr Ala Val Tyr
 65                  70                  75                  80

Gln Ser Trp Met Thr Gly Ile Asn Tyr Trp Leu Met Leu Lys Glu Val
                 85                  90                  95

Thr Glu Val Gly Ser Ala Gly Ala Ser Met Leu Asp Lys Leu Trp Leu
             100                 105                 110

Pro Ala Leu Trp Gly Val Ala Glu Val Met Leu Phe Cys Ser Leu Ala
         115                 120                 125

Lys Phe Arg Arg Lys Thr His Phe Ser Ala Asp Ile Leu Phe Ala Phe
    130                 135                 140

Leu Met Leu Met Ile Phe Val Arg Ser Phe Asp Thr Lys Gln Glu His
145                 150                 155                 160

Gly Ile Ser Pro Lys Pro Thr Tyr Ser Arg Ile Lys Ala Asn Tyr Phe
                165                 170                 175

Ser Phe Gly Tyr Phe Val Gly Arg Val Leu Pro Tyr Gln Leu Phe Asp
            180                 185                 190

Leu Ser Lys Ile Pro Val Phe Lys Gln Pro Ala Pro Ser Lys Ile Gly
        195                 200                 205

Gln Gly Ser Ile Gln Asn Ile Val Leu Ile Met Gly Glu Ser Glu Ser
    210                 215                 220

Ala Ala His Leu Lys Leu Phe Gly Tyr Gly Arg Glu Thr Ser Pro Phe
225                 230                 235                 240

Leu Thr Arg Leu Ser Gln Ala Asp Phe Lys Pro Ile Val Lys Gln Ser
                245                 250                 255

Tyr Ser Ala Gly Phe Met Thr Ala Val Ser Leu Pro Ser Phe Phe Asn
            260                 265                 270

Val Ile Pro His Ala Asn Gly Leu Glu Gln Ile Ser Gly Gly Asp Thr
        275                 280                 285

Asn Met Phe Arg Leu Ala Lys Glu Gln Gly Tyr Glu Thr Tyr Phe Tyr
    290                 295                 300

Ser Ala Gln Ala Glu Asn Gln Met Ala Ile Leu Asn Leu Ile Gly Lys
305                 310                 315                 320

Lys Trp Ile Asp His Leu Ile Gln Pro Thr Gln Leu Gly Tyr Gly Asn
                325                 330                 335

Gly Asp Asn Met Pro Asp Glu Lys Leu Leu Pro Leu Phe Asp Lys Ile
            340                 345                 350

Asn Leu Gln Gln Gly Arg His Phe Ile Val Leu His Gln Arg Gly Ser
        355                 360                 365

His Ala Pro Tyr Gly Ala Leu Leu Gln Pro Gln Asp Lys Val Phe Gly

-continued

```
                    370                 375                 380
Glu Ala Asp Ile Val Asp Lys Tyr Asp Asn Thr Ile His Lys Thr Asp
385                 390                 395                 400

Gln Met Ile Gln Thr Val Phe Glu Gln Leu Gln Lys Gln Pro Asp Gly
                405                 410                 415

Asn Trp Leu Phe Ala Tyr Thr Ser Asp His Gly Gln Tyr Val Arg Gln
                420                 425                 430

Asp Ile Tyr Asn Gln Gly Thr Val Gln Pro Asp Ser Tyr Ile Val Pro
            435                 440                 445

Leu Val Leu Tyr Ser Pro Asp Lys Ala Val Gln Ala Ala Asn Gln
450                 455                 460

Ala Phe Ala Pro Cys Glu Ile Ala Phe His Gln Gln Leu Ser Thr Phe
465                 470                 475                 480

Leu Ile His Thr Leu Gly Tyr Asp Met Pro Val Ser Gly Cys Arg Glu
                485                 490                 495

Gly Ser Val Thr Gly Asn Leu Ile Thr Gly Asp Ala Gly Ser Leu Asn
                500                 505                 510

Ile Arg Asn Gly Lys Ala Glu Tyr Val Tyr Pro Gln
            515                 520
```

<210> SEQ ID NO 58
<211> LENGTH: 1314
<212> TYPE: DNA
<213> ORGANISM: Neisseria gonorrhoeae
<220> FEATURE:
<221> NAME/KEY: CDS
<222> LOCATION: (1)..(1311)

<400> SEQUENCE: 58

```
atg ctg acg ttt atc gga ttg ctg att atc ggg gtc atc gta tgg ctg     48
Met Leu Thr Phe Ile Gly Leu Leu Ile Ile Gly Val Ile Val Trp Leu
  1               5                  10                  15 ttg ctg acg gaa aaa gtg tcg ccc atc atc gca tta atc ttg gtg ccg     96
Leu Leu Thr Glu Lys Val Ser Pro Ile Ile Ala Leu Ile Leu Val Pro
             20                  25                  30 ctg att ggg gcg ttg ctg gcg ggg ttt gat gta tcc caa tta aaa gaa    144
Leu Ile Gly Ala Leu Leu Ala Gly Phe Asp Val Ser Gln Leu Lys Glu
         35                  40                  45 ttt tat tcg ggc ggc acg aaa tcg gtg acg cag att gtg att atg ttt    192
Phe Tyr Ser Gly Gly Thr Lys Ser Val Thr Gln Ile Val Ile Met Phe
     50                  55                  60 atg ttt tcc att ttg ttt ttt gga atc atg aac gat gtg ggg ctg ttc    240
Met Phe Ser Ile Leu Phe Phe Gly Ile Met Asn Asp Val Gly Leu Phe
 65                  70                  75                  80 cgt ccg atg ata ggc ggt ttg att aag ctg act cgg ggt aat atc gtg    288
Arg Pro Met Ile Gly Gly Leu Ile Lys Leu Thr Arg Gly Asn Ile Val
                 85                  90                  95 gca gtg agt gtg ggg acg gtc ttg gtg tcg gtg gtg gca cag ttg gac    336
Ala Val Ser Val Gly Thr Val Leu Val Ser Val Val Ala Gln Leu Asp
            100                 105                 110 ggg gcg ggc gcg acg acg ttt tta tcg gtc gtc ccc gcc ctt ttg ccg    384
Gly Ala Gly Ala Thr Thr Phe Leu Ser Val Val Pro Ala Leu Leu Pro
        115                 120                 125 ctt tac aag cgt ctg cat atg aat cct tac ctg ctg ttt ttg ctg ctg    432
Leu Tyr Lys Arg Leu His Met Asn Pro Tyr Leu Leu Phe Leu Leu Leu
    130                 135                 140 act tcc agc gcg ggg cta atc aac ctt ttg ccg cgg ggc ggg ccg atc    480
Thr Ser Ser Ala Gly Leu Ile Asn Leu Leu Pro Arg Gly Gly Pro Ile
145                 150                 155                 160
```

```
ggg cgg gtt gca agc gtg ttg ggc gca gat gtg ggc gaa tta tat aaa     528
Gly Arg Val Ala Ser Val Leu Gly Ala Asp Val Gly Glu Leu Tyr Lys
            165                 170                 175 cct ttg ttg acg gtg caa att atc ggt gtg gtg ttt atc ctt gtg ctg     576
Pro Leu Leu Thr Val Gln Ile Ile Gly Val Val Phe Ile Leu Val Leu
        180                 185                 190 tcc ctg ttt ttg ggt gtg cgt gaa aaa agg cgg att gtc cgg gag ttg     624
Ser Leu Phe Leu Gly Val Arg Glu Lys Arg Arg Ile Val Arg Glu Leu
    195                 200                 205 ggc gcg ttg ccc gcc gtg gcg gat ttg ata aag ccg gcg cct ttg tcg     672
Gly Ala Leu Pro Ala Val Ala Asp Leu Ile Lys Pro Ala Pro Leu Ser
210                 215                 220 gaa gaa gaa caa aaa ttg gcg cgt ccg aaa ctg ttt tgg tgg aat gtc     720
Glu Glu Glu Gln Lys Leu Ala Arg Pro Lys Leu Phe Trp Trp Asn Val
225                 230                 235                 240 ctg ctg ttt ttg gcg gcg atg agc ctg ctt ttt tcg ggc atc ttc ccg     768
Leu Leu Phe Leu Ala Ala Met Ser Leu Leu Phe Ser Gly Ile Phe Pro
                245                 250                 255 ccg ggt tat gta ttt atg ctg gct gca acg gcg gcg ttg ctt ttg aat     816
Pro Gly Tyr Val Phe Met Leu Ala Ala Thr Ala Ala Leu Leu Leu Asn
            260                 265                 270 tac cgc agc ccg cag gaa cag atg gag cgg att tat gcc cac gcc ggc     864
Tyr Arg Ser Pro Gln Glu Gln Met Glu Arg Ile Tyr Ala His Ala Gly
        275                 280                 285 ggc gcg gtg atg atg gcg tcc att att ttg gcg gca ggt acg ttt ttg     912
Gly Ala Val Met Met Ala Ser Ile Ile Leu Ala Ala Gly Thr Phe Leu
    290                 295                 300 ggg att ttg aag ggc gcg ggg atg ttg gac gcg att tcc aaa gac ctt     960
Gly Ile Leu Lys Gly Ala Gly Met Leu Asp Ala Ile Ser Lys Asp Leu
305                 310                 315                 320 gtg cat atc ctg ccg gac gcg ttg ctg cct tat ctg cat att gcc atc    1008
Val His Ile Leu Pro Asp Ala Leu Leu Pro Tyr Leu His Ile Ala Ile
                325                 330                 335 ggt gtg ttg ggt att ccg ctt gag ttg gtt ttg agt acg gac gct tat    1056
Gly Val Leu Gly Ile Pro Leu Glu Leu Val Leu Ser Thr Asp Ala Tyr
            340                 345                 350 tat ttc gga ctg ttt ccg att gtg gaa cag att acc tcg cag gcg ggc    1104
Tyr Phe Gly Leu Phe Pro Ile Val Glu Gln Ile Thr Ser Gln Ala Gly
        355                 360                 365 gtt gca ccc gaa gcg gca ggc tat gcg atg ttg atc ggc agt atc gtc    1152
Val Ala Pro Glu Ala Ala Gly Tyr Ala Met Leu Ile Gly Ser Ile Val
    370                 375                 380 ggt act ttt gtt acg ccg ctt tcg ccg gct ttg tgg atg ggt ttg ggt    1200
Gly Thr Phe Val Thr Pro Leu Ser Pro Ala Leu Trp Met Gly Leu Gly
385                 390                 395                 400 ttg gcg aaa ttg tcg atg ggc aaa cac atc cgt tat tcg ttt ttc tgg    1248
Leu Ala Lys Leu Ser Met Gly Lys His Ile Arg Tyr Ser Phe Phe Trp
                405                 410                 415 gcg tgg ggt ttg tcg ctg gcg ata ttg gtc agt tcg ata gcg gca gga    1296
Ala Trp Gly Leu Ser Leu Ala Ile Leu Val Ser Ser Ile Ala Ala Gly
            420                 425                 430 atc gtg cct ctg ccg taa                                            1314
Ile Val Pro Leu Pro
        435
```

<210> SEQ ID NO 59
<211> LENGTH: 437
<212> TYPE: PRT
<213> ORGANISM: Neisseria gonorrhoeae

<400> SEQUENCE: 59

| | | | | | | | | | | | | | | |
|---|---|---|---|---|---|---|---|---|---|---|---|---|---|---|
|Met|Leu|Thr|Phe|Ile|Gly|Leu|Leu|Ile|Ile|Gly|Val|Ile|Val|Trp|Leu|
|1| | | |5| | | | |10| | | | |15| |
|Leu|Leu|Thr|Glu|Lys|Val|Ser|Pro|Ile|Ile|Ala|Leu|Ile|Leu|Val|Pro|
| | | |20| | | | |25| | | | |30| | |
|Leu|Ile|Gly|Ala|Leu|Leu|Ala|Gly|Phe|Asp|Val|Ser|Gln|Leu|Lys|Glu|
| | |35| | | | |40| | | | |45| | | |
|Phe|Tyr|Ser|Gly|Gly|Thr|Lys|Ser|Val|Thr|Gln|Ile|Val|Ile|Met|Phe|
| |50| | | | |55| | | | |60| | | | |
|Met|Phe|Ser|Ile|Leu|Phe|Phe|Gly|Ile|Met|Asn|Asp|Val|Gly|Leu|Phe|
|65| | | | |70| | | | |75| | | | |80|
|Arg|Pro|Met|Ile|Gly|Gly|Leu|Ile|Lys|Leu|Thr|Arg|Gly|Asn|Ile|Val|
| | | | |85| | | | |90| | | | |95| |
|Ala|Val|Ser|Val|Gly|Thr|Val|Leu|Val|Ser|Val|Val|Ala|Gln|Leu|Asp|
| | | |100| | | | |105| | | | |110| | |
|Gly|Ala|Gly|Ala|Thr|Thr|Phe|Leu|Ser|Val|Val|Pro|Ala|Leu|Leu|Pro|
| | |115| | | | |120| | | | |125| | | |
|Leu|Tyr|Lys|Arg|Leu|His|Met|Asn|Pro|Tyr|Leu|Leu|Phe|Leu|Leu|Leu|
| |130| | | | |135| | | | |140| | | | |
|Thr|Ser|Ser|Ala|Gly|Leu|Ile|Asn|Leu|Leu|Pro|Arg|Gly|Gly|Pro|Ile|
|145| | | | |150| | | | |155| | | | |160|
|Gly|Arg|Val|Ala|Ser|Val|Leu|Gly|Ala|Asp|Val|Gly|Glu|Leu|Tyr|Lys|
| | | | |165| | | | |170| | | | |175| |
|Pro|Leu|Leu|Thr|Val|Gln|Ile|Ile|Gly|Val|Val|Phe|Ile|Leu|Val|Leu|
| | | |180| | | | |185| | | | |190| | |
|Ser|Leu|Phe|Leu|Gly|Val|Arg|Glu|Lys|Arg|Arg|Ile|Val|Arg|Glu|Leu|
| | |195| | | | |200| | | | |205| | | |
|Gly|Ala|Leu|Pro|Ala|Val|Ala|Asp|Leu|Ile|Lys|Pro|Ala|Pro|Leu|Ser|
| |210| | | | |215| | | | |220| | | | |
|Glu|Glu|Glu|Gln|Lys|Leu|Ala|Arg|Pro|Lys|Leu|Phe|Trp|Trp|Asn|Val|
|225| | | | |230| | | | |235| | | | |240|
|Leu|Leu|Phe|Leu|Ala|Ala|Met|Ser|Leu|Leu|Phe|Ser|Gly|Ile|Phe|Pro|
| | | | |245| | | | |250| | | | |255| |
|Pro|Gly|Tyr|Val|Phe|Met|Leu|Ala|Ala|Thr|Ala|Ala|Leu|Leu|Leu|Asn|
| | | |260| | | | |265| | | | |270| | |
|Tyr|Arg|Ser|Pro|Gln|Glu|Gln|Met|Glu|Arg|Ile|Tyr|Ala|His|Ala|Gly|
| | |275| | | | |280| | | | |285| | | |
|Gly|Ala|Val|Met|Met|Ala|Ser|Ile|Ile|Leu|Ala|Ala|Gly|Thr|Phe|Leu|
| |290| | | | |295| | | | |300| | | | |
|Gly|Ile|Leu|Lys|Gly|Ala|Gly|Met|Leu|Asp|Ala|Ile|Ser|Lys|Asp|Leu|
|305| | | | |310| | | | |315| | | | |320|
|Val|His|Ile|Leu|Pro|Asp|Ala|Leu|Leu|Pro|Tyr|Leu|His|Ile|Ala|Ile|
| | | | |325| | | | |330| | | | |335| |
|Gly|Val|Leu|Gly|Ile|Pro|Leu|Glu|Leu|Val|Leu|Ser|Thr|Asp|Ala|Tyr|
| | | |340| | | | |345| | | | |350| | |
|Tyr|Phe|Gly|Leu|Phe|Pro|Ile|Val|Glu|Gln|Ile|Thr|Ser|Gln|Ala|Gly|
| | |355| | | | |360| | | | |365| | | |
|Val|Ala|Pro|Glu|Ala|Ala|Gly|Tyr|Ala|Met|Leu|Ile|Gly|Ser|Ile|Val|
| |370| | | | |375| | | | |380| | | | |
|Gly|Thr|Phe|Val|Thr|Pro|Leu|Ser|Pro|Ala|Leu|Trp|Met|Gly|Leu|Gly|
|385| | | | |390| | | | |395| | | | |400|
|Leu|Ala|Lys|Leu|Ser|Met|Gly|Lys|His|Ile|Arg|Tyr|Ser|Phe|Phe|Trp|
| | | | |405| | | | |410| | | | |415| |

```
Ala Trp Gly Leu Ser Leu Ala Ile Leu Val Ser Ser Ile Ala Ala Gly
            420                 425                 430

Ile Val Pro Leu Pro
            435

<210> SEQ ID NO 60
<211> LENGTH: 1155
<212> TYPE: DNA
<213> ORGANISM: Neisseria gonorrhoeae
<220> FEATURE:
<221> NAME/KEY: CDS
<222> LOCATION: (1)..(1152)

<400> SEQUENCE: 60 atg ggc atc cat ctc gac ttc ggc att agt cct aaa acg ttc cga cag       48
Met Gly Ile His Leu Asp Phe Gly Ile Ser Pro Lys Thr Phe Arg Gln
  1               5                  10                  15 act tat ctg tat caa aag ccc aag ctc ttt aaa gga gcg gtt cgg aat       96
Thr Tyr Leu Tyr Gln Lys Pro Lys Leu Phe Lys Gly Ala Val Arg Asn
                 20                  25                  30 ctc gaa gcc gca tct tgt aaa tat atc aac gag ata tac caa cga gca      144
Leu Glu Ala Ala Ser Cys Lys Tyr Ile Asn Glu Ile Tyr Gln Arg Ala
             35                  40                  45 gac cca acc gca ccg ctg ttt cat ctg cgt aaa aaa ggc gca atc gtt      192
Asp Pro Thr Ala Pro Leu Phe His Leu Arg Lys Lys Gly Ala Ile Val
         50                  55                  60 cct aaa gaa gaa tac gtc gaa agt ttc gac gat ttg ggc aaa act cgc      240
Pro Lys Glu Glu Tyr Val Glu Ser Phe Asp Asp Leu Gly Lys Thr Arg
 65                  70                  75                  80 tac cgt ttt att aaa tcc gtt atc tac gaa cat atg aag aat ggt gcg      288
Tyr Arg Phe Ile Lys Ser Val Ile Tyr Glu His Met Lys Asn Gly Ala
                 85                  90                  95 tcg tta gtc tat aac cat att aac aac gag ccg ttt tca gac cat atc      336
Ser Leu Val Tyr Asn His Ile Asn Asn Glu Pro Phe Ser Asp His Ile
                100                 105                 110 gcc cgt caa gtc gcc cgc ttt gcc ggc gca cat act att gtt agt gga      384
Ala Arg Gln Val Ala Arg Phe Ala Gly Ala His Thr Ile Val Ser Gly
            115                 120                 125 tat ctt gct ttt ggc agc gac gaa tct tat aaa aac cat tgg gat acc      432
Tyr Leu Ala Phe Gly Ser Asp Glu Ser Tyr Lys Asn His Trp Asp Thr
        130                 135                 140 cgc gat gtg tat gcc atc cag ctt ttc ggc aag aaa cgt tgg caa ctt      480
Arg Asp Val Tyr Ala Ile Gln Leu Phe Gly Lys Lys Arg Trp Gln Leu
145                 150                 155                 160 act gcc cct gat ttc cct atg cca ttg tat atg caa cag act aaa gat      528
Thr Ala Pro Asp Phe Pro Met Pro Leu Tyr Met Gln Gln Thr Lys Asp
                165                 170                 175 act gat att tcc att cct gaa cat atc gat atg gat att atc ctt gaa      576
Thr Asp Ile Ser Ile Pro Glu His Ile Asp Met Asp Ile Ile Leu Glu
            180                 185                 190 gca ggt gat gtc ctc tac atc cca cgc ggt tgg tgg cac aga cct atc      624
Ala Gly Asp Val Leu Tyr Ile Pro Arg Gly Trp Trp His Arg Pro Ile
        195                 200                 205 ccg ctc ggc tgt gaa acc ttc cac ttc gct gtc ggt acc ttc cca cca      672
Pro Leu Gly Cys Glu Thr Phe His Phe Ala Val Gly Thr Phe Pro Pro
    210                 215                 220 aac ggc tat aat tac ctc gag tgg cta atg aag aaa ttt ccc acc ata      720
Asn Gly Tyr Asn Tyr Leu Glu Trp Leu Met Lys Lys Phe Pro Thr Ile
225                 230                 235                 240 gaa agt ctg cgc cac agt ttc tca gac tgg gag caa gat agg acg cgt      768
```

-continued

| | | | | | | | | | | | | | | |
|---|---|---|---|---|---|---|---|---|---|---|---|---|---|---|
| Glu | Ser | Leu | Arg | His | Ser | Phe | Ser | Asp | Trp | Glu | Gln | Asp | Arg | Thr | Arg |
| | | | | 245 | | | | | 250 | | | | | 255 | |

| atc aac gat act gcc gca caa att gct gcc atg att gcc gac ccc gtc | 816 |
|---|---|
| Ile Asn Asp Thr Ala Ala Gln Ile Ala Ala Met Ile Ala Asp Pro Val | |
|           260               265             270 | |
| aat tat gaa gcc ttc agt gaa gac ttt ctc ggc aaa gaa cgt acc gat | 864 |
| Asn Tyr Glu Ala Phe Ser Glu Asp Phe Leu Gly Lys Glu Arg Thr Asp | |
|    275                280               285 | |
| acc gct ttt cat ctc gaa cag ttc gcg aat ccc aac gct act ccg ctt | 912 |
| Thr Ala Phe His Leu Glu Gln Phe Ala Asn Pro Asn Ala Thr Pro Leu | |
|           290               295             300 | |
| tca gac gac gtc agg ttg aga tta aat gcc aat aat ttg gat acg ttg | 960 |
| Ser Asp Asp Val Arg Leu Arg Leu Asn Ala Asn Asn Leu Asp Thr Leu | |
| 305                    310               315              320 | |
| gaa aag gga tat ttg att ggg aat ggg atg aag ata agc gta gat gag | 1008 |
| Glu Lys Gly Tyr Leu Ile Gly Asn Gly Met Lys Ile Ser Val Asp Glu | |
|                 325               330             335 | |
| ttg ggg aaa aaa gtg tta gaa cac atc ggt aag aat gaa ccg tta ttg | 1056 |
| Leu Gly Lys Lys Val Leu Glu His Ile Gly Lys Asn Glu Pro Leu Leu | |
|               340                345             350 | |
| ttg aaa aat cta ctg gtt aac ttc aat cag gca aaa cat gaa gaa gtt | 1104 |
| Leu Lys Asn Leu Leu Val Asn Phe Asn Gln Ala Lys His Glu Glu Val | |
|    355                360               365 | |
| agg aag ttg atc tat cag ttg ata gag tta gat ttt ctg gaa att ttg | 1152 |
| Arg Lys Leu Ile Tyr Gln Leu Ile Glu Leu Asp Phe Leu Glu Ile Leu | |
| 370                    375               380 | |
| tga | 1155 |

<210> SEQ ID NO 61
<211> LENGTH: 384
<212> TYPE: PRT
<213> ORGANISM: Neisseria gonorrhoeae

<400> SEQUENCE: 61

Met Gly Ile His Leu Asp Phe Gly Ile Ser Pro Lys Thr Phe Arg Gln
 1               5                  10                  15

Thr Tyr Leu Tyr Gln Lys Pro Lys Leu Phe Lys Gly Ala Val Arg Asn
            20                  25                  30

Leu Glu Ala Ala Ser Cys Lys Tyr Ile Asn Glu Ile Tyr Gln Arg Ala
        35                  40                  45

Asp Pro Thr Ala Pro Leu Phe His Leu Arg Lys Lys Gly Ala Ile Val
    50                  55                  60

Pro Lys Glu Glu Tyr Val Glu Ser Phe Asp Asp Leu Gly Lys Thr Arg
65                  70                  75                  80

Tyr Arg Phe Ile Lys Ser Val Ile Tyr Glu His Met Lys Asn Gly Ala
                85                  90                  95

Ser Leu Val Tyr Asn His Ile Asn Asn Glu Pro Phe Ser Asp His Ile
            100                 105                 110

Ala Arg Gln Val Ala Arg Phe Ala Gly Ala His Thr Ile Val Ser Gly
        115                 120                 125

Tyr Leu Ala Phe Gly Ser Asp Glu Ser Tyr Lys Asn His Trp Asp Thr
    130                 135                 140

Arg Asp Val Tyr Ala Ile Gln Leu Phe Gly Lys Lys Arg Trp Gln Leu
145                 150                 155                 160

Thr Ala Pro Asp Phe Pro Met Pro Leu Tyr Met Gln Gln Thr Lys Asp
                165                 170                 175

Thr Asp Ile Ser Ile Pro Glu His Ile Asp Met Asp Ile Ile Leu Glu

-continued

```
              180                 185                 190
Ala Gly Asp Val Leu Tyr Ile Pro Arg Gly Trp Trp His Arg Pro Ile
        195                 200                 205

Pro Leu Gly Cys Glu Thr Phe His Phe Ala Val Gly Thr Phe Pro Pro
    210                 215                 220

Asn Gly Tyr Asn Tyr Leu Glu Trp Leu Met Lys Lys Phe Pro Thr Ile
225                 230                 235                 240

Glu Ser Leu Arg His Ser Phe Ser Asp Trp Glu Gln Asp Arg Thr Arg
                245                 250                 255

Ile Asn Asp Thr Ala Ala Gln Ile Ala Ala Met Ile Ala Asp Pro Val
            260                 265                 270

Asn Tyr Glu Ala Phe Ser Glu Asp Phe Leu Gly Lys Glu Arg Thr Asp
        275                 280                 285

Thr Ala Phe His Leu Glu Gln Phe Ala Asn Pro Asn Ala Thr Pro Leu
    290                 295                 300

Ser Asp Asp Val Arg Leu Arg Leu Asn Ala Asn Leu Asp Thr Leu
305                 310                 315                 320

Glu Lys Gly Tyr Leu Ile Gly Asn Gly Met Lys Ile Ser Val Asp Glu
                325                 330                 335

Leu Gly Lys Lys Val Leu Glu His Ile Gly Lys Asn Glu Pro Leu Leu
            340                 345                 350

Leu Lys Asn Leu Leu Val Asn Phe Asn Gln Ala Lys His Glu Val
        355                 360                 365

Arg Lys Leu Ile Tyr Gln Leu Ile Glu Leu Asp Phe Leu Glu Ile Leu
    370                 375                 380

<210> SEQ ID NO 62
<211> LENGTH: 717
<212> TYPE: DNA
<213> ORGANISM: Neisseria meningitidis
<220> FEATURE:
<221> NAME/KEY: CDS
<222> LOCATION: (1)..(714)

<400> SEQUENCE: 62 atg aat aga ccc aag caa ccc ttc ttc cgt ccc gaa gtc gcc gtt gcc    48
Met Asn Arg Pro Lys Gln Pro Phe Phe Arg Pro Glu Val Ala Val Ala
1               5                   10                  15 cgc caa acc agc ctg acg ggt aaa gtg att ctg aca cga ccg ttg tca    96
Arg Gln Thr Ser Leu Thr Gly Lys Val Ile Leu Thr Arg Pro Leu Ser
            20                  25                  30 ttt tcc cta tgg acg aca ttt gca tcg ata tct gcg tta ttg att atc   144
Phe Ser Leu Trp Thr Thr Phe Ala Ser Ile Ser Ala Leu Leu Ile Ile
        35                  40                  45 ctg ttt ttg ata ttt ggt aac tat acg cga aag aca aca gtg gag gga   192
Leu Phe Leu Ile Phe Gly Asn Tyr Thr Arg Lys Thr Thr Val Glu Gly
    50                  55                  60 caa att tta cct gca tcg ggc gta atc agg gtg tat gca ccg gat acg   240
Gln Ile Leu Pro Ala Ser Gly Val Ile Arg Val Tyr Ala Pro Asp Thr
65                  70                  75                  80 ggg aca att aca gcg aaa ttc gtg gaa gat gga gaa aag gtt aag gct   288
Gly Thr Ile Thr Ala Lys Phe Val Glu Asp Gly Glu Lys Val Lys Ala
                85                  90                  95 ggc gac aag cta ttt gcg ctt tcg acc tca cgt ttc ggc gca gga gat   336
Gly Asp Lys Leu Phe Ala Leu Ser Thr Ser Arg Phe Gly Ala Gly Asp
            100                 105                 110 agc gtg cag cag cag ttg aaa acg gag gca gtt ttg aag aaa acg ttg   384
Ser Val Gln Gln Gln Leu Lys Thr Glu Ala Val Leu Lys Lys Thr Leu
```

```
                115                 120                 125
gca gaa cag gaa ctg ggt cgt ctg aag ctg ata cac ggg aat gaa acg        432
Ala Glu Gln Glu Leu Gly Arg Leu Lys Leu Ile His Gly Asn Glu Thr
            130                 135                 140 cgc agc ctt aaa gca act gtc gaa cgt ttg gaa aac cag gaa ctc cat        480
Arg Ser Leu Lys Ala Thr Val Glu Arg Leu Glu Asn Gln Glu Leu His
145                 150                 155                 160 att tcg caa cag ata gac ggt cag aaa agg cgc att aga ctt gcg gaa        528
Ile Ser Gln Gln Ile Asp Gly Gln Lys Arg Arg Ile Arg Leu Ala Glu
                165                 170                 175 gaa atg ttg cag aaa tat cgt ttc cta tcc gcc aat gat gca gtg cca        576
Glu Met Leu Gln Lys Tyr Arg Phe Leu Ser Ala Asn Asp Ala Val Pro
            180                 185                 190 aaa caa gaa atg atg aat gtc aag gca gag ctt tta gag cag aaa gcc        624
Lys Gln Glu Met Met Asn Val Lys Ala Glu Leu Leu Glu Gln Lys Ala
        195                 200                 205 aaa ctt gat gcc tac cgc cga gaa gaa gtc ggg ctg ctt cag gaa atc        672
Lys Leu Asp Ala Tyr Arg Arg Glu Glu Val Gly Leu Leu Gln Glu Ile
210                 215                 220 cgc acg cag aat ctg aca ttg gcc agc ctc ccc caa gcg gca tga            717
Arg Thr Gln Asn Leu Thr Leu Ala Ser Leu Pro Gln Ala Ala
225                 230                 235

<210> SEQ ID NO 63
<211> LENGTH: 238
<212> TYPE: PRT
<213> ORGANISM: Neisseria meningitidis

<400> SEQUENCE: 63

Met Asn Arg Pro Lys Gln Pro Phe Phe Arg Pro Glu Val Ala Val Ala
1               5                   10                  15

Arg Gln Thr Ser Leu Thr Gly Lys Val Ile Leu Thr Arg Pro Leu Ser
                20                  25                  30

Phe Ser Leu Trp Thr Thr Phe Ala Ser Ile Ser Ala Leu Leu Ile Ile
            35                  40                  45

Leu Phe Leu Ile Phe Gly Asn Tyr Thr Arg Lys Thr Thr Val Glu Gly
        50                  55                  60

Gln Ile Leu Pro Ala Ser Gly Val Ile Arg Val Tyr Ala Pro Asp Thr
65                  70                  75                  80

Gly Thr Ile Thr Ala Lys Phe Val Glu Asp Gly Lys Val Lys Ala
                85                  90                  95

Gly Asp Lys Leu Phe Ala Leu Ser Ser Arg Phe Gly Ala Gly Asp
            100                 105                 110

Ser Val Gln Gln Gln Leu Lys Thr Glu Ala Val Leu Lys Lys Thr Leu
        115                 120                 125

Ala Glu Gln Glu Leu Gly Arg Leu Lys Leu Ile His Gly Asn Glu Thr
130                 135                 140

Arg Ser Leu Lys Ala Thr Val Glu Arg Leu Glu Asn Gln Glu Leu His
145                 150                 155                 160

Ile Ser Gln Gln Ile Asp Gly Gln Lys Arg Arg Ile Arg Leu Ala Glu
                165                 170                 175

Glu Met Leu Gln Lys Tyr Arg Phe Leu Ser Ala Asn Asp Ala Val Pro
            180                 185                 190

Lys Gln Glu Met Met Asn Val Lys Ala Glu Leu Leu Glu Gln Lys Ala
        195                 200                 205

Lys Leu Asp Ala Tyr Arg Arg Glu Glu Val Gly Leu Leu Gln Glu Ile
210                 215                 220
```

Arg Thr Gln Asn Leu Thr Leu Ala Ser Leu Pro Gln Ala Ala
225                 230                 235

<210> SEQ ID NO 64
<211> LENGTH: 690
<212> TYPE: DNA
<213> ORGANISM: Neisseria gonorrhoeae
<220> FEATURE:
<221> NAME/KEY: CDS
<222> LOCATION: (1)..(687)

<400> SEQUENCE: 64

| | |
|---|---|
| atg atg aat gtc gag gca gag ctt tta gag cag aaa gcc aaa ctt gat<br>Met Met Asn Val Glu Ala Glu Leu Leu Glu Gln Lys Ala Lys Leu Asp<br>1               5                   10                  15 | 48 |
| gcc tac ggc cga gaa gaa gcc ggg ctg ctt cag gaa atc cgc acg cag<br>Ala Tyr Gly Arg Glu Glu Ala Gly Leu Leu Gln Glu Ile Arg Thr Gln<br>            20                  25                  30 | 96 |
| aat ctg aca ttg gcc agc ctc ccc aaa cgg cat gag aca gaa caa agc<br>Asn Leu Thr Leu Ala Ser Leu Pro Lys Arg His Glu Thr Glu Gln Ser<br>        35                  40                  45 | 144 |
| cag ctt gaa cgc acc atg gcc gat att tct caa gaa gtt ttg gat ttt<br>Gln Leu Glu Arg Thr Met Ala Asp Ile Ser Gln Glu Val Leu Asp Phe<br>50                  55                  60 | 192 |
| gaa atg cgc tct gaa caa atc atc cgt gca gga cgg tcg ggt tat ata<br>Glu Met Arg Ser Glu Gln Ile Ile Arg Ala Gly Arg Ser Gly Tyr Ile<br>65              70                  75                  80 | 240 |
| gca ata ccg aac gtc gaa gtc gga cgg cag gtt gat cct tcc aaa ctg<br>Ala Ile Pro Asn Val Glu Val Gly Arg Gln Val Asp Pro Ser Lys Leu<br>                85                  90                  95 | 288 |
| ctc ttg agc att gtt ccc gaa cgt acc gag tta tat gcc cat cta tat<br>Leu Leu Ser Ile Val Pro Glu Arg Thr Glu Leu Tyr Ala His Leu Tyr<br>            100                 105                 110 | 336 |
| atc ccc agc agt gca gca ggc ttt atc aag ccg aaa gac aag gtt gtc<br>Ile Pro Ser Ser Ala Ala Gly Phe Ile Lys Pro Lys Asp Lys Val Val<br>        115                 120                 125 | 384 |
| cta cgt tat cag gca tat ccc tat cag aaa ttc ggg ctt gct tcc ggc<br>Leu Arg Tyr Gln Ala Tyr Pro Tyr Gln Lys Phe Gly Leu Ala Ser Gly<br>130                 135                 140 | 432 |
| agt gtc gta tca gtg gca aaa acg gca ctg ggc aga cag gaa ttg tcg<br>Ser Val Val Ser Val Ala Lys Thr Ala Leu Gly Arg Gln Glu Leu Ser<br>145                 150                 155                 160 | 480 |
| gga ttg ggc atg gta tcc tcc gat ttg gcg aag agc aac gaa cct gtt<br>Gly Leu Gly Met Val Ser Ser Asp Leu Ala Lys Ser Asn Glu Pro Val<br>                165                 170                 175 | 528 |
| tat ctc gtg aaa ata aaa ccc gac aaa cca acc atc act gca tac ggt<br>Tyr Leu Val Lys Ile Lys Pro Asp Lys Pro Thr Ile Thr Ala Tyr Gly<br>            180                 185                 190 | 576 |
| gag gaa aaa ccg ctg caa atc ggc atg acg ctg gaa gca gac atc cta<br>Glu Glu Lys Pro Leu Gln Ile Gly Met Thr Leu Glu Ala Asp Ile Leu<br>        195                 200                 205 | 624 |
| cac gag aaa cgg cgg ctg tac gaa tgg gta ttg gag ccg att tac agt<br>His Glu Lys Arg Arg Leu Tyr Glu Trp Val Leu Glu Pro Ile Tyr Ser<br>210                 215                 220 | 672 |
| atg tcg ggc agg ttg taa<br>Met Ser Gly Arg Leu<br>225 | 690 |

<210> SEQ ID NO 65
<211> LENGTH: 229
<212> TYPE: PRT

-continued

<213> ORGANISM: Neisseria gonorrhoeae

<400> SEQUENCE: 65

```
Met Met Asn Val Glu Ala Glu Leu Leu Glu Gln Lys Ala Lys Leu Asp
 1               5                  10                  15

Ala Tyr Gly Arg Glu Ala Gly Leu Leu Gln Glu Ile Arg Thr Gln
            20                  25                  30

Asn Leu Thr Leu Ala Ser Leu Pro Lys Arg His Glu Thr Glu Gln Ser
        35                  40                  45

Gln Leu Glu Arg Thr Met Ala Asp Ile Ser Gln Glu Val Leu Asp Phe
    50                  55                  60

Glu Met Arg Ser Glu Gln Ile Ile Arg Ala Gly Arg Ser Gly Tyr Ile
65                  70                  75                  80

Ala Ile Pro Asn Val Glu Val Gly Arg Gln Val Asp Pro Ser Lys Leu
                85                  90                  95

Leu Leu Ser Ile Val Pro Glu Arg Thr Glu Leu Tyr Ala His Leu Tyr
            100                 105                 110

Ile Pro Ser Ser Ala Ala Gly Phe Ile Lys Pro Lys Asp Lys Val Val
        115                 120                 125

Leu Arg Tyr Gln Ala Tyr Pro Tyr Gln Lys Phe Gly Leu Ala Ser Gly
    130                 135                 140

Ser Val Ser Val Ala Lys Thr Ala Leu Gly Arg Gln Glu Leu Ser
145                 150                 155                 160

Gly Leu Gly Met Val Ser Ser Asp Leu Ala Lys Ser Asn Glu Pro Val
                165                 170                 175

Tyr Leu Val Lys Ile Lys Pro Asp Lys Pro Thr Ile Thr Ala Tyr Gly
            180                 185                 190

Glu Glu Lys Pro Leu Gln Ile Gly Met Thr Leu Glu Ala Asp Ile Leu
        195                 200                 205

His Glu Lys Arg Arg Leu Tyr Glu Trp Val Leu Glu Pro Ile Tyr Ser
    210                 215                 220

Met Ser Gly Arg Leu
225
```

<210> SEQ ID NO 66
<211> LENGTH: 924
<212> TYPE: DNA
<213> ORGANISM: Neisseria gonorrhoeae
<220> FEATURE:
<221> NAME/KEY: CDS
<222> LOCATION: (1)..(921)

<400> SEQUENCE: 66

```
atg caa tac agc aca ctg gca gga caa acc gac aac tcc ctc gtt tcc      48
Met Gln Tyr Ser Thr Leu Ala Gly Gln Thr Asp Asn Ser Leu Val Ser
 1               5                  10                  15 aat aat ttc ggg ttt ttg cgc ctg ccg ctt aat ttt atg ccg tat gaa      96
Asn Asn Phe Gly Phe Leu Arg Leu Pro Leu Asn Phe Met Pro Tyr Glu
            20                  25                  30 agc cat gcc gat tgg gtt att acc ggc gtg cct tat gat atg gcg gtt     144
Ser His Ala Asp Trp Val Ile Thr Gly Val Pro Tyr Asp Met Ala Val
        35                  40                  45 tca ggg cgt tcc ggc gcg cgt ttc ggt cct gaa gcc atc cgg cgc gcc     192
Ser Gly Arg Ser Gly Ala Arg Phe Gly Pro Glu Ala Ile Arg Arg Ala
    50                  55                  60 tcc gtc aac ctc gct tgg gag cac cgc agg ttt ccg tgg aca ttt gat     240
Ser Val Asn Leu Ala Trp Glu His Arg Arg Phe Pro Trp Thr Phe Asp
65                  70                  75                  80
```

```
gtg cgc gaa cgc ctg aac att att gat tgc ggc gac ttg gtt ttt tct    288
Val Arg Glu Arg Leu Asn Ile Ile Asp Cys Gly Asp Leu Val Phe Ser
             85                  90                  95 ttt ggc gac agc agg gat ttt gtc gaa aaa atg gaa gcg cac gcc ggc    336
Phe Gly Asp Ser Arg Asp Phe Val Glu Lys Met Glu Ala His Ala Gly
        100                 105                 110 aaa tta ctt tct ttc ggc aaa cgc tgt ttg agt ttg ggc ggc gac cat    384
Lys Leu Leu Ser Phe Gly Lys Arg Cys Leu Ser Leu Gly Gly Asp His
            115                 120                 125 ttc att acc ctc ccg ttg ttg cgc gcc cac gcc cgc tat ttc ggc aaa    432
Phe Ile Thr Leu Pro Leu Leu Arg Ala His Ala Arg Tyr Phe Gly Lys
130                 135                 140 ctc gca ctg att cat ttt gac gcg cac acc gac acc tac gac aac ggc    480
Leu Ala Leu Ile His Phe Asp Ala His Thr Asp Thr Tyr Asp Asn Gly
145                 150                 155                 160 agc gaa tac gac cac ggc acg atg ttt tat acc gcc ccc aag gaa ggc    528
Ser Glu Tyr Asp His Gly Thr Met Phe Tyr Thr Ala Pro Lys Glu Gly
                165                 170                 175 ctc atc gac ccg tcc cgt tcc gta caa atc ggc ata cgc acc gaa cac    576
Leu Ile Asp Pro Ser Arg Ser Val Gln Ile Gly Ile Arg Thr Glu His
            180                 185                 190 agt aaa aaa ttg cct ttt act gtg ttg tcc gcc ccc aaa gtc aat gaa    624
Ser Lys Lys Leu Pro Phe Thr Val Leu Ser Ala Pro Lys Val Asn Glu
        195                 200                 205 gac agt gtt gaa gag acc gtc cgt aaa atc aaa gaa acc gtc ggc aat    672
Asp Ser Val Glu Glu Thr Val Arg Lys Ile Lys Glu Thr Val Gly Asn
    210                 215                 220 atg ccc gtt tac ctg act ttc gac ata gac tgt ctc gac ccg tcg ttc    720
Met Pro Val Tyr Leu Thr Phe Asp Ile Asp Cys Leu Asp Pro Ser Phe
225                 230                 235                 240 gcc ccc ggg acc ggt acg ccc gta tgc ggc ggc ttg agc agc gac agg    768
Ala Pro Gly Thr Gly Thr Pro Val Cys Gly Gly Leu Ser Ser Asp Arg
                245                 250                 255 gca tta aaa atc cta cgt ggg ctg acg gat ctc gac atc gtc ggt atg    816
Ala Leu Lys Ile Leu Arg Gly Leu Thr Asp Leu Asp Ile Val Gly Met
            260                 265                 270 gat gtt gta gaa gtt gcc ccc tct tac gac caa tcc gac att acc gct    864
Asp Val Val Glu Val Ala Pro Ser Tyr Asp Gln Ser Asp Ile Thr Ala
        275                 280                 285 ttg gcc ggc gcc aca att gcc ttg gaa atg ctt tac ctt caa ggt gcg    912
Leu Ala Gly Ala Thr Ile Ala Leu Glu Met Leu Tyr Leu Gln Gly Ala
    290                 295                 300 aaa aag gac tga                                                    924
Lys Lys Asp
305
```

<210> SEQ ID NO 67
<211> LENGTH: 307
<212> TYPE: PRT
<213> ORGANISM: Neisseria gonorrhoeae

<400> SEQUENCE: 67

```
Met Gln Tyr Ser Thr Leu Ala Gly Gln Thr Asp Asn Ser Leu Val Ser
  1               5                  10                  15

Asn Asn Phe Gly Phe Leu Arg Leu Pro Leu Asn Phe Met Pro Tyr Glu
             20                  25                  30

Ser His Ala Asp Trp Val Ile Thr Gly Val Pro Tyr Asp Met Ala Val
         35                  40                  45

Ser Gly Arg Ser Gly Ala Arg Phe Gly Pro Glu Ala Ile Arg Arg Ala
```

```
                 50                   55                  60
Ser Val Asn Leu Ala Trp Glu His Arg Arg Phe Pro Trp Thr Phe Asp
 65                  70                  75                  80

Val Arg Glu Arg Leu Asn Ile Ile Asp Cys Gly Asp Leu Val Phe Ser
                 85                  90                  95

Phe Gly Asp Ser Arg Asp Phe Val Glu Lys Met Glu Ala His Ala Gly
                100                 105                 110

Lys Leu Leu Ser Phe Gly Lys Arg Cys Leu Ser Leu Gly Gly Asp His
                115                 120                 125

Phe Ile Thr Leu Pro Leu Leu Arg Ala His Ala Arg Tyr Phe Gly Lys
    130                 135                 140

Leu Ala Leu Ile His Phe Asp Ala His Thr Asp Thr Tyr Asp Asn Gly
145                 150                 155                 160

Ser Glu Tyr Asp His Gly Thr Met Phe Tyr Thr Ala Pro Lys Glu Gly
                165                 170                 175

Leu Ile Asp Pro Ser Arg Ser Val Gln Ile Gly Ile Arg Thr Glu His
                180                 185                 190

Ser Lys Lys Leu Pro Phe Thr Val Leu Ser Ala Pro Lys Val Asn Glu
    195                 200                 205

Asp Ser Val Glu Glu Thr Val Arg Lys Ile Lys Glu Thr Val Gly Asn
210                 215                 220

Met Pro Val Tyr Leu Thr Phe Asp Ile Asp Cys Leu Asp Pro Ser Phe
225                 230                 235                 240

Ala Pro Gly Thr Gly Thr Pro Val Cys Gly Gly Leu Ser Ser Asp Arg
                245                 250                 255

Ala Leu Lys Ile Leu Arg Gly Leu Thr Asp Leu Asp Ile Val Gly Met
                260                 265                 270

Asp Val Val Glu Val Ala Pro Ser Tyr Asp Gln Ser Asp Ile Thr Ala
    275                 280                 285

Leu Ala Gly Ala Thr Ile Ala Leu Glu Met Leu Tyr Leu Gln Gly Ala
    290                 295                 300

Lys Lys Asp
305

<210> SEQ ID NO 68
<211> LENGTH: 1404
<212> TYPE: DNA
<213> ORGANISM: Neisseria meningitidis
<220> FEATURE:
<221> NAME/KEY: CDS
<222> LOCATION: (1)..(1401)

<400> SEQUENCE: 68 atg aca ttg ctc aat cta atg ata atg caa gat tac ggt att tcc gtt      48
Met Thr Leu Leu Asn Leu Met Ile Met Gln Asp Tyr Gly Ile Ser Val
 1               5                  10                  15 tgc ctg aca ctg acg ccc tat ttg caa cat gaa cta ttt tcg gct atg      96
Cys Leu Thr Leu Thr Pro Tyr Leu Gln His Glu Leu Phe Ser Ala Met
                20                  25                  30 aaa tcc tat ttt tcc aaa tat atc cta ccc gtt tca ctt ttt acc ttg     144
Lys Ser Tyr Phe Ser Lys Tyr Ile Leu Pro Val Ser Leu Phe Thr Leu
            35                  40                  45 cca cta tcc ctt tcc cca tcc gtt tcg gct ttt acg ctg cct gaa gca     192
Pro Leu Ser Leu Ser Pro Ser Val Ser Ala Phe Thr Leu Pro Glu Ala
        50                  55                  60 tgg cgg gcg gcg cag caa cat tcg gct gat ttt caa gcg tcc cat tac     240
Trp Arg Ala Ala Gln Gln His Ser Ala Asp Phe Gln Ala Ser His Tyr
```

-continued

```
                65                  70                  75                  80
cag cgt gat gca gtg cgc gca cgg caa caa caa gcc aag gcc gca ttc      288
Gln Arg Asp Ala Val Arg Ala Arg Gln Gln Gln Ala Lys Ala Ala Phe
                        85                  90                  95 ctt ccc cat gta tcc gcc aat gcc agc tac cag cgc cag ccg cca tcg      336
Leu Pro His Val Ser Ala Asn Ala Ser Tyr Gln Arg Gln Pro Pro Ser
                100                 105                 110 att tct tcc acc cgc gaa aca cag gga tgg agc gtg cag gtg gga caa      384
Ile Ser Ser Thr Arg Glu Thr Gln Gly Trp Ser Val Gln Val Gly Gln
            115                 120                 125 acc tta ttt gac gct gcc aaa ttt gca caa tac cgc caa agc agg ttc      432
Thr Leu Phe Asp Ala Ala Lys Phe Ala Gln Tyr Arg Gln Ser Arg Phe
        130                 135                 140 gat acg cag gct gca gaa cag cgt ttc gat gcg gca cgc gaa gaa ttg      480
Asp Thr Gln Ala Ala Glu Gln Arg Phe Asp Ala Ala Arg Glu Glu Leu
145                 150                 155                 160 ctg ttg aaa gtt gcc gaa agt tat ttc aac gtt tta ctc agc cga gac      528
Leu Leu Lys Val Ala Glu Ser Tyr Phe Asn Val Leu Leu Ser Arg Asp
                165                 170                 175 acc gtt gcc gcc cat gcg gcg gaa aaa gag gct tat gcc cag cag gta      576
Thr Val Ala Ala His Ala Ala Glu Lys Glu Ala Tyr Ala Gln Gln Val
                180                 185                 190 agg cag gcg cag gct tta ttc aat aaa ggt gct gcc acc gcg ctg gat      624
Arg Gln Ala Gln Ala Leu Phe Asn Lys Gly Ala Ala Thr Ala Leu Asp
            195                 200                 205 att cac gaa gcc aaa gcc ggt tac gac aat gcc ctg gcc caa gaa atc      672
Ile His Glu Ala Lys Ala Gly Tyr Asp Asn Ala Leu Ala Gln Glu Ile
        210                 215                 220 gcc gta ttg gct gag aaa caa acc tat gaa aac cag ttg aac gac tac      720
Ala Val Leu Ala Glu Lys Gln Thr Tyr Glu Asn Gln Leu Asn Asp Tyr
225                 230                 235                 240 acc gac ctg gat agc aaa caa atc gag gcc ata gat acc gcc aac ctg      768
Thr Asp Leu Asp Ser Lys Gln Ile Glu Ala Ile Asp Thr Ala Asn Leu
                245                 250                 255 ttg gca cgc tat ctg ccc aag ctg gaa cgt tac agt ctg gat gaa tgg      816
Leu Ala Arg Tyr Leu Pro Lys Leu Glu Arg Tyr Ser Leu Asp Glu Trp
                260                 265                 270 cag cgc att gcc tta tcc aac aat cat gaa tac cgg atg cag cag ctt      864
Gln Arg Ile Ala Leu Ser Asn Asn His Glu Tyr Arg Met Gln Gln Leu
            275                 280                 285 gcc ctg caa agc agc gga cag gcg ctt cgg gca gca cag aac agc cgc      912
Ala Leu Gln Ser Ser Gly Gln Ala Leu Arg Ala Ala Gln Asn Ser Arg
        290                 295                 300 tat ccc acc gtt tct gcc cat gtc ggc tat cag aat aac ctc tac act      960
Tyr Pro Thr Val Ser Ala His Val Gly Tyr Gln Asn Asn Leu Tyr Thr
305                 310                 315                 320 tca tct gcg cag aat aat gac tac cac tat cgg ggc aaa ggg atg agc     1008
Ser Ser Ala Gln Asn Asn Asp Tyr His Tyr Arg Gly Lys Gly Met Ser
                325                 330                 335 gtc ggc gta cag ttg aat ttg ccg ctt tat acc ggc gga gaa ttg tcg     1056
Val Gly Val Gln Leu Asn Leu Pro Leu Tyr Thr Gly Gly Glu Leu Ser
                340                 345                 350 ggc aaa atc cat gaa gcc gaa gcg caa tac ggg gcc gcc gaa gca cag     1104
Gly Lys Ile His Glu Ala Glu Ala Gln Tyr Gly Ala Ala Glu Ala Gln
            355                 360                 365 ctg acc gca acc gag cgg cac atc aaa ctc gcc gta cgc cag gct tat     1152
Leu Thr Ala Thr Glu Arg His Ile Lys Leu Ala Val Arg Gln Ala Tyr
        370                 375                 380 acc gaa agc ggt gcg gcg cgt tac caa atc atg gcg caa gaa cgg gtt     1200
```

-continued

```
Thr Glu Ser Gly Ala Ala Arg Tyr Gln Ile Met Ala Gln Glu Arg Val
385                 390                 395                 400 ttg gaa agc agc cgt ttg aaa ctg aaa tcg acc gaa acc ggc caa caa    1248
Leu Glu Ser Ser Arg Leu Lys Leu Lys Ser Thr Glu Thr Gly Gln Gln
                405                 410                 415 tac ggc atc cgc aac cgg ctg gaa gta ata cgg gcg cgg cag gaa gtc    1296
Tyr Gly Ile Arg Asn Arg Leu Glu Val Ile Arg Ala Arg Gln Glu Val
            420                 425                 430 gcc caa gca gaa cag aaa ctg gct caa gca cgg tat aaa ttc atg ctg    1344
Ala Gln Ala Glu Gln Lys Leu Ala Gln Ala Arg Tyr Lys Phe Met Leu
        435                 440                 445 gct tat ttg cgc ttg gtg aaa gag agc ggg tta ggg ttg gaa acg gta    1392
Ala Tyr Leu Arg Leu Val Lys Glu Ser Gly Leu Gly Leu Glu Thr Val
    450                 455                 460 ttt gcg gaa taa                                                    1404
Phe Ala Glu
465
```

<210> SEQ ID NO 69
<211> LENGTH: 467
<212> TYPE: PRT
<213> ORGANISM: Neisseria meningitidis

<400> SEQUENCE: 69

```
Met Thr Leu Leu Asn Leu Met Ile Met Gln Asp Tyr Gly Ile Ser Val
1               5                   10                  15

Cys Leu Thr Leu Thr Pro Tyr Leu Gln His Glu Leu Phe Ser Ala Met
            20                  25                  30

Lys Ser Tyr Phe Ser Lys Tyr Ile Leu Pro Val Ser Leu Phe Thr Leu
        35                  40                  45

Pro Leu Ser Leu Ser Pro Ser Val Ser Ala Phe Thr Leu Pro Glu Ala
    50                  55                  60

Trp Arg Ala Ala Gln Gln His Ser Ala Asp Phe Gln Ala Ser His Tyr
65                  70                  75                  80

Gln Arg Asp Ala Val Arg Ala Arg Gln Gln Ala Lys Ala Ala Phe
                85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255
```

```
Leu Ala Arg Tyr Leu Pro Lys Leu Glu Arg Tyr Ser Leu Asp Glu Trp
        260                 265                 270

Gln Arg Ile Ala Leu Ser Asn Asn His Glu Tyr Arg Met Gln Gln Leu
    275                 280                 285

Ala Leu Gln Ser Ser Gly Gln Ala Leu Arg Ala Gln Asn Ser Arg
290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
            355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465

<210> SEQ ID NO 70
<211> LENGTH: 696
<212> TYPE: DNA
<213> ORGANISM: Neisseria gonorrhoeae
<220> FEATURE:
<221> NAME/KEY: CDS
<222> LOCATION: (1)..(693)

<400> SEQUENCE: 70 atg aaa caa tcc gcc cga ata aaa aat atg gat cag aca tta aaa aat    48
Met Lys Gln Ser Ala Arg Ile Lys Asn Met Asp Gln Thr Leu Lys Asn
 1               5                  10                  15 aca ttg ggc att tgc gcg ctt tta gcc ttt tgt ttt ggc gcg gcc atc    96
Thr Leu Gly Ile Cys Ala Leu Leu Ala Phe Cys Phe Gly Ala Ala Ile
            20                  25                  30 gca tca ggt tat cac ttg gaa tat gaa tac ggc tac cgt tat tct gcc   144
Ala Ser Gly Tyr His Leu Glu Tyr Glu Tyr Gly Tyr Arg Tyr Ser Ala
        35                  40                  45 gtg ggc gct ttg gct tcg gtt gta ttt tta tta ttg gca cgc ggc        192
Val Gly Ala Leu Ala Ser Val Val Phe Leu Leu Leu Ala Arg Gly
    50                  55                  60 ttc ccg cgc gtt tct tca gtt gtt tta ctg att tac gtc ggc aca acc   240
Phe Pro Arg Val Ser Ser Val Val Leu Leu Ile Tyr Val Gly Thr Thr
65                  70                  75                  80 gcc cta tat ttg ccg gtc ggc tgg ctg tat ggt gcg cct tct tat cag   288
Ala Leu Tyr Leu Pro Val Gly Trp Leu Tyr Gly Ala Pro Ser Tyr Gln
                85                  90                  95 ata gtc ggt tcg ata ttg gaa agc aat cct gcc gag gcg cgt gaa ttt   336
Ile Val Gly Ser Ile Leu Glu Ser Asn Pro Ala Glu Ala Arg Glu Phe
```

```
                100                 105                  110
gtc ggc aat ctt ccc ggg tcg ctt tat ttt gtg cag gca tta ttt ttc       384
Val Gly Asn Leu Pro Gly Ser Leu Tyr Phe Val Gln Ala Leu Phe Phe
            115                 120                 125 att ttt ggc ttg aca gtt tgg aaa tat tgt gta tct gtg ggg gta ttt       432
Ile Phe Gly Leu Thr Val Trp Lys Tyr Cys Val Ser Val Gly Val Phe
130                 135                 140 gct gac gta aaa aac tat aaa cgt cgc agc aaa ata tgg ctg acc ata       480
Ala Asp Val Lys Asn Tyr Lys Arg Arg Ser Lys Ile Trp Leu Thr Ile
145                 150                 155                 160 tta ttg act ttg att ttg tcc tgc gcg gtg atg gag aaa atc gcc ggc       528
Leu Leu Thr Leu Ile Leu Ser Cys Ala Val Met Glu Lys Ile Ala Gly
                165                 170                 175 gat aaa gat tgg cga gaa cct gat gcc ggc ctg ttg ttg aat att ttc       576
Asp Lys Asp Trp Arg Glu Pro Asp Ala Gly Leu Leu Leu Asn Ile Phe
            180                 185                 190 gac ctg tat tac gac ttg gct ttc cgc gcc ggc aca ata tgc cgc caa       624
Asp Leu Tyr Tyr Asp Leu Ala Phe Arg Ala Gly Thr Ile Cys Arg Gln
            195                 200                 205 gcg cgc cca cat ttt gga agc agc aaa aaa agc gtc aac atg gca tat       672
Ala Arg Pro His Phe Gly Ser Ser Lys Lys Ser Val Asn Met Ala Tyr
210                 215                 220 ccg cca act tgc gcc caa gta taa                                        696
Pro Pro Thr Cys Ala Gln Val
225                 230

<210> SEQ ID NO 71
<211> LENGTH: 231
<212> TYPE: PRT
<213> ORGANISM: Neisseria gonorrhoeae

<400> SEQUENCE: 71

Met Lys Gln Ser Ala Arg Ile Lys Asn Met Asp Gln Thr Leu Lys Asn
  1               5                  10                  15

Thr Leu Gly Ile Cys Ala Leu Leu Ala Phe Cys Phe Gly Ala Ala Ile
                 20                  25                  30

Ala Ser Gly Tyr His Leu Glu Tyr Glu Tyr Gly Tyr Arg Tyr Ser Ala
             35                  40                  45

Val Gly Ala Leu Ala Ser Val Val Phe Leu Leu Leu Ala Arg Gly
         50                  55                  60

Phe Pro Arg Val Ser Ser Val Val Leu Leu Ile Tyr Val Gly Thr Thr
 65                  70                  75                  80

Ala Leu Tyr Leu Pro Val Gly Trp Leu Tyr Gly Ala Pro Ser Tyr Gln
                 85                  90                  95

Ile Val Gly Ser Ile Leu Glu Ser Asn Pro Ala Glu Ala Arg Glu Phe
            100                 105                 110

Val Gly Asn Leu Pro Gly Ser Leu Tyr Phe Val Gln Ala Leu Phe Phe
            115                 120                 125

Ile Phe Gly Leu Thr Val Trp Lys Tyr Cys Val Ser Val Gly Val Phe
130                 135                 140

Ala Asp Val Lys Asn Tyr Lys Arg Arg Ser Lys Ile Trp Leu Thr Ile
145                 150                 155                 160

Leu Leu Thr Leu Ile Leu Ser Cys Ala Val Met Glu Lys Ile Ala Gly
                165                 170                 175

Asp Lys Asp Trp Arg Glu Pro Asp Ala Gly Leu Leu Leu Asn Ile Phe
            180                 185                 190

Asp Leu Tyr Tyr Asp Leu Ala Phe Arg Ala Gly Thr Ile Cys Arg Gln
```

```
                     195                 200                 205
Ala Arg Pro His Phe Gly Ser Ser Lys Lys Ser Val Asn Met Ala Tyr
    210                 215                 220

Pro Pro Thr Cys Ala Gln Val
225                 230

<210> SEQ ID NO 72
<211> LENGTH: 2607
<212> TYPE: DNA
<213> ORGANISM: Neisseria meningitidis
<220> FEATURE:
<221> NAME/KEY: CDS
<222> LOCATION: (1)..(2604)

<400> SEQUENCE: 72 atg gct gcc aac caa cgt tac cgc aaa ccg ctg ccc ggt acg gat ttg     48
Met Ala Ala Asn Gln Arg Tyr Arg Lys Pro Leu Pro Gly Thr Asp Leu
 1               5                  10                  15 gaa tac tac gac gcg cgt gcg gcg tgt gag ggc atc aaa ccc ggc tct     96
Glu Tyr Tyr Asp Ala Arg Ala Ala Cys Glu Gly Ile Lys Pro Gly Ser
                20                  25                  30 tac gac aag ctg cct tac acg agc cgc att ttg gcg gag aat ttg gtc    144
Tyr Asp Lys Leu Pro Tyr Thr Ser Arg Ile Leu Ala Glu Asn Leu Val
            35                  40                  45 aac cgc gcg gac aaa gtc gat ttg ccg acg ctg caa agc tgg ctg ggt    192
Asn Arg Ala Asp Lys Val Asp Leu Pro Thr Leu Gln Ser Trp Leu Gly
        50                  55                  60 cag ctg att gag gga aaa cag gaa atc gac ttt cct tgg tat ccg gcg    240
Gln Leu Ile Glu Gly Lys Gln Glu Ile Asp Phe Pro Trp Tyr Pro Ala
 65                  70                  75                  80 cgg gtg gtg tgc cac gat att ctg ggg cag acc gcg ttg gtg gat ttg    288
Arg Val Val Cys His Asp Ile Leu Gly Gln Thr Ala Leu Val Asp Leu
                 85                  90                  95 gca ggt ctg cgc gat gcg att gcc gaa aaa ggc ggc gat cct gcc aaa    336
Ala Gly Leu Arg Asp Ala Ile Ala Glu Lys Gly Gly Asp Pro Ala Lys
                100                 105                 110 gtg aat ccg gtg gtg caa acc cag ctc atc gtc gac cac tcg ctg gcg    384
Val Asn Pro Val Val Gln Thr Gln Leu Ile Val Asp His Ser Leu Ala
            115                 120                 125 gtg gaa tgc ggc ggc tac gac ccc gat gcg ttc cgc aaa aac cgc gaa    432
Val Glu Cys Gly Gly Tyr Asp Pro Asp Ala Phe Arg Lys Asn Arg Glu
        130                 135                 140 atc gaa gac aga cgt aac gaa gac cgt ttc cac ttc atc aac tgg aca    480
Ile Glu Asp Arg Arg Asn Glu Asp Arg Phe His Phe Ile Asn Trp Thr
145                 150                 155                 160 aaa acc gct ttt gaa aat gtg gac gtg att ccg gcg ggc aac ggc atc    528
Lys Thr Ala Phe Glu Asn Val Asp Val Ile Pro Ala Gly Asn Gly Ile
                165                 170                 175 atg cac caa atc aat cta gaa aaa atg tcg ccc gtc gtc caa gtc aaa    576
Met His Gln Ile Asn Leu Glu Lys Met Ser Pro Val Val Gln Val Lys
                180                 185                 190 aac ggc gtg gct ttc ccc gat acc tgc gtc ggc acg gat tcg cac acg    624
Asn Gly Val Ala Phe Pro Asp Thr Cys Val Gly Thr Asp Ser His Thr
            195                 200                 205 cca cac gtc gat gcg ctg ggc gtg att tcc gtg ggc gtg ggc gga ttg    672
Pro His Val Asp Ala Leu Gly Val Ile Ser Val Gly Val Gly Gly Leu
        210                 215                 220 gaa gcg gaa acc gta atg ctg gga cgc gcg tcc atg atg cgc ctg ccc    720
Glu Ala Glu Thr Val Met Leu Gly Arg Ala Ser Met Met Arg Leu Pro
225                 230                 235                 240
```

```
gat att gtc ggc gtt gag ctg aac ggc aaa cgg aag gcg ggc att acg        768
Asp Ile Val Gly Val Glu Leu Asn Gly Lys Arg Lys Ala Gly Ile Thr
            245                 250                 255 gcg acg gat att gtg ttg gca ctg acc gag ttt ctg cgc aaa gaa cgc        816
Ala Thr Asp Ile Val Leu Ala Leu Thr Glu Phe Leu Arg Lys Glu Arg
            260                 265                 270 gtg gtc ggg gcg ttt gtc gaa ttc ttc ggc gag ggc gcg aga agc ctg        864
Val Val Gly Ala Phe Val Glu Phe Phe Gly Glu Gly Ala Arg Ser Leu
            275                 280                 285 tct atc ggc gac cgc gcg acc att tcc aac atg acg ccg gag ttc ggc        912
Ser Ile Gly Asp Arg Ala Thr Ile Ser Asn Met Thr Pro Glu Phe Gly
        290                 295                 300 gcg act gcc gcg atg ttc gct att gat gag caa acc att gat tat ttg        960
Ala Thr Ala Ala Met Phe Ala Ile Asp Glu Gln Thr Ile Asp Tyr Leu
305                 310                 315                 320 aaa ctg acc gga cgc gac gac gcg cag gtg aaa ttg gtg gaa acc tac       1008
Lys Leu Thr Gly Arg Asp Asp Ala Gln Val Lys Leu Val Glu Thr Tyr
            325                 330                 335 gcc aaa acc gca ggc ttg tgg gca gat gcc ttg aaa acc gcc gtt tat       1056
Ala Lys Thr Ala Gly Leu Trp Ala Asp Ala Leu Lys Thr Ala Val Tyr
            340                 345                 350 ccg cgc gtt ttg aaa ttt gat ttg agc agc gta acg cgc aat atg gca       1104
Pro Arg Val Leu Lys Phe Asp Leu Ser Ser Val Thr Arg Asn Met Ala
            355                 360                 365 ggc ccg agc aac ccg cac gcg cgt ttt gcg acc gcc gat ttg gcc ggc       1152
Gly Pro Ser Asn Pro His Ala Arg Phe Ala Thr Ala Asp Leu Ala Gly
        370                 375                 380 aaa ggc ttg gct aaa cct tac gaa gag cct tca gac ggc caa atg cct       1200
Lys Gly Leu Ala Lys Pro Tyr Glu Glu Pro Ser Asp Gly Gln Met Pro
385                 390                 395                 400 gac ggt gca gtg att att gcc gcg att act tcc tgt acc aat act tcc       1248
Asp Gly Ala Val Ile Ile Ala Ala Ile Thr Ser Cys Thr Asn Thr Ser
            405                 410                 415 aat ccg cgc aac gtt gtc gcc gcc gcg ctg ttg gca cgc aat gcc aac       1296
Asn Pro Arg Asn Val Val Ala Ala Ala Leu Leu Ala Arg Asn Ala Asn
            420                 425                 430 cgc ctc ggc ttg caa cgc aaa cct tgg gtg aaa tct tcg ttt gcc ccg       1344
Arg Leu Gly Leu Gln Arg Lys Pro Trp Val Lys Ser Ser Phe Ala Pro
            435                 440                 445 ggt tca aaa gta gcc gaa atc tat ttg aaa gaa gca gat ctg ctg ccc       1392
Gly Ser Lys Val Ala Glu Ile Tyr Leu Lys Glu Ala Asp Leu Leu Pro
        450                 455                 460 gaa atg gaa aaa ctc ggc ttc ggt atc gtt gcc ttc gca tgt acc acc       1440
Glu Met Glu Lys Leu Gly Phe Gly Ile Val Ala Phe Ala Cys Thr Thr
465                 470                 475                 480 tgt aac ggc atg agc ggc gcg ctg gat ccg aaa atc cag aaa gaa atc       1488
Cys Asn Gly Met Ser Gly Ala Leu Asp Pro Lys Ile Gln Lys Glu Ile
            485                 490                 495 atc gac cgc gat ttg tac gcc acc gcc gta ttg tca ggc aac cgc aac       1536
Ile Asp Arg Asp Leu Tyr Ala Thr Ala Val Leu Ser Gly Asn Arg Asn
            500                 505                 510 ttt gac ggc cgt atc cat ccg tat gcg aaa cag gct ttc ctc gct tcg       1584
Phe Asp Gly Arg Ile His Pro Tyr Ala Lys Gln Ala Phe Leu Ala Ser
            515                 520                 525 cct ccg ttg gtc gtt gcc tac gcg ctg gca ggc agc atc cgt ttc gat       1632
Pro Pro Leu Val Val Ala Tyr Ala Leu Ala Gly Ser Ile Arg Phe Asp
        530                 535                 540 att gaa aac gac gta ctc ggc gtt gca gac ggc aaa gaa atc cgc ctg       1680
Ile Glu Asn Asp Val Leu Gly Val Ala Asp Gly Lys Glu Ile Arg Leu
545                 550                 555                 560
```

```
aaa gac att tgg cct acc gat gaa gaa atc gat gcc atc gtt gcc gaa    1728
Lys Asp Ile Trp Pro Thr Asp Glu Glu Ile Asp Ala Ile Val Ala Glu
            565                 570                 575 tat gtg aaa ccg cag caa ttt cgc gac gtt tat atc ccg atg ttc gac    1776
Tyr Val Lys Pro Gln Gln Phe Arg Asp Val Tyr Ile Pro Met Phe Asp
        580                 585                 590 acc ggc aca gcg caa aaa gca cca agc ccg ctg tac gac tgg cgt cca    1824
Thr Gly Thr Ala Gln Lys Ala Pro Ser Pro Leu Tyr Asp Trp Arg Pro
    595                 600                 605 atg tct acc tat atc cgc cgc cca cct tac tgg gaa ggc gca ctg gca    1872
Met Ser Thr Tyr Ile Arg Arg Pro Pro Tyr Trp Glu Gly Ala Leu Ala
610                 615                 620 ggg gaa cgc aca tta agc ggt atg cgt ccg ctg gcg att ttg ccc gac    1920
Gly Glu Arg Thr Leu Ser Gly Met Arg Pro Leu Ala Ile Leu Pro Asp
625                 630                 635                 640 aac atc acc acc gac cat ctc tcg cca tcc aat gcg att ttg gca agc    1968
Asn Ile Thr Thr Asp His Leu Ser Pro Ser Asn Ala Ile Leu Ala Ser
                645                 650                 655 agt gcc gca ggc gaa tat ttg gca aaa atg ggt ttg cct gaa gaa gac    2016
Ser Ala Ala Gly Glu Tyr Leu Ala Lys Met Gly Leu Pro Glu Glu Asp
            660                 665                 670 ttc aac tct tac gca acc cac cgt ggc gac cac ttg acc gcc caa cgc    2064
Phe Asn Ser Tyr Ala Thr His Arg Gly Asp His Leu Thr Ala Gln Arg
        675                 680                 685 gca acc ttc gcc aat ccg aaa ctg ttt aac gaa atg gtg aga aac gaa    2112
Ala Thr Phe Ala Asn Pro Lys Leu Phe Asn Glu Met Val Arg Asn Glu
    690                 695                 700 gac ggc agc gta cgc caa ggt tcg ctg gca cgc gtt gaa ccc gaa ggc    2160
Asp Gly Ser Val Arg Gln Gly Ser Leu Ala Arg Val Glu Pro Glu Gly
705                 710                 715                 720 caa acc atg cgc atg tgg gaa gcc atc gaa acc tat atg aac cgc aaa    2208
Gln Thr Met Arg Met Trp Glu Ala Ile Glu Thr Tyr Met Asn Arg Lys
                725                 730                 735 cag ccg ctc atc atc att gcc ggc gcg gac tac ggt caa ggc tca agc    2256
Gln Pro Leu Ile Ile Ile Ala Gly Ala Asp Tyr Gly Gln Gly Ser Ser
            740                 745                 750 cgc gac tgg gct gca aaa ggc gta cgc ctc gcc ggc gtg gaa gcg att    2304
Arg Asp Trp Ala Ala Lys Gly Val Arg Leu Ala Gly Val Glu Ala Ile
        755                 760                 765 gtt gcc gaa ggc ttc gag cgt atc cac cgc acc aac ttg atc ggt atg    2352
Val Ala Glu Gly Phe Glu Arg Ile His Arg Thr Asn Leu Ile Gly Met
    770                 775                 780 ggc gtg ttg ccg ctg cag ttc aaa ccg ggt acc aac cgc cac acc ctg    2400
Gly Val Leu Pro Leu Gln Phe Lys Pro Gly Thr Asn Arg His Thr Leu
785                 790                 795                 800 caa ctg gac ggt acg gaa acc tac gac gtt gtc ggc gaa cgc aca ccg    2448
Gln Leu Asp Gly Thr Glu Thr Tyr Asp Val Val Gly Glu Arg Thr Pro
                805                 810                 815 cgc tgc gac ctg acc ctt gtg att cac cgt aaa aac ggc gag acc gtc    2496
Arg Cys Asp Leu Thr Leu Val Ile His Arg Lys Asn Gly Glu Thr Val
            820                 825                 830 gaa gtc ccc att acc tgc cgc ctc gat acc gca gaa gaa gtg ttg gta    2544
Glu Val Pro Ile Thr Cys Arg Leu Asp Thr Ala Glu Glu Val Leu Val
        835                 840                 845 tat gaa gcc ggt ggc gta ttg caa cgg ttt gca cag gat ttt ttg gaa    2592
Tyr Glu Ala Gly Gly Val Leu Gln Arg Phe Ala Gln Asp Phe Leu Glu
    850                 855                 860 ggg aac gcg gct tag                                                2607
Gly Asn Ala Ala
```

865

<210> SEQ ID NO 73
<211> LENGTH: 868
<212> TYPE: PRT
<213> ORGANISM: Neisseria meningitidis

<400> SEQUENCE: 73

```
Met Ala Ala Asn Gln Arg Tyr Arg Lys Pro Leu Pro Gly Thr Asp Leu
  1               5                  10                  15

Glu Tyr Tyr Asp Ala Arg Ala Ala Cys Glu Gly Ile Lys Pro Gly Ser
             20                  25                  30

Tyr Asp Lys Leu Pro Tyr Thr Ser Arg Ile Leu Ala Glu Asn Leu Val
         35                  40                  45

Asn Arg Ala Asp Lys Val Asp Leu Pro Thr Leu Gln Ser Trp Leu Gly
 50                  55                  60

Gln Leu Ile Glu Gly Lys Gln Glu Ile Asp Phe Pro Trp Tyr Pro Ala
 65                  70                  75                  80

Arg Val Val Cys His Asp Ile Leu Gly Gln Thr Ala Leu Val Asp Leu
                 85                  90                  95

Ala Gly Leu Arg Asp Ala Ile Ala Glu Lys Gly Gly Asp Pro Ala Lys
            100                 105                 110

Val Asn Pro Val Val Gln Thr Gln Leu Ile Val Asp His Ser Leu Ala
        115                 120                 125

Val Glu Cys Gly Gly Tyr Asp Pro Asp Ala Phe Arg Lys Asn Arg Glu
130                 135                 140

Ile Glu Asp Arg Arg Asn Glu Asp Arg Phe His Phe Ile Asn Trp Thr
145                 150                 155                 160

Lys Thr Ala Phe Glu Asn Val Asp Val Ile Pro Ala Gly Asn Gly Ile
                165                 170                 175

Met His Gln Ile Asn Leu Glu Lys Met Ser Pro Val Val Gln Val Lys
            180                 185                 190

Asn Gly Val Ala Phe Pro Asp Thr Cys Val Gly Thr Asp Ser His Thr
        195                 200                 205

Pro His Val Asp Ala Leu Gly Val Ile Ser Val Gly Val Gly Gly Leu
    210                 215                 220

Glu Ala Glu Thr Val Met Leu Gly Arg Ala Ser Met Met Arg Leu Pro
225                 230                 235                 240

Asp Ile Val Gly Val Glu Leu Asn Gly Lys Arg Lys Ala Gly Ile Thr
                245                 250                 255

Ala Thr Asp Ile Val Leu Ala Leu Thr Glu Phe Leu Arg Lys Glu Arg
            260                 265                 270

Val Val Gly Ala Phe Val Glu Phe Gly Glu Gly Ala Arg Ser Leu
        275                 280                 285

Ser Ile Gly Asp Arg Ala Thr Ile Ser Asn Met Thr Pro Glu Phe Gly
    290                 295                 300

Ala Thr Ala Ala Met Phe Ala Ile Asp Glu Gln Thr Ile Asp Tyr Leu
305                 310                 315                 320

Lys Leu Thr Gly Arg Asp Asp Ala Gln Val Lys Leu Val Glu Thr Tyr
                325                 330                 335

Ala Lys Thr Ala Gly Leu Trp Ala Asp Ala Leu Lys Thr Ala Val Tyr
            340                 345                 350

Pro Arg Val Leu Lys Phe Asp Leu Ser Ser Val Thr Arg Asn Met Ala
        355                 360                 365
```

-continued

```
Gly Pro Ser Asn Pro His Ala Arg Phe Ala Thr Ala Asp Leu Ala Gly
    370                 375                 380

Lys Gly Leu Ala Lys Pro Tyr Glu Glu Pro Ser Asp Gly Gln Met Pro
385                 390                 395                 400

Asp Gly Ala Val Ile Ile Ala Ala Ile Thr Ser Cys Thr Asn Thr Ser
                405                 410                 415

Asn Pro Arg Asn Val Val Ala Ala Ala Leu Leu Ala Arg Asn Ala Asn
            420                 425                 430

Arg Leu Gly Leu Gln Arg Lys Pro Trp Val Lys Ser Ser Phe Ala Pro
        435                 440                 445

Gly Ser Lys Val Ala Glu Ile Tyr Leu Lys Glu Ala Asp Leu Leu Pro
    450                 455                 460

Glu Met Glu Lys Leu Gly Phe Gly Ile Val Ala Phe Ala Cys Thr Thr
465                 470                 475                 480

Cys Asn Gly Met Ser Gly Ala Leu Asp Pro Lys Ile Gln Lys Glu Ile
                485                 490                 495

Ile Asp Arg Asp Leu Tyr Ala Thr Ala Val Leu Ser Gly Asn Arg Asn
            500                 505                 510

Phe Asp Gly Arg Ile His Pro Tyr Ala Lys Gln Ala Phe Leu Ala Ser
        515                 520                 525

Pro Pro Leu Val Val Ala Tyr Ala Leu Ala Gly Ser Ile Arg Phe Asp
    530                 535                 540

Ile Glu Asn Asp Val Leu Gly Val Ala Asp Gly Lys Glu Ile Arg Leu
545                 550                 555                 560

Lys Asp Ile Trp Pro Thr Asp Glu Glu Ile Asp Ala Ile Val Ala Glu
                565                 570                 575

Tyr Val Lys Pro Gln Gln Phe Arg Asp Val Tyr Ile Pro Met Phe Asp
            580                 585                 590

Thr Gly Thr Ala Gln Lys Ala Pro Ser Pro Leu Tyr Asp Trp Arg Pro
        595                 600                 605

Met Ser Thr Tyr Ile Arg Arg Pro Pro Tyr Trp Glu Gly Ala Leu Ala
    610                 615                 620

Gly Glu Arg Thr Leu Ser Gly Met Arg Pro Leu Ala Ile Leu Pro Asp
625                 630                 635                 640

Asn Ile Thr Thr Asp His Leu Ser Pro Ser Asn Ala Ile Leu Ala Ser
                645                 650                 655

Ser Ala Ala Gly Glu Tyr Leu Ala Lys Met Gly Leu Pro Glu Glu Asp
            660                 665                 670

Phe Asn Ser Tyr Ala Thr His Arg Gly Asp His Leu Thr Ala Gln Arg
        675                 680                 685

Ala Thr Phe Ala Asn Pro Lys Leu Phe Asn Glu Met Val Arg Asn Glu
    690                 695                 700

Asp Gly Ser Val Arg Gln Gly Ser Leu Ala Arg Val Glu Pro Glu Gly
705                 710                 715                 720

Gln Thr Met Arg Met Trp Glu Ala Ile Glu Thr Tyr Met Asn Arg Lys
                725                 730                 735

Gln Pro Leu Ile Ile Ala Gly Ala Asp Tyr Gly Gln Gly Ser Ser
            740                 745                 750

Arg Asp Trp Ala Ala Lys Gly Val Arg Leu Ala Gly Val Glu Ala Ile
        755                 760                 765

Val Ala Glu Gly Phe Glu Arg Ile His Arg Thr Asn Leu Ile Gly Met
    770                 775                 780

Gly Val Leu Pro Leu Gln Phe Lys Pro Gly Thr Asn Arg His Thr Leu
```

```
                785                 790                 795                 800

Gln Leu Asp Gly Thr Glu Thr Tyr Asp Val Val Gly Glu Arg Thr Pro
                    805                 810                 815

Arg Cys Asp Leu Thr Leu Val Ile His Arg Lys Asn Gly Glu Thr Val
                    820                 825                 830

Glu Val Pro Ile Thr Cys Arg Leu Asp Thr Ala Glu Glu Val Leu Val
                    835                 840                 845

Tyr Glu Ala Gly Gly Val Leu Gln Arg Phe Ala Gln Asp Phe Leu Glu
                    850                 855                 860

Gly Asn Ala Ala
865

<210> SEQ ID NO 74
<211> LENGTH: 1170
<212> TYPE: DNA
<213> ORGANISM: Neisseria meningitidis
<220> FEATURE:
<221> NAME/KEY: CDS
<222> LOCATION: (1)..(1167)

<400> SEQUENCE: 74 atg ccg caa att aaa att ccc gcc gtt tac tac cgt ggc ggt aca tca      48
Met Pro Gln Ile Lys Ile Pro Ala Val Tyr Tyr Arg Gly Gly Thr Ser
 1               5                  10                  15 aaa ggc gtg ttt ttc aaa cgt tcc gac ctg ccc gag gcg gcg cgg gaa      96
Lys Gly Val Phe Phe Lys Arg Ser Asp Leu Pro Glu Ala Ala Arg Glu
                20                  25                  30 gcg gga agc gca cgc gac aaa atc ctc ttg cgc gta ctc ggc agc ccg     144
Ala Gly Ser Ala Arg Asp Lys Ile Leu Leu Arg Val Leu Gly Ser Pro
            35                  40                  45 gat ccc tac ggc aag cag ata gac ggt ttg ggc aac gcc agc tcg tcc     192
Asp Pro Tyr Gly Lys Gln Ile Asp Gly Leu Gly Asn Ala Ser Ser Ser
        50                  55                  60 acc agc aag gcg gtg att ttg gac aag tcc gaa cgc gcc gat cac gat     240
Thr Ser Lys Ala Val Ile Leu Asp Lys Ser Glu Arg Ala Asp His Asp
65                  70                  75                  80 gtc gat tac ctt ttc ggg caa gtt tcc atc gac aaa cct ttt gtc gat     288
Val Asp Tyr Leu Phe Gly Gln Val Ser Ile Asp Lys Pro Phe Val Asp
                85                  90                  95 tgg agt ggc aac tgc ggc aac ctc acc gcc gcc gtg ggc gca ttt gcc     336
Trp Ser Gly Asn Cys Gly Asn Leu Thr Ala Ala Val Gly Ala Phe Ala
            100                 105                 110 atc gag caa ggc ttg gtc gat aaa ggc aag att cct tca gac ggc atc     384
Ile Glu Gln Gly Leu Val Asp Lys Gly Lys Ile Pro Ser Asp Gly Ile
        115                 120                 125 tgc aca gtc aaa atc tgg cag aaa aac atc ggc aaa acc att att gcc     432
Cys Thr Val Lys Ile Trp Gln Lys Asn Ile Gly Lys Thr Ile Ile Ala
    130                 135                 140 cat gta ccg atg caa aac ggc gca gtt ttg gaa aca ggc gat ttt gag     480
His Val Pro Met Gln Asn Gly Ala Val Leu Glu Thr Gly Asp Phe Glu
145                 150                 155                 160 ctc gac ggc gta acg ttc ccg gca gcc gaa gta caa atc gaa ttt ctt     528
Leu Asp Gly Val Thr Phe Pro Ala Ala Glu Val Gln Ile Glu Phe Leu
                165                 170                 175 gat cca gcc gac ggc gaa ggc agt atg ttc cca acc ggc aat ttg gtc     576
Asp Pro Ala Asp Gly Glu Gly Ser Met Phe Pro Thr Gly Asn Leu Val
            180                 185                 190 gat gaa att gat gtg ccg aat ata ggc cgt ttg aaa gcc acg ctc atc     624
Asp Glu Ile Asp Val Pro Asn Ile Gly Arg Leu Lys Ala Thr Leu Ile
        195                 200                 205
```

| | | |
|---|---|---|
| aac gcg ggc att ccg acc gtt ttc ctg aat gcc gcc gac ttg ggc tac<br>Asn Ala Gly Ile Pro Thr Val Phe Leu Asn Ala Ala Asp Leu Gly Tyr<br>210 215 220 | | 672 |
| acg ggc aaa gag ttg caa gac gac atc aac aac gat gcc gca gct ttg<br>Thr Gly Lys Glu Leu Gln Asp Asp Ile Asn Asn Asp Ala Ala Ala Leu<br>225 230 235 240 | | 720 |
| gaa aaa ttc gag aaa atc cgc gct tac ggt gcg ctg aaa atg ggt ctg<br>Glu Lys Phe Glu Lys Ile Arg Ala Tyr Gly Ala Leu Lys Met Gly Leu<br>245 250 255 | | 768 |
| atc agc gac gta tcc gaa gct gcc gcc cgc gcg cac acg ccg aaa gtc<br>Ile Ser Asp Val Ser Glu Ala Ala Ala Arg Ala His Thr Pro Lys Val<br>260 265 270 | | 816 |
| gcc ttc gtc gcg ccc gcc gcc gat tac acc gcc tcc agt ggc aaa acc<br>Ala Phe Val Ala Pro Ala Ala Asp Tyr Thr Ala Ser Ser Gly Lys Thr<br>275 280 285 | | 864 |
| gtg aat gcc gcc gac atc gat ttg ctg gta cgc gcc ctg agc atg ggc<br>Val Asn Ala Ala Asp Ile Asp Leu Leu Val Arg Ala Leu Ser Met Gly<br>290 295 300 | | 912 |
| aaa ttg cac cac gcg atg atg ggt acc gcc tct gtt gcc att gcg acc<br>Lys Leu His His Ala Met Met Gly Thr Ala Ser Val Ala Ile Ala Thr<br>305 310 315 320 | | 960 |
| gcc gcc gcc gtg ccc ggt acg ctg gtc aac ctt gcc gca ggc ggc gga<br>Ala Ala Ala Val Pro Gly Thr Leu Val Asn Leu Ala Ala Gly Gly Gly<br>325 330 335 | | 1008 |
| acg cgt aaa gaa gtg cgc ttc ggg cat cct tcc ggc aca ttg cgc gtc<br>Thr Arg Lys Glu Val Arg Phe Gly His Pro Ser Gly Thr Leu Arg Val<br>340 345 350 | | 1056 |
| ggt gca gcc gcc gaa tgt cag gac gga caa tgg acg gcc acc aaa gcg<br>Gly Ala Ala Ala Glu Cys Gln Asp Gly Gln Trp Thr Ala Thr Lys Ala<br>355 360 365 | | 1104 |
| gtt atg agc cgc agc gca cgc gtg atg atg gaa ggt tgg gtc agg gtg<br>Val Met Ser Arg Ser Ala Arg Val Met Met Glu Gly Trp Val Arg Val<br>370 375 380 | | 1152 |
| ccg gaa gat tgt ttt taa<br>Pro Glu Asp Cys Phe<br>385 | | 1170 |

<210> SEQ ID NO 75
<211> LENGTH: 389
<212> TYPE: PRT
<213> ORGANISM: Neisseria meningitidis

<400> SEQUENCE: 75

Met Pro Gln Ile Lys Ile Pro Ala Val Tyr Tyr Arg Gly Gly Thr Ser
1               5                   10                  15

Lys Gly Val Phe Phe Lys Arg Ser Asp Leu Pro Glu Ala Ala Arg Glu
            20                  25                  30

Ala Gly Ser Ala Arg Asp Lys Ile Leu Leu Arg Val Leu Gly Ser Pro
        35                  40                  45

Asp Pro Tyr Gly Lys Gln Ile Asp Gly Leu Gly Asn Ala Ser Ser Ser
    50                  55                  60

Thr Ser Lys Ala Val Ile Leu Asp Lys Ser Glu Arg Ala Asp His Asp
65                  70                  75                  80

Val Asp Tyr Leu Phe Gly Gln Val Ser Ile Asp Lys Pro Phe Val Asp
                85                  90                  95

Trp Ser Gly Asn Cys Gly Asn Leu Thr Ala Ala Val Gly Ala Phe Ala
            100                 105                 110

Ile Glu Gln Gly Leu Val Asp Lys Gly Lys Ile Pro Ser Asp Gly Ile

```
                115                 120                 125
Cys Thr Val Lys Ile Trp Gln Lys Asn Ile Gly Lys Thr Ile Ile Ala
            130                 135                 140

His Val Pro Met Gln Asn Gly Ala Val Leu Glu Thr Gly Asp Phe Glu
145                 150                 155                 160

Leu Asp Gly Val Thr Phe Pro Ala Ala Glu Val Gln Ile Glu Phe Leu
                165                 170                 175

Asp Pro Ala Asp Gly Glu Gly Ser Met Phe Pro Thr Gly Asn Leu Val
            180                 185                 190

Asp Glu Ile Asp Val Pro Asn Ile Gly Arg Leu Lys Ala Thr Leu Ile
                195                 200                 205

Asn Ala Gly Ile Pro Thr Val Phe Leu Asn Ala Ala Asp Leu Gly Tyr
            210                 215                 220

Thr Gly Lys Glu Leu Gln Asp Asp Ile Asn Asn Asp Ala Ala Ala Leu
225                 230                 235                 240

Glu Lys Phe Glu Lys Ile Arg Ala Tyr Gly Ala Leu Lys Met Gly Leu
                245                 250                 255

Ile Ser Asp Val Ser Glu Ala Ala Ala Arg Ala His Thr Pro Lys Val
            260                 265                 270

Ala Phe Val Ala Pro Ala Ala Asp Tyr Thr Ala Ser Ser Gly Lys Thr
                275                 280                 285

Val Asn Ala Ala Asp Ile Asp Leu Leu Val Arg Ala Leu Ser Met Gly
            290                 295                 300

Lys Leu His His Ala Met Met Gly Thr Ala Ser Val Ala Ile Ala Thr
305                 310                 315                 320

Ala Ala Ala Val Pro Gly Thr Leu Val Asn Leu Ala Ala Gly Gly Gly
                325                 330                 335

Thr Arg Lys Glu Val Arg Phe Gly His Pro Ser Gly Thr Leu Arg Val
            340                 345                 350

Gly Ala Ala Ala Glu Cys Gln Asp Gly Gln Trp Thr Ala Thr Lys Ala
                355                 360                 365

Val Met Ser Arg Ser Ala Arg Val Met Met Glu Gly Trp Val Arg Val
            370                 375                 380

Pro Glu Asp Cys Phe
385

<210> SEQ ID NO 76
<211> LENGTH: 2094
<212> TYPE: DNA
<213> ORGANISM: Neisseria gonorrhoeae
<220> FEATURE:
<221> NAME/KEY: CDS
<222> LOCATION: (1)..(2091)

<400> SEQUENCE: 76 atg aat tcg acc gca agt aaa acc ctg aaa gga ttg tcg ctg gtg ttt    48
Met Asn Ser Thr Ala Ser Lys Thr Leu Lys Gly Leu Ser Leu Val Phe
  1               5                  10                  15 ttc gcc tct ggc ttc tgc gcc ctg att tac cag gtc agc tgg cag agg    96
Phe Ala Ser Gly Phe Cys Ala Leu Ile Tyr Gln Val Ser Trp Gln Arg
             20                  25                  30 ctt cta ttc agc cac ata ggt atc gat ttg agt tcg att act gtc att   144
Leu Leu Phe Ser His Ile Gly Ile Asp Leu Ser Ser Ile Thr Val Ile
         35                  40                  45 att tct gta ttt atg gtc ggc ttg ggt gta ggt gcg tat ttc ggc gga   192
Ile Ser Val Phe Met Val Gly Leu Gly Val Gly Ala Tyr Phe Gly Gly
     50                  55                  60
```

| | |
|---|---|
| cgc att gct gac cgt ttt cct tca agt atc atc ccc ctg ttt tgc atc<br>Arg Ile Ala Asp Arg Phe Pro Ser Ser Ile Ile Pro Leu Phe Cys Ile<br>65                 70                    75                   80 | 240 |
| gct gaa gta tcc atc ggt ctg ttc ggt ttg gta agc aag ggt ctg att<br>Ala Glu Val Ser Ile Gly Leu Phe Gly Leu Val Ser Lys Gly Leu Ile<br>               85                      90                    95 | 288 |
| tcc ggc ttg ggg cat ctt tta gtt gag gct gat ttg ccc atc atc gct<br>Ser Gly Leu Gly His Leu Leu Val Glu Ala Asp Leu Pro Ile Ile Ala<br>          100                    105                    110 | 336 |
| gct gcc aat ttc ctc tta ttg ctg ctt cct acc ttt atg atg ggc gcg<br>Ala Ala Asn Phe Leu Leu Leu Leu Leu Pro Thr Phe Met Met Gly Ala<br>               115                    120                    125 | 384 |
| acc ttg ccc ttg ctg acc tgt ttt ttt aac cgg aaa ata cat aat gtt<br>Thr Leu Pro Leu Leu Thr Cys Phe Phe Asn Arg Lys Ile His Asn Val<br>130                    135                    140 | 432 |
| ggc gag tct atc ggt acc tta tat ttt ttc aac act ttg ggt gcg gca<br>Gly Glu Ser Ile Gly Thr Leu Tyr Phe Phe Asn Thr Leu Gly Ala Ala<br>145                    150                    155                   160 | 480 |
| ctc gga tcg ctt gcc gcc gcc gaa ttt ttc tac gtc ttt ttt acc ctc<br>Leu Gly Ser Leu Ala Ala Ala Glu Phe Phe Tyr Val Phe Phe Thr Leu<br>               165                    170                    175 | 528 |
| tcc caa acc att gcg ctg aca gcc tgc ctt aac ctt ctg att gct gct<br>Ser Gln Thr Ile Ala Leu Thr Ala Cys Leu Asn Leu Leu Ile Ala Ala<br>          180                    185                    190 | 576 |
| tca gta tgc tgc gtt aca gaa agg atg gat atg gtg aac act aaa ccg<br>Ser Val Cys Cys Val Thr Glu Arg Met Asp Met Val Asn Thr Lys Pro<br>               195                    200                    205 | 624 |
| aat act agt gtg att aat atg ctt tct ttc ctt acc gga tta ttg agc<br>Asn Thr Ser Val Ile Asn Met Leu Ser Phe Leu Thr Gly Leu Leu Ser<br>210                    215                    220 | 672 |
| ttg ggt ata gaa gtc ttg tgg gta agg atg ttt tcg ttc gca gca cag<br>Leu Gly Ile Glu Val Leu Trp Val Arg Met Phe Ser Phe Ala Ala Gln<br>225                    230                    235                   240 | 720 |
| tcc gtg cct cag gca ttt tca ttt att ctt gcc tgt ttt ctg acc ggt<br>Ser Val Pro Gln Ala Phe Ser Phe Ile Leu Ala Cys Phe Leu Thr Gly<br>               245                    250                    255 | 768 |
| atc gcc gtc ggc gcg tat ttt ggc aaa cgg att tgc cgc agc cgc ttt<br>Ile Ala Val Gly Ala Tyr Phe Gly Lys Arg Ile Cys Arg Ser Arg Phe<br>          260                    265                    270 | 816 |
| gtt gat att ccc ttt atc ggg cag tgc ttc ttg tgg gcg ggt att gcc<br>Val Asp Ile Pro Phe Ile Gly Gln Cys Phe Leu Trp Ala Gly Ile Ala<br>               275                    280                    285 | 864 |
| gat ttt ttg att ttg ggt gct gcg tgg ttg ttg acg ggt ttt tcc ggt<br>Asp Phe Leu Ile Leu Gly Ala Ala Trp Leu Leu Thr Gly Phe Ser Gly<br>          290                    295                    300 | 912 |
| ttc gtc cac cac gcc ggt att ttc att acc ctg tct gcc gtc gtc agg<br>Phe Val His His Ala Gly Ile Phe Ile Thr Leu Ser Ala Val Val Arg<br>305                    310                    315                   320 | 960 |
| ggg ttg att ttc cca ctt gta cac cat gtg ggt acg gat ggc aac aaa<br>Gly Leu Ile Phe Pro Leu Val His His Val Gly Thr Asp Gly Asn Lys<br>               325                    330                    335 | 1008 |
| tcc gga cga cag gtt tcc aat gtt tat ttc gcc aac gtt gcc ggc agt<br>Ser Gly Arg Gln Val Ser Asn Val Tyr Phe Ala Asn Val Ala Gly Ser<br>          340                    345                    350 | 1056 |
| gca ttg ggt ccg gtc ctt atc ggc ttt gtg ata ctt gat ttg ttg tcc<br>Ala Leu Gly Pro Val Leu Ile Gly Phe Val Ile Leu Asp Leu Leu Ser<br>               355                    360                    365 | 1104 |
| acc caa cag att tac ctg ctc atc tgt ttg att tct gct gct gtc cct<br>Thr Gln Gln Ile Tyr Leu Leu Ile Cys Leu Ile Ser Ala Ala Val Pro | 1152 |

-continued

```
              370                 375                 380
ttg ttt tgt aca ctg ttc caa aaa agt ctc cga ctg aat gca gtg tcg    1200
Leu Phe Cys Thr Leu Phe Gln Lys Ser Leu Arg Leu Asn Ala Val Ser
385                 390                 395                 400 gta gca gtt tcc cta atg ttc ggc atc ctc atg ttc cta ctg ccg gat    1248
Val Ala Val Ser Leu Met Phe Gly Ile Leu Met Phe Leu Leu Pro Asp
                405                 410                 415 tct gtc ttt caa aat att gct ggc cgt ccg gat agg ttg att gaa aac    1296
Ser Val Phe Gln Asn Ile Ala Gly Arg Pro Asp Arg Leu Ile Glu Asn
            420                 425                 430 aaa cac ggc att gtt gcg gtt tac cat aga gat ggt gat aag gtt gtt    1344
Lys His Gly Ile Val Ala Val Tyr His Arg Asp Gly Asp Lys Val Val
        435                 440                 445 tat ggg gcg aat gta tac gac ggc gca tac aat acc gat ata ttc aat    1392
Tyr Gly Ala Asn Val Tyr Asp Gly Ala Tyr Asn Thr Asp Ile Phe Asn
    450                 455                 460 agt gtc aac ggc atc gaa cgt gcc tat ctg cta ccc tcc ctg aag tcc    1440
Ser Val Asn Gly Ile Glu Arg Ala Tyr Leu Leu Pro Ser Leu Lys Ser
465                 470                 475                 480 ggc ata cgc cgc att ttc gtc gtt gga ttg agt aca ggt tcg tgg gcg    1488
Gly Ile Arg Arg Ile Phe Val Val Gly Leu Ser Thr Gly Ser Trp Ala
                485                 490                 495 cgc gtc ttg tct gcc att ccg gaa atg cag tcg atg atc gtt gcg gaa    1536
Arg Val Leu Ser Ala Ile Pro Glu Met Gln Ser Met Ile Val Ala Glu
            500                 505                 510 atc aat ccg gca tac cgt agc ctt atc gcg gac gag ccg caa atc gca    1584
Ile Asn Pro Ala Tyr Arg Ser Leu Ile Ala Asp Glu Pro Gln Ile Ala
        515                 520                 525 ccg ctt ttg cag gac aaa cgt gtt gaa att gta ttg gat gac ggt agg    1632
Pro Leu Leu Gln Asp Lys Arg Val Glu Ile Val Leu Asp Asp Gly Arg
    530                 535                 540 aaa tgg ctg cgt cgc cat cct gat gaa aaa ttc gac ctg att ttg atg    1680
Lys Trp Leu Arg Arg His Pro Asp Glu Lys Phe Asp Leu Ile Leu Met
545                 550                 555                 560 aat tcg act tgg tac tgg cgt gcc tat tcc act aac ctg ttg agt gcg    1728
Asn Ser Thr Trp Tyr Trp Arg Ala Tyr Ser Thr Asn Leu Leu Ser Ala
                565                 570                 575 gaa ttt tta aaa cag gtg caa agc cac ctt acc ccg gat ggt att gta    1776
Glu Phe Leu Lys Gln Val Gln Ser His Leu Thr Pro Asp Gly Ile Val
            580                 585                 590 atg ttt aat acc acg cac agc ccg cat gct ttt gct acc gcc gta cac    1824
Met Phe Asn Thr Thr His Ser Pro His Ala Phe Ala Thr Ala Val His
        595                 600                 605 agt att ccc tat gca tac cgc tac ggg cat atg gta gtc ggc tcg gca    1872
Ser Ile Pro Tyr Ala Tyr Arg Tyr Gly His Met Val Val Gly Ser Ala
    610                 615                 620 acc ccg gta gtt ttc cct aat aaa gaa ctg ctc aag caa cgc ctt tcc    1920
Thr Pro Val Val Phe Pro Asn Lys Glu Leu Leu Lys Gln Arg Leu Ser
625                 630                 635                 640 cgg ttg att tgg ccg gaa agc ggc agg cac gta ttt gac agc agc acc    1968
Arg Leu Ile Trp Pro Glu Ser Gly Arg His Val Phe Asp Ser Ser Thr
                645                 650                 655 gtg gat gct gca gca caa aag gtt gtc tct cgt atg ctg att cgg atg    2016
Val Asp Ala Ala Ala Gln Lys Val Val Ser Arg Met Leu Ile Arg Met
            660                 665                 670 acg gaa cct tcg gct ggg gcg gaa gtc att act gac gat aat atg att    2064
Thr Glu Pro Ser Ala Gly Ala Glu Val Ile Thr Asp Asp Asn Met Ile
        675                 680                 685 gta gaa tac aaa tac ggc aga ggg att taa                            2094
Val Glu Tyr Lys Tyr Gly Arg Gly Ile
```

Val Glu Tyr Lys Tyr Gly Arg Gly Ile
    690                 695

<210> SEQ ID NO 77
<211> LENGTH: 697
<212> TYPE: PRT
<213> ORGANISM: Neisseria gonorrhoeae

<400> SEQUENCE: 77

Met Asn Ser Thr Ala Ser Lys Thr Leu Lys Gly Leu Ser Leu Val Phe
 1               5                  10                  15

Phe Ala Ser Gly Phe Cys Ala Leu Ile Tyr Gln Val Ser Trp Gln Arg
                20                  25                  30

Leu Leu Phe Ser His Ile Gly Ile Asp Leu Ser Ser Ile Thr Val Ile
            35                  40                  45

Ile Ser Val Phe Met Val Gly Leu Gly Val Gly Ala Tyr Phe Gly Gly
 50                  55                  60

Arg Ile Ala Asp Arg Phe Pro Ser Ser Ile Ile Pro Leu Phe Cys Ile
 65                  70                  75                  80

Ala Glu Val Ser Ile Gly Leu Phe Gly Leu Val Ser Lys Gly Leu Ile
                85                  90                  95

Ser Gly Leu Gly His Leu Leu Val Glu Ala Asp Leu Pro Ile Ile Ala
            100                 105                 110

Ala Ala Asn Phe Leu Leu Leu Leu Pro Thr Phe Met Met Gly Ala
            115                 120                 125

Thr Leu Pro Leu Leu Thr Cys Phe Phe Asn Arg Lys Ile His Asn Val
130                 135                 140

Gly Glu Ser Ile Gly Thr Leu Tyr Phe Phe Asn Thr Leu Gly Ala Ala
145                 150                 155                 160

Leu Gly Ser Leu Ala Ala Ala Glu Phe Phe Tyr Val Phe Phe Thr Leu
                165                 170                 175

Ser Gln Thr Ile Ala Leu Thr Ala Cys Leu Asn Leu Leu Ile Ala Ala
            180                 185                 190

Ser Val Cys Cys Val Thr Glu Arg Met Asp Met Val Asn Thr Lys Pro
        195                 200                 205

Asn Thr Ser Val Ile Asn Met Leu Ser Phe Leu Thr Gly Leu Leu Ser
210                 215                 220

Leu Gly Ile Glu Val Leu Trp Val Arg Met Phe Ser Phe Ala Ala Gln
225                 230                 235                 240

Ser Val Pro Gln Ala Phe Ser Phe Ile Leu Ala Cys Phe Leu Thr Gly
                245                 250                 255

Ile Ala Val Gly Ala Tyr Phe Gly Lys Arg Ile Cys Arg Ser Arg Phe
            260                 265                 270

Val Asp Ile Pro Phe Ile Gly Gln Cys Phe Leu Trp Ala Gly Ile Ala
        275                 280                 285

Asp Phe Leu Ile Leu Gly Ala Ala Trp Leu Leu Thr Gly Phe Ser Gly
    290                 295                 300

Phe Val His His Ala Gly Ile Phe Ile Thr Leu Ser Ala Val Val Arg
305                 310                 315                 320

Gly Leu Ile Phe Pro Leu Val His Val Gly Thr Asp Gly Asn Lys
                325                 330                 335

Ser Gly Arg Gln Val Ser Asn Val Tyr Phe Ala Asn Val Ala Gly Ser
            340                 345                 350

Ala Leu Gly Pro Val Leu Ile Gly Phe Val Ile Leu Asp Leu Leu Ser
        355                 360                 365

-continued

```
Thr Gln Gln Ile Tyr Leu Leu Ile Cys Leu Ile Ser Ala Ala Val Pro
    370             375             380
Leu Phe Cys Thr Leu Phe Gln Lys Ser Leu Arg Leu Asn Ala Val Ser
385             390             395             400
Val Ala Val Ser Leu Met Phe Gly Ile Leu Met Phe Leu Leu Pro Asp
                405             410             415
Ser Val Phe Gln Asn Ile Ala Gly Arg Pro Asp Arg Leu Ile Glu Asn
            420             425             430
Lys His Gly Ile Val Ala Val Tyr His Arg Asp Gly Asp Lys Val Val
        435             440             445
Tyr Gly Ala Asn Val Tyr Asp Gly Ala Tyr Asn Thr Asp Ile Phe Asn
    450             455             460
Ser Val Asn Gly Ile Glu Arg Ala Tyr Leu Leu Pro Ser Leu Lys Ser
465             470             475             480
Gly Ile Arg Arg Ile Phe Val Val Gly Leu Ser Thr Gly Ser Trp Ala
                485             490             495
Arg Val Leu Ser Ala Ile Pro Glu Met Gln Ser Met Ile Val Ala Glu
            500             505             510
Ile Asn Pro Ala Tyr Arg Ser Leu Ile Ala Asp Glu Pro Gln Ile Ala
        515             520             525
Pro Leu Leu Gln Asp Lys Arg Val Glu Ile Val Leu Asp Asp Gly Arg
    530             535             540
Lys Trp Leu Arg Arg His Pro Asp Glu Lys Phe Asp Leu Ile Leu Met
545             550             555             560
Asn Ser Thr Trp Tyr Trp Arg Ala Tyr Ser Thr Asn Leu Leu Ser Ala
                565             570             575
Glu Phe Leu Lys Gln Val Gln Ser His Leu Thr Pro Asp Gly Ile Val
            580             585             590
Met Phe Asn Thr Thr His Ser Pro His Ala Phe Ala Thr Ala Val His
        595             600             605
Ser Ile Pro Tyr Ala Tyr Arg Tyr Gly His Met Val Val Gly Ser Ala
    610             615             620
Thr Pro Val Val Phe Pro Asn Lys Glu Leu Leu Lys Gln Arg Leu Ser
625             630             635             640
Arg Leu Ile Trp Pro Glu Ser Gly Arg His Val Phe Asp Ser Ser Thr
                645             650             655
Val Asp Ala Ala Ala Gln Lys Val Val Ser Arg Met Leu Ile Arg Met
            660             665             670
Thr Glu Pro Ser Ala Gly Ala Glu Val Ile Thr Asp Asp Asn Met Ile
        675             680             685
Val Glu Tyr Lys Tyr Gly Arg Gly Ile
    690             695
```

<210> SEQ ID NO 78
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 78
gctctagacc accatgtctg aagaaaaatt gaaaatgag                           39

<210> SEQ ID NO 79
<211> LENGTH: 32

```
<212> TYPE: DNA
<213> ORGANISM: Artificial Sequence
<220> FEATURE:
<223> OTHER INFORMATION: Description of Artificial Sequence: primer

<400> SEQUENCE: 79
cgggatccag aaatggctgg attcgctatc ag                              32

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 80
gctctagacc accatgaaac acttactcat cg                              32

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 81
cgggatccaa tacgtaggac ttgggtc                                    27

<210> SEQ ID NO 82
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 82
gctctagacc accatgaaaa aatccctttt cgttc                           35

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 83
cgggatccat tgcggataaa catattccgc c                               31

<210> SEQ ID NO 84
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 84
gctctagacc accatgcgaa cgaccccaac cttc                            34

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 85
```
cgggatccag aaccggtagc ctacgccgac                                              30

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 86
gctctagacc accatgaaca cacgcatcat cgtttc                                       36

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 87
cgggatccag caacggcctg ccgctttaag                                              30

<210> SEQ ID NO 88
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 88
gctctagacc accatgctga cgtttatcgg actg                                         34

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 89
cgggatccac ggcagaggca cgattcc                                                 27

<210> SEQ ID NO 90
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 90
gctctagacc accatgggca tccatctcga cttc                                         34

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 91
cgggatccac aaaagttcca gaaaatctaa ctc                                          33

<210> SEQ ID NO 92
<211> LENGTH: 33
<212> TYPE: DNA
<213> ORGANISM: Artificial Sequence

```
<220> FEATURE:
<223> OTHER INFORMATION: Description of Artificial Sequence: primer

<400> SEQUENCE: 92
gctctagacc accatgaata gacccaagca acc                           33

<210> SEQ ID NO 93
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 93
cgggatccat gccgcttggg ggaggc                                   26

<210> SEQ ID NO 94
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 94
gctctagacc accatgatga atgtcgaggc agag                          34

<210> SEQ ID NO 95
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 95
cgggatccac agtttgcccg acatac                                   26

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 96
gctctagacc accatgaaat tttttcctgc tcc                           33

<210> SEQ ID NO 97
<211> LENGTH: 62
<212> TYPE: DNA
<213> ORGANISM: Artificial Sequence
<220> FEATURE:
<223> OTHER INFORMATION: Description of Artificial Sequence: primer

<400> SEQUENCE: 97
gaagatctag aaactgtaat tcaagttgaa ggaagatcta gaaactgtaa ttcaagttga    60
ag                                                             62

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 98
```

-continued

```
gctctagacc accatgattg aatttgtccg agc                              33
```

<210> SEQ ID NO 99
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 99

```
cgggatccaa ccctgcgacg agttgcgcgg gatccaaccc tgcgacgagt tgcg       54
```

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 100

```
gctctagacc accatgcaat acagcacact ggc                              33
```

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 101

```
cgggatccag tccttttttcg caccttgaag                                 30
```

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 102

```
gctctagacc accatggagc agtcgggcaa attc                             34
```

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 103

```
cgggatccaa gctgtttggc gatttcggtg                                  30
```

<210> SEQ ID NO 104
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 104

```
gctctagacc accatgcaaa acggcggggg aaag                             34
```

<210> SEQ ID NO 105
<211> LENGTH: 30
<212> TYPE: DNA
<213> ORGANISM: Artificial Sequence

```
<220> FEATURE:
<223> OTHER INFORMATION: Description of Artificial Sequence: primer

<400> SEQUENCE: 105
cgggatccag tgcctgcgca gcttggaatc                                    30

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 106
gctctagacc accatgacat tgctcaatct aatgataatg                         40

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 107
cgggatccat tccgcaaata cctgtttcca acc                                33

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 108
gctctagacc accatgaaac aatccgcccg                                    30

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 109
cgggatccat acttgggcgc aacatgac                                      28

<210> SEQ ID NO 110
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 110
gctctagacc accatgaatg tttacggttt ccc                                33

<210> SEQ ID NO 111
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 111
cgggatccat tttttagacg tatttttagt cg                                 32
```

```
<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 112
gctctagacc accatgatga gtcaacactc tgcc                              34

<210> SEQ ID NO 113
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 113
cgggatccat ccagttttg ctcgaaggc                                     29

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 114
gctctagacc accatgcctt cgagcaaaaa ctgg                              34

<210> SEQ ID NO 115
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 115
cgggatccat cgttcttcaa tctccacaaa cg                                32

<210> SEQ ID NO 116
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 116
gctctagacc accatgcacc tatgtggaaa g                                 31

<210> SEQ ID NO 117
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 117
cgggatccat tcaattcgct tcaacaatg                                    29

<210> SEQ ID NO 118
<211> LENGTH: 36
<212> TYPE: DNA
<213> ORGANISM: Artificial Sequence
<220> FEATURE:
<223> OTHER INFORMATION: Description of Artificial Sequence: primer
```

```
<400> SEQUENC
ggactagtcc accatggctg ccaaccaacg ttaccg                                    36

<210> SEQ ID NO 119
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 119
gaagatctaa gccgcgttcc cttccaaaaa atc                                       33

<210> SEQ ID NO 120
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 120
gctctagacc accatgccgc aaattaaaat tccc                                      34

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 121
cgggatccaa aaacaatctt ccggcaccc                                            29

<210> SEQ ID NO 122
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 122
gctctagacc accatgcgca cgccgttttg ttg                                       33

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 123
cgggatccat tgggcaacga cgaaggcac                                            29

<210> SEQ ID NO 124
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 124
gctctagacc accatgagaa tagagatcac acc                                       33

<210> SEQ ID NO 125
<211> LENGTH: 27
```

```
<212> TYPE: DNA
<213> ORGANISM: Artificial Sequence
<220> FEATURE:
<223> OTHER INFORMATION: Description of Artificial Sequence: primer

<400> SEQUENCE: 125
cgggatccat ggctcaatcc tttctgc                                              27

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 126
gctctagacc accatgattc acgtttcggc agtg                                      34

<210> SEQ ID NO 127
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 127
cgggatccaa cctgcttcat gggtgattc                                            29

<210> SEQ ID NO 128
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 128
gctctagacc accatgaatt cgaccgcaag taaaac                                    36

<210> SEQ ID NO 129
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 129
cgggatccaa atccctctgc cgtatttg                                             28
```